United States Patent
Jang et al.

(10) Patent No.: US 11,024,812 B2
(45) Date of Patent: Jun. 1, 2021

(54) COMPOUND FOR ORGANIC-ELECTRIC ELEMENT, ORGANIC-ELECTRIC ELEMENT USING SAME, AND ELECTRONIC DEVICE FOR SAME

(71) Applicant: DUK SAN NEOLUXCO., LTD., Cheonan-si (KR)

(72) Inventors: Jae Wan Jang, Cheonan-si (KR); Seul-gi Kim, Daejeon (KR); Wonsam Kim, Hwaseong-si (KR); Bo Ram Park, Mokpo-si (KR); Seung-won Choi, Yongin-si (KR); Jong-Jin Ha, Cheonan-si (KR); Seungwon Yeo, Daejeon (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 198 days.

(21) Appl. No.: 15/781,212

(22) PCT Filed: Nov. 22, 2016

(86) PCT No.: PCT/KR2016/013456
§ 371 (c)(1),
(2) Date: Jun. 4, 2018

(87) PCT Pub. No.: WO2017/095054
PCT Pub. Date: Jun. 8, 2017

(65) Prior Publication Data
US 2019/0013479 A1    Jan. 10, 2019

(30) Foreign Application Priority Data

Dec. 4, 2015  (KR) .................. 10-2015-0172036

(51) Int. Cl.
*H01L 51/00* (2006.01)
*C07D 401/14* (2006.01)
(Continued)

(52) U.S. Cl.
CPC ........ *H01L 51/0072* (2013.01); *C07D 209/56* (2013.01); *C07D 209/94* (2013.01);
(Continued)

(58) Field of Classification Search
CPC ..... H01L 51/0072–0074; H01L 51/006; H01L 51/0061; C07D 403/00–14;
(Continued)

(56) References Cited

FOREIGN PATENT DOCUMENTS

JP    4-329547 A    11/1992
JP    2009-9966 A    1/2009
(Continued)

OTHER PUBLICATIONS

Machine translation of KR10-2015-0111106 (Year: 2015).*
(Continued)

*Primary Examiner* — Eric R Smith
(74) *Attorney, Agent, or Firm* — Vorys, Sater, Seymour & Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and electronic device thereof, and by comprising the compound represented by Formula 1 in the organic material layer, the driving voltage of the organic electronic device can be lowered, and the luminous efficiency and life time of the organic electronic device can be improved.

12 Claims, 1 Drawing Sheet

(51) Int. Cl.
| | |
|---|---|
| C09K 11/06 | (2006.01) |
| C07D 409/12 | (2006.01) |
| C07D 491/048 | (2006.01) |
| C07D 409/04 | (2006.01) |
| C07D 405/04 | (2006.01) |
| C07D 487/04 | (2006.01) |
| C07D 405/12 | (2006.01) |
| C07D 495/04 | (2006.01) |
| C07D 403/04 | (2006.01) |
| C07D 403/12 | (2006.01) |
| C07D 487/06 | (2006.01) |
| C07D 209/94 | (2006.01) |
| C07D 405/14 | (2006.01) |
| C07D 209/56 | (2006.01) |
| C07D 403/10 | (2006.01) |
| C07D 403/14 | (2006.01) |
| C07D 405/10 | (2006.01) |
| C07D 409/14 | (2006.01) |
| H01L 51/50 | (2006.01) |

(52) U.S. Cl.
CPC ......... *C07D 401/14* (2013.01); *C07D 403/04* (2013.01); *C07D 403/10* (2013.01); *C07D 403/12* (2013.01); *C07D 403/14* (2013.01); *C07D 405/04* (2013.01); *C07D 405/10* (2013.01); *C07D 405/12* (2013.01); *C07D 405/14* (2013.01); *C07D 409/04* (2013.01); *C07D 409/12* (2013.01); *C07D 409/14* (2013.01); *C07D 487/04* (2013.01); *C07D 487/06* (2013.01); *C07D 491/048* (2013.01); *C07D 495/04* (2013.01); *C09K 11/06* (2013.01); *H01L 51/006* (2013.01); *H01L 51/0054* (2013.01); *H01L 51/0059* (2013.01); *H01L 51/0061* (2013.01); *H01L 51/0067* (2013.01); *H01L 51/0073* (2013.01); *H01L 51/0074* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1048* (2013.01); *C09K 2211/1051* (2013.01); *C09K 2211/1088* (2013.01); *C09K 2211/1092* (2013.01); *C09K 2211/185* (2013.01); *H01L 51/0052* (2013.01); *H01L 51/0058* (2013.01); *H01L 51/5016* (2013.01); *H01L 51/5056* (2013.01); *H01L 51/5072* (2013.01); *H01L 51/5088* (2013.01)

(58) Field of Classification Search
CPC .... C07D 405/00–14; C07D 409/00–14; C07D 209/56–96; C07D 401/14; C07D 409/04; C07D 409/14; C07D 405/04; C07D 405/12; C07D 405/10; C07D 487/04; C07D 487/06; C07D 209/94; C07D 403/10; C07D 403/14; C07D 403/04; C07D 405/14; C09K 2211/1029; C09K 2211/1007; C09K 2211/1088; C09K 2211/1092; C09K 2211/1014; C09K 2211/1048; C09K 2211/1051; C09K 2211/185; C09K 2211/1044; C09K 2211/1011

See application file for complete search history.

(56) References Cited

FOREIGN PATENT DOCUMENTS

| | | | |
|---|---|---|---|
| JP | 2009-49088 A | | 3/2009 |
| JP | 2009123740 A | * | 6/2009 |
| KR | 10-2015-0111106 A | | 10/2015 |

OTHER PUBLICATIONS

Machine translation of JP H03-128412 (Year: 1991).*
W. Fan, et al., "Domino reactions of cyclic enaminones leading to selective synthesis of pentacyclic indoles and its functionalization", Tetrahedron 72, p. 4867-4877 (Year: 2016).*
Machine translation of JP2009-123740A (Year: 2009).*
P. A. Blair, S-J. Chang, H. Schechter, "Photolytic, thermal, addition and cycloaddition reactions of 2-diazo-5,6- and -3,8-disubstituted acenaphthenones", Journal of Organic Chemistry 69, p. 7123-7133 (Year: 2004).*
Wrobel et al., "Synthesis of 1-Hydroxyindoles and Indoles from ortho-Nitroarylethanes", Tetrahedron, vol. 53, No. 15, pp. 5501-5514, 1997.

* cited by examiner

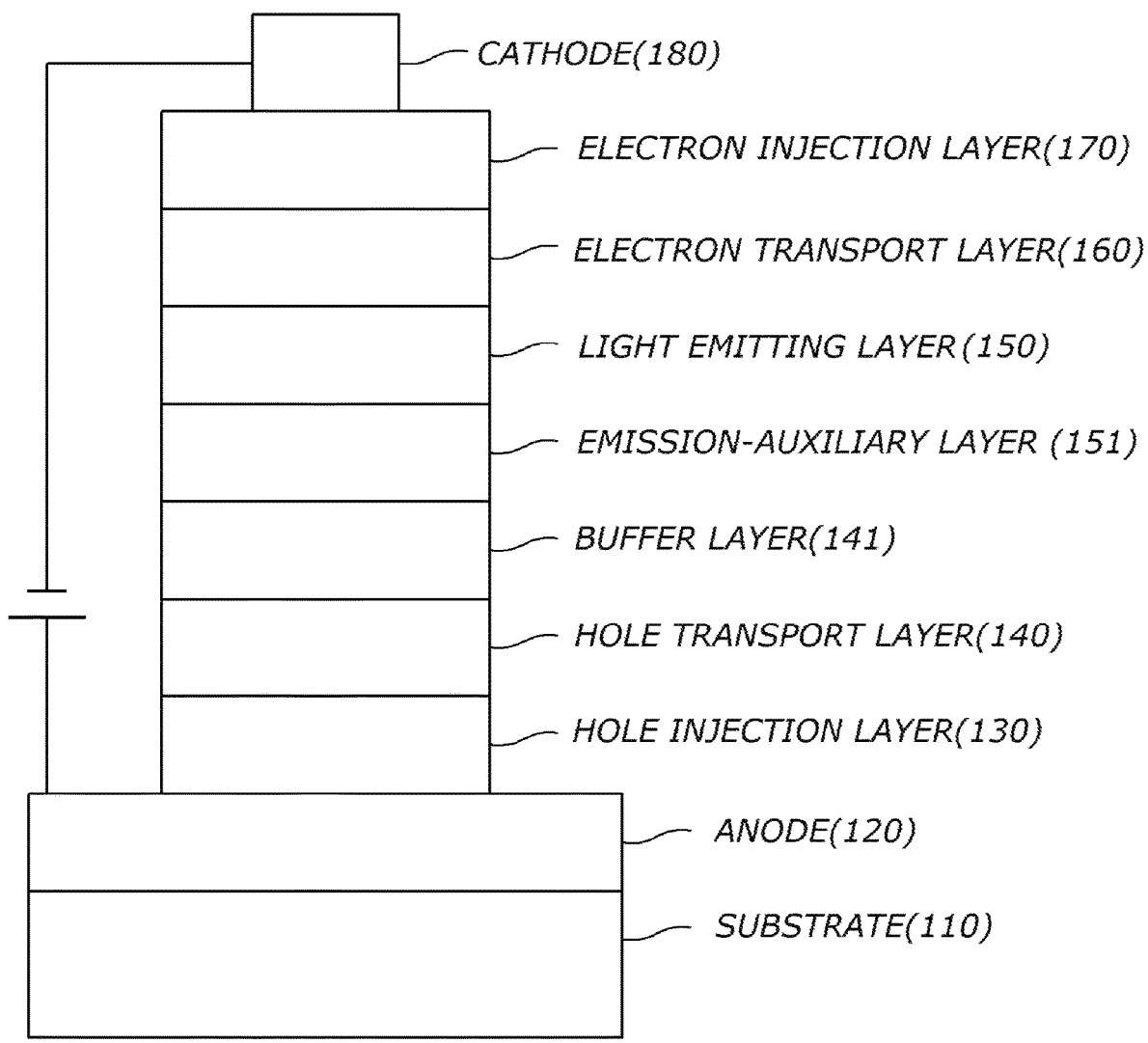

COMPOUND FOR ORGANIC-ELECTRIC ELEMENT, ORGANIC-ELECTRIC ELEMENT USING SAME, AND ELECTRONIC DEVICE FOR SAME

CROSS-REFERENCE TO RELATED APPLICATION

This patent application claims priority from and the benefit under 35 U.S.C. § 119 to § 121, and § 365 of Korean Patent Application No. 10-2015-0172036, filed on Dec. 4, 2015, which is hereby incorporated by reference for all purposes as if fully set forth herein. Further, this application claims the benefit of priority in countries other than U.S., which is hereby incorporated by reference herein.

BACKGROUND

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there are problems that the maximum emission wavelength shifts to a long wavelength and the color purity is reduced due to intermolecular interactions or the efficiency of device is reduced due to the light emission attenuating effect. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. Therefore, there is a need to develop the material of a hole transport layer and/or light emitting material capable of achieving a charge balance in the light emitting layer efficiently.

On the other hand, it is required to develop the material of a hole transport layer that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In addition, deposition is a main method of forming an OLED, and thus there is an actual need to develop a material that is durable to such a deposition method, that is, a highly heat-resistant material.

That is, it should be preceded that the materials consisting an organic material layer of the element, for example, a hole injection material, a hole transport material, a light emitting material, an electron transport material, an electron injection material, material of an emission-auxiliary layer and the like, are supported by a stable and efficient material. However, such a stable and efficient organic material layer material for an organic electric element has not yet been fully developed. Accordingly, there is a continuous need to develop new materials for an organic material layer, particularly, it is strongly required to develop host material for a light emitting layer and material of the hole transport layer.

Object, Technical Solution and Effects of the Invention

The present invention is to provide a compound lowering driving voltage of the element, improving luminous efficiency, color purity and lifetime of the element, an organic electric element comprising the same, and an electronic device thereof.

In an aspect of the present invention, the present invention provides the compound represented by the following formula.

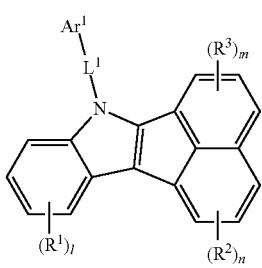

In another aspect of the present invention, the present invention provides an organic electric element using the compound represented by formula above and an electric device thereof.

By using the compound according to embodiments of the present invention, the driving voltage of element can be lowered and the luminous efficiency, color purity and lifetime of the element can be g significantly improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

The FIGURE illustrates an example of an organic electric element according to an embodiment of the present invention.

Hereinafter, some embodiments of the present invention will be described in detail with reference to the accompanying illustrative drawings. In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means the saturated aliphatic functional radicals including a linear alkyl group, a branched chain alkyl group, a cycloalkyl group (alicyclic), or an alkyl group substituted with a cycloalkyl or with a cycloalkyl substituted with an alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an oxygen radical attached to an alkyl group, but not limited to, and has 1 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises spiro compound formed by linking R and R' together with the carbon bonded to them.

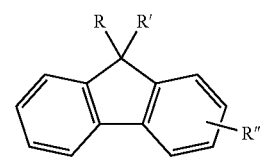

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

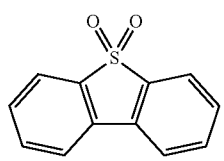 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic ring" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula:

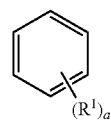

Wherein, the substituent $R^1$ is absent when a is an integer of zero, the sole $R^1$ is bonded to any one of the carbon atoms constituting the benzene ring when a is an integer of 1, when a is an integer of 2 or 3, the substituent $R^1$s may be bonded as follows and the substituents $R^1$s may be the same or different each other, and the substituent $R^1$s may be bonded to the carbon of the benzene ring in a similar manner when a is an integer of 4 to 6. Herein, the indication of the hydrogen bonded to the carbon which forms the benzene ring is omitted.

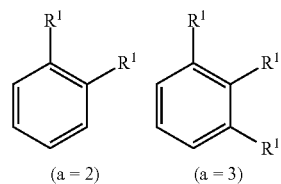

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

Although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170 and the like, as a host or a dopant material of a light emitting layer 150, or as a material of a layer for improving luminous efficiency. For example, the inventive compound may be used as material of the light emitting layer 150, the hole transport layer 140, and/or the emission-auxiliary layer 151, preferably, as material of the hole transport layer 140 and/or the light emitting layer 150.

On the other hand, even if the core is the same core, the band gap, the electrical characteristics, the interface characteristics, and the like may be different depending on which substituent is bonded at which position. Therefore, it is necessary to study the selection of the core and the combination of the core and the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, according to the present invention, energy level and $T_1$ value between the respective layers of the organic material layer, inherent material properties (mobility, interfacial properties, etc.) and the like can be optimized by forming a hole transport layer 140 and/or a light emitting layer 150 which comprises the compound represented by the Formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

[Formula 1]

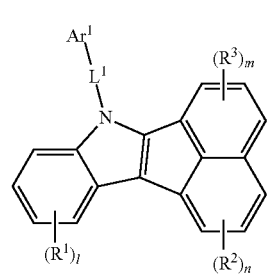

In the formula 1, each of symbols may be defined as follows.

$R^1$ to $R^3$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -$L^a$-N($R^a$)($R^b$).

When $R^1$ is an aryl group, $R^1$ may be preferably a $C_6$-$C_{30}$ aryl group, more preferably a $C_6$-$C_{18}$ aryl group, for example, phenyl, biphenyl, terphenyl, naphthyl, triphenylene and the like. When $R^1$ is a heterocyclic group, $R^1$ may be preferably a $C_2$-$C_{30}$ heterocyclic group, more preferably a $C_2$-$C_{12}$ heterocyclic group, for example, pyridine, pyrimidine, triazine, quinazoline, carbazole, benzothienopyridine, di benzofuran, dibenzothiophene and the like.

When $R^1$ is a fluorenyl group, for example, $R^1$ may be 9,9-dimethyl-9H-fluorene and when $R^1$ is an alkyl group, $R^1$ may be tert-butyl group.

When $R^2$ and $R^3$ are a heterocyclic group, $R^2$ and $R^3$ may be preferably a $C_2$-$C_{30}$ heterocyclic group, more preferably a $C_2$-$C_{18}$ heterocyclic group, for example, pyridine, carbazole, dibenzothiophene, acenaphthoindole and the like.

Further, neighboring $R^1$s to neighboring $R^3$s, or $R^2$ and $R^3$ may be each independently linked to each other to form at least one ring. That is, neighboring $R^1$ groups, neighboring $R^2$ groups, neighboring $R^3$ groups, or $R^2$ and $R^3$ groups are optionally linked to each other to form at least one ring. Here, the formed ring may be a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring and the combination of these. For example, they, particularly, $R^2$ and $R^3$ may be linked to each other to form a ring such as benzene or naphthalene, or the like.

l is an integer of 0 to 4, m and n are each an integer of 0 to 3, and a plurality of $R^1$s to $R^3$s may be each the same or different from each other when they are each an integer of 2 or more.

$Ar^1$ may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-N($R^a$)($R^b$), a $C_1$-$C_{30}$ alkoxyl group, and a $C_6$-$C_{30}$ aryloxyl group.

When $Ar^1$ is an aryl group, $Ar^1$ may be preferably a $C_6$-$C_{30}$ aryl group, more preferably a $C_6$-$C_{18}$ aryl group, for example, phenyl, biphenyl, terphenyl, naphthyl, phenanthrene, triphenylene and the like. When $Ar^1$ is a heterocyclic group, $Ar^1$ may be preferably a $C_2$-$C_{30}$ heterocyclic group, more preferably a $C_2$-$C_{18}$ heterocyclic group, for example, pyridine, pyrimidine, triazine, quinazoline, quinoxaline, benzoquinazoline, dibenzoquinazoline, carbazole, dibenzothiophene, dibenzofuran, benzothienopyrimidine, naphtofuropyrimidine, acenaphthoindole, pyrimidoindole, 5,5-dimethyl-5H-indenopyrimidine, and the like. When $Ar^1$ is a fluorenyl group, $Ar^1$ may be 9,9-dimethyl-9H-fluorene and when $Ar^1$ is an alkenyl group, $Ar^1$ may be ethenyl group.

$L^1$ may be selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P.

When $L^1$ is an arylene group, $L^1$ may be preferably a $C_6$-$C_{30}$ arylene group, more preferably a $C_6$-$C_{12}$ arylene group, for example, phenyl, naphthalene, biphenyl and the like. When $L^1$ is a heterocyclic group, $L^1$ may be preferably a $C_2$-$C_{30}$ heterocyclic group, more preferably a $C_2$-$C_{18}$ heterocyclic group, for example, pyridine, pyrimidine, triazine, quinazoline, quinoxaline, benzoquinazoline, dibenzoquinazoline, carbazole, benzothienopyrimidine, benzofuropyrimidine, naphthofuropyrimidine, acenaphthoindole, pyrimidoindole, 5,5-dimethyl-5H-indenopyrimidine and the like. When $L^1$ is a fluorenylene group, $L^1$ may be 9,9-dimethyl-9H-fluorene.

$L^a$ may be selected from the group consisting of a single bond, a $C_6$-$C_{60}$ arylene group, a fluorenylene group; and a $C_2$-$C_{60}$ heterocyclic group containing at least one heteroatom selected from the group consisting of O, N, S, Si, and P.

When $L^a$ is an arylene group, $L^a$ may be preferably a $C_6$-$C_{30}$ arylene group, more preferably a $C_6$-$C_{12}$ arylene group, for example, phenyl, naphthalene, biphenyl and the like. When $L^a$ is a heterocyclic group, $L^a$ may be preferably a $C_2$-$C_{30}$ heterocyclic group, more preferably a $C_2$-$C_{12}$ heterocyclic group, for example, dibenzothiophene. When $L^a$ is a fluorenylene group, $L^a$ may be 9,9-dimethyl-9H-fluorene.

$R^a$ and $R^b$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, -L'-N(R')(R"), and a $C_6$-$C_{30}$ aryloxyl group.

When $R^a$ and $R^b$ are an aryl group, $R^a$ and $R^b$ may be preferably a $C_6$-$C_{30}$ aryl group, more preferably a $C_6$-$C_{18}$ aryl group, for example, phenyl, biphenyl, terphenyl, naphthyl, phenanthrene and the like. When $R^a$ and $R^b$ are a heterocyclic group, $R^a$ and $R^b$ may be preferably a $C_2$-$C_{30}$ heterocyclic group, more preferably a $C_2$-$C_{12}$ heterocyclic group, for example, pyridine, carbazole, dibenzothiophene, dibenzofuran and the like. When $R^a$ and $R^b$ are a fluorenyl group, $R^a$ and $R^b$ may be 9,9-dimethyl-9H-fluorene, 9,9-diphenyl-9H-fluorene, 9,9'-spirofluorene or the like.

L' may be selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P. When L' is an arylene group, L' may be preferably a $C_6$-$C_{30}$ arylene group, more preferably a $C_6$-$C_{12}$ arylene group, for example, phenyl, biphenyl and the like.

R' and R" may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group.

When R' and R" are an aryl group, R' and R" may be preferably a $C_6$-$C_{30}$ aryl group, more preferably a $C_6$-$C_{12}$ aryl group, for example, phenyl, naphthyl, biphenyl and the like.

Meanwhile, the case where $R^1$ to $R^3$ are all hydrogen when $L^1$ is a single bond and $Ar^1$ is methyl or phenyl is excluded. Preferably, when $L^1$ is a single bond and $Ar^1$ is methyl or phenyl, at least one of $R^1$ to $R^3$ is selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and -$L^a$-N($R^a$)($R^b$); or at least one couple of neighboring $R^1$s to neighboring $R^3$s may be linked to each other to form at least one ring; or $R^2$ and $R^3$ may be linked to each other to form at least one ring.

The above aryl group, fluorenyl group, heterocyclic group, alkyl group, fused ring group, alkenyl group, alkynyl group, alkoxyl group, aryloxyl group, arylene group, fluorenylene group, ring formed by linking between neighboring groups of $R^1$s to $R^3$s, and ring formed by linking between $R^2$ and $R^3$ are each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group, and the combination of these.

For example, $R^1$ to $R^3$ may be each independently further substituted with phenyl, triphenylene, carbazole, quinazoline, triazine, benzothienopyrimidine, pyrimidoindole, benzocarbazole, methyl, fluoro, cyano group and the like, $Ar^1$ may be further substituted with deuterium, phenyl, pyridine, dibenzothiophene, naphthyl, carbazole, dibenzofuran, biphenyl, fluorene, phenyl substituted with deuterium, methyl, ethoxy, propene and the like, $L^1$, $L^a$, $L'$ may be each further substituted with deuterium, phenyl, naphthyl, dibenzofuran, methoxy, methyl, t-butyl and the like, and $R^a$ and $R^b$ may be each further substituted with deuterium, phenyl, naphthyl, dibenzofuran, methoxy, methyl, t-butyl and the like.

Preferably, the formula 1 may be represented by the following formula 2.

[Formula 2]

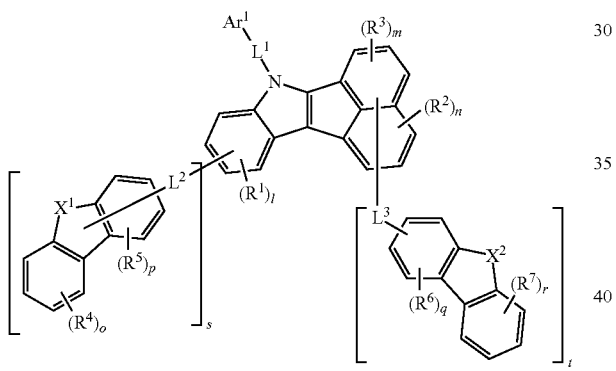

In formula 2, $Ar^1$, $L^1$, $R^1$ to $R^3$, l, m, and n are the same as defined in the Formula 1.

s is an integer of 0 to 4, t is an integer of 0 to 6, and s+t is an integer of 1 or more.

$L^2$ and $L^3$ may be each independently selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P.

$X^1$ and $X^2$ may be each independently N, N-$L^4$-$Ar^2$, O, S, $C(R^8)(R^9)$ or $Si(R^{10})(R^{11})$. Here, $X^1$ may be bonded to $L^2$ when $X^1$ is N, and $X^2$ may be bonded to $L^3$ when $X^2$ is N.

$R^4$ to $R^7$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -$L^a$-N$(R^a)(R^b)$. Further, neighboring groups of $R^4$s to neighboring groups $R^7$s may be optionally linked to each other to form at least one ring.

o, p, q and r are each an integer of 0 to 4, and, and a plurality of $R^4$s to $R^7$s may be each the same or different from each other when o, p, q and r are each an integer of 2 or more.

$R^8$ to $R^{11}$ may be each independently selected from the group consisting of hydrogen, deuterium, a $C_1$-$C_{50}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group, a $C_1$-$C_{30}$ silyl group, a $C_6$-$C_{60}$ aryl group, a $C_2$-$C_{60}$ heterocyclic group containing at least one heteroatom selected from the group consisting of O, N, S, Si, and P, a fluorenyl group, and -$L^a$-N$(R^a)(R^b)$. Here, $R^8$ and $R^9$ may be linked to each other to form a spiro compound together with C to which they are bonded, and $R^{10}$ and $R^{11}$ may be linked to each other to form a spiro compound together with C to which they are bonded.

$L^4$ may be independently selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P.

$Ar^2$ may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-N$(R^a)(R^b)$, a $C_1$-$C_{30}$ alkoxyl group, and a $C_6$-$C_{30}$ aryloxyl group.

$L^a$, $R^a$ and $R^b$ are the same as defined in the formula 1.

Further, $Ar^1$ in the Formula 1 may be selected from the following group.

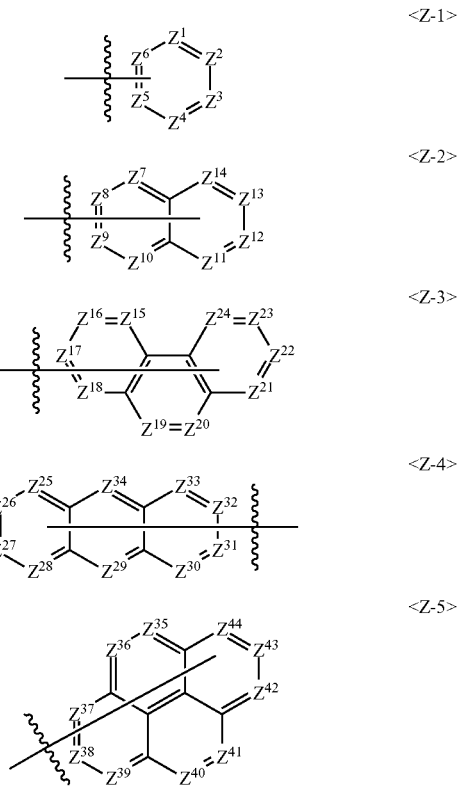

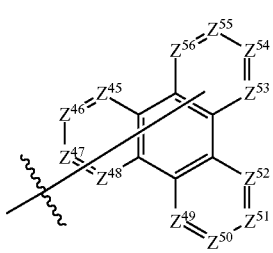

<Z-6>

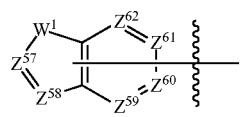

<Z-7>

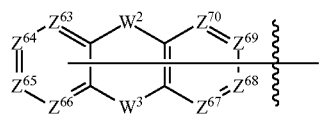

<Z-8>

In the above group of Z-1 to Z-8, $Z^1$ to $Z^{70}$ may be each independently C, $CR^{12}$ or N, and C is bonded to $L^1$ or N of the formula 1 when $Z^1$ to $Z^{70}$ are C.

Preferably, one of $Z^1$ to $Z^6$ in formula Z-1 may be C and at least one of $Z^1$ to $Z^6$ may be N, one of $Z^7$ to $Z^{14}$ in formula Z-2 may be C and at least one of $Z^7$ to $Z^{14}$ may be N, one of $Z^{15}$ to $Z^{24}$ in formula Z-3 may be C and at least one of $Z^5$ to $Z^{24}$ may be N, one of $Z^{25}$ to $Z^{34}$ in formula Z-4 may be C and at least one of $Z^{25}$ to $Z^{34}$ may be N, one of $Z^{35}$ to $Z^{44}$ in formula Z-5 may be C and at least one of $Z^{35}$ to $Z^{44}$ may be N, one of $Z^{45}$ to $Z^{56}$ in formula Z-6 may be C and at least one of $Z^{45}$ to $Z^{56}$ may be N, one of $Z^{57}$ to $Z^{62}$ in formula Z-7 may be C and at least one of $Z^{57}$ to $Z^{62}$ may be N, and one of $Z^{63}$ to $Z^{70}$ in formula Z-8 may be C and at least one of $Z^{63}$ to $Z^{70}$ may be N.

$W^1$ to $W^3$ may be each independently a single bond, $C(R^{13})(R^{14})$, $N(Ar^3)$, O, S or $Si(R^{15})(R^{16})$.

R 2, and $R^{13}$ to $R^{16}$ may be each independently selected from the group consisting of hydrogen, deuterium, a $C_1$-$C_{50}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group, a $C_1$-$C_{30}$ silyl group, a $C_6$-$C_{60}$ aryl group, a $C_2$-$C_{60}$ heterocyclic group containing at least one heteroatom selected from the group consisting of O, N, S, Si, and P, a fluorenyl group and -$L^a$-$N(R^a)(R^b)$, and $R^{13}$ and $R^{14}$, or $R^{15}$ and $R^{16}$ may be optionally linked to each other to form a ring.

$Ar^3$ may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-$N(R^a)(R^b)$, a $C_1$-$C_{30}$ alkoxyl group, and a $C_6$-$C_{30}$ aryloxyl group, $L^a$, $R^a$ and $R^b$ are the same as defined in the formula 1.

Specifically, the compound represented by formula 1 above may be any one of the following compounds.

1-1

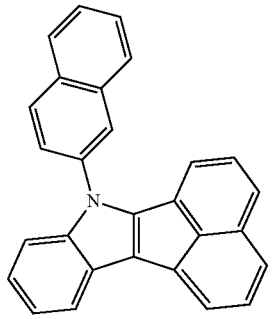

1-2

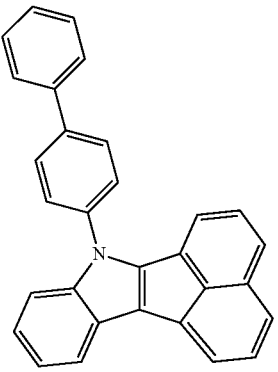

1-3

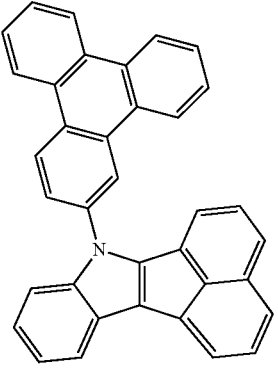

1-4

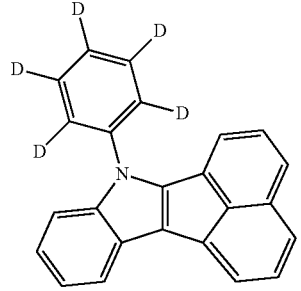

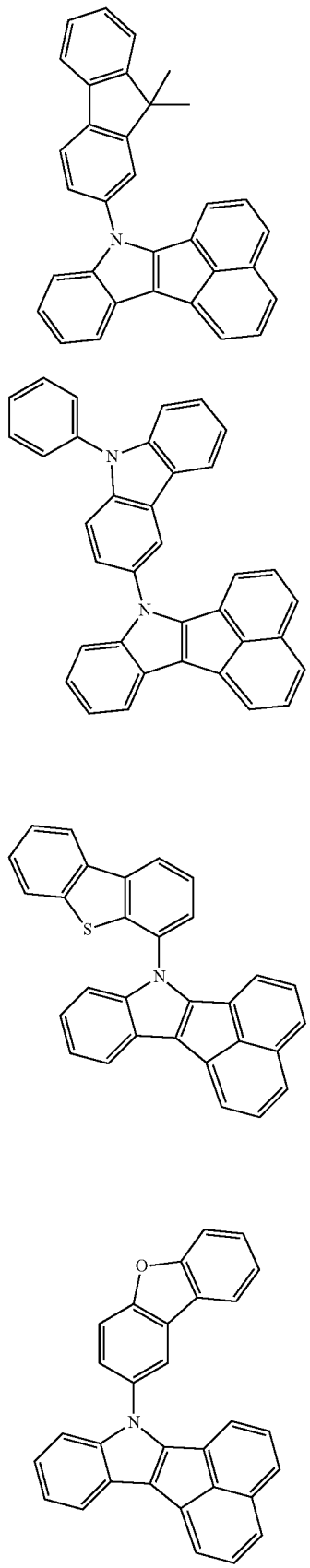
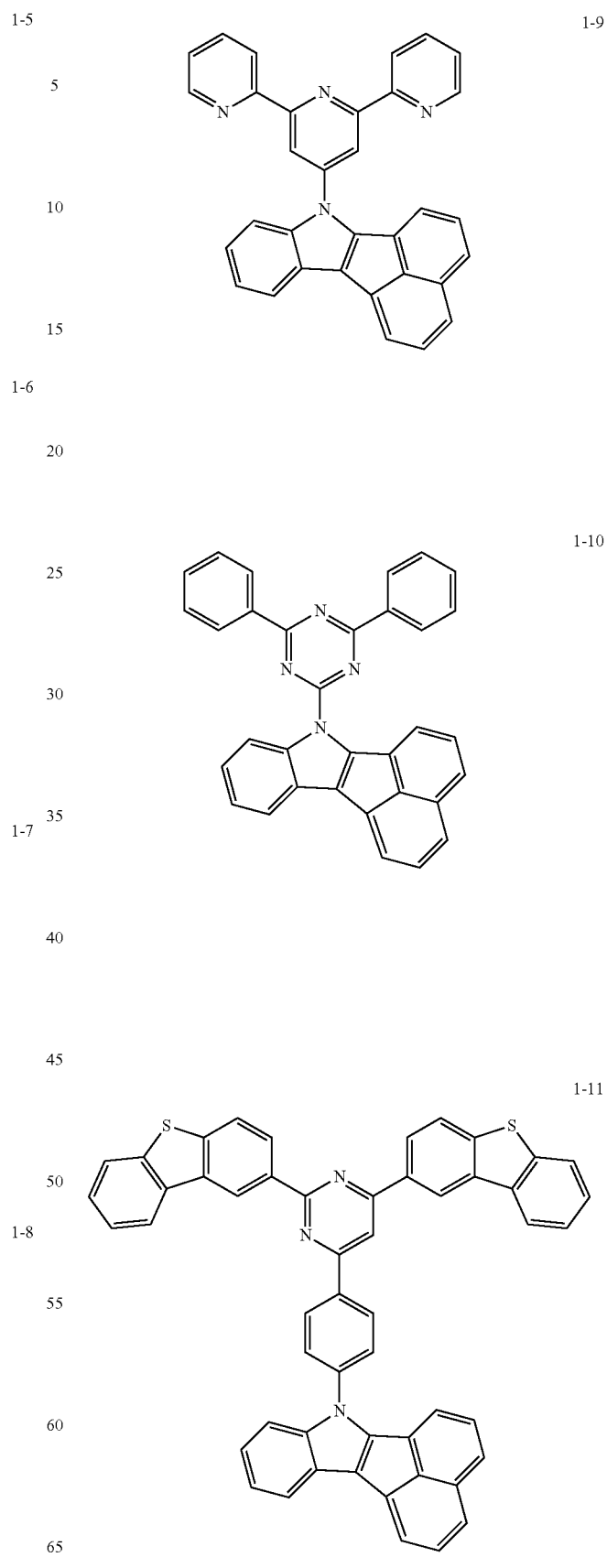

1-12
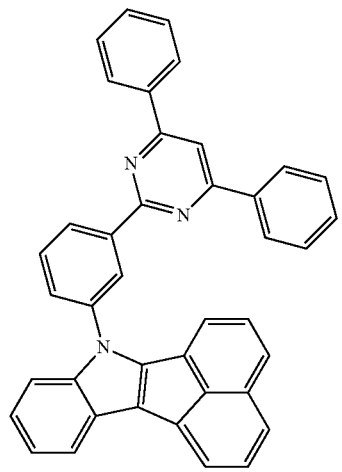
1-13
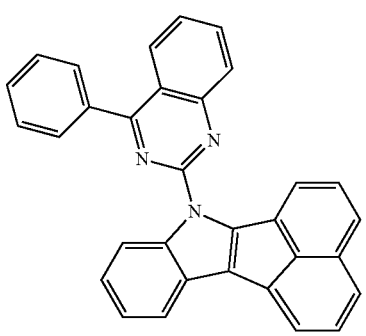
1-14
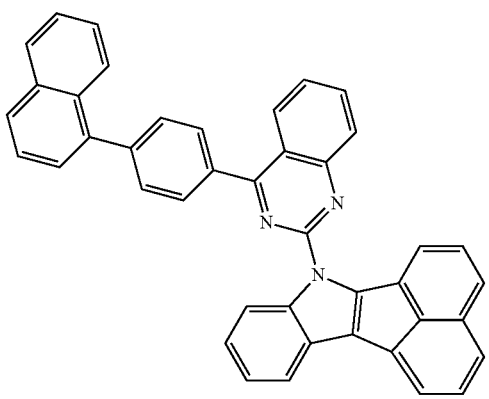
1-15
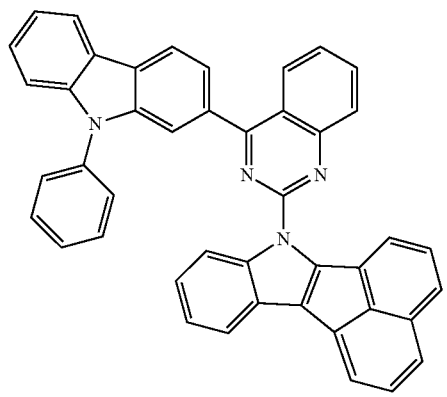
1-16
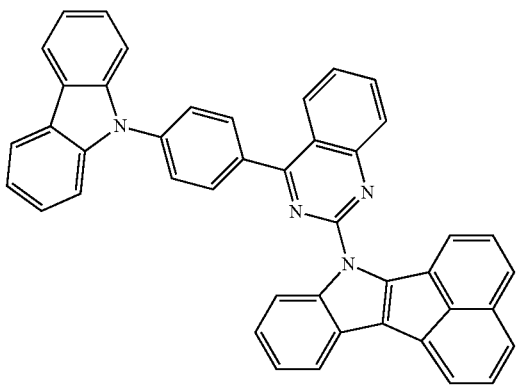
1-17
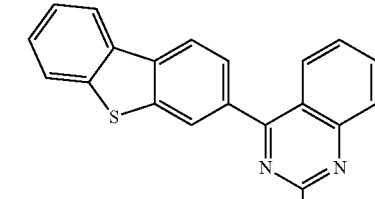
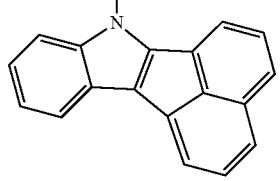
1-18
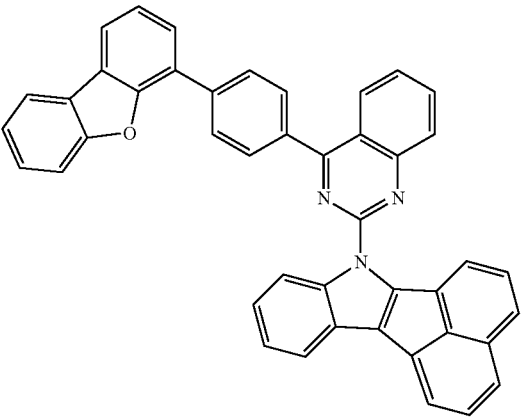

1-19
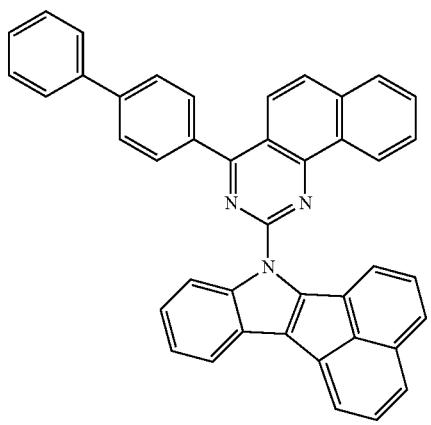
1-20
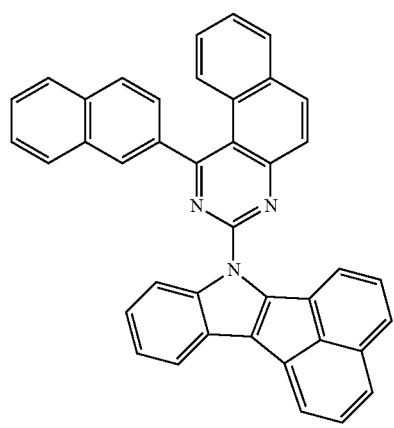
1-21
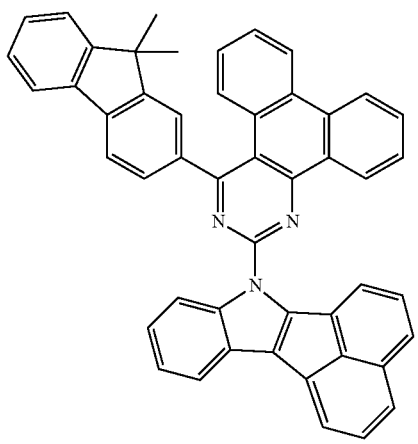
1-22
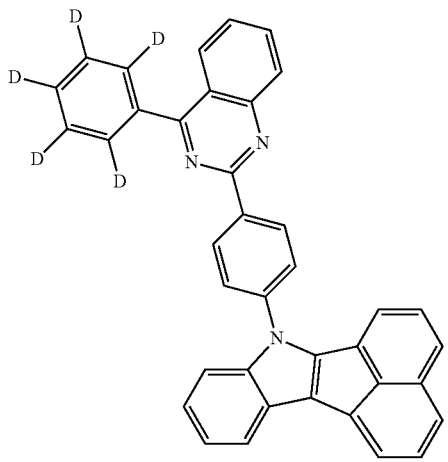
1-23
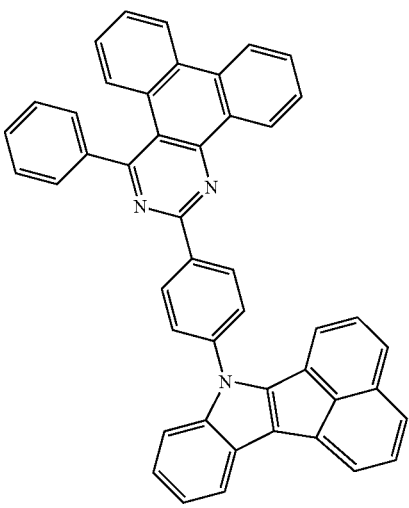
1-24
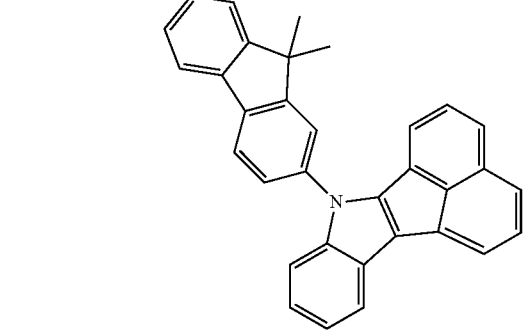

1-25
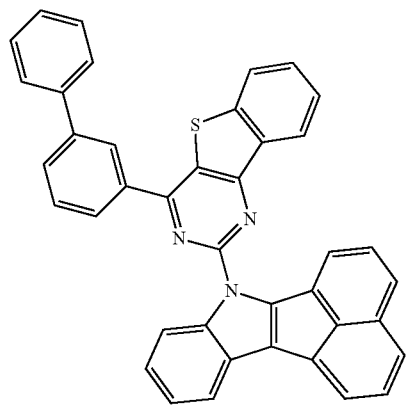
1-26
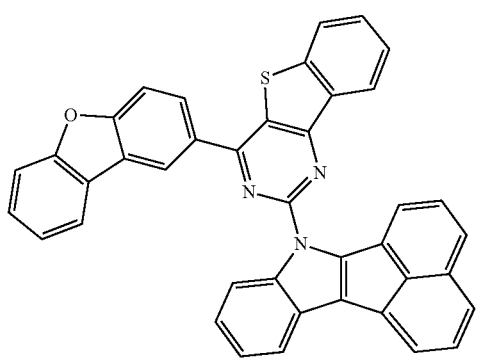
1-27
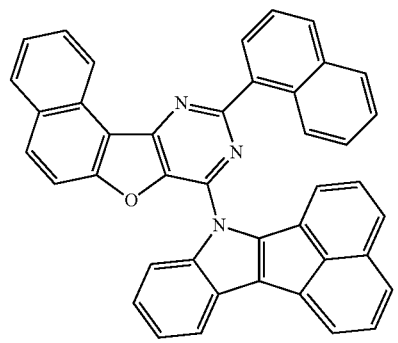
1-28
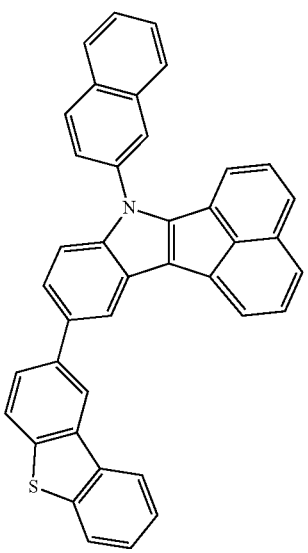
1-29
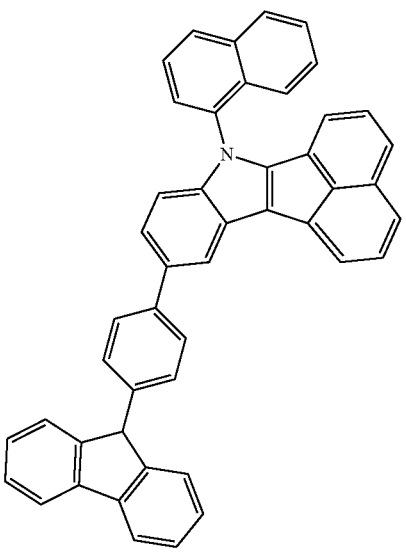
1-30
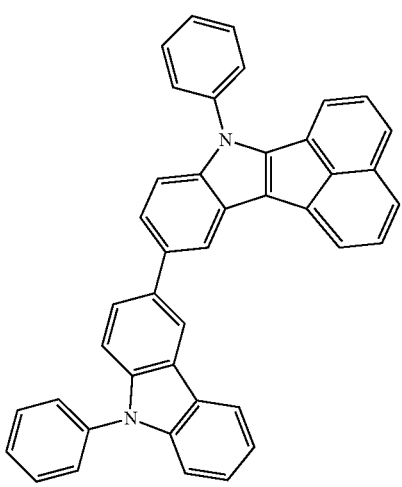
1-31
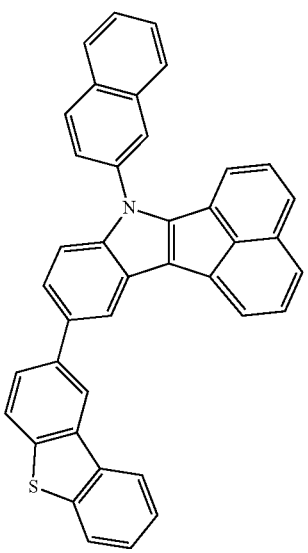

-continued
I-32
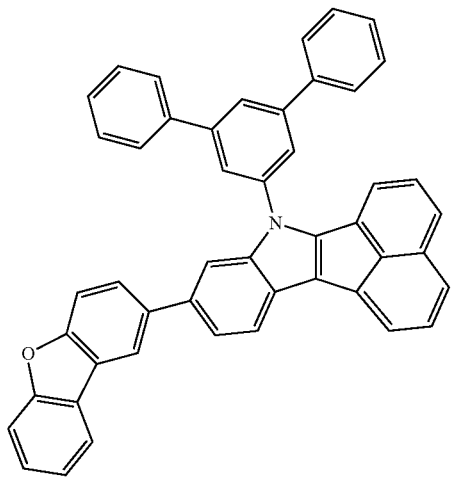
I-33
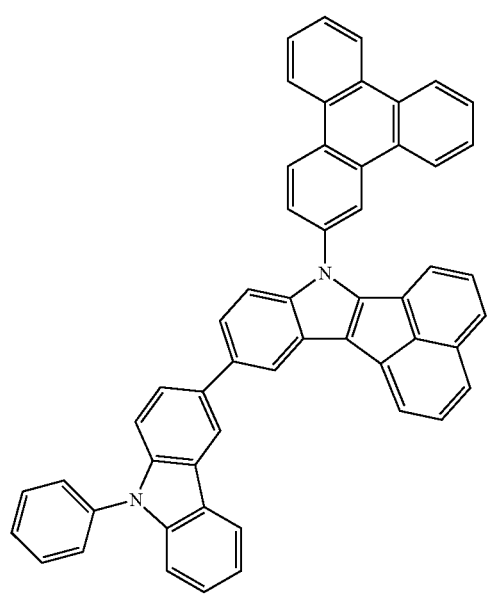
I-34
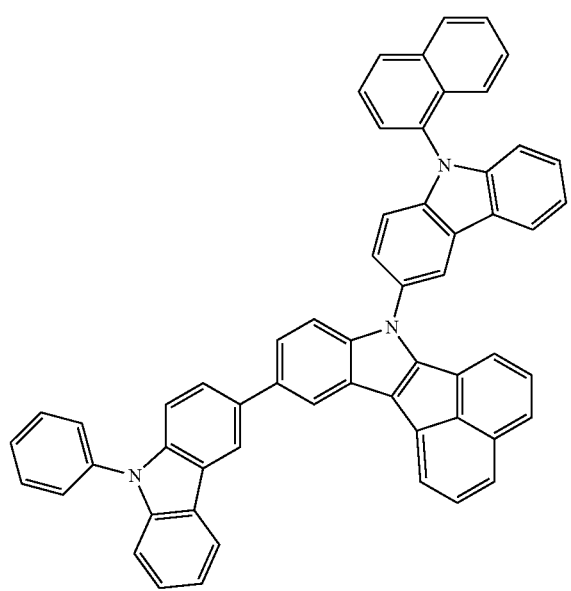
-continued
I-35
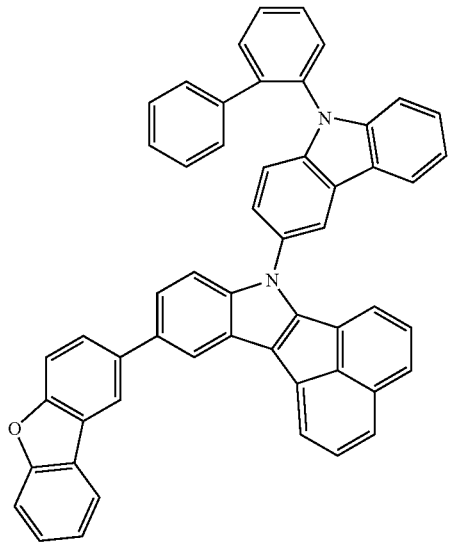
I-36
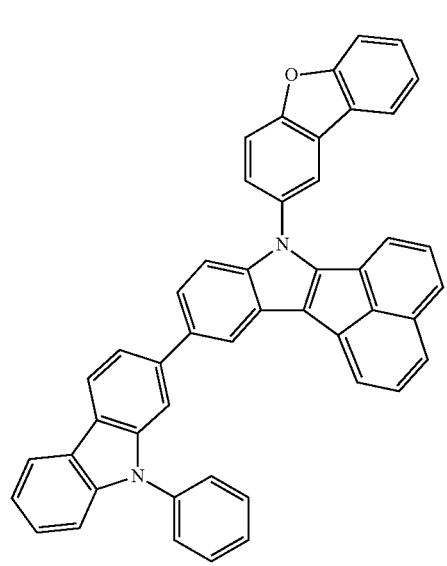
I-37
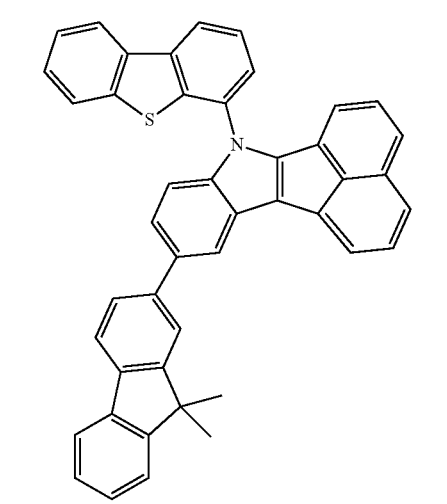

I-38
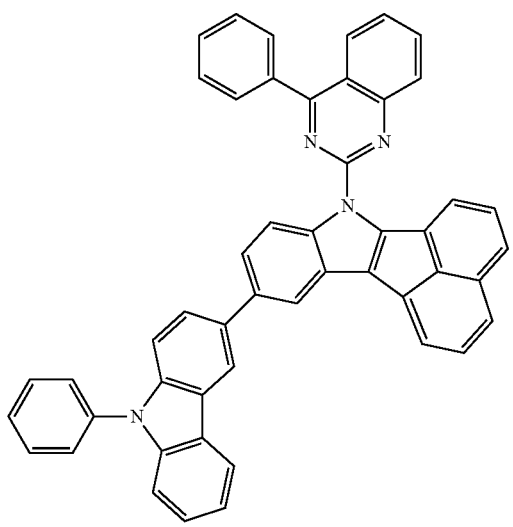
I-40
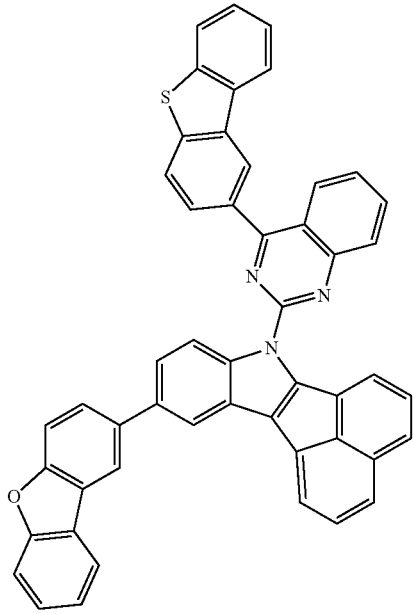
I-39
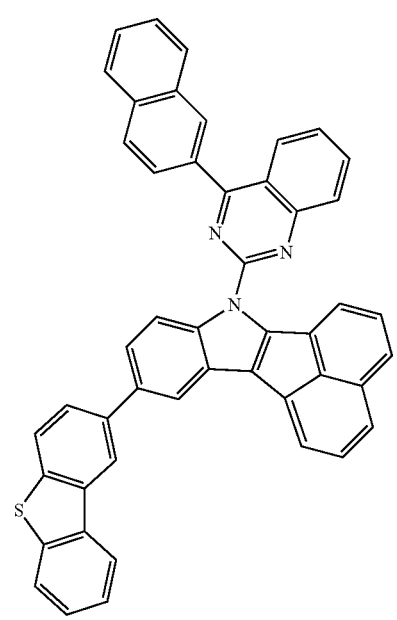
I-41
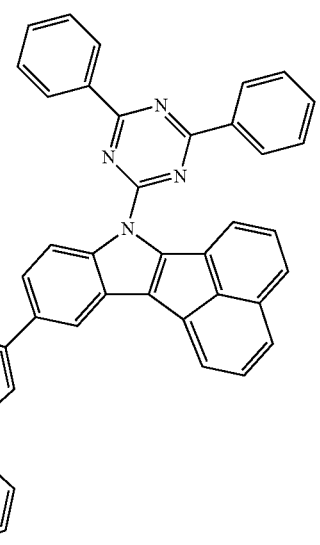
I-42

I-43
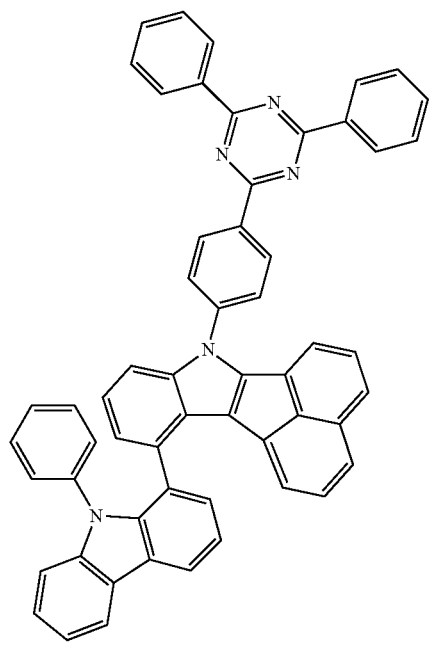
I-44
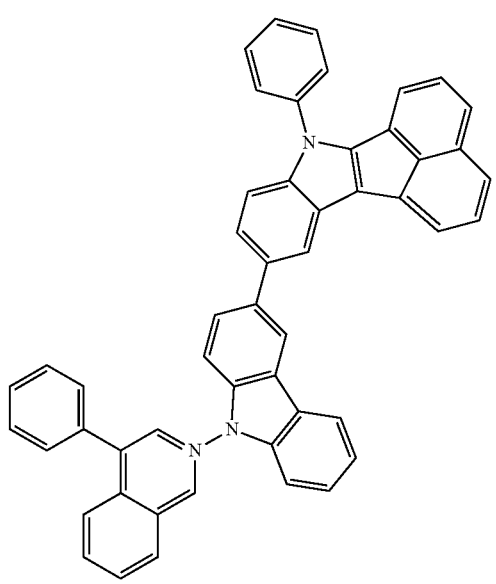
I-45
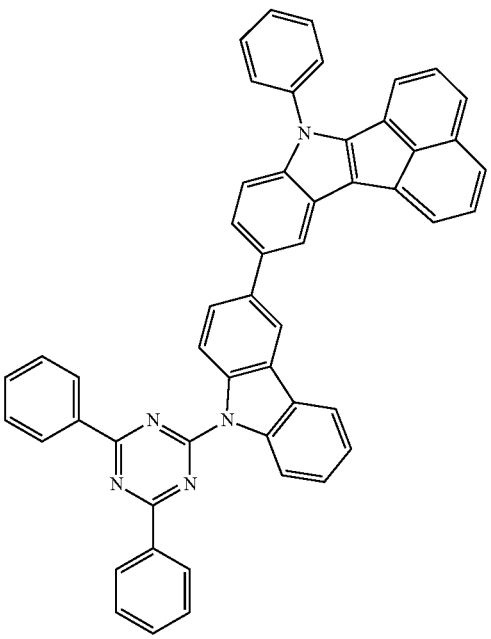
I-46
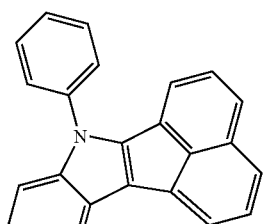
I-47
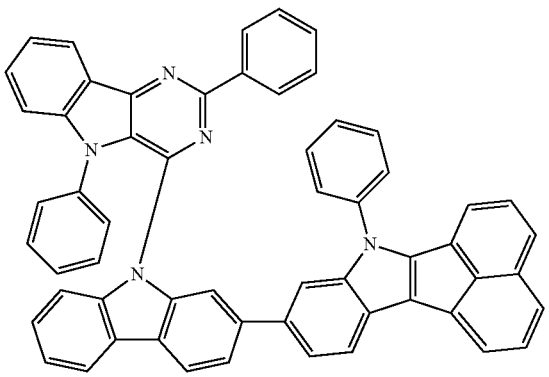

-continued
I-48
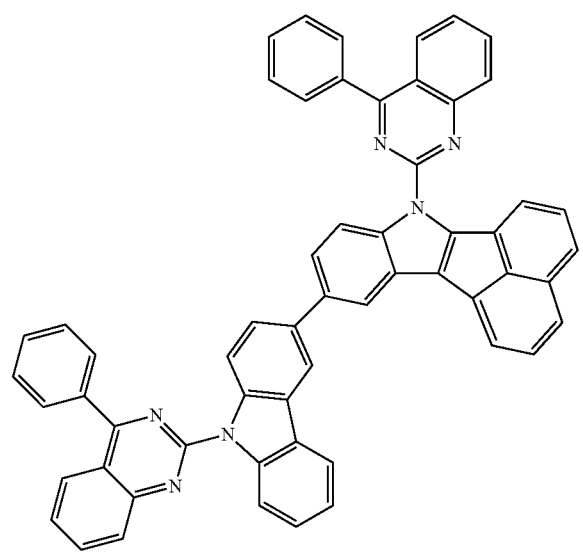
I-49
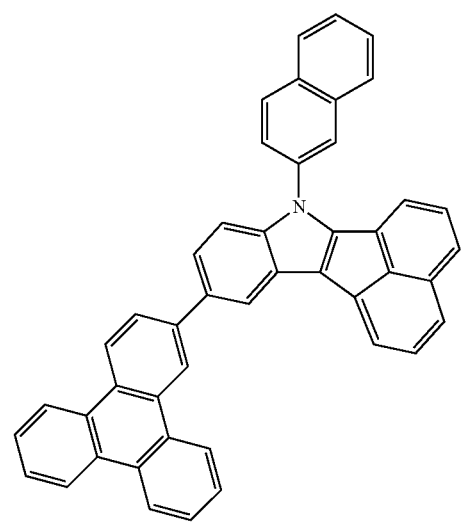
I-50
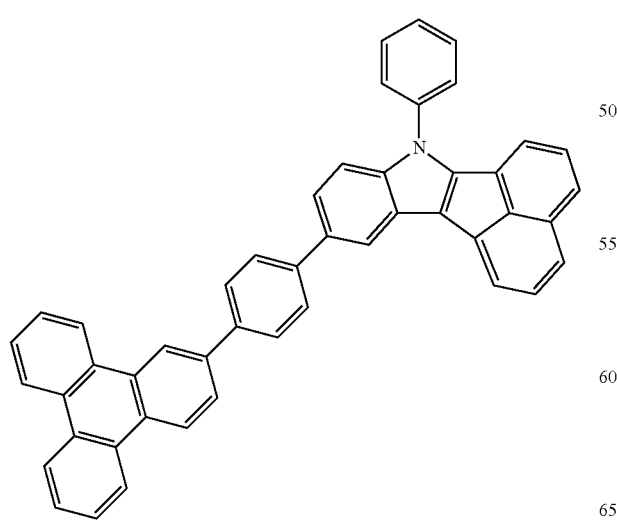
-continued
I-51
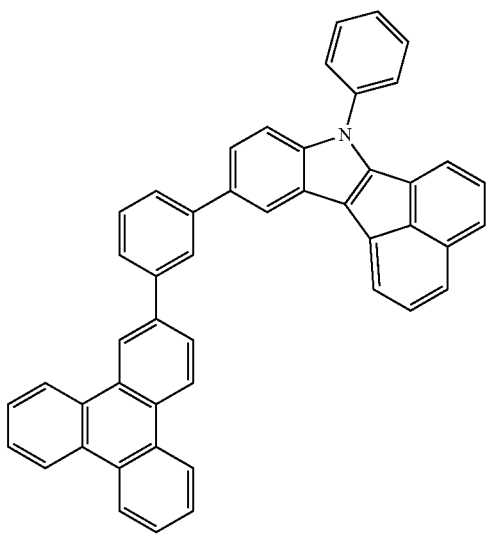
I-52
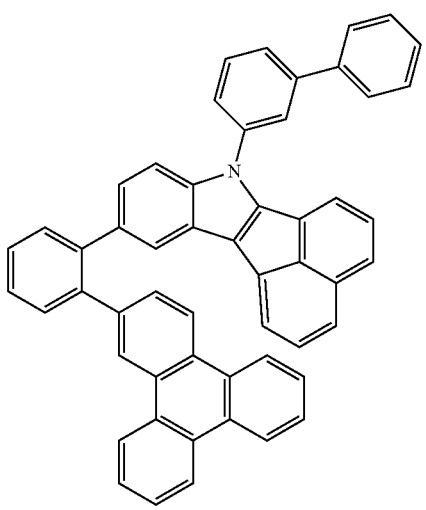
I-53
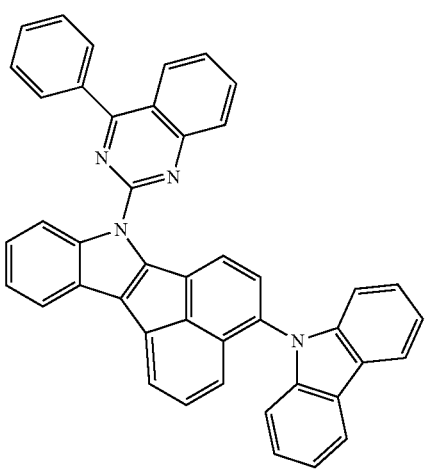

I-54
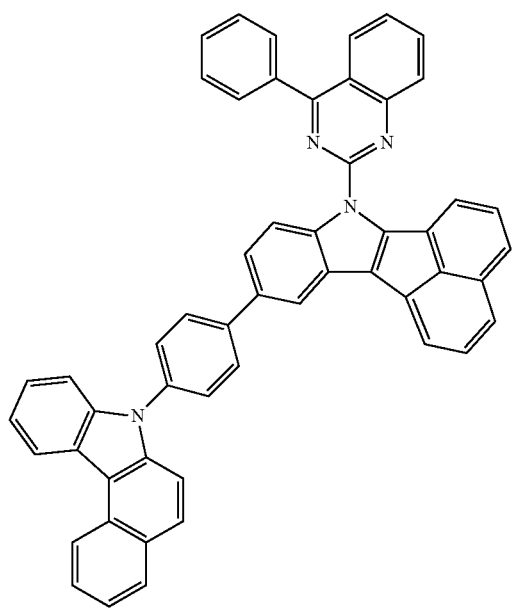
I-55
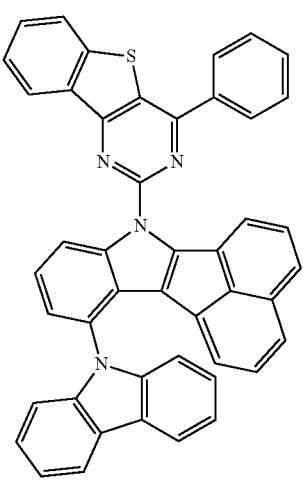
I-56
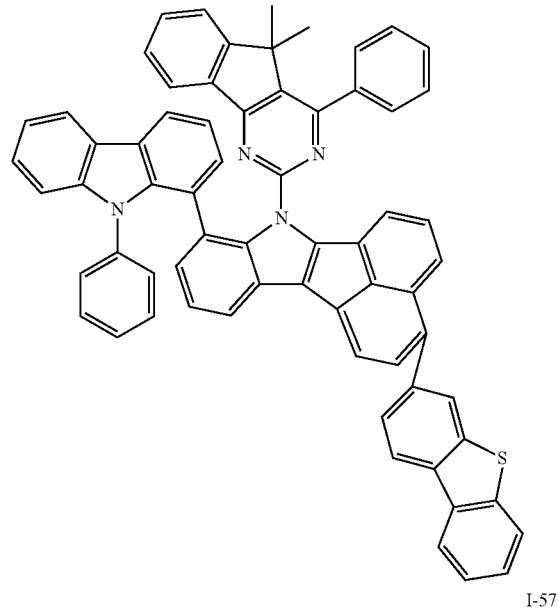
I-57
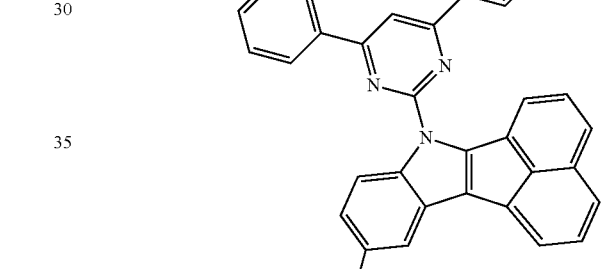
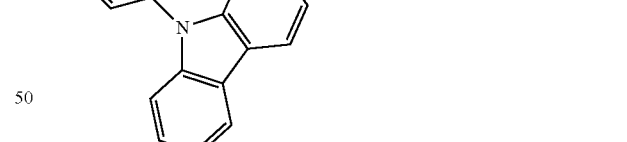
I-58
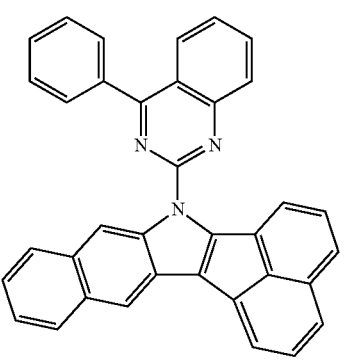

I-59
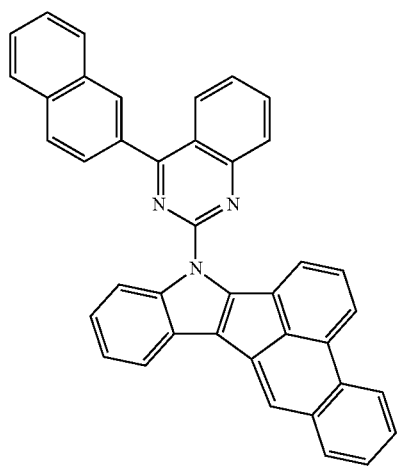
I-60
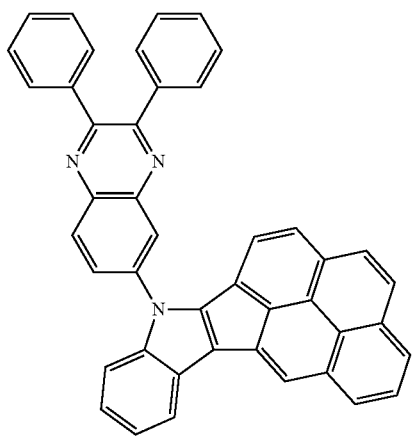
I-61
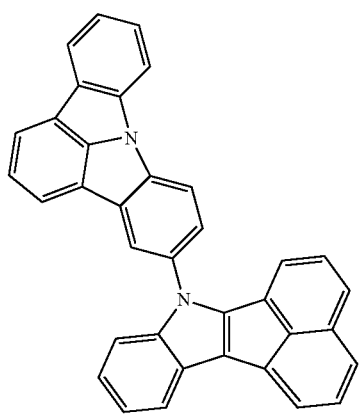
I-62
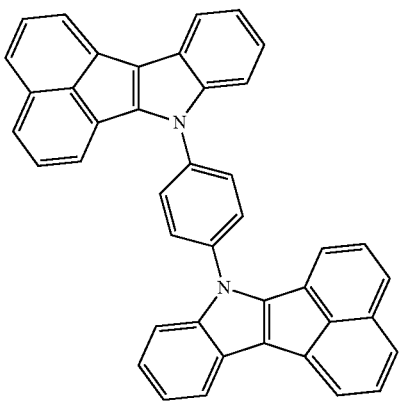
I-63
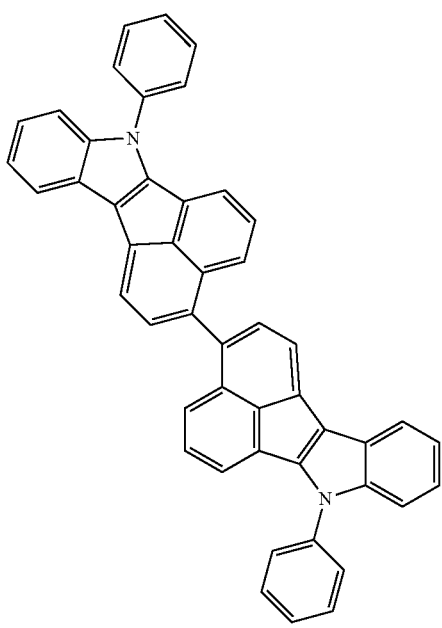

-continued
I-64
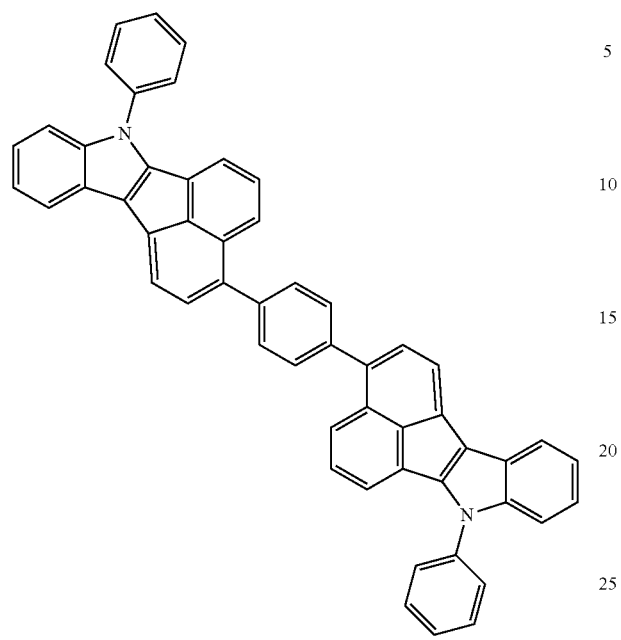
I-65
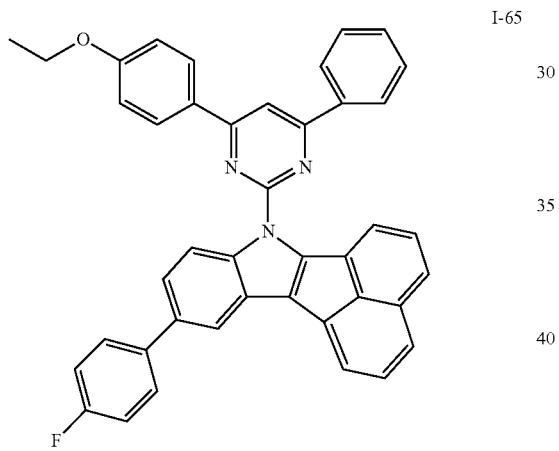
I-66
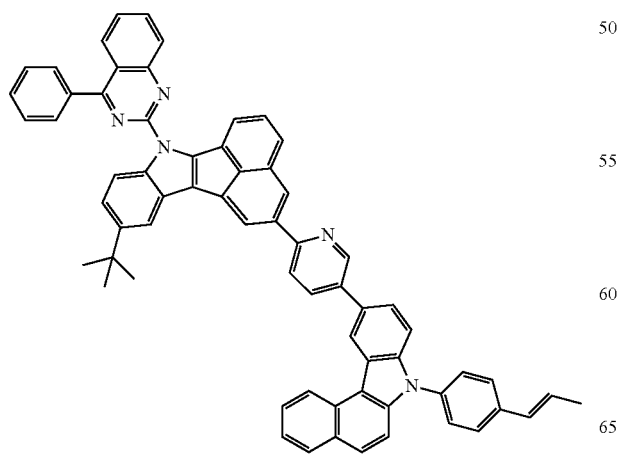
-continued
I-67
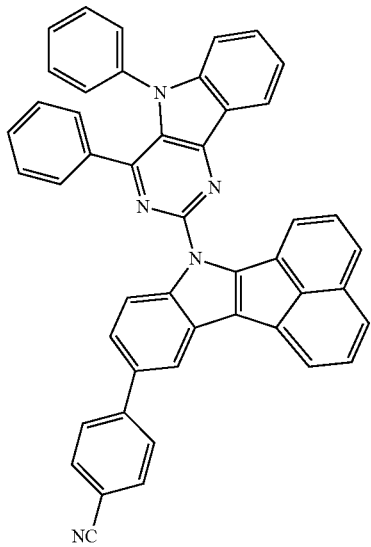
I-68
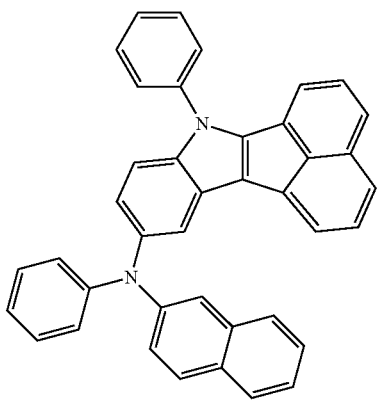
I-69
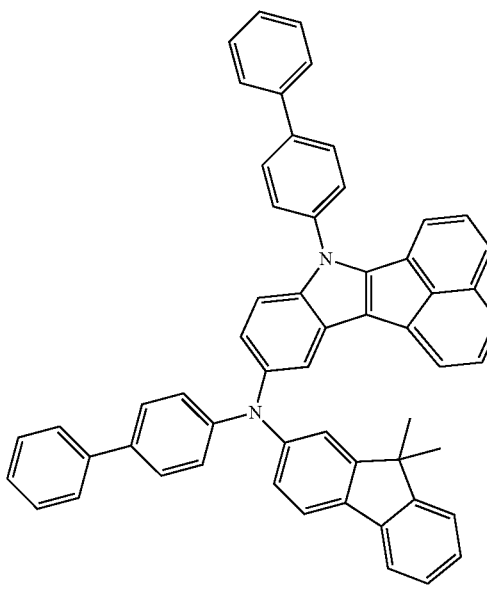

-continued
I-70
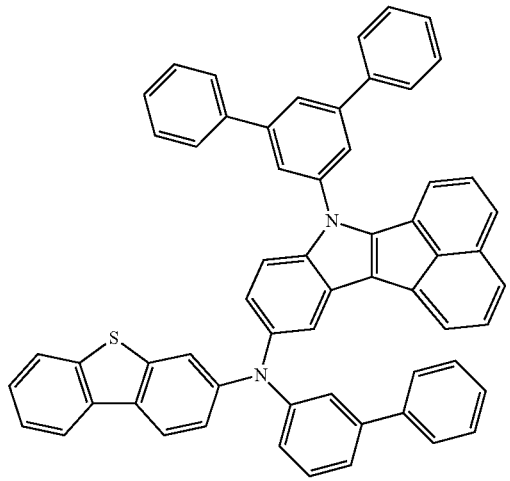
I-72
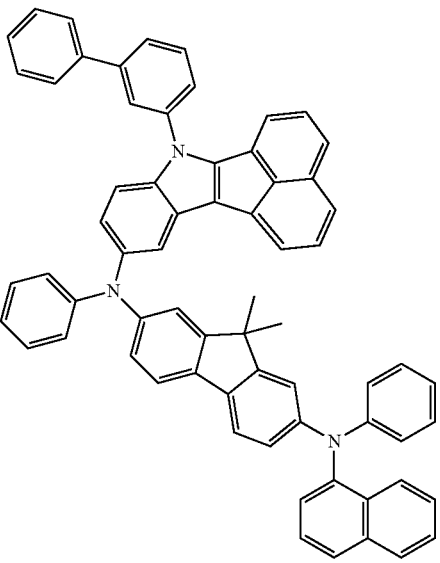
I-71
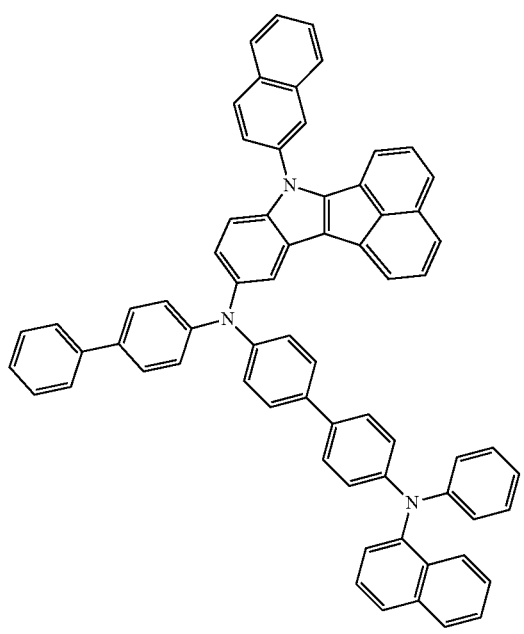
I-73
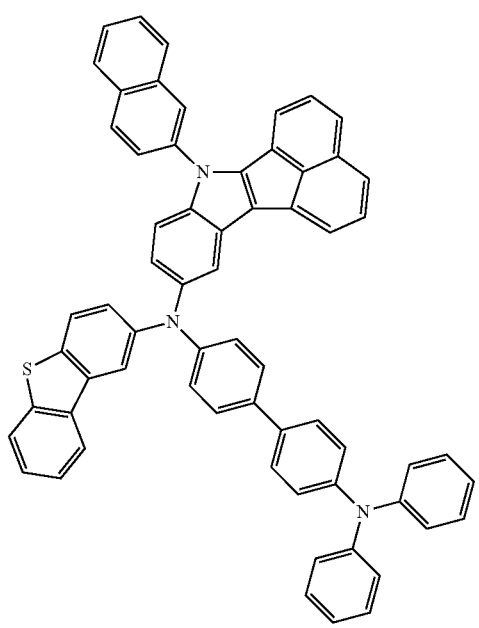

I-74
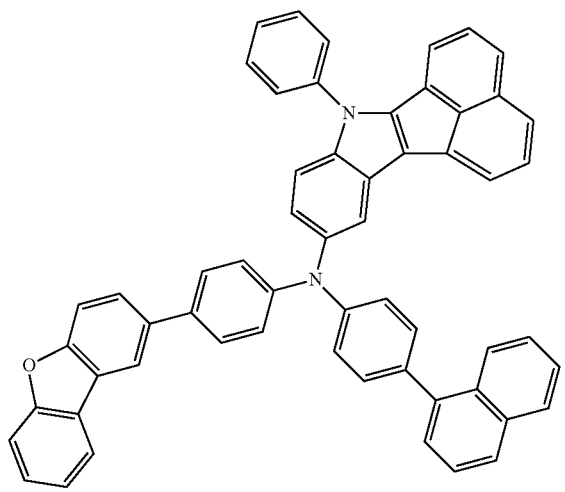
I-75
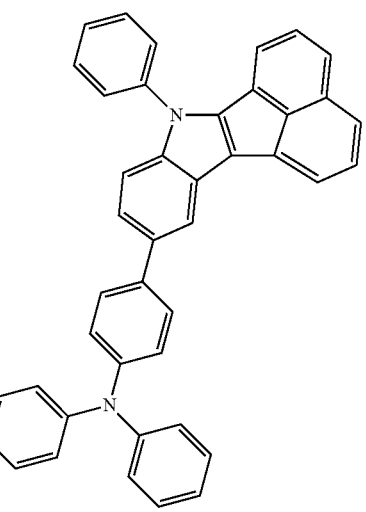
I-76
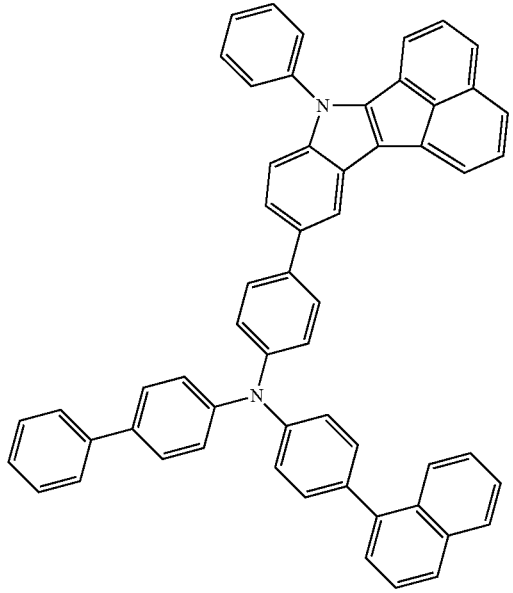
I-77
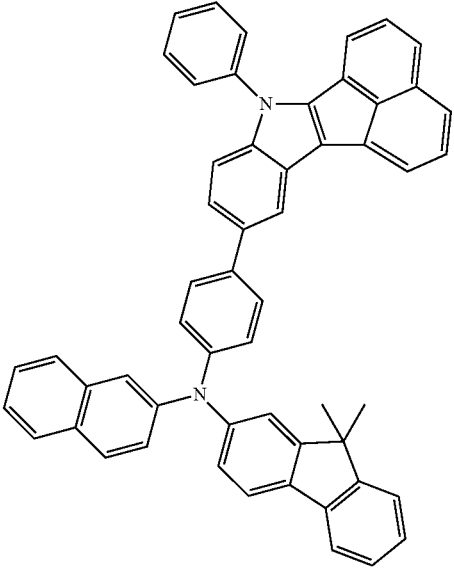
I-78
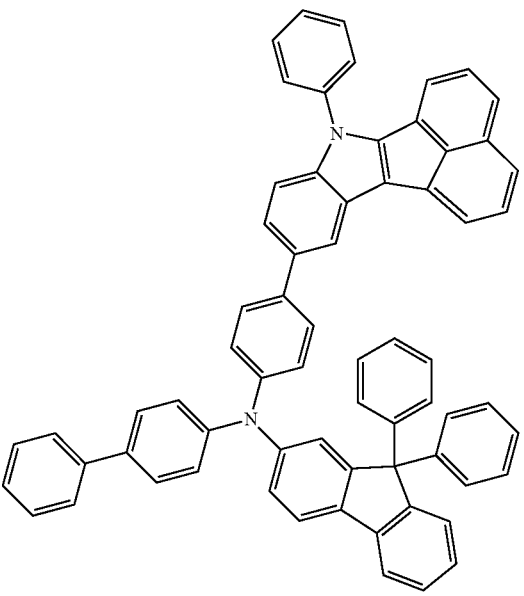

I-79
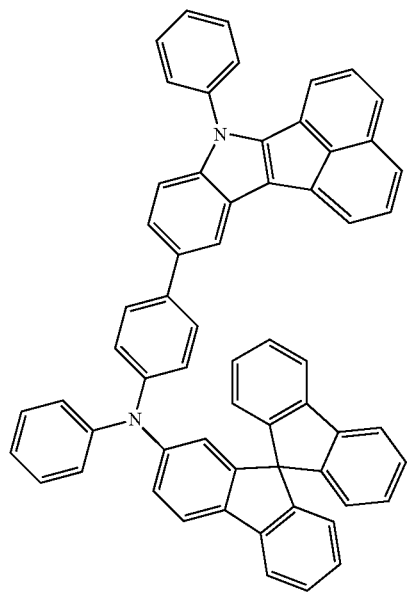
I-81
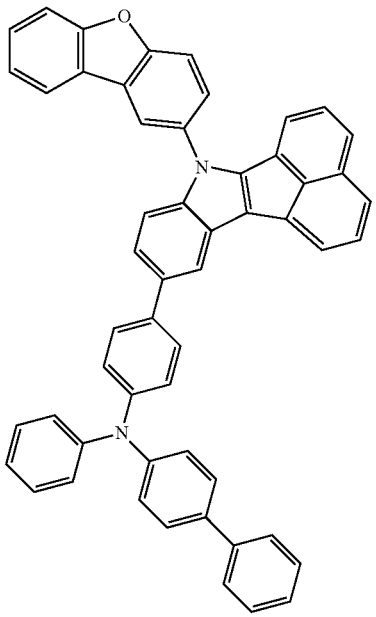
I-80
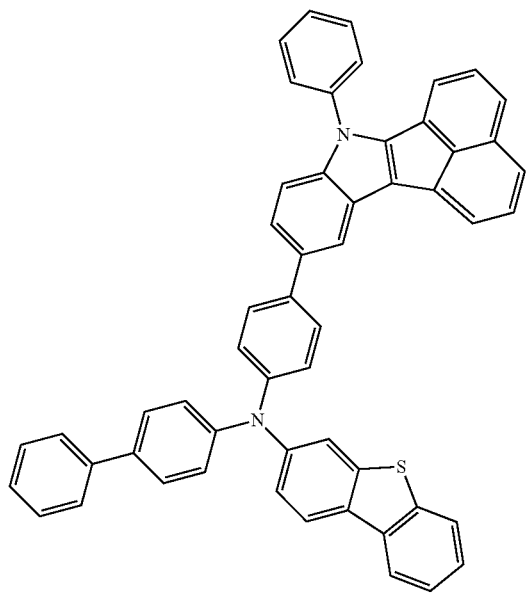
I-82
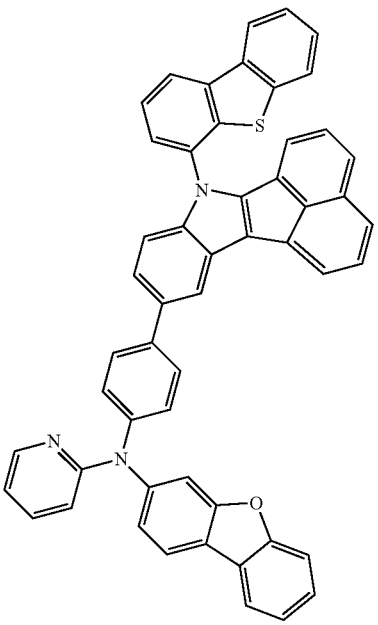

I-83
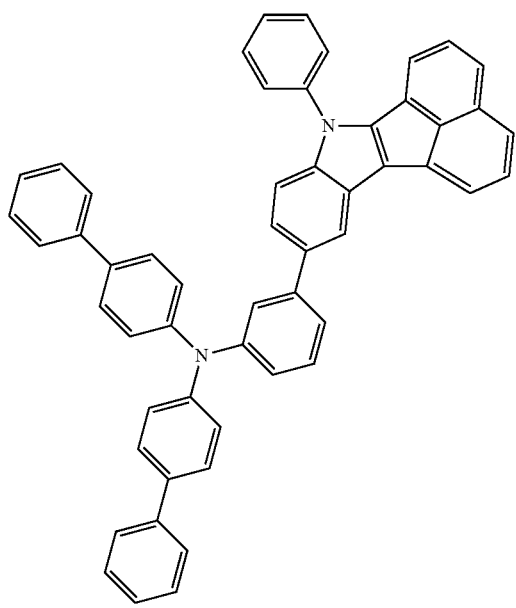
I-85
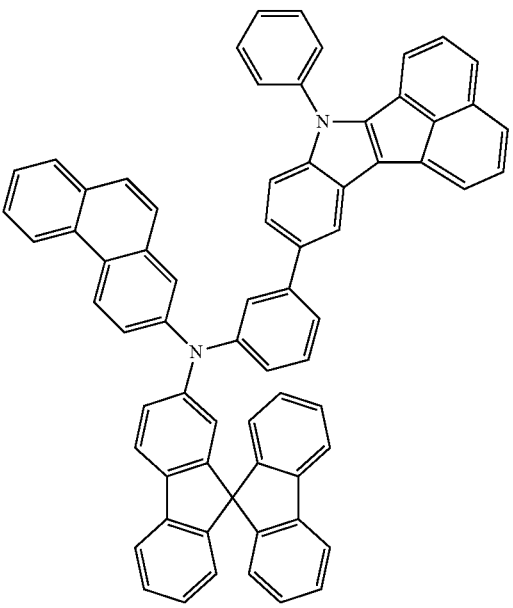
I-84
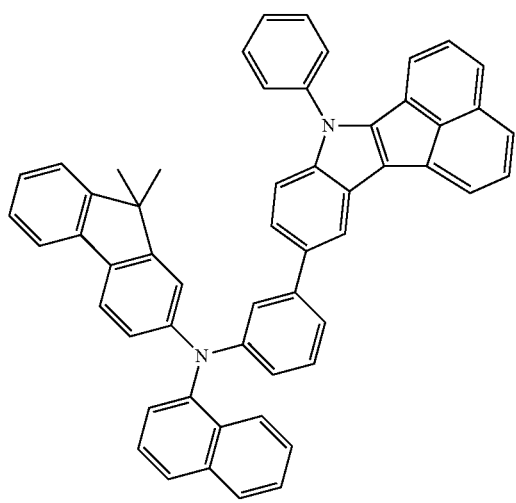
I-86
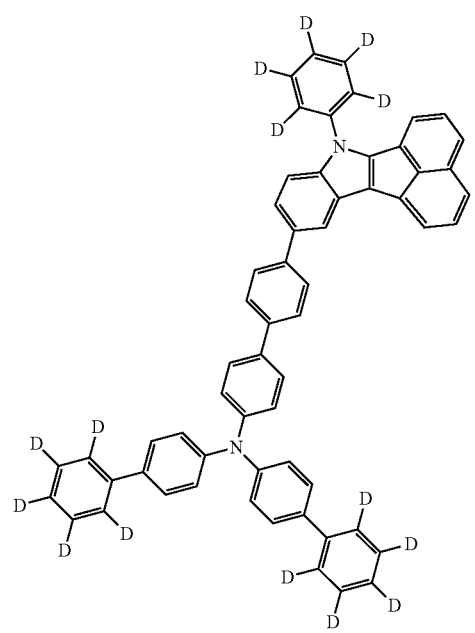

I-87
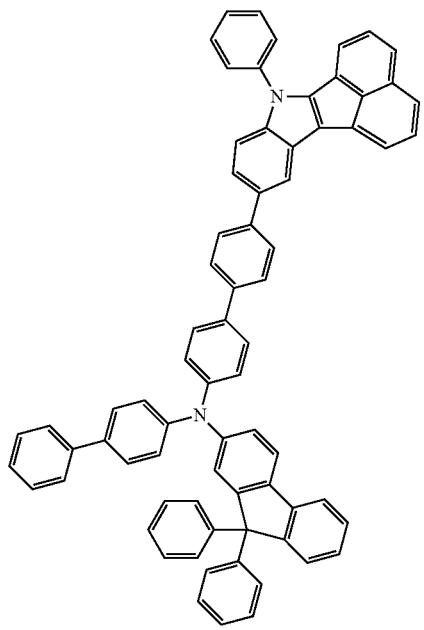
I-88
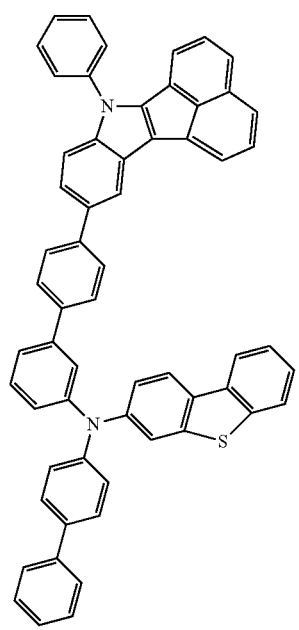
I-89
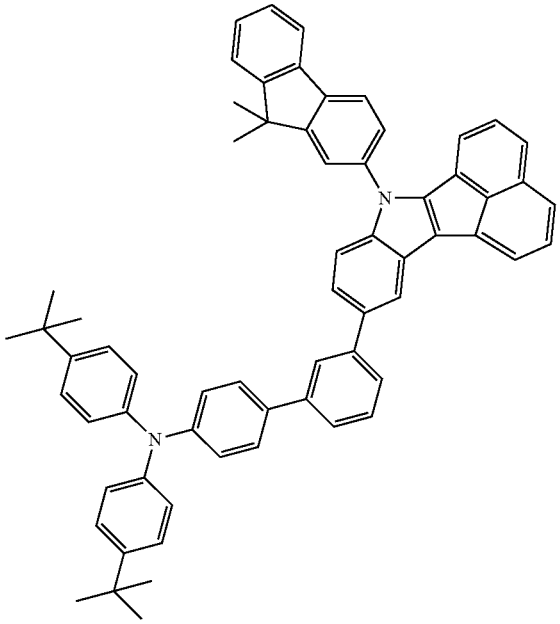
I-90
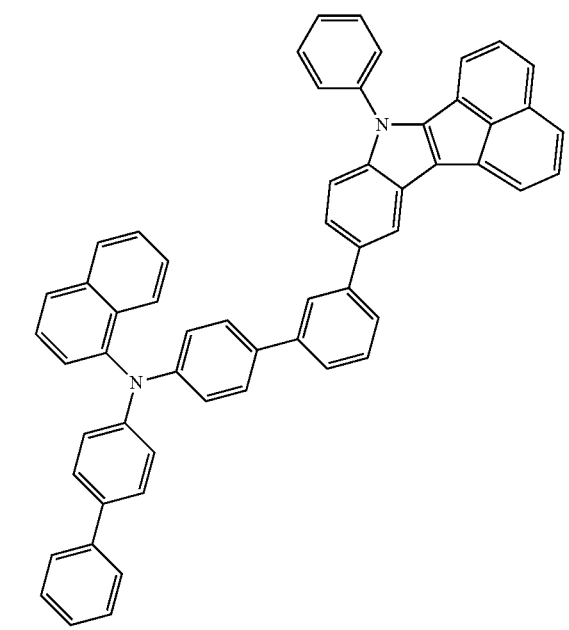

I-91
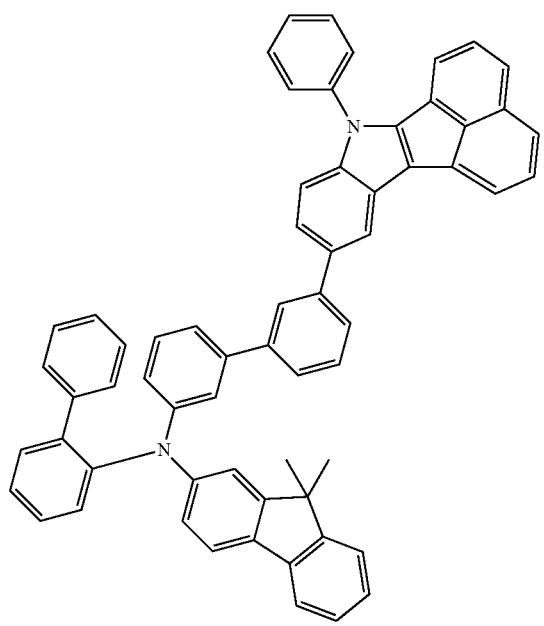
I-92
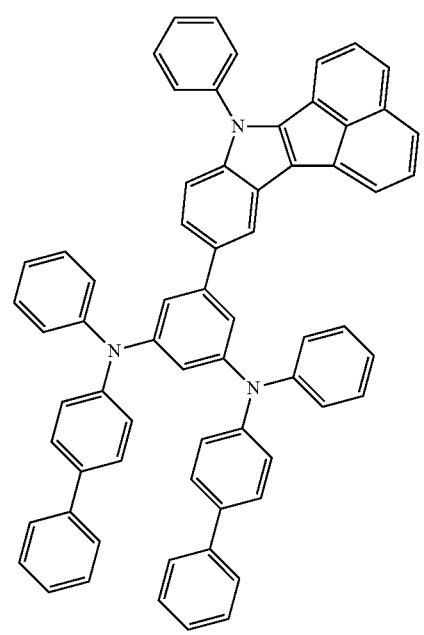
I-93
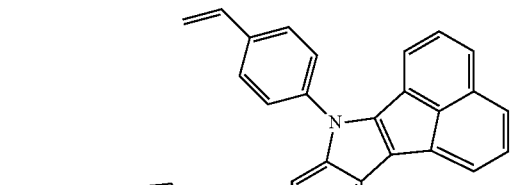
I-94
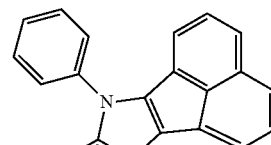
I-95
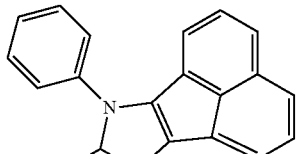

I-96
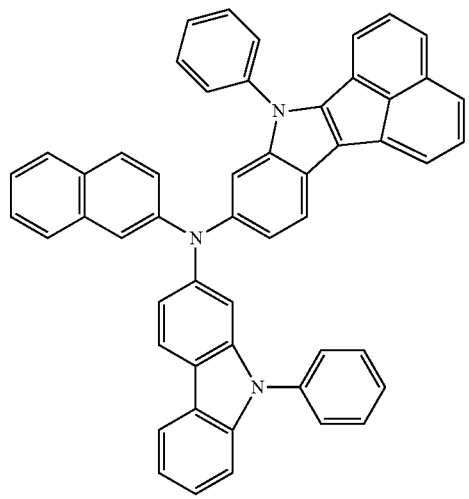
I-97
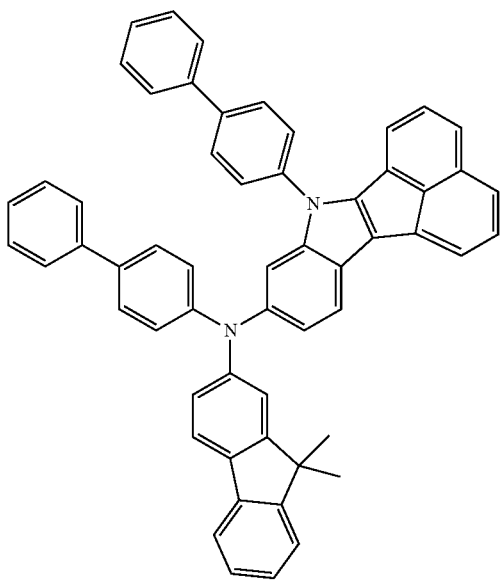
I-98
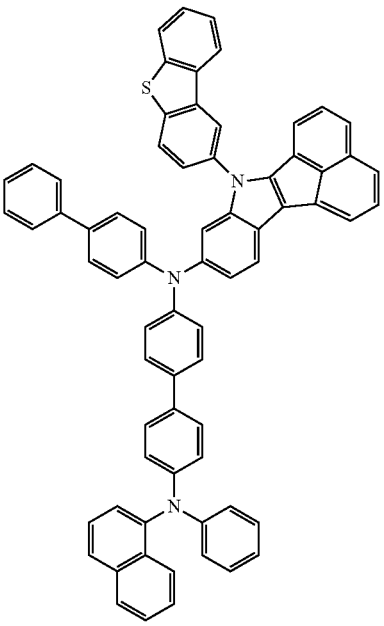
I-99
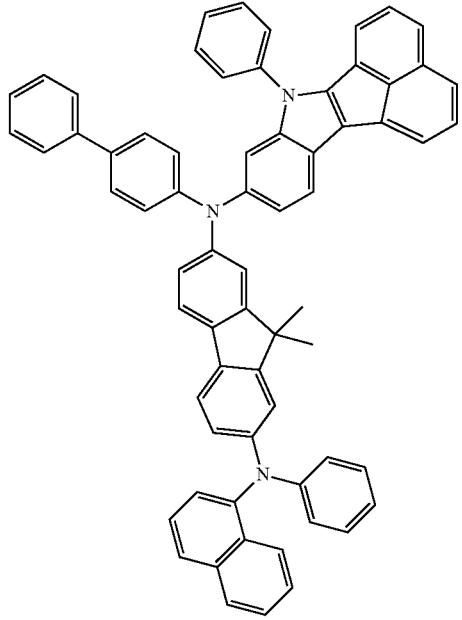

I-100
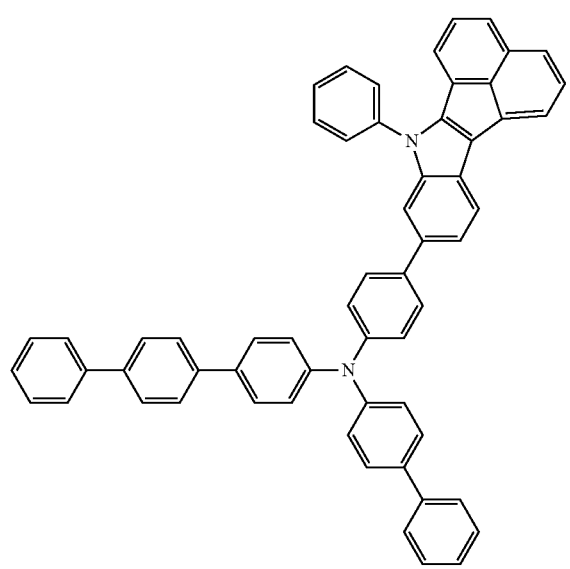
I-101
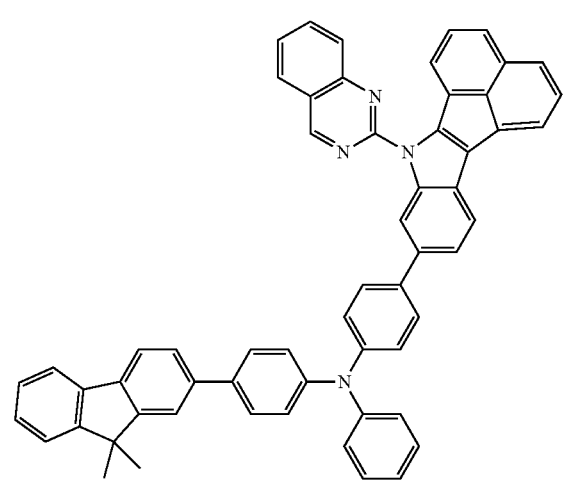
I-102
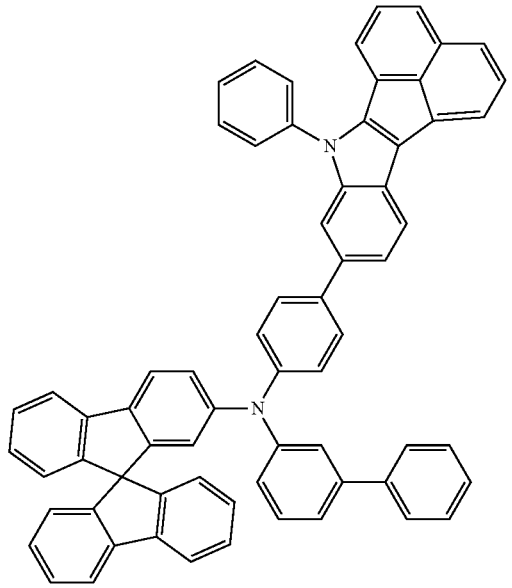
I-103
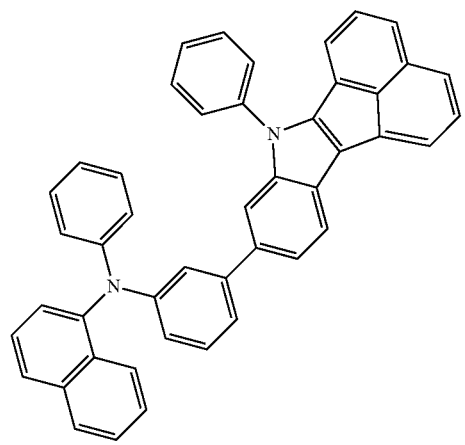
I-104
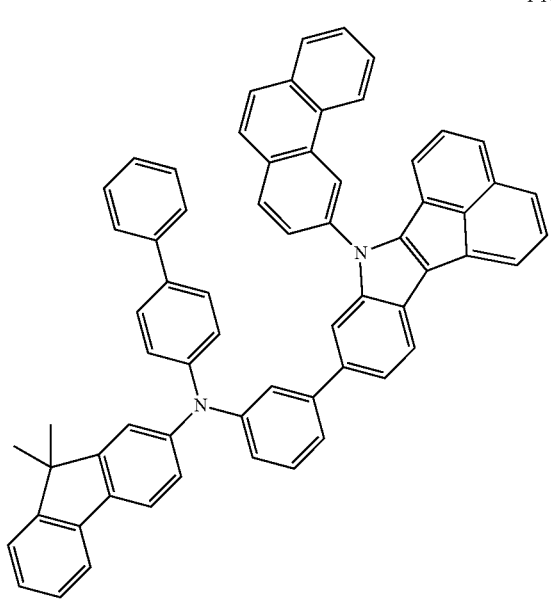
I-105
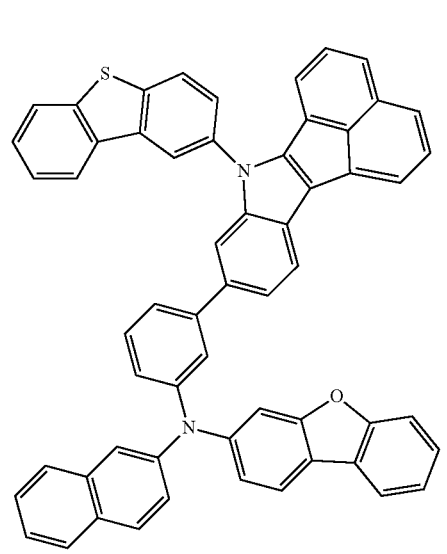

I-106
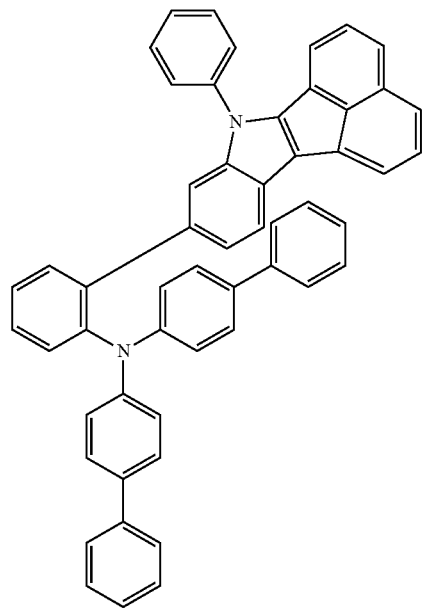
I-108
I-107
I-109
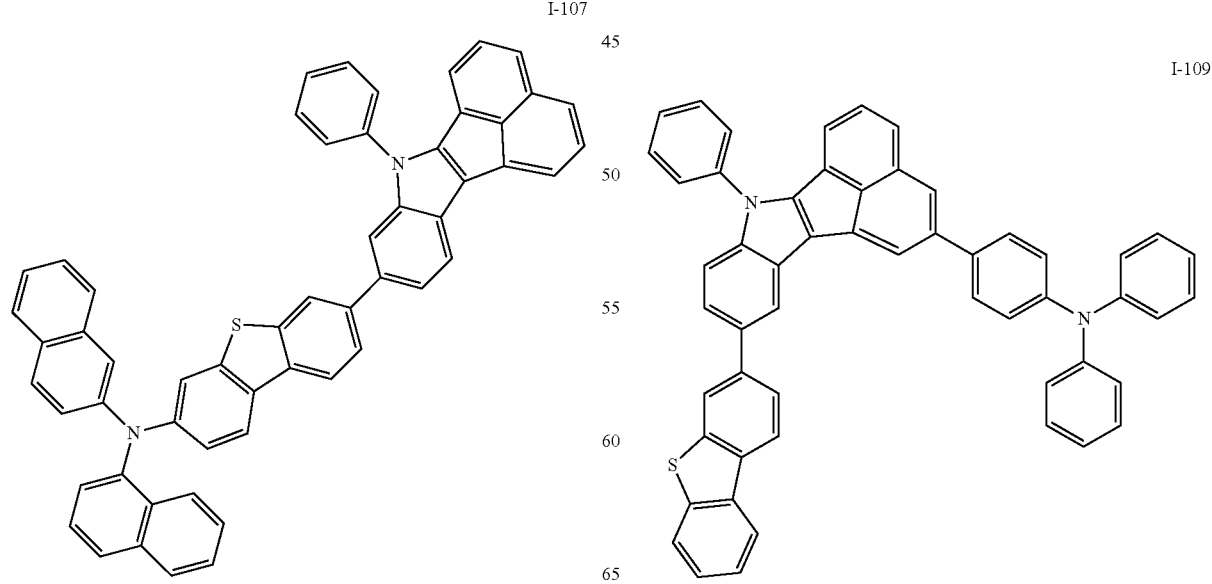

I-110

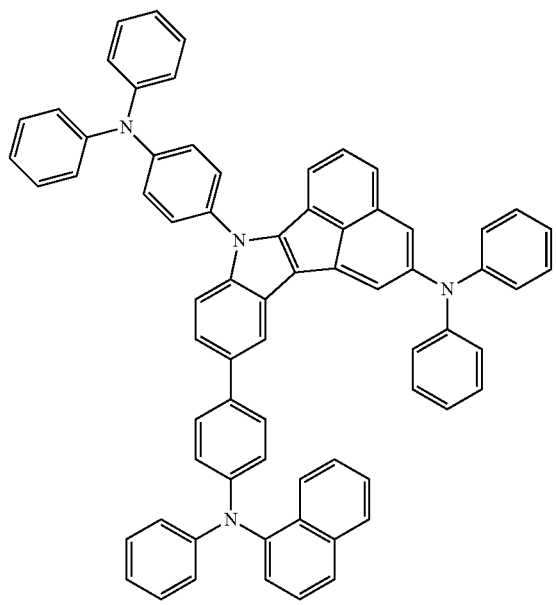

I-112

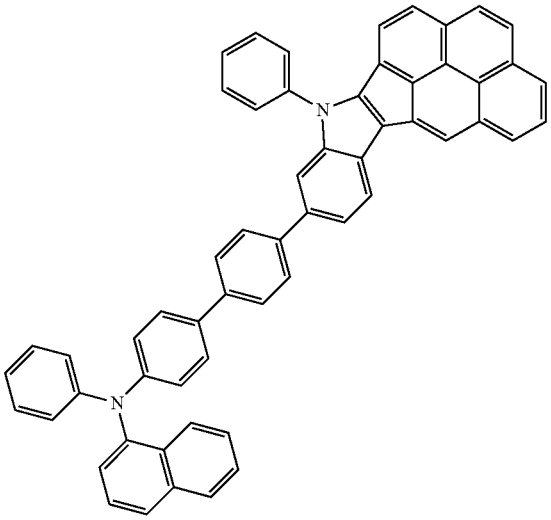

I-111

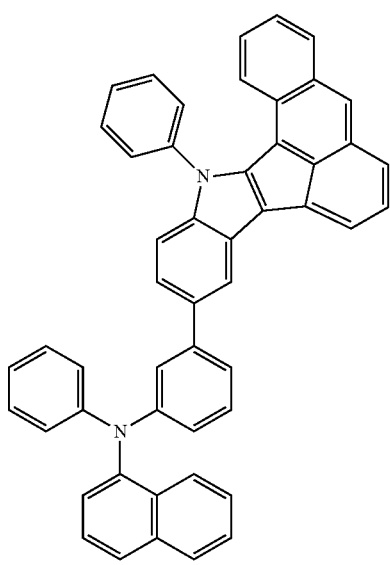

In accordance with an aspect of the present invention, the present invention provides a compound for the organic electric element represented by formula 1 above.

In accordance with another aspect of the present invention, the present invention provides an organic electric element comprising the compound represented by the formula 1.

Here, the organic electric element may comprise a first electrode, a second electrode, and an organic material layer formed between the first electrode and the second electrode, wherein the organic material layer may comprise the compound represented by the formula 1, the compound may be comprised in at least one layer of a hole injection layer, a hole transport layer, an emission-auxiliary layer or a light emitting layer, and the compound may be comprised as a single compound or a mixture of two or more kinds. That is, the compound represented by the formula 1 may be used as material of a hole injection layer, a hole transport layer, an emission-auxiliary layer or a light emitting layer. Preferably, the compound represented by the formula 1 may be used as phosphorescent host material and/or as material of a hole transport layer.

In accordance with another embodiment of the present invention, the present invention provides an organic electric element comprising a layer for improving luminous efficiency formed on one side of the first electrode and/or one side of the second electrode, the side not facing the organic material layer.

Hereinafter, Synthesis example of the compound represented by Formula 1 according to one embodiment of the present invention and manufacturing of an organic electric element will be described in detail by way of examples. However, the present invention is not limited to the following examples.

SYNTHESIS EXAMPLE

For example, as shown in Reaction Scheme 1 below, the compound (final products) according to the present invention is synthesized by reacting Sub 1 with Sub 2, but there is no limitation thereto.

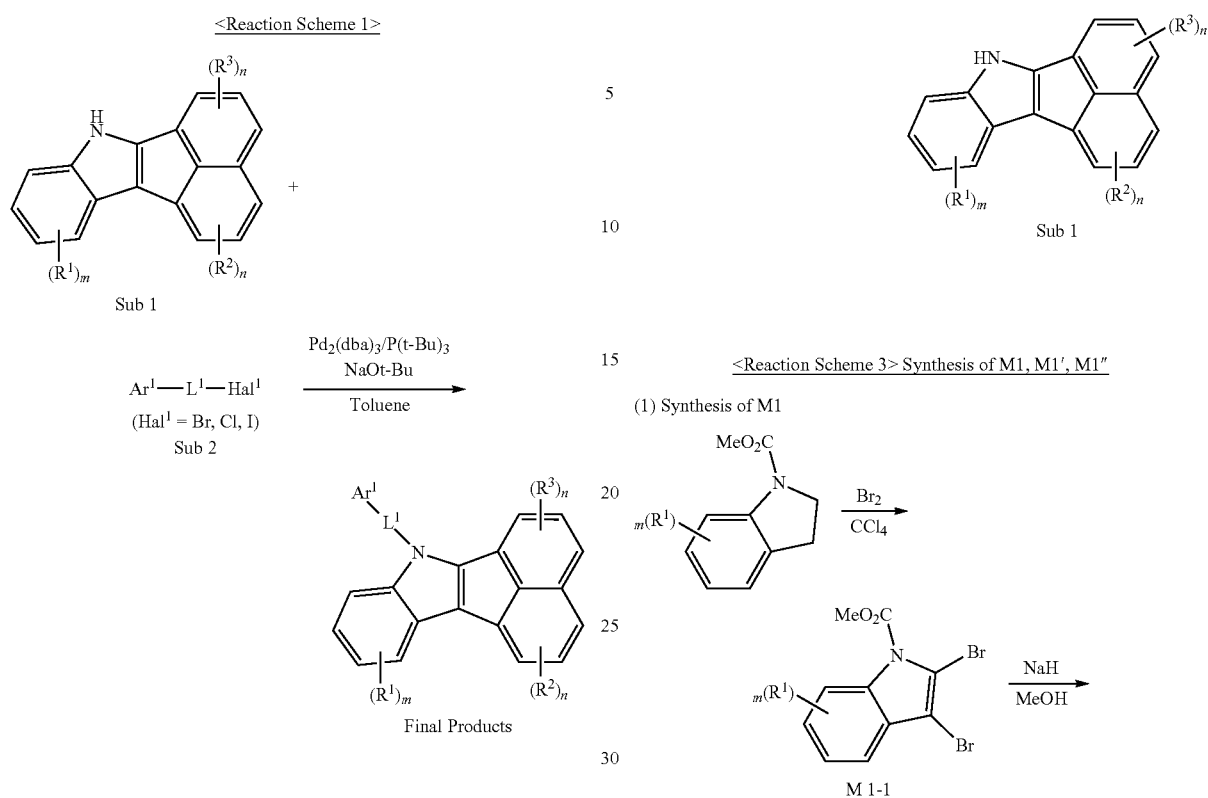
I. Synthesis of Sub 1
Sub 1 of the Reaction Scheme 1 can be synthesized according to, but not limited to, the reaction route of the following Reaction Schemes 2 and 3.
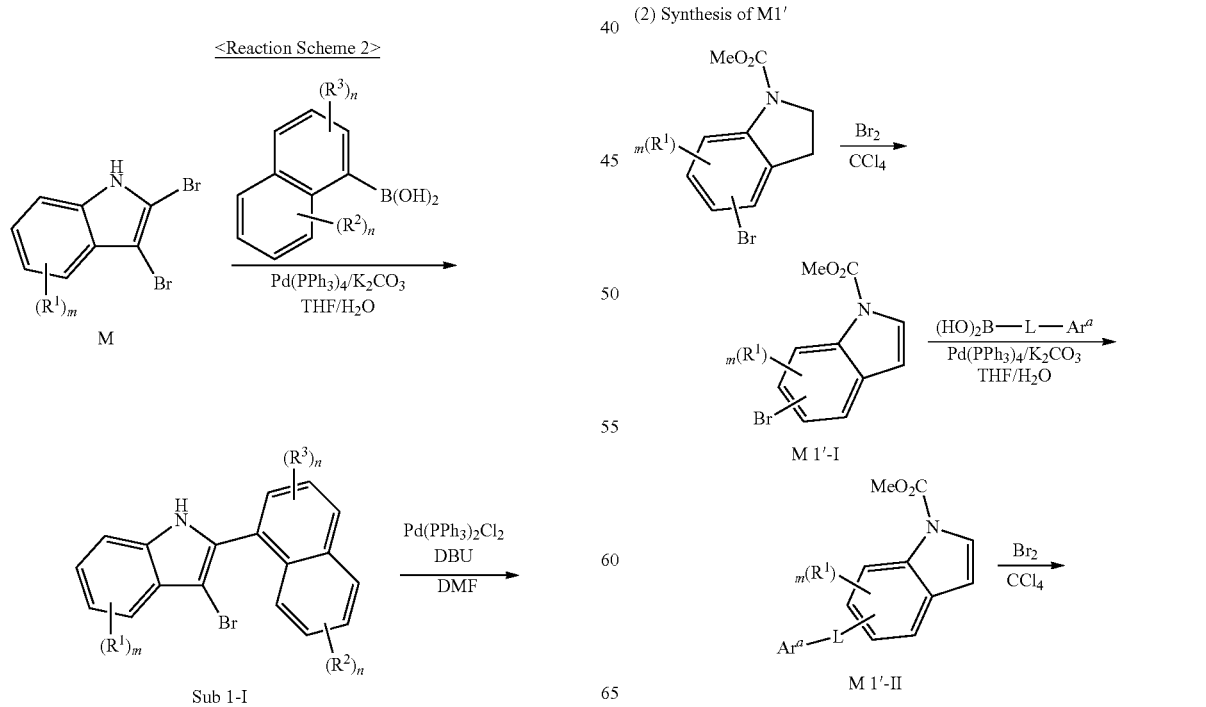

-continued

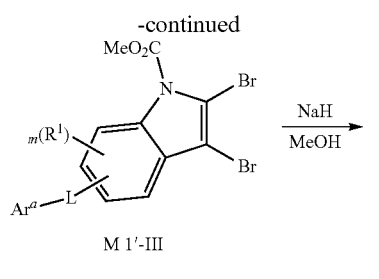

M 1'-III

M 1'

(3) Synthesis of M1''

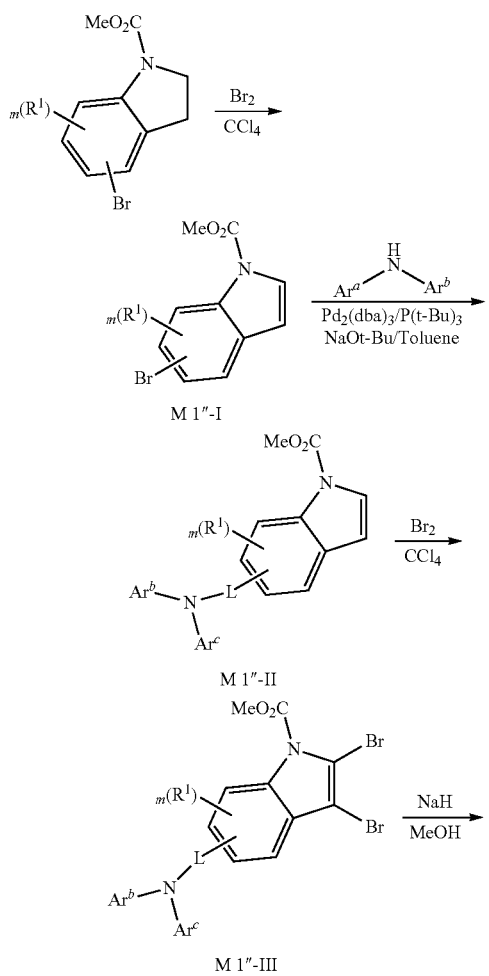

M 1''-I

M 1''-II

M 1''-III

M 1''

1. Synthesis Example of Sub 1-1

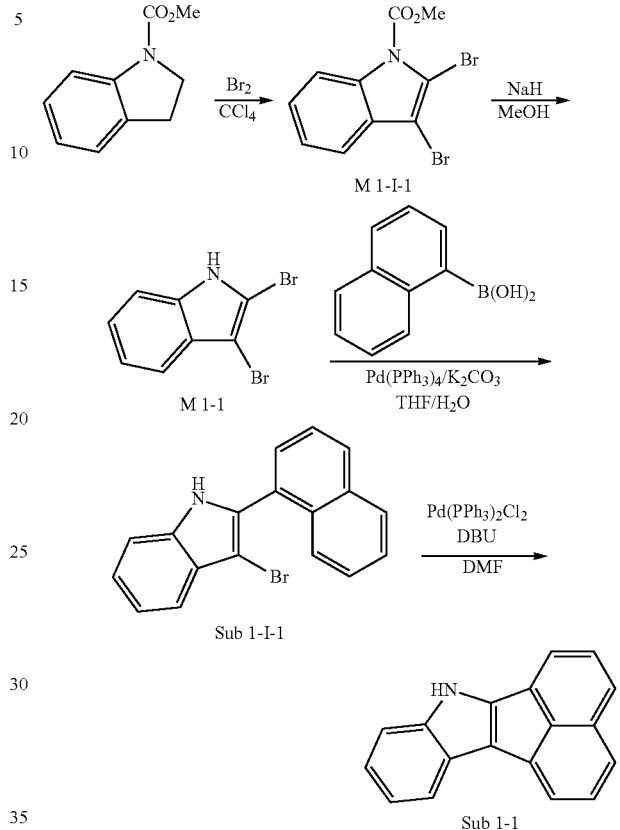

Sub 1-I-1

Sub 1-1

1) Synthesis of M 1-I-1

CCl$_4$ (847 ml) and methyl indoline-1-carboxylate (10 g, 56.43 mmol) were placed in a round bottom flask and the solution of CCl$_4$ (395 ml) and Br$_2$ (72.15 g, 451.47 mmol) was added, and then the mixture was stirred at room temperature. When the reaction was completed, aqueous solution of 10% NaHSO$_3$ was added and the mixture was extracted with CH$_2$Cl$_2$ and water. The organic layer was dried with MgSO$_4$ and concentrated. The concentrate was applied to silica gel column and recrystallized to obtain 17.66 g (yield: 94%) of the product.

2) Synthesis of M 1-1

After M 1-I-1 (17.66 g, 53.04 mmol) was added to MeOH (1326 ml), NaH (2.55 g, 106.07 mmol) was added and the mixture was stirred under reflux. When the reaction was completed, the reaction mixture was cooled to room temperature. Then, MeOH was removed by using a decompression apparatus, and the resultant was dissolved in EtOAc. The organic layer was wished with the saturated solution of NH$_4$Cl and brine, and then dried with MgSO$_4$ and concentrated. The concentrate was applied to silica gel column and recrystallized to obtain 13.42 g (yield: 92%) of the product.

3) Synthesis of Sub 1-I-1

After naphthalen-1-ylboronic acid (75.07 g, 436.46 mmol) was dissolved in THF (1920 ml) in a round bottom flask, M 1-1 (120.00 g, 436.46 mmol), Pd(PPh$_3$)$_4$ (7.57 g, 6.55 mmol), K$_2$CO$_3$ (90.48 g, 654.69 mmol) and water (960 ml) was added, and then the mixture was refluxed under heating at 80° C. When the reaction was completed, distilled water was added to dilute at room temperature. Then, the reaction product was extracted with methylene chloride and water and the organic layer was dried with MgSO$_4$ and concentrated. The concentrate was applied to silica gel column and recrystallized to obtain 88.60 g (yield: 63%) of the product.

4) Synthesis of Sub 1-1

After Sub 1-I-1 (88.60 g, 322.25 mmol), Pd(PPh$_3$)$_2$Cl$_2$ (22.62 g, 32.23 mmol) and 1,8-Diazabicyclo[5.4.0]undec-7-ene (68.68 g, 451.15 mmol) were dissolved in anhydrous DMF (644 ml), the mixture was stirred at 140° C. When the reaction was completed, toluene was added to dilute and Pd was removed by using celite, and then the resultant was washed with water. Then, the organic layer was dried with MgSO$_4$ and concentrated. The concentrate was applied to silica gel column and recrystallized to obtain 84.10 g (yield: 81%) of the product.

2. Synthesis Example of Sub 1-2

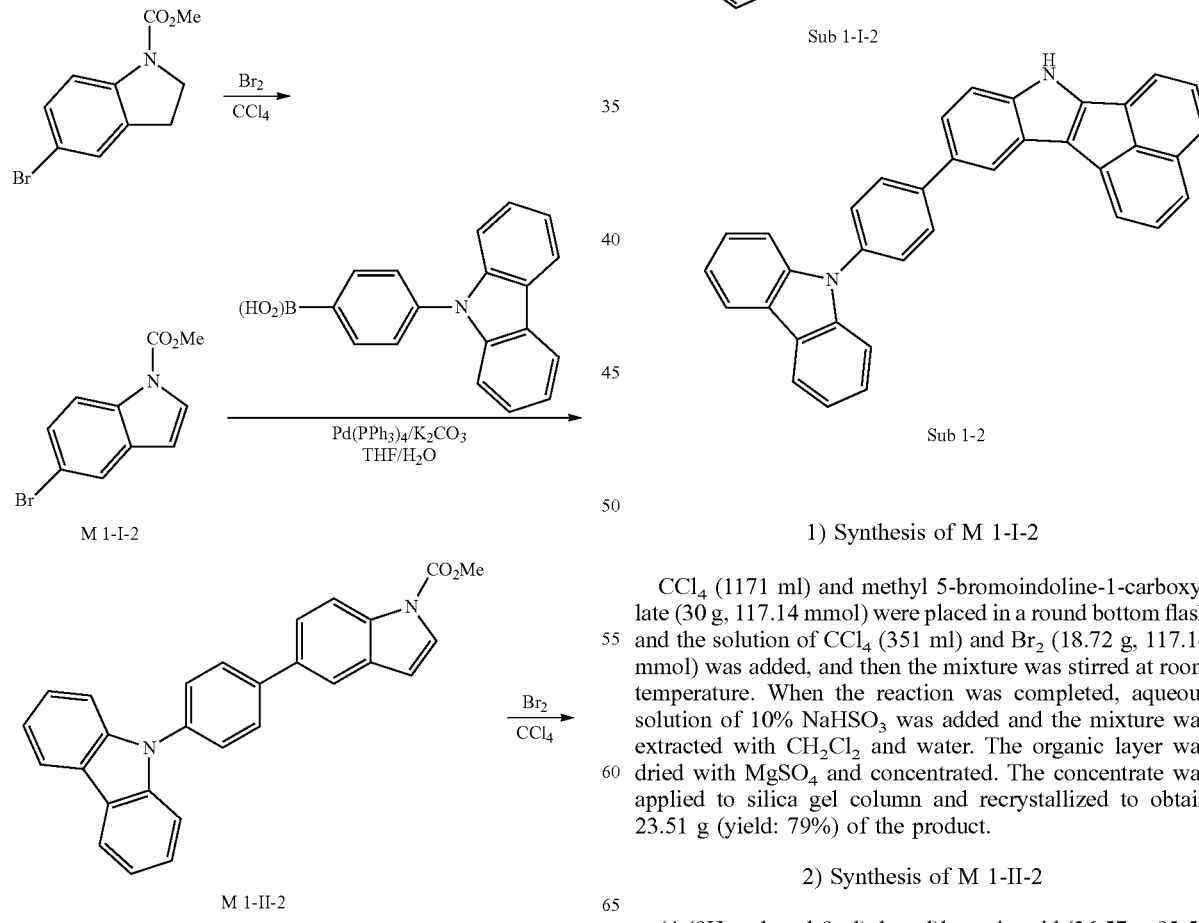

1) Synthesis of M 1-I-2

CCl$_4$ (1171 ml) and methyl 5-bromoindoline-1-carboxylate (30 g, 117.14 mmol) were placed in a round bottom flask and the solution of CCl$_4$ (351 ml) and Br$_2$ (18.72 g, 117.14 mmol) was added, and then the mixture was stirred at room temperature. When the reaction was completed, aqueous solution of 10% NaHSO$_3$ was added and the mixture was extracted with CH$_2$Cl$_2$ and water. The organic layer was dried with MgSO$_4$ and concentrated. The concentrate was applied to silica gel column and recrystallized to obtain 23.51 g (yield: 79%) of the product.

2) Synthesis of M 1-II-2

(4-(9H-carbazol-9-yl)phenyl)boronic acid (26.57 g, 92.53 mmol) was placed in a round bottom flask and M 1-I-2

(23.51 g, 92.53 mmol), Pd(PPh$_3$)$_4$ (3.21 g, 2.78 mmol), K$_2$CO$_3$ (38.37 g, 277.59 mmol), THF (407 mL) and water (203 mL) were added. Then, 33.53 g (yield: 87%) of the product was obtained by the same method as in synthesis of Sub 1-I-1.

3) Synthesis of M 1-III-2

CCl$_4$ (396 ml) and M 1-II-2 (11 g, 26.41 mmol) were placed in a round bottom flask and the solution of CCl$_4$ (185 ml) and Br$_2$ (33.77 g, 211.3 mmol) were added. Then, 13.95 (yield: 92%) of the product was obtained by the same method as in synthesis of M 1-I-1.

4) Synthesis of M 1-2

After M 1-III-2 (13.95 g, 24.29 mmol) was added to MeOH (607 ml), NaH (1.17 g, 48.58 mmol) was added to the mixture. Then, 11.29 g (yield: 90%) of the product was obtained by the same method as in synthesis of M 1-1.

5) Synthesis of Sub 1-I-2

Naphthalen-1-ylboronic acid (3.76 g, 21.87 mmol) was placed in a round bottom flask and M 1-2 (11.29 g, 21.87 mmol), Pd(PPh$_3$)$_4$ (0.38 g, 0.33 mmol), K$_2$CO$_3$ (4.53 g, 32.8 mmol), THF (96 ml) and water (48 ml) were added. Then, 9.0 g (yield: 73%) of the product was obtained by the same method as in synthesis of Sub 1-I-1.

6) Synthesis of Sub 1-2

Pd(PPh$_3$)$_2$Cl$_2$ (2.48 g, 3.53 mmol), 1,8-Diazabicyclo[5.4.0]undec-7-ene (7.53 g, 49.46 mmol) and anhydrous DMF (71 ml) were added to Sub 1-I-2 (14 g, 35.33 mmol). Then, 6.91 g (yield: 62%) of the product was obtained by the same method as in synthesis of Sub 1-1.

3. Synthesis Example of Sub 1-7

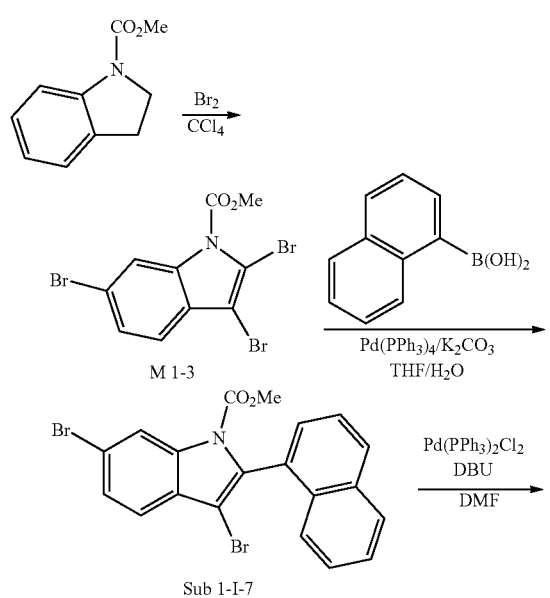

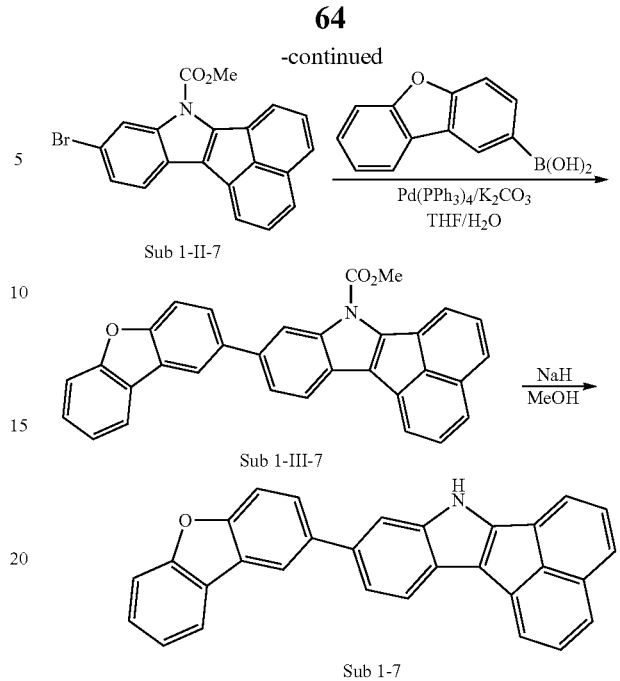

1) Synthesis of M 1-3

CCl$_4$ (998 ml) and methyl 1H-indole-1-carboxylate (25 g, 142.7 mmol) were placed in a round bottom flask and the solution of CCl$_4$ (428 ml) and Br$_2$ (182 g, 1141.62 mmol) was added, and then the mixture was stirred at room temperature for 10 days or longer. When the reaction was completed, aqueous solution of 10% NaHSO$_3$ was added and the mixture was extracted with CH$_2$Cl$_2$ and water. The organic layer was dried with MgSO$_4$ and concentrated. The concentrate was applied to silica gel column and recrystallized to obtain 42.29 g (yield: 89%) of the product.

2) Synthesis of Sub 1-I-7

Naphthalen-1-ylboronic acid (35.08 g, 203.94 mmol) was placed in a round bottom flask and M 1-3 (84 g, 203.94 mmol), Pd(PPh$_3$)$_4$ (2.36 g, 2.04 mmol), K$_2$CO$_3$ (28.19 g, 203.94 mmol), THF (897 ml) and water (448 ml) were added. Then, 29.96 g (yield: 32%) of the product was obtained by the same method as in synthesis of Sub 1-I-1.

3) Synthesis of Sub 1-II-7

Pd(PPh$_3$)$_2$Cl$_2$ (4.59 g, 6.53 mmol), 1,8-Diazabicyclo[5.4.0]undec-7-ene (13.93 g, 91.48 mmol), anhydrous DMF (131 ml) were added to Sub 1-I-7 (30 g, 35.34 mmol). Then, 15.08 g (yield: 60%) of the product was obtained by the same method as in synthesis of Sub 1-1.

4) Synthesis of Sub 1-III-7

Dibenzo[b,d]furan-2-ylboronic acid (8.45 g, 39.87 mmol) was placed in a round bottom flask and Sub 1-II-7 (15.08 g, 39.87 mmol), Pd(PPh$_3$)$_4$ (1.38 g, 1.2 mmol), K$_2$CO$_3$ (16.53 g, 119.61 mmol), THF (175 mL) and water (88 mL) were added. Then, 16.52 g (yield: 89%) of the product was obtained by the same method as in synthesis of Sub 1-I-1.

5) Synthesis of Sub 1-7

After Sub 1-III-7 (16.52 g, 35.49 mmol) was added to MeOH (887 ml), NaH (1.70 g, 70.98 mmol) was added to the mixture. Then, 13.30 g (yield: 92%) of the product was obtained by the same method as in synthesis of M 1-1.

4. Synthesis Example of Sub 1-11

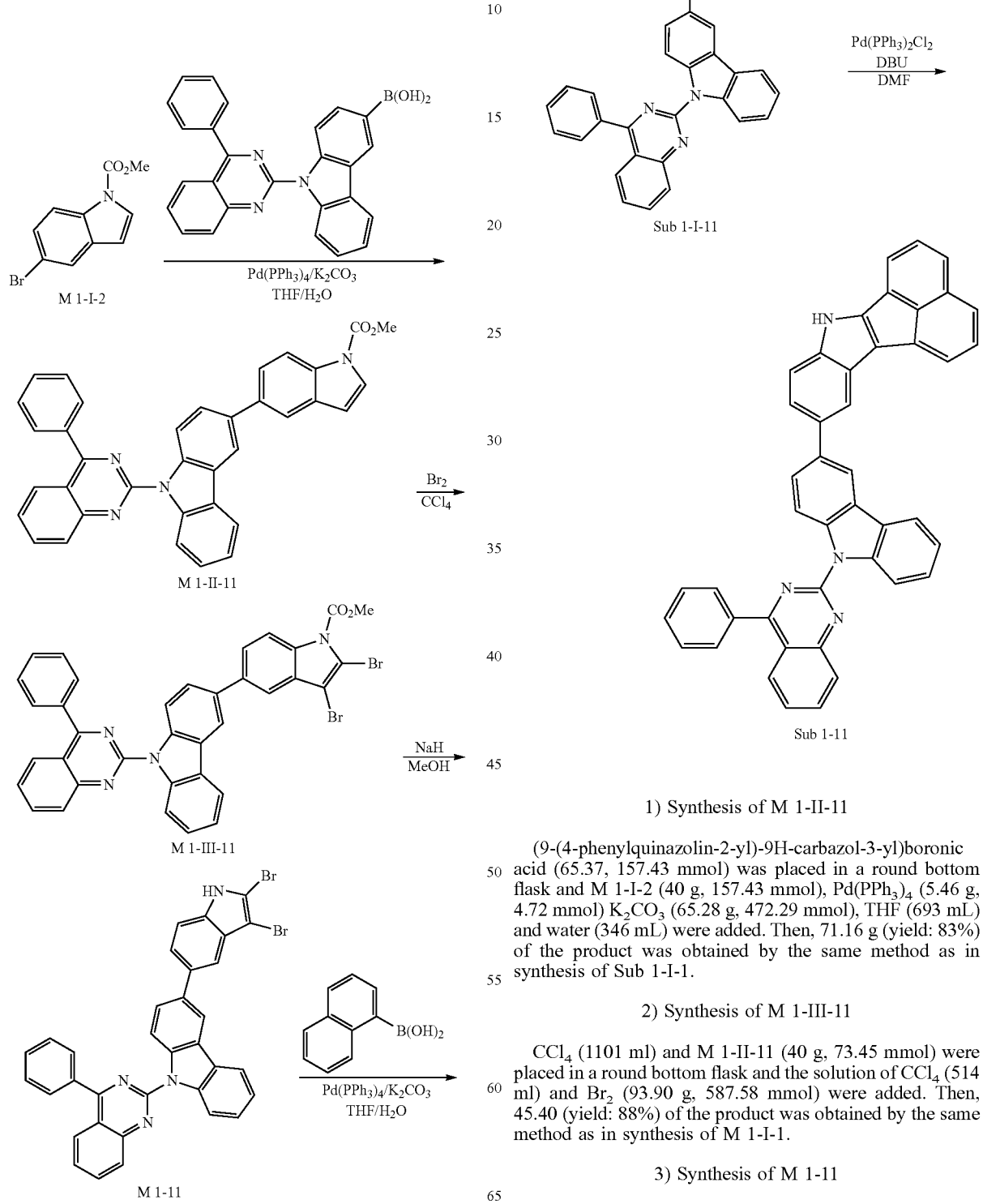

1) Synthesis of M 1-II-11

(9-(4-phenylquinazolin-2-yl)-9H-carbazol-3-yl)boronic acid (65.37, 157.43 mmol) was placed in a round bottom flask and M 1-I-2 (40 g, 157.43 mmol), Pd(PPh$_3$)$_4$ (5.46 g, 4.72 mmol) K$_2$CO$_3$ (65.28 g, 472.29 mmol), THF (693 mL) and water (346 mL) were added. Then, 71.16 g (yield: 83%) of the product was obtained by the same method as in synthesis of Sub 1-I-1.

2) Synthesis of M 1-III-11

CCl$_4$ (1101 ml) and M 1-II-11 (40 g, 73.45 mmol) were placed in a round bottom flask and the solution of CCl$_4$ (514 ml) and Br$_2$ (93.90 g, 587.58 mmol) were added. Then, 45.40 (yield: 88%) of the product was obtained by the same method as in synthesis of M 1-I-1.

3) Synthesis of M 1-11

After M 1-III-11 (45.40 g, 64.64 mmol) was added to MeOH (1616 ml), NaH (3.10 g, 129.27 mmol) was added to the mixture. Then, 36.23 g (yield: 87%) of the product was obtained by the same method as in synthesis of M 1-1.

4) Synthesis of Sub 1-I-11

M 1-11 (36.23 g, 56.23 mmol), Pd(PPh$_3$)$_4$ (0.97 g, 0.84 mmol), K$_2$CO$_3$ (11.66 g, 84.34 mmol), THF (247 ml) and water (124 ml) were added to naphthalen-1-ylboronic acid (9.67 g, 56.23 mmol). Then, 28.78 g (yield: 74%) of the product was obtained by the same method as in synthesis of Sub 1-I-1.

5) Synthesis of Sub 1-11

Pd(PPh$_3$)$_2$Cl$_2$ (2.92 g, 4.16 mmol), 1,8-Diazabicyclo[5.4.0]undec-7-ene (8.87 g, 58.26 mmol), anhydrous DMF (83 ml) were added to Sub 1-I-11 (28.78 g, 41.61 mmol). Then, 14.99 g (yield: 59%) of the product was obtained by the same method as in synthesis of Sub 1-1.

5. Synthesis Example of Sub 1-18

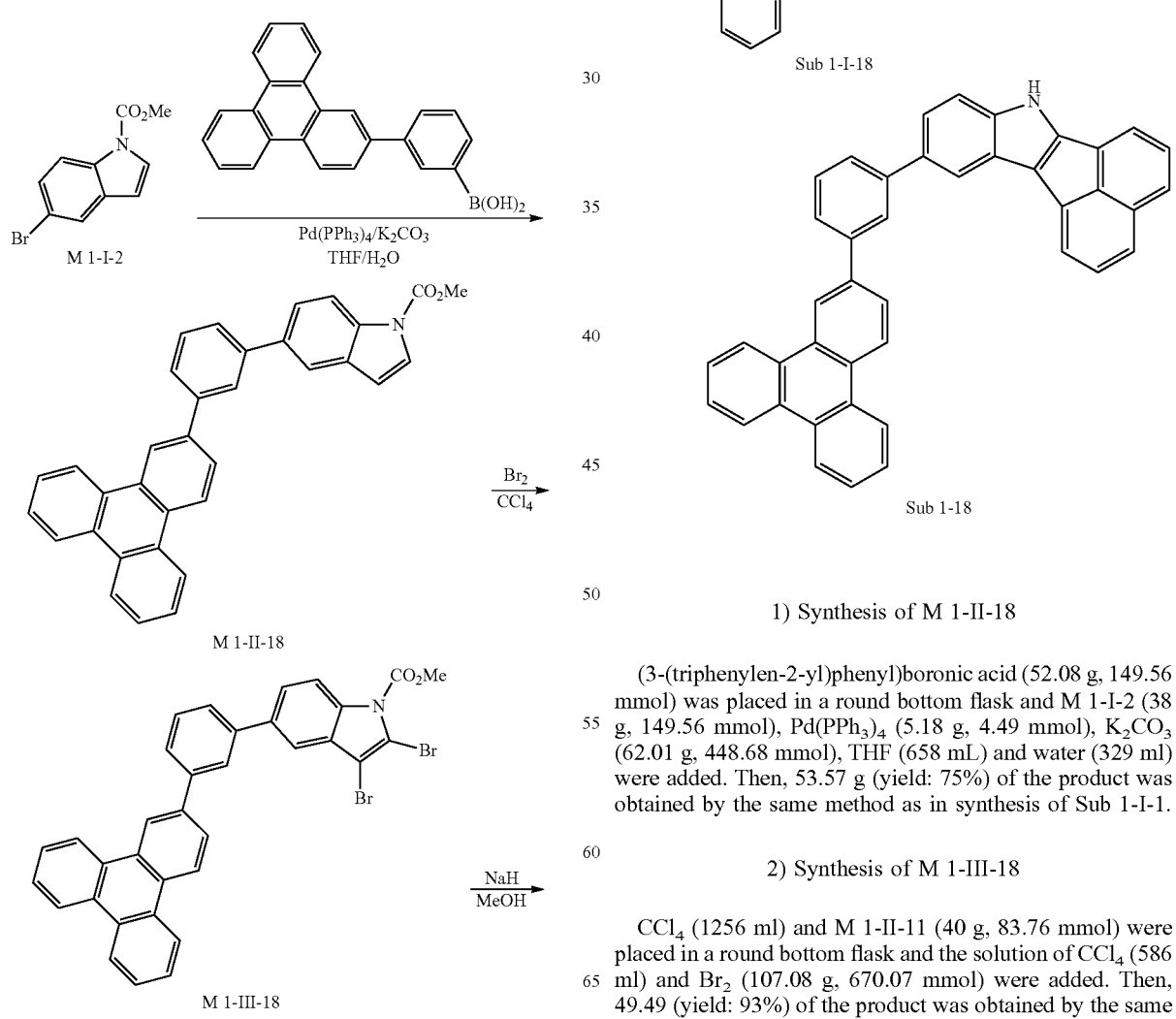

1) Synthesis of M 1-II-18

(3-(triphenylen-2-yl)phenyl)boronic acid (52.08 g, 149.56 mmol) was placed in a round bottom flask and M 1-I-2 (38 g, 149.56 mmol), Pd(PPh$_3$)$_4$ (5.18 g, 4.49 mmol), K$_2$CO$_3$ (62.01 g, 448.68 mmol), THF (658 mL) and water (329 ml) were added. Then, 53.57 g (yield: 75%) of the product was obtained by the same method as in synthesis of Sub 1-I-1.

2) Synthesis of M 1-III-18

CCl$_4$ (1256 ml) and M 1-II-11 (40 g, 83.76 mmol) were placed in a round bottom flask and the solution of CCl$_4$ (586 ml) and Br$_2$ (107.08 g, 670.07 mmol) were added. Then, 49.49 (yield: 93%) of the product was obtained by the same method as in synthesis of M 1-I-1.

3) Synthesis of M 1-18

After M 1-III-18 (49.49 g, 77.89 mmol) was added to MeOH (1947 ml), NaH (3.74 g, 155.79 mmol) was added to the mixture. Then, 40.47 g (yield: 90%) of the product was obtained by the same method as in synthesis of M 1-1.

4) Synthesis of Sub 1-I-18

M 1-18 (40.47 g, 70.1 mmol), Pd(PPh$_3$)$_4$ (1.22 g, 1.05 mmol), K$_2$CO$_3$ (14.53 g, 105.15 mmol), THF (308 ml) and water (154 ml) were added to naphthalen-1-ylboronic acid (12.06 g, 70.1 mmol). Then, 33.28 g (yield: 76%) of the product was obtained by the same method as in synthesis of Sub 1-I-1.

5) Synthesis of Sub 1-18

Pd(PPh$_3$)$_2$Cl$_2$ (3.74 g, 5.33 mmol), 1,8-Diazabicyclo[5.4.0]undec-7-ene (11.36 g, 74.6 mmol) and anhydrous DMF (107 ml) were added to Sub 1-I-18 (33.28 g, 53.28 mmol). Then, 18.25 g (yield: 63%) of the product was obtained by the same method as in synthesis of Sub 1-1.

6. Synthesis Example of Sub 1-20

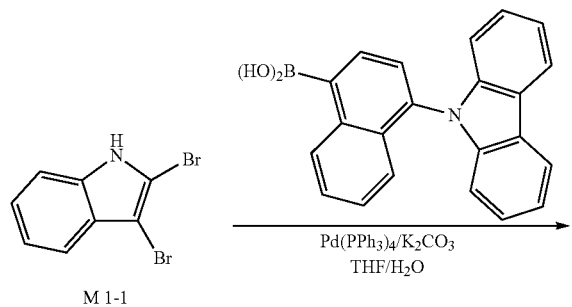

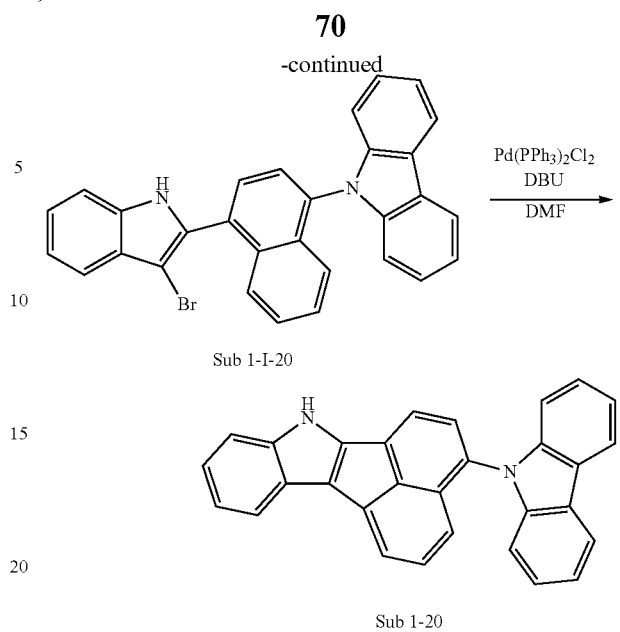

1) Synthesis of Sub 1-I-20

THF (320 ml), M 1-1 (20.00 g, 72.74 mmol), Pd(PPh$_3$)$_4$ (1.26 g, 1.09 mmol), K$_2$CO$_3$ (15.08 g, 109.11 mmol) and water (160 ml) were added to (4-(9H-carbazol-9-yl)naphthalen-1-yl)boronic acid (24.53 g, 72.74 mmol). Then, 21.27 g (yield: 60%) of the product was obtained by the same method as in synthesis of Sub 1-I-1.

2) Synthesis of Sub 1-20

Pd(PPh$_3$)$_2$Cl$_2$ (3.06 g, 4.36 mmol), 1,8-Diazabicyclo[5.4.0]undec-7-ene (9.30 g, 61.10 mmol) and anhydrous DMF (87 ml) were added to Sub 1-I-20 (21.27 g, 43.64 mmol). Then, 13.84 g (yield: 78%) of the product was obtained by the same method as in synthesis of Sub 1-1.

7. Synthesis Example of Sub 1-23

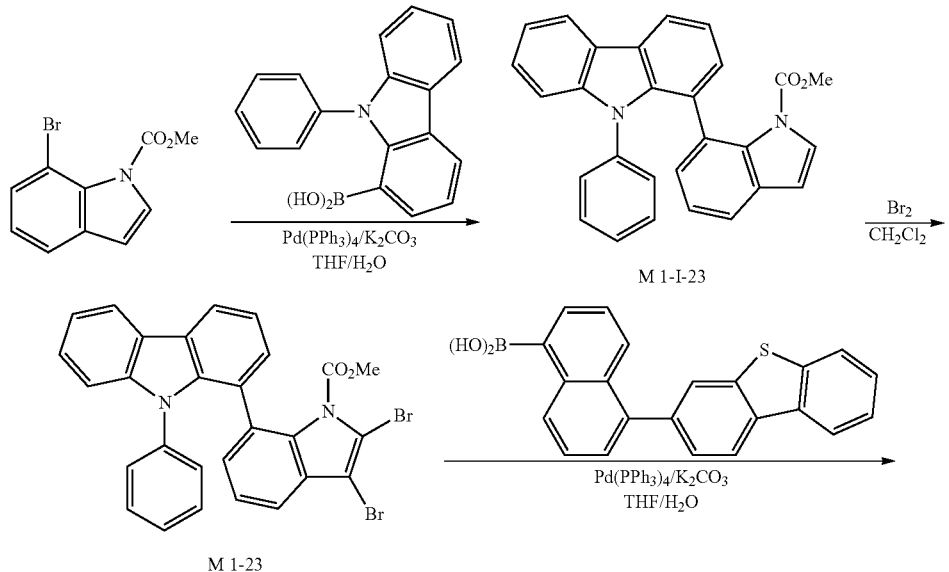

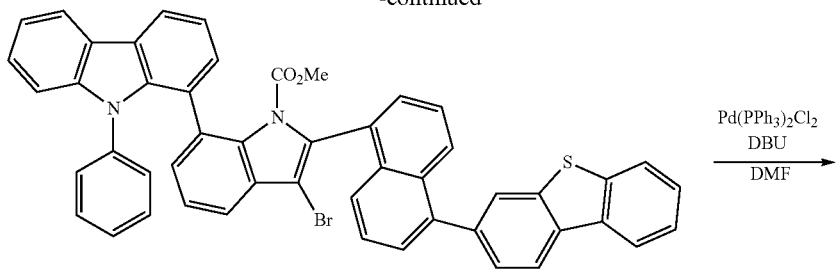

Sub 1-I-23

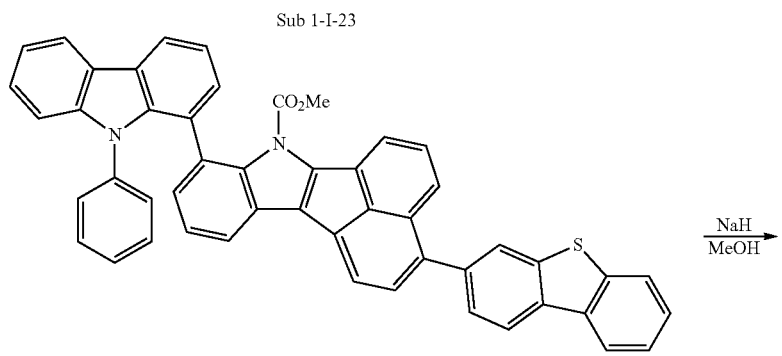

Sub 1-II-23

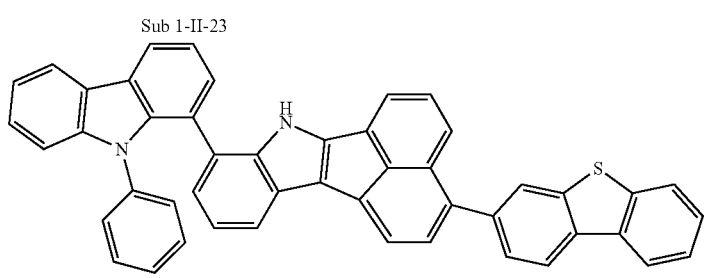

Sub 1-23

1) Synthesis of M 1-I-23

Methyl 7-bromo-1H-indole-1-carboxylate (25 g, 98.39 mmol), Pd(PPh₃)₄ (3.41 g, 2.95 mmol), K₂CO₃ (40.8 g, 295.18 mmol), THF (433 ml) and water (216 ml) were added to (9-phenyl-9H-carbazol-1-yl)boronic acid (28.25 g, 98.39 mmol). Then, 35.65 g (yield: 87%) of the product was obtained by the same method as in synthesis of Sub 1-I-1.

2) Synthesis of M 1-23

CH₂Cl₂ (588 ml) and M 1-I-23 (35 g, 84.04 mmol) were placed in a round bottom flask and the reactor was placed in an ice bath to provide an ice atmosphere. Then, the solution of CH₂Cl₂ and Br₂ (53.72 g, 336.15 mmol) was slowly added. A cold aqueous 5% NaHSO₃ solution was added 5 minutes after the addition was completed. Then, the organic layer was washed with cold NaHCO₃ and then washed with a saturated aqueous NaCl solution. The organic layer was extracted with CH₂Cl₂ and water. Then organic layer was dried with MgSO₄ and concentrated. The concentrate was applied to silica gel column and recrystallized to obtain 40.54 g (yield: 84%) of the product.

3) Synthesis of Sub 1-I-23

M 1-23 (40.54 g, 70.59 mmol), Pd(PPh₃)₄ (2.45 g, 2.12 mmol), K₂CO₃ (29.27 g, 211.78 mmol), THF (311 ml) and water (155 ml) were added to (5-(dibenzo[b,d]thiophen-3-yl)naphthalen-1-yl)boronic acid (25.01 g, 70.59 mmol). Then, 43.69 g (yield: 77%) of the product was obtained by the same method as in synthesis of Sub 1-I-1.

4) Synthesis of Sub 1-II-23

Pd(PPh₃)₂Cl₂ (3.82 g, 5.44 mmol), 1,8-Diazabicyclo[5.4.0]undec-7-ene (11.59 g, 76.10 mmol) and anhydrous DMF (109 ml) were added to Sub 1-I-23 (43.69 g, 54.36 mmol). Then, 24.36 g (yield: 62%) of the product was obtained by the same method as in synthesis of Sub 1-1.

5) Synthesis of Sub 1-23

After Sub 1-II-23 (20 g, 27.67 mmol) was added to MeOH (692 ml), NaH (1.33 g, 55.34 mmol) was added to the mixture. Then, 16.37 g (yield: 89%) of the product was obtained by the same method as in synthesis of M 1-1.

8. Synthesis Example of Sub 1-27

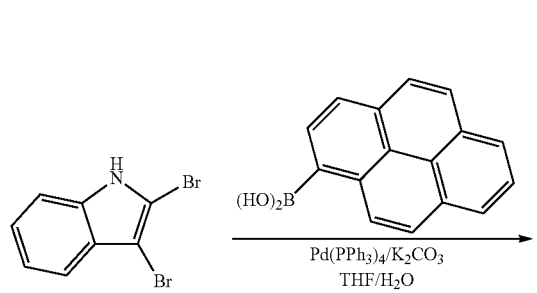

M 1-1

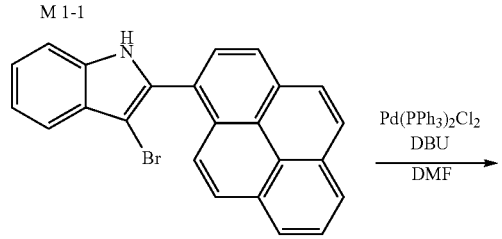

Sub 1-I-27

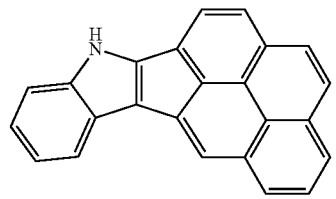

Sub 1-27

1) Synthesis of Sub 1-I-27

THF (416 ml), M 1-1 (26.00 g, 94.57 mmol), Pd(PPh$_3$)$_4$ (1.64 g, 1.42 mmol), K$_2$CO$_3$ (19.60 g, 141.85 mmol) and water (208 ml) were added to pyren-1-ylboronic acid (23.27 g, 94.57 mmol). Then, 21.36 g (yield: 57%) of the product was obtained by the same method as in synthesis of Sub 1-I-1.

2) Synthesis of Sub 1-27

Pd(PPh$_3$)$_2$Cl$_2$ (3.78 g, 5.39 mmol), 1,8-Diazabicyclo[5.4.0]undec-7-ene (11.49 g, 75.46 mmol) and anhydrous DMF (108 ml) were added to Sub 1-I-27 (21.36 g, 53.90 mmol). Then, 12.92 g (yield: 76%) of the product was obtained by the same method as in synthesis of Sub 1-1.

9. Synthesis Example of Sub 1-34

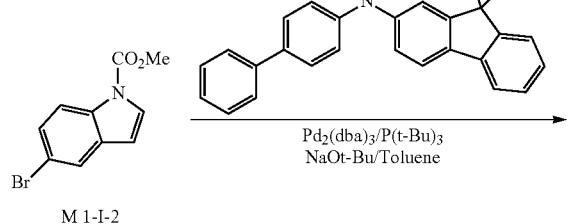

M 1-I-2

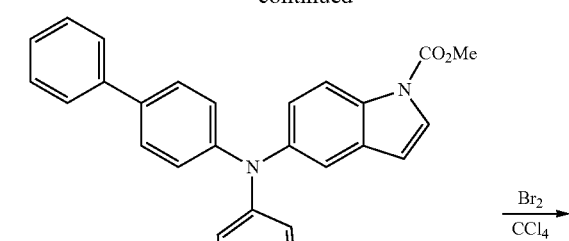

M 1-I-34

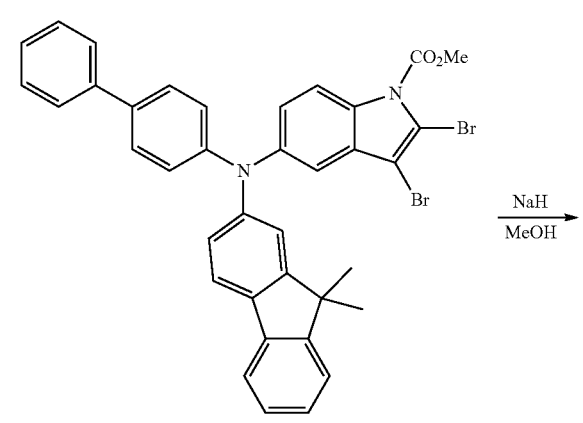

M 1-II-34

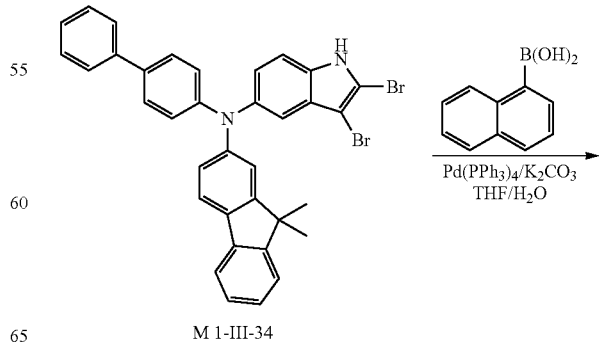

M 1-III-34

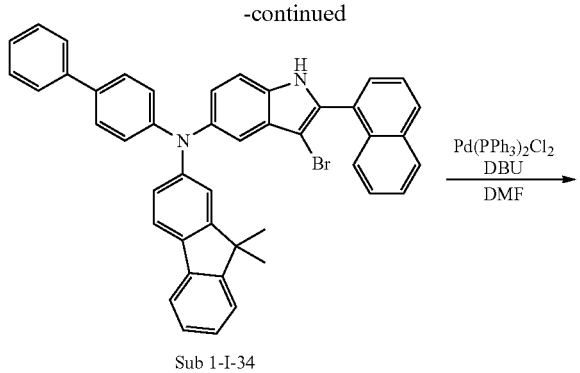

Sub 1-I-34

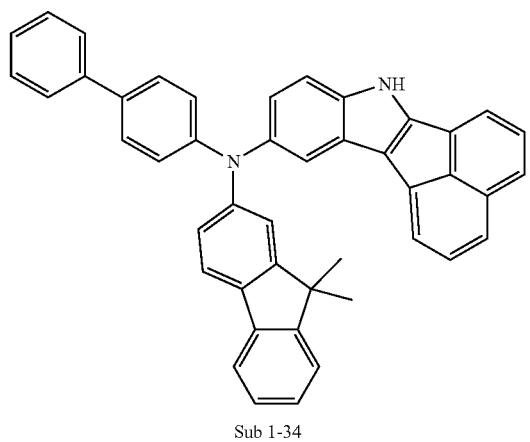

Sub 1-34

1) Synthesis of M 1-I-34

After M-I-2 (15.60 g, 61.40 mmol) was dissolved in Toluene (645 ml) in a round bottom flask, N-([1,1'-biphenyl]-4-yl)-9,9-dimethyl-9H-fluoren-2-amine (22.19 g, 61.40 mmol), $Pd_2(dba)_3$ (1.69 g, 1.84 mmol), $P(t-Bu)_3$ (0.99 g, 4.91 mmol) and NaOt-Bu (17.70 g, 184.19 mmol) were added and the mixture was stirred at 100° C. When the reaction was completed, the organic layer was extracted with $CH_2Cl_2$ and water. Then organic layer was dried with $MgSO_4$ and concentrated. The concentrate was applied to silica gel column and recrystallized to obtain 27.25 g (yield: 83%) of the product.

2) Synthesis of M 1-II-34

$CCl_4$ (1017 ml) and M 1-I-34 (27.2 g, 50.87 mmol) were placed in a round bottom flask and the solution of $CCl_4$ (356 ml) and $Br_2$ (65.04 g, 406.99 mmol) were added. Then, 31.70 g (yield: 90%) of the product was obtained by the same method as in synthesis of M 1-I-1.

3) Synthesis of M 1-III-34

After M 1-II-34 (31.70 g, 45.78 mmol) was added to MeOH (1144 ml), NaH (2.20 g, 91.56 mmol) was added to the mixture. Then, 25.27 g (yield: 87%) of the product was obtained by the same method as in synthesis of M 1-1.

4) Synthesis of Sub 1-I-34

After naphthalen-1-ylboronic acid (6.83 g, 39.72 mmol) was dissolved in THF (1751), Sub 1-I-34 (25.20 g, 39.72 mmol), $Pd(PPh_3)_4$ (0.69 g, 0.6 mmol), $K_2CO_3$ (8.23 g, 59.58 mmol), THF (175 ml) and water (87 ml) were added to the mixture. Then, 20.04 g (yield: 74%) of the product was obtained by the same method as in synthesis of Sub 1-I-1.

5) Synthesis of Sub 1-34

$Pd(PPh_3)_2Cl_2$ (2.06 g, 2.93 mmol), 1,8-Diazabicyclo[5.4.0]undec-7-ene (6.25 g, 41.07 mmol), anhydrous DMF (59 ml) were added to Sub 1-I-34 (20 g, 29.34 mmol). Then, 10.22 g (yield: 58%) of the product was obtained by the same method as in synthesis of Sub 1-1.

10. Synthesis Example of Sub 1-37

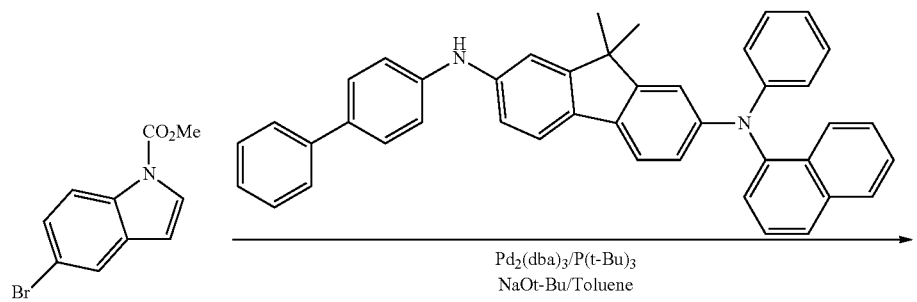

M 1-I-2

-continued
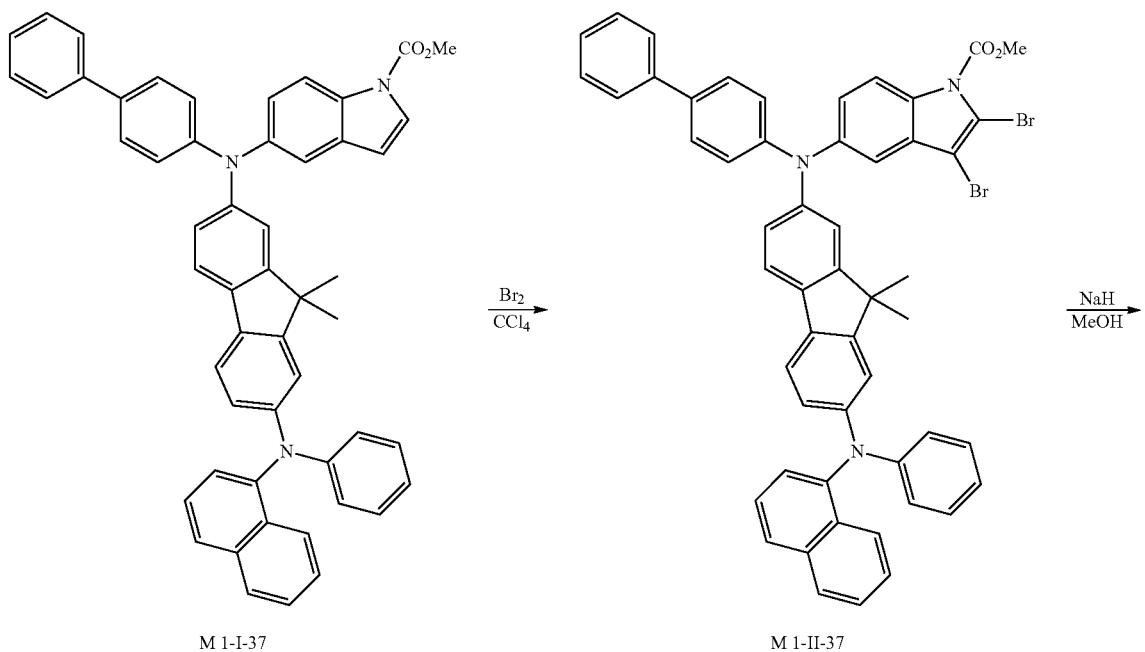
M 1-I-37 → M 1-II-37
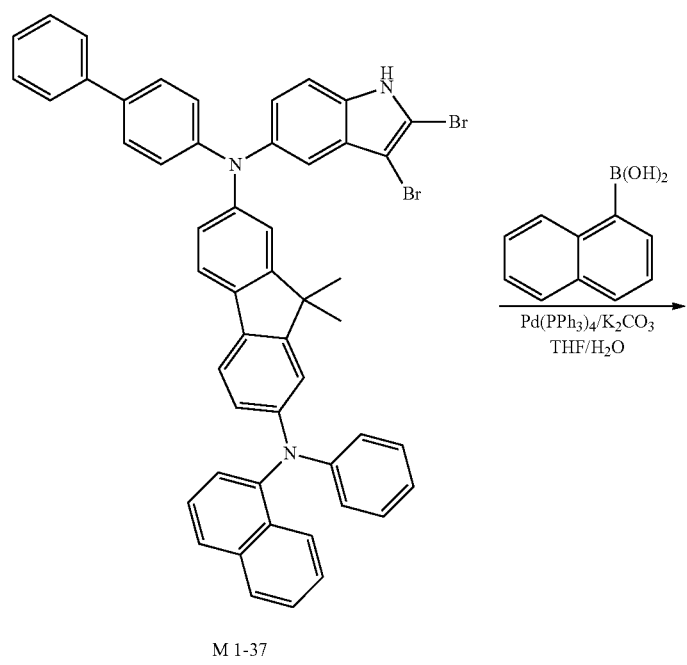
M 1-37

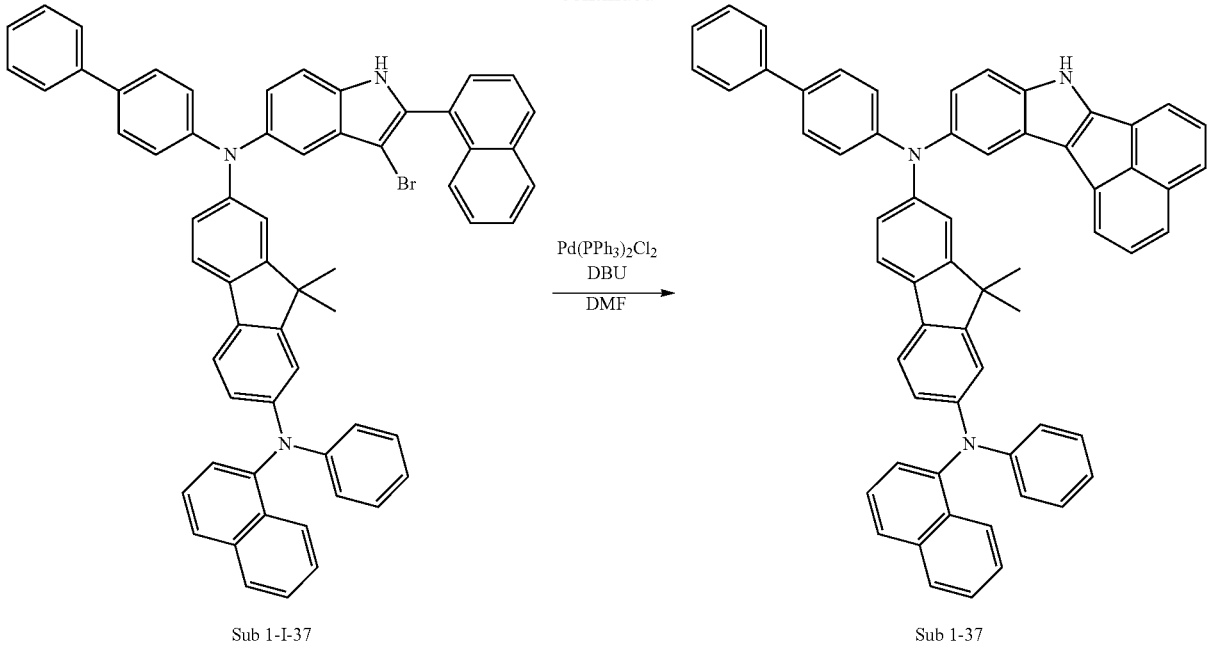

Sub 1-I-37 → Sub 1-37

1) Synthesis of M 1-I-37

After M-I-2 (12.60 g, 49.59 mmol) was dissolved in Toluene (521 ml) in a round bottom flask, N2-([1,1'-biphenyl]-4-yl)-9,9-dimethyl-N7-(naphthalen-1-yl)-N7-phenyl-9H-fluorene-2,7-diamine (28.70 g, 49.59 mmol), $Pd_2(dba)_3$ (1.36 g, 1.49 mmol), P(t-Bu)$_3$ (0.80 g, 3.97 mmol) and NaOt-Bu (14.30 g, 148.77 mmol) were added, and then 29.46 g (yield: 79%) of the product was obtained by the same method as in synthesis of M 1-I-34.

2) Synthesis of M 1-II-37

$CCl_4$ (779 ml) and M 1-I-37 (29.3 g, 38.97 mmol) were placed in a round bottom flask and the solution of $CCl_4$ (272 ml) and $Br_2$ (49.82 g, 311.73 mmol) were added. Then, 31.19 g (yield: 88%) of the product was obtained by the same method as in synthesis of M 1-I-1.

3) Synthesis of M 1-III-37

After M 1-II-37 (31.1 g, 34.19 mmol) was added to MeOH (854 ml), NaH (1.64 g, 68.37 mmol) was added to the mixture. Then, 24.17 g (yield: 83%) of the product was obtained by the same method as in synthesis of M 1-1.

4) Synthesis of Sub 1-I-37

Sub 1-I-37 (24.10 g, 28.3 mmol), Pd(PPh$_3$)$_4$ (0.49 g, 0.42 mmol), $K_2CO_3$ (5.87 g, 42.45 mmol), THF (125 ml) and water (62 ml) were added to naphthalen-1-ylboronic acid (4.87 g, 28.3 mmol). Then, 18.06 g (yield: 71%) of the product was obtained by the same method as in synthesis of Sub 1-I-1.

5) Synthesis of Sub 1-37

Pd(PPh$_3$)$_2$Cl$_2$ (1.41 g, 2 mmol), 1,8-iazabicyclo[5.4.0]undec-7-ene (4.27 g, 28.03 mmol) and anhydrous DMF (40 ml) were added to Sub 1-I-37 (18 g, 20.02 mmol). Then, 10.11 g (yield: 55%) of the product was obtained by the same method as in synthesis of Sub 1-1.

11. Synthesis Example of Sub 1-41

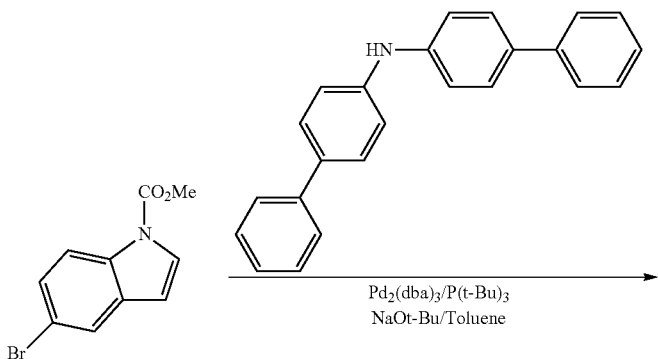

M 1-I-2

-continued
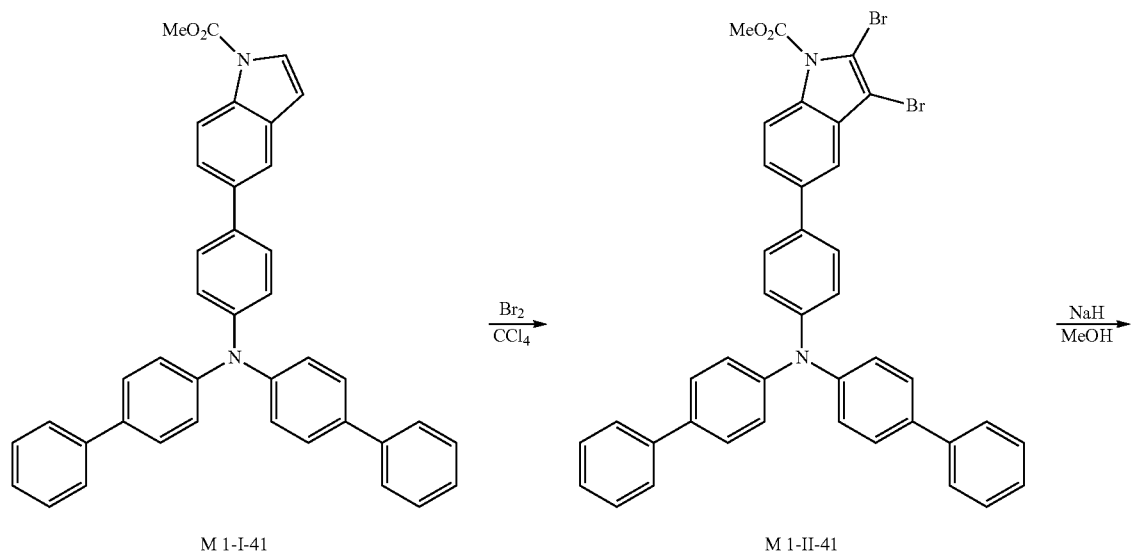
M 1-I-41  M 1-II-41
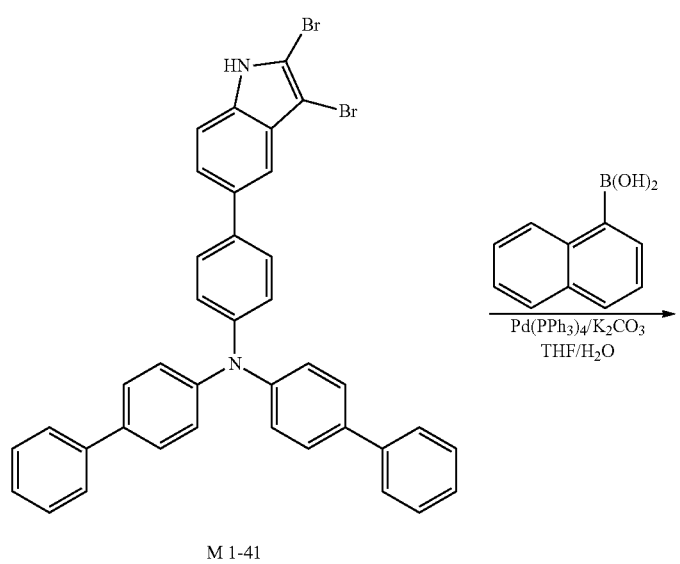
M 1-41
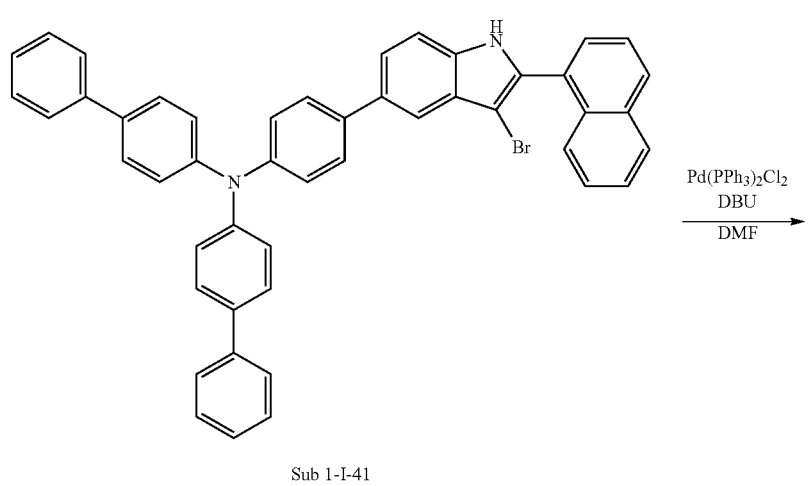
Sub 1-I-41

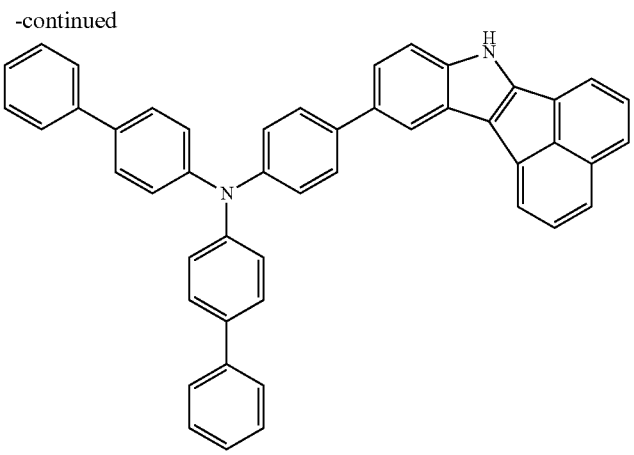

Sub 1-41

1) Synthesis of M 1-I-41

After M-I-2 (13 g, 51.16 mmol) was dissolved in Toluene (537 ml) in a round bottom flask, di([1,1'-biphenyl]-4-yl) amine (16.45 g, 51.16 mmol), Pd$_2$(dba)$_3$ (1.41 g, 1.53 mmol), P(t-Bu)$_3$ (0.83 g, 4.09 mmol) and NaOt-Bu (14.75 g, 153.49 mmol) were added, and then 25.11 g (yield: 86%) of the product was obtained by the same method as in synthesis of M 1-I-34.

2) Synthesis of M 1-II-41

CCl$_4$ (872 ml) and M 1-I-41 (24.9 g, 43.63 mmol) were placed in a round bottom flask and the solution of CCl$_4$ (305 ml) and Br$_2$ (55.78 g, 349.05 mmol) were added. Then, 28.92 g (yield: 91%) of the product was obtained by the same method as in synthesis of M 1-I-1.

3) Synthesis of M 1-41

After M 1-II-41 (28.9 g, 39.67 mmol) was added to MeOH (991 ml), NaH (1.90 g, 79.34 mmol) was added to the mixture. Then, 23.14 g (yield: 87%) of the product was obtained by the same method as in synthesis of M 1-1.

4) Synthesis of Sub 1-I-41

M 1-41 (23.10 g, 34.45 mmol), Pd(PPh$_3$)$_4$ (0.60 g, 0.52 mmol), K$_2$CO$_3$ (7.14 g, 51.68 mmol), THF (152 ml) and water (76 ml) were added to naphthalen-1-ylboronic acid (5.93 g, 34.45 mmol). Then, 19.04 g (yield: 77%) of the product was obtained by the same method as in synthesis of Sub 1-I-1.

5) Synthesis of Sub 1-41

Pd(PPh$_3$)$_2$Cl$_2$ (1.86 g, 2.65 mmol), 1,8-iazabicyclo[5.4.0]undec-7-ene (5.64 g, 37.06 mmol) and anhydrous DMF (53 ml) were added to Sub 1-I-41 (19 g, 26.47 mmol). Then, 10.1 g (yield: 60%) of the product was obtained by the same method as in synthesis of Sub 1-1.

12. Synthesis Example of Sub 1-50

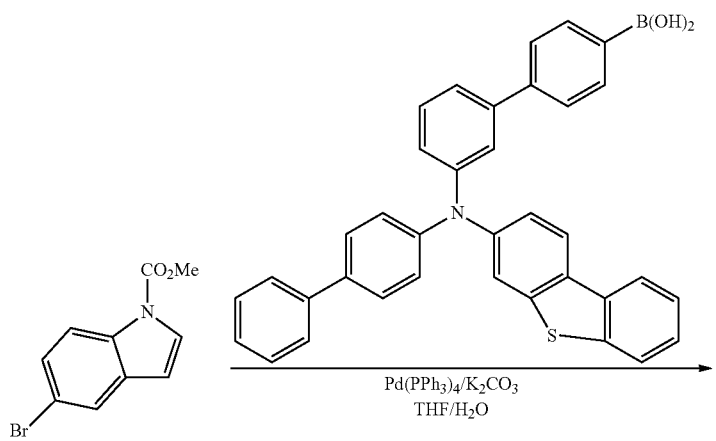

-continued
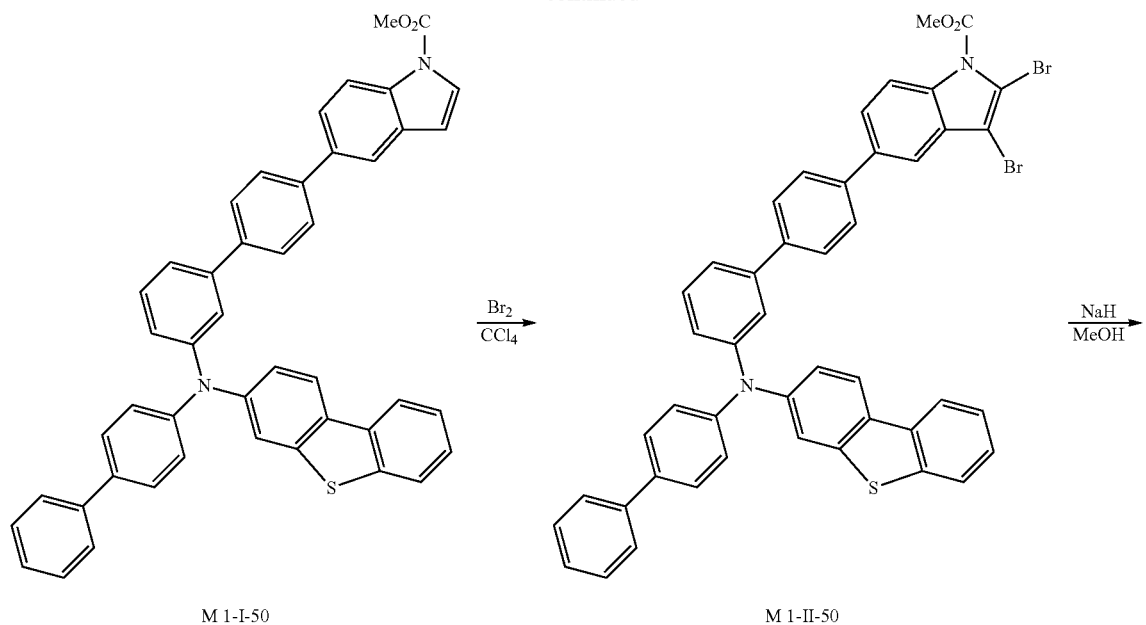
M 1-I-50
M 1-II-50
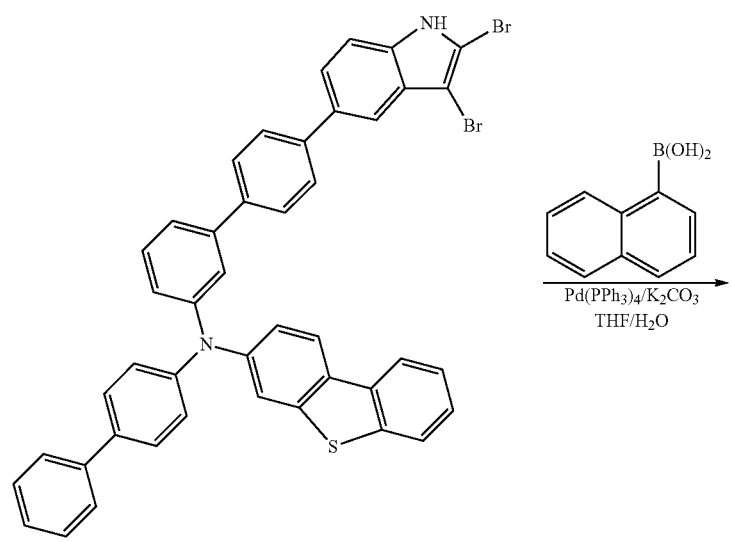
M 1-50

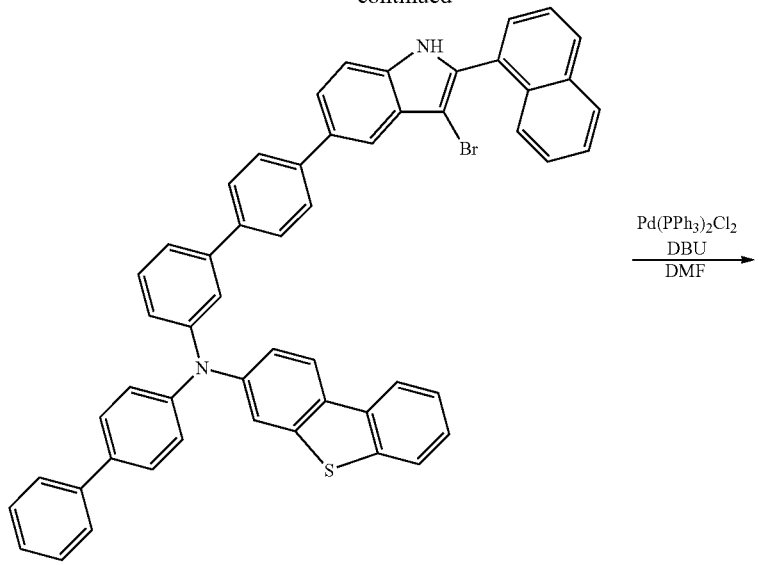

Sub 1-I-50

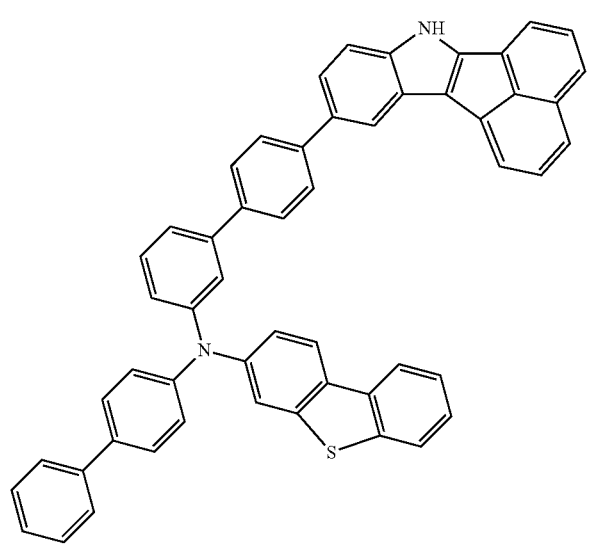

Sub 1-50

1) Synthesis of M 1-I-50

(3'-([1,1'-biphenyl]-4-yl(dibenzo[b,d]thiophen-3-yl)amino)-[1,1'-biphenyl]-4-yl)boronic acid (35.77 g, 65.33 mmol) was placed in a round bottom flask and M 1-I-2 (16.6 g, 65.33 mmol), $Pd(PPh_3)_4$ (2.26 g, 1.96 mmol), $K_2CO_3$ (27.09 g, 196 mmol), THF (287 mL) and water (144 ml) were added. Then, 33.58 g (yield: 76%) of the product was obtained by the same method as in synthesis of Sub 1-I-1.

2) Synthesis of M 1-II-50

$CCl_4$ (987 ml) and M 1-I-50 (33.4 g, 49.35 mmol) were placed in a round bottom flask and the solution of $CCl_4$ (345 ml) and $Br_2$ (63.09 g, 395.78 mmol) were added. Then, 35.01 g (yield: 85%) of the product was obtained by the same method as in synthesis of M 1-I-1.

3) Synthesis of M 1-50

After M 1-II-50 (35 g, 41.94 mmol) was added to MeOH (1048 ml), NaH (2.01 g, 83.87 mmol) was added to the mixture. Then, 26.70 g (yield: 82%) of the product was obtained by the same method as in synthesis of M 1-1.

4) Synthesis of Sub 1-I-50

M 1-50 (26.70 g, 34.38 mmol), $Pd(PPh_3)_4$ (0.60 g, 0.52 mmol), $K_2CO_3$ (7.13 g, 51.57 mmol), THF (151 ml) and water (76 ml) were added to naphthalen-1-ylboronic acid (5.91 g, 34.38 mmol). Then, 20.11 g (yield: 71%) of the product was obtained by the same method as in synthesis of Sub 1-I-1.

5) Synthesis of Sub 1-50

$Pd(PPh_3)_2Cl_2$ (1.70 g, 2.43 mmol), 1,8-iazabicyclo[5.4.0]undec-7-ene (5.17 g, 33.99 mmol), and anhydrous DMF (53 ml) were added to Sub 1-I-50 (20 g, 24.28 mmol). Then, 9.92 g (yield: 55%) of the product was obtained by the same method as in synthesis of Sub 1-1.

13. Synthesis Example of Sub 1-69
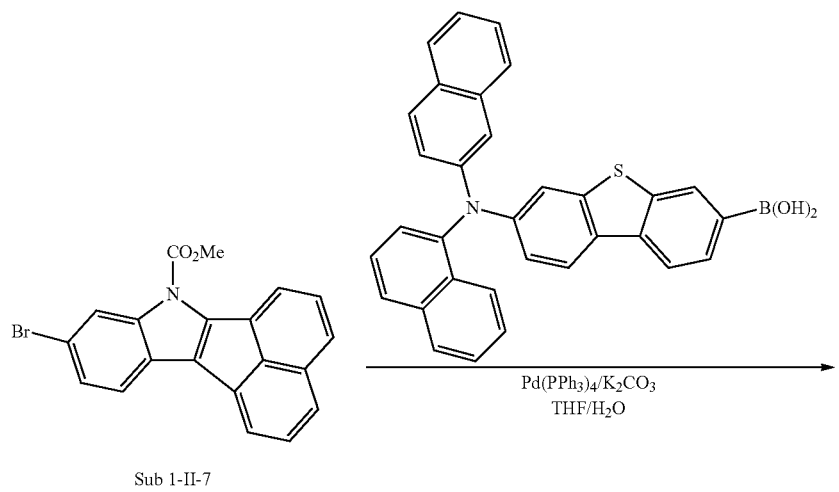
Sub 1-II-7
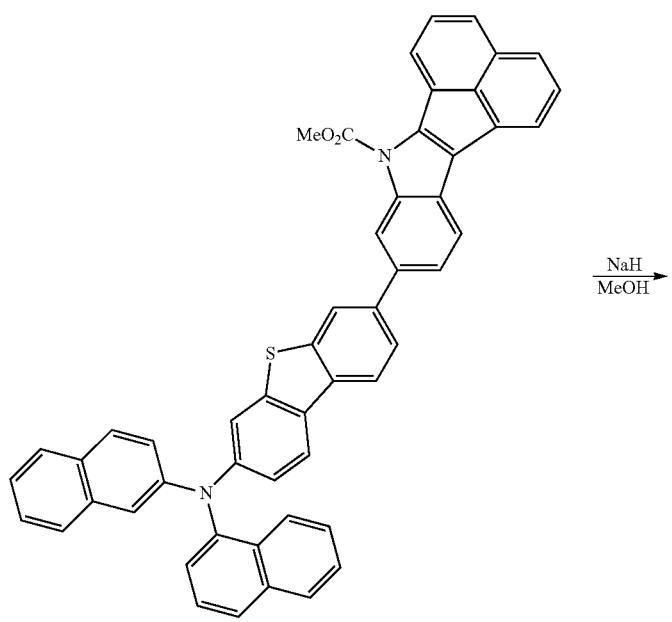
Sub 1-III-69

-continued

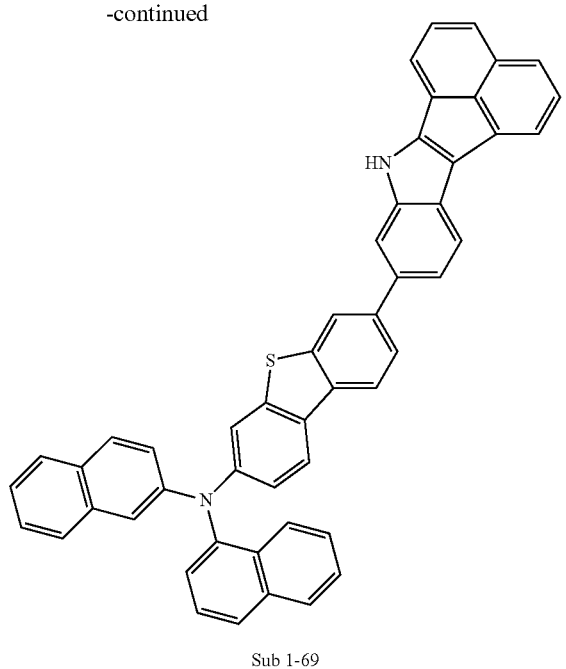
Sub 1-69

1) Synthesis of Sub 1-III-69

(7-(naphthalen-1-yl(naphthalen-2-yl)amino)dibenzo[b,d]thiophen-3-yl)boronic acid (11.77 g, 23.76 mmol) was placed in a round bottom flask and Sub 1-II-7 (9.2 g, 23.76 mmol), Pd(PPh$_3$)$_4$ (0.82 g, 0.71 mmol), K$_2$CO$_3$ (9.85 g, 71.28 mmol), THF (105 mL) and water (52 ml) were added. Then, 14.06 g (yield: 79%) of the product was obtained by the same method as in synthesis of Sub 1-I-1.

2) Synthesis of Sub 1-69

After Sub 1-III-69 (14 g, 18.69 mmol) was added to MeOH (467 ml), NaH (0.90 g, 37.39 mmol) was added to the mixture. Then, 10.33 g (yield: 80%) of the product was obtained by the same method as in synthesis of M 1-1.

14. Synthesis Example of Sub 1-70

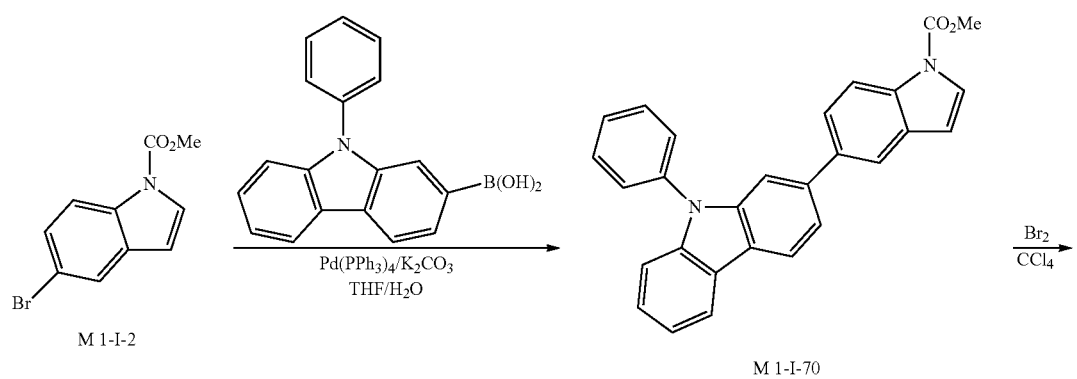

-continued
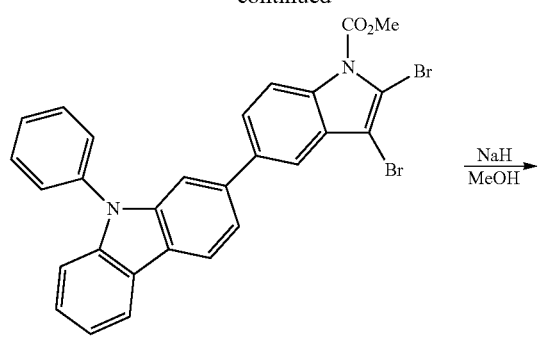
M 1-II-70
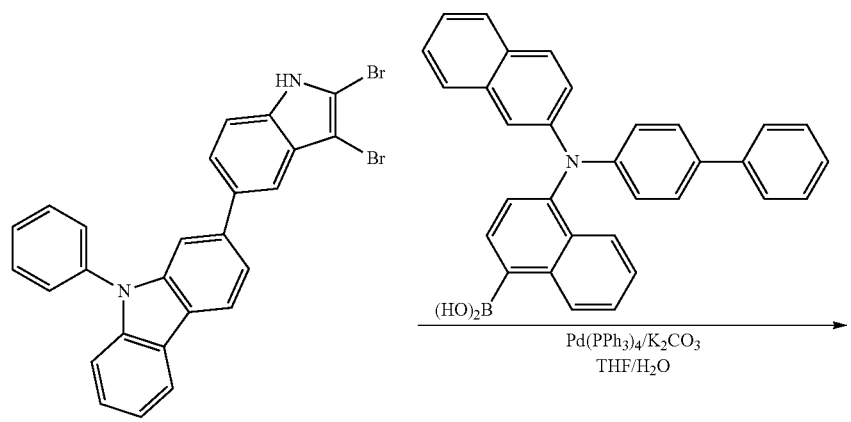
M 1-70
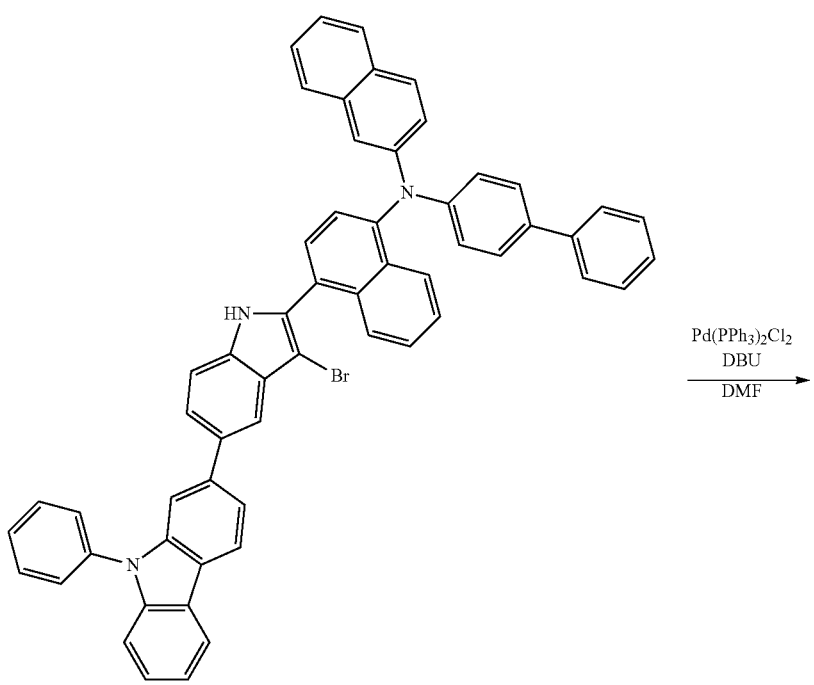
Sub 1-I-70

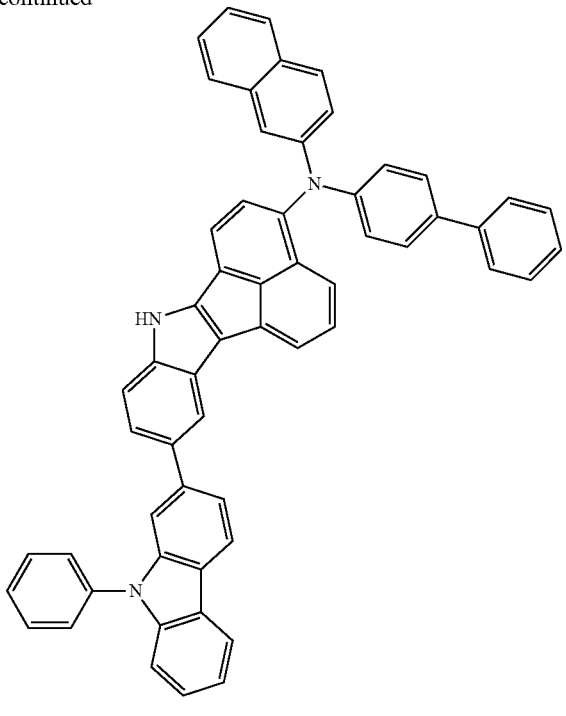

Sub 1-70

1) Synthesis of M 1-I-70

(9-phenyl-9H-carbazol-2-yl)boronic acid (13.56 g, 47.23 mmol) was placed in a round bottom flask and M 1-I-2 (12 g, 47.23 mmol), Pd(PPh$_3$)$_4$ (1.64 g, 1.42 mmol), K$_2$CO$_3$ (19.58 g, 141.63 mmol), THF (208 mL) and water (104 ml) were added. Then, 17.90 g (yield: 91%) of the product was obtained by the same method as in synthesis of Sub 1-I-1.

2) Synthesis of M 1-II-70

CCl$_4$ (850 ml) and M 1-I-70 (17.7 g, 42.5 mmol) were placed in a round bottom flask and the solution of CCl$_4$ (297 ml) and Br$_2$ (54.33 g, 339.99 mmol) were added. Then, 22.45 g (yield: 92%) of the product was obtained by the same method as in synthesis of M 1-I-1.

3) Synthesis of M 1-70

After M 1-II-70 (22.4 g, 39.01 mmol) was added to MeOH (975 ml), NaH (1.87 g, 78.01 mmol) was added to the mixture. Then, 16.91 g (yield: 84%) of the product was obtained by the same method as in synthesis of M 1-1.

4) Synthesis of Sub 1-I-70

M 1-70 (16.90 g, 32.74 mmol), Pd(PPh$_3$)$_4$ (0.57 g, 0.49 mmol), K$_2$CO$_3$ (6.79 g, 49.11 mmol), THF (144 ml) and water (72 ml) were added to (4-([1,1'-biphenyl]-4-yl(naphthalen-2-yl)amino)naphthalen-1-yl)boronic acid (15.23 g, 32.74 mmol). Then, 21.04 g (yield: 75%) of the product was obtained by the same method as in synthesis of Sub 1-I-1.

5) Synthesis of Sub 1-70

Pd(PPh$_3$)$_2$Cl$_2$ (1.72 g, 2.45 mmol), 1,8-iazabicyclo[5.4.0]undec-7-ene (5.22 g, 34.31 mmol) and anhydrous DMF (49 ml) were added to Sub 1-I-70 (21 g, 24.51 mmol). Then, 9.7 g (yield: 51%) of the product was obtained by the same method as in synthesis of Sub 1-1.

15. Synthesis Example of Sub 1-74

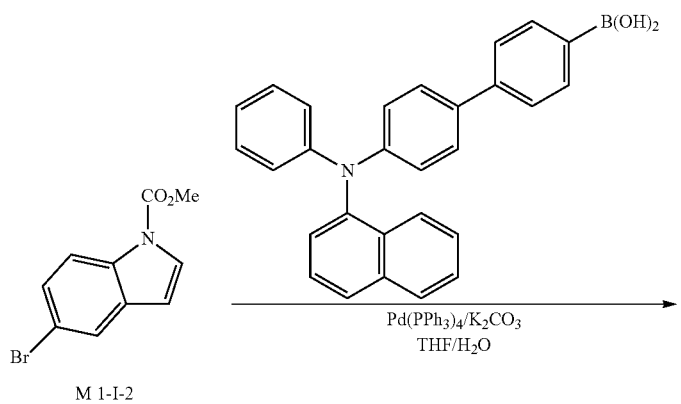

-continued
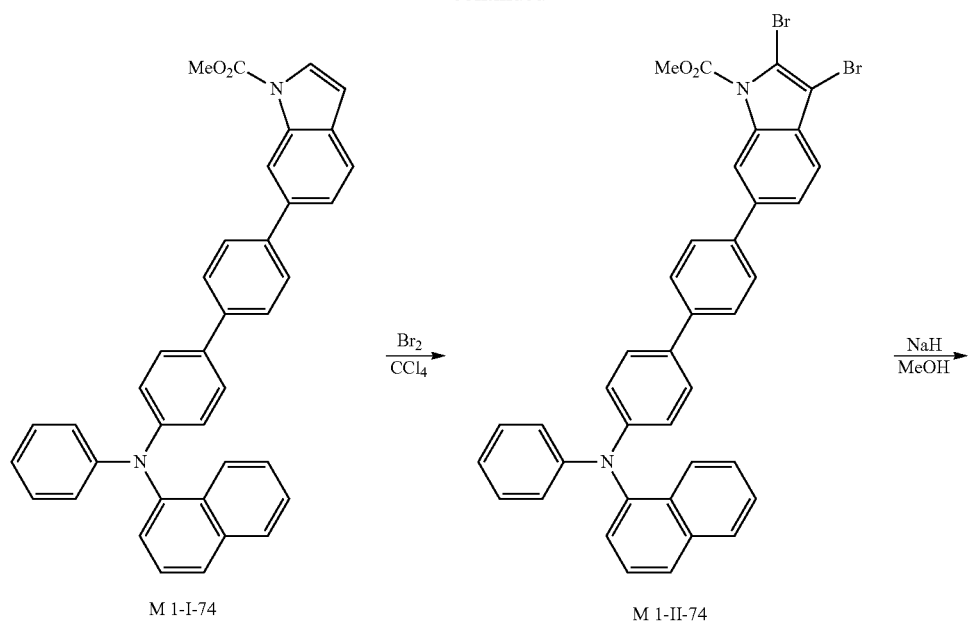
M 1-I-74 → M 1-II-74
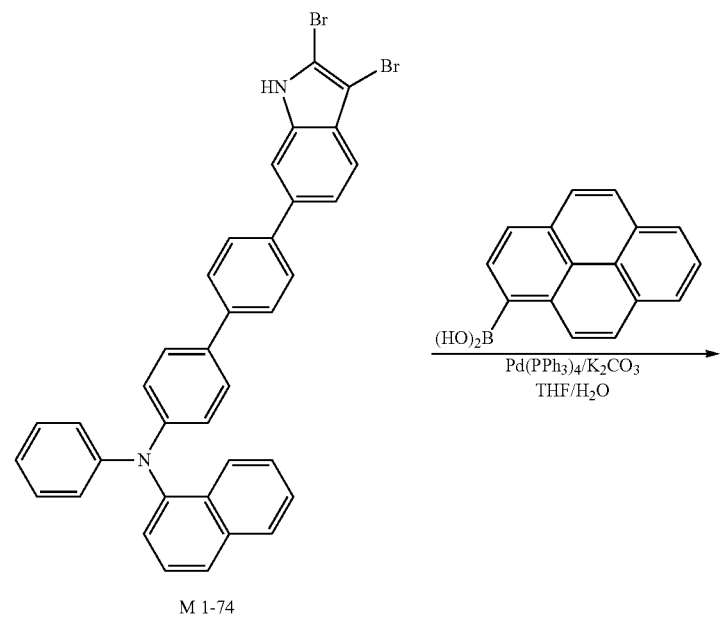
M 1-74

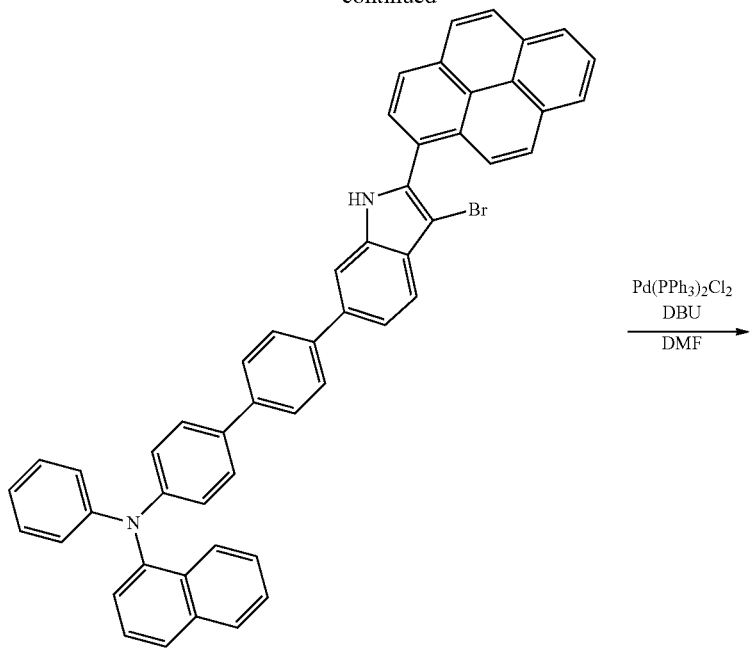

Sub 1-I-74

Pd(PPh₃)₂Cl₂
DBU
$\xrightarrow{\text{DMF}}$

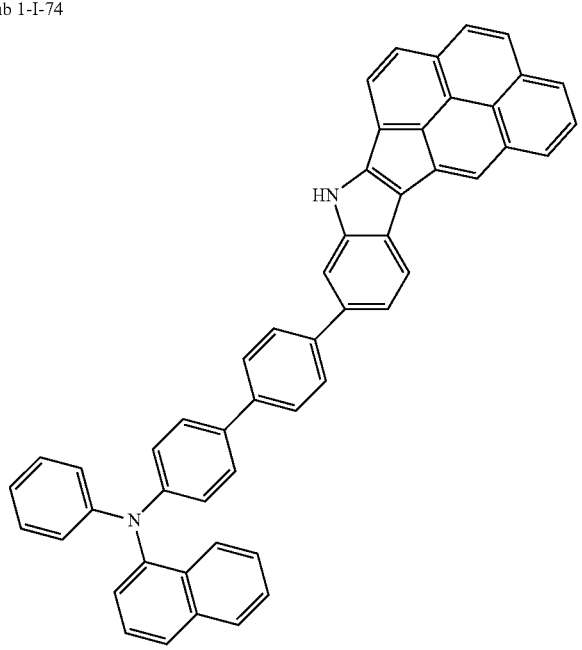

Sub 1-74

1) Synthesis of M 1-I-74

(4'-(naphthalen-1-yl(phenyl)amino)-[1,1'-biphenyl]-4-yl) boronic acid (26.64 g, 64.15 mmol) was placed in a round bottom flask and M 1-I-2 (16.30 g, 64.15 mmol), Pd(PPh₃)₄ (2.22 g, 1.92 mmol), K₂CO₃ (26.60 g, 192.46 mmol), THF (282 mL) and water (141 ml) were added. Then, 30.05 g (yield: 86%) of the product was obtained by the same method as in synthesis of Sub 1-I-1.

2) Synthesis of M 1-II-74

CCl₄ (1098 ml) and M 1-I-74 (29.9 g, 54.9 mmol) were placed in a round bottom flask and the solution of CCl₄ (384 ml) and Br₂ (70.19 g, 439.18 mmol) were added. Then, 34.32 g (yield: 89%) of the product was obtained by the same method as in synthesis of M 1-I-1.

3) Synthesis of M 1-74

After M 1-II-74 (34.3 g, 48.83 mmol) was added to MeOH (1220 ml), NaH (2.34 g, 97.66 mmol) was added to the mixture. Then, 24.86 g (yield: 79%) of the product was obtained by the same method as in synthesis of M 1-1.

4) Synthesis of Sub 1-I-74

M 1-74 (24.80 g, 38.49 mmol), Pd(PPh₃)₄ (0.67 g, 0.58 mmol), K₂CO₃ (7.98 g, 57.73 mmol), THF (169 ml) and water (85 ml) were added to pyren-1-ylboronic acid (9.47 g, 38.49 mmol). Then, 20.04 g (yield: 68%) of the product was obtained by the same method as in synthesis of Sub 1-I-1.

5) Synthesis of Sub 1-74

Pd(PPh₃)₂Cl₂ (1.83 g, 2.61 mmol), 1,8-iazabicyclo[5.4.0]undec-7-ene (5.57 g, 36.57 mmol) and anhydrous DMF (52 ml) were added to Sub 1-I-74 (20 g, 26.12 mmol). Then, 10.02 g (yield: 56%) of the product was obtained by the same method as in synthesis of Sub 1-1.

The compound belonging to Sub 1 may be, but not limited to, the following compounds, and Table 1 shows FD-MS (Field Desorption-Mass Spectrometry) values of compounds belonging to Sub 1.

Sub 1-1

Sub 1-2

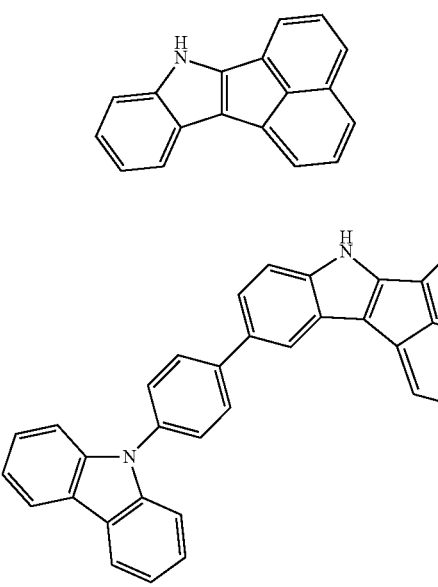

Sub 1-3

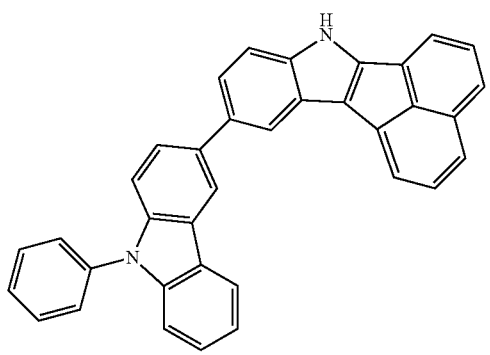

Sub 1-4

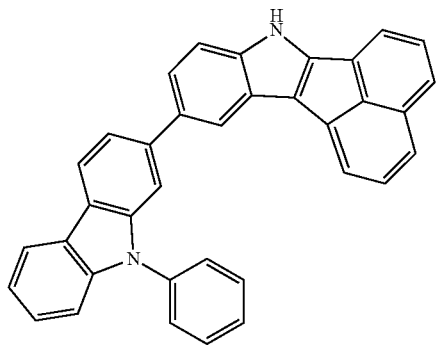

Sub 1-5

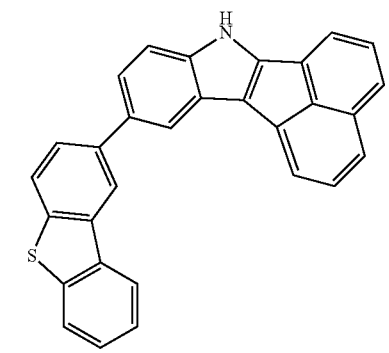

Sub 1-6

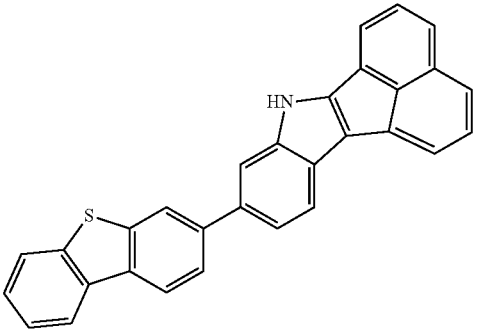

Sub 1-7

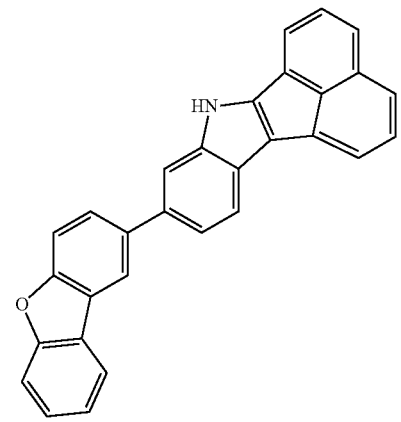

Sub 1-8
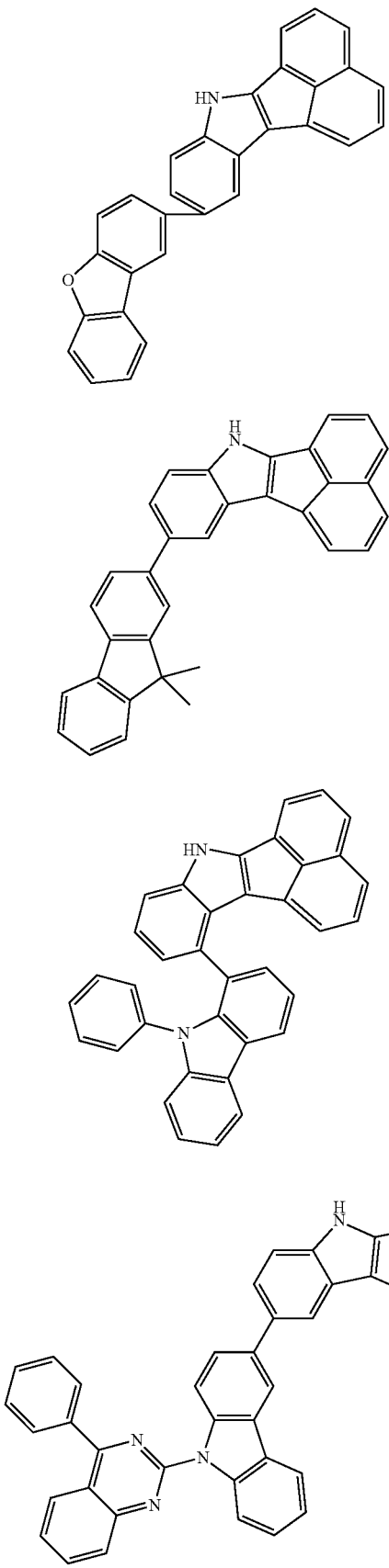
Sub 1-9
Sub 1-10
Sub 1-11
Sub 1-12
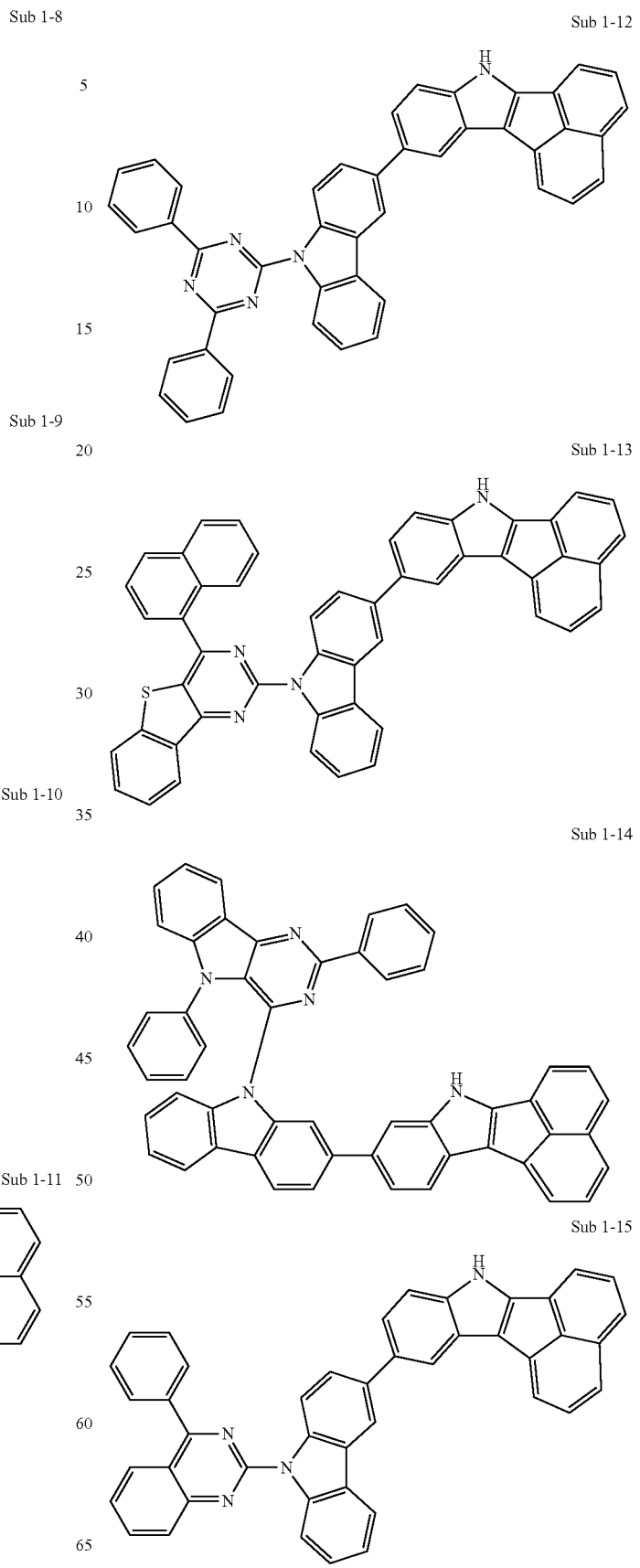
Sub 1-13
Sub 1-14
Sub 1-15

105
-continued
Sub 1-16
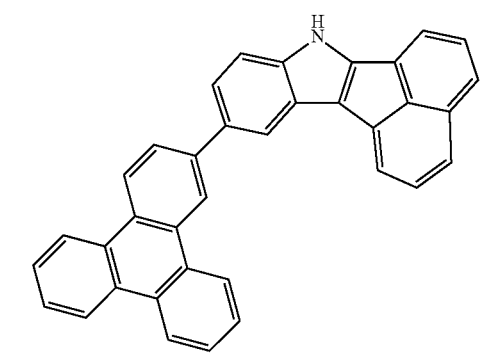
Sub 1-17
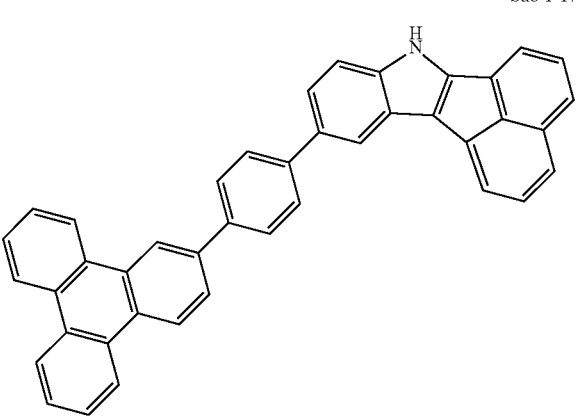
Sub 1-18
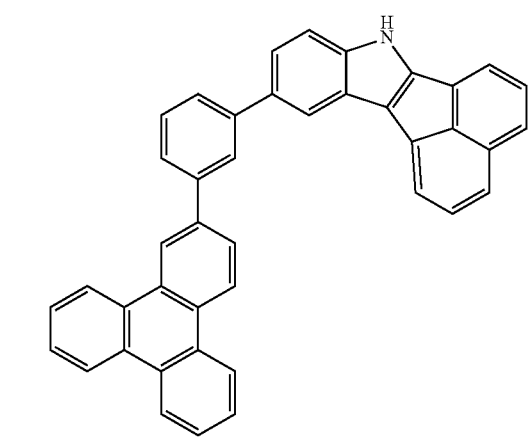
Sub 1-19
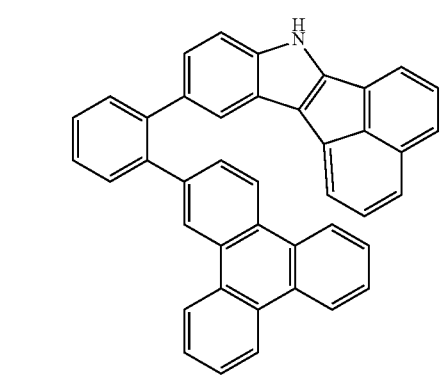
106
-continued
Sub 1-20
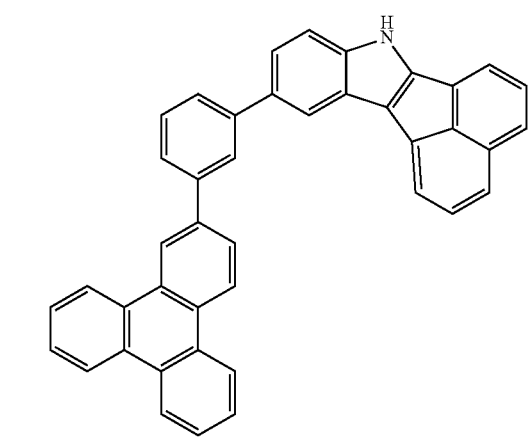
Sub 1-21
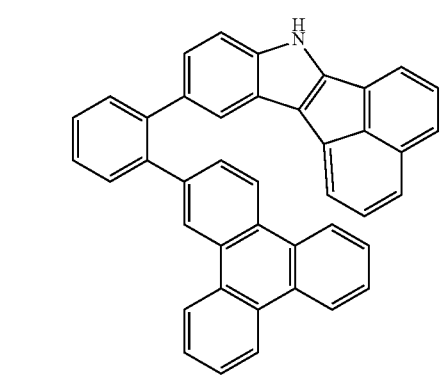
Sub 1-22
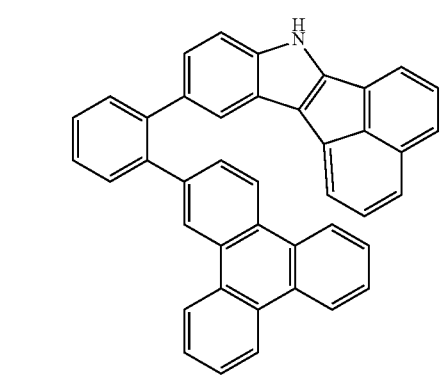
Sub 1-23
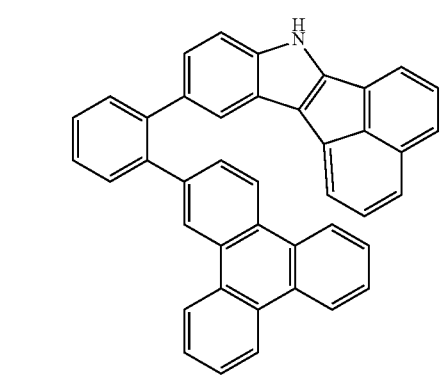

Sub 1-24
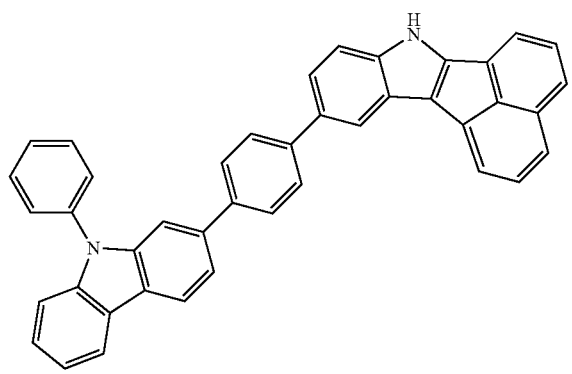
Sub 1-25
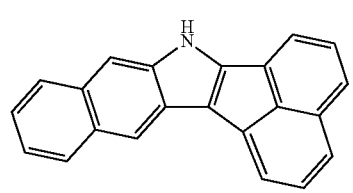
Sub 1-26
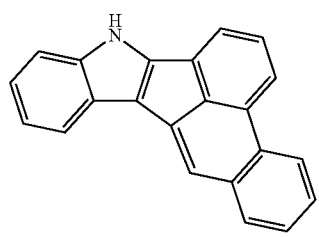
Sub 1-27
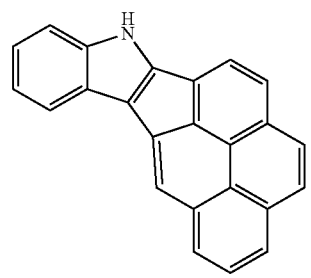
Sub 1-28
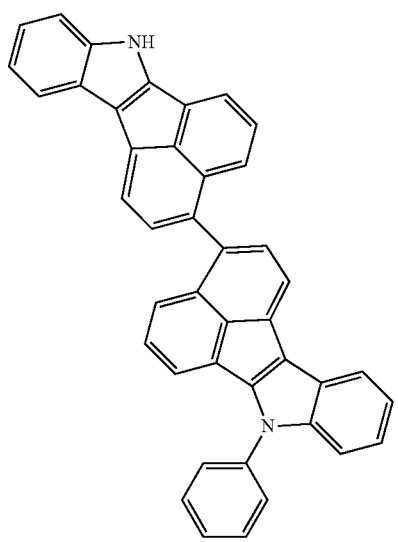
Sub 1-29
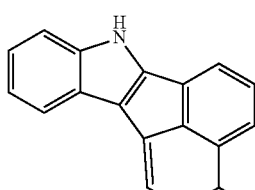
Sub 1-30
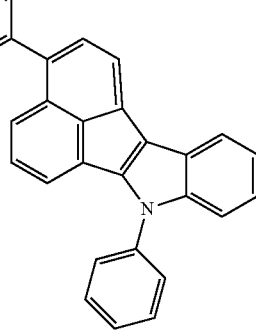
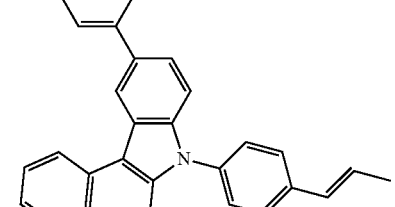
Sub 1-31
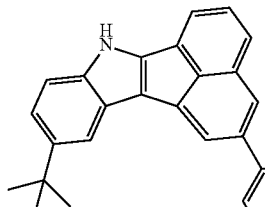
Sub 1-32
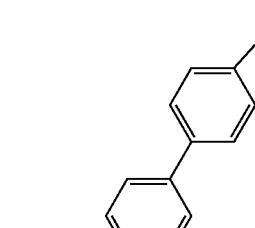

Sub 1-33
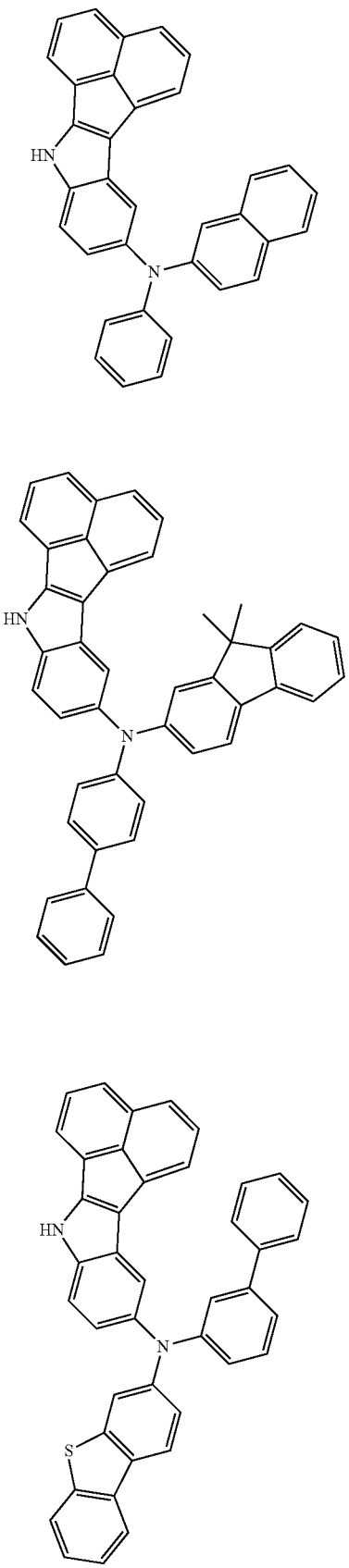
Sub 1-34
Sub 1-35
Sub 1-36
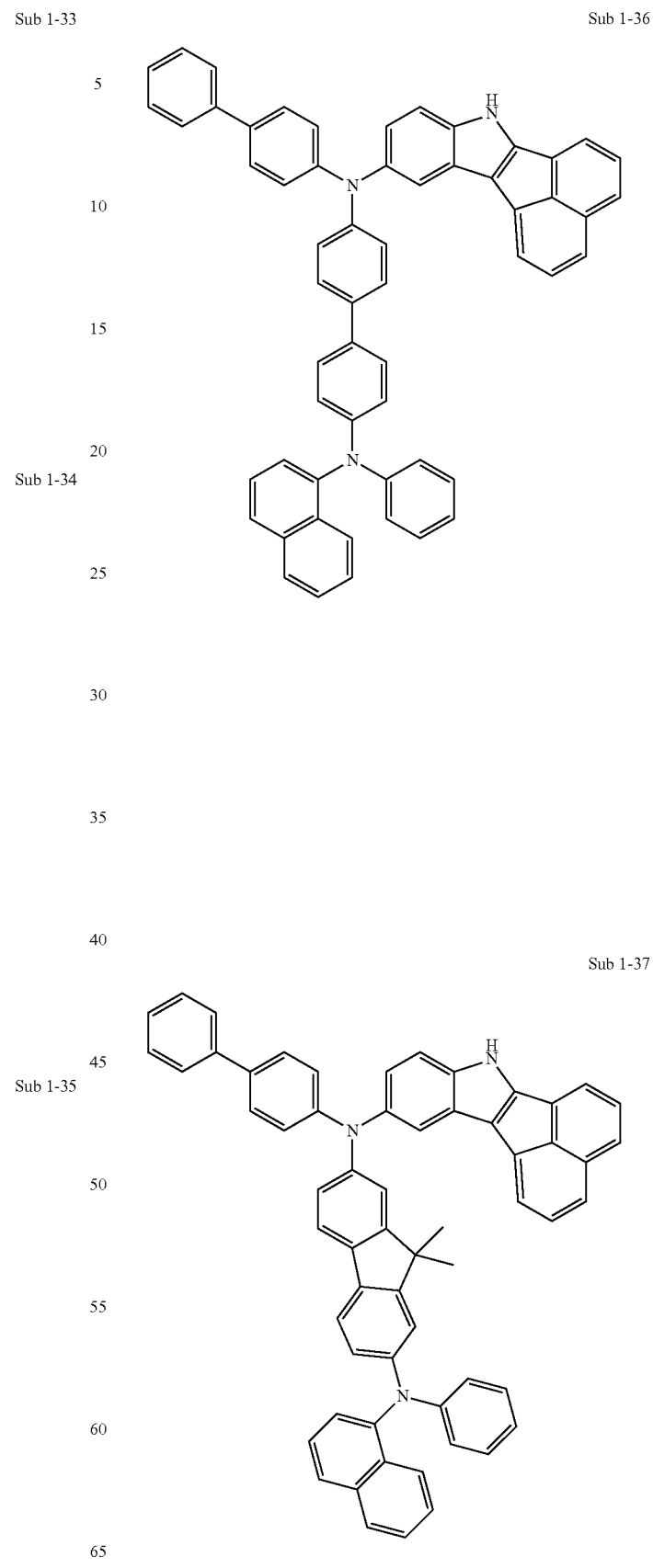
Sub 1-37

Sub 1-38
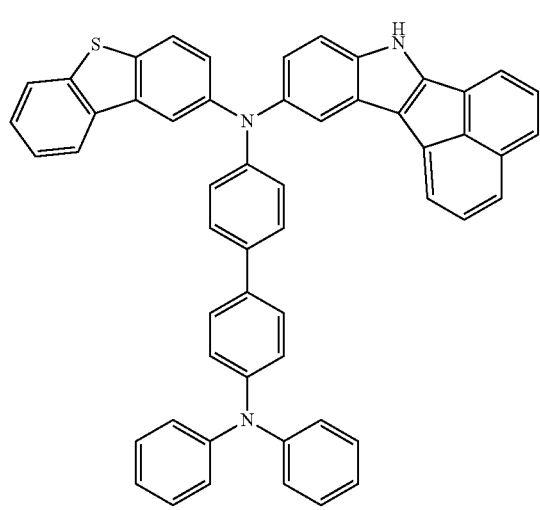
Sub 1-40
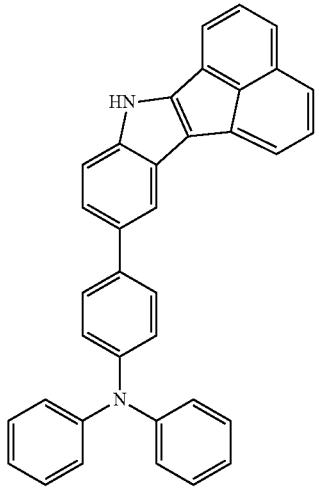
Sub 1-39
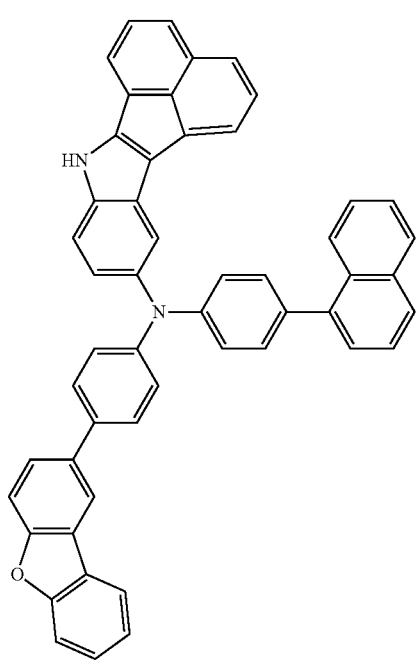
Sub 1-41
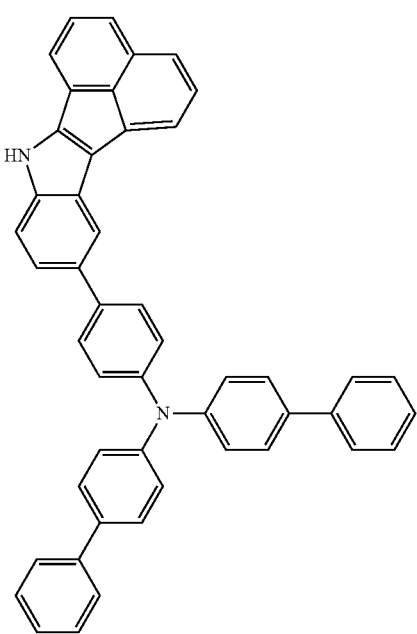

Sub 1-42
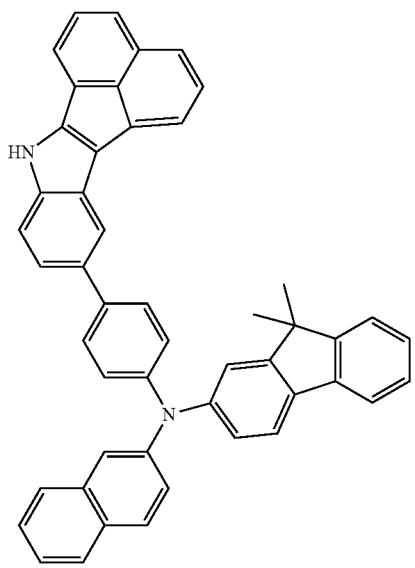
Sub 1-43
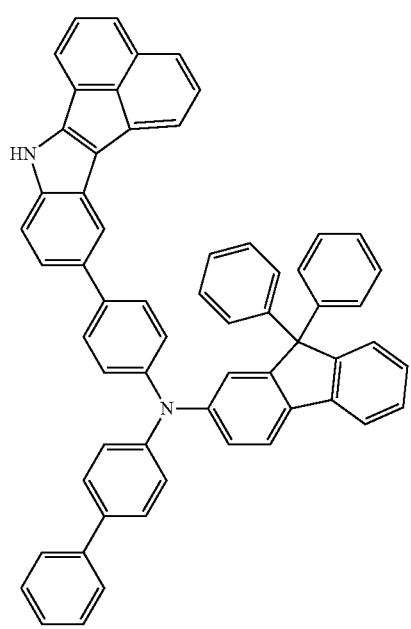
Sub 1-44
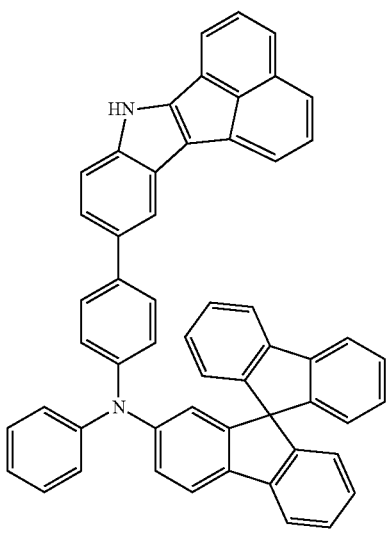
Sub 1-45
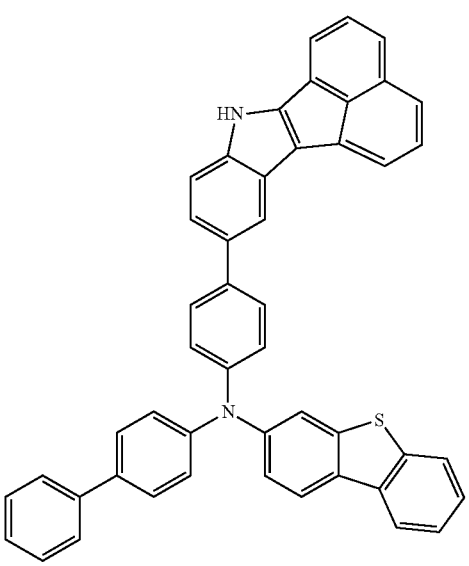
Sub 1-46
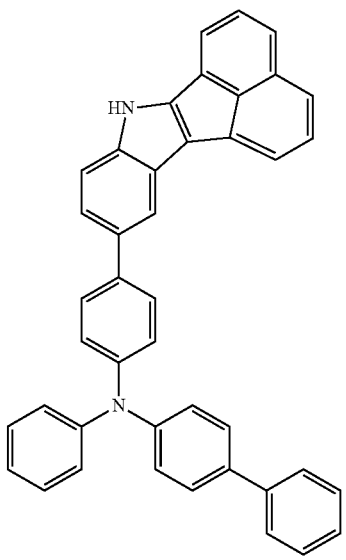

Sub 1-47
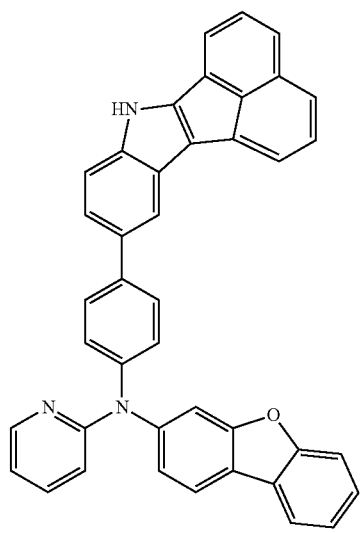
Sub 1-49
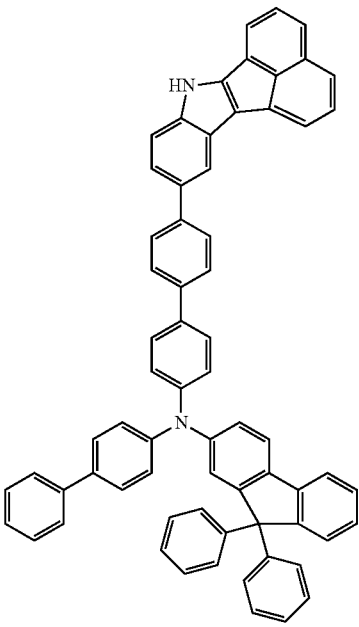
Sub 1-48
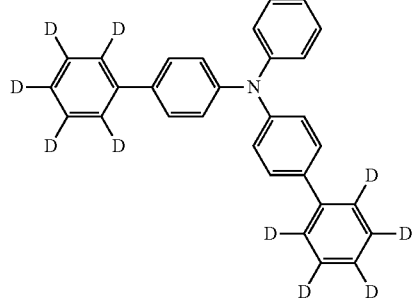
Sub 1-50
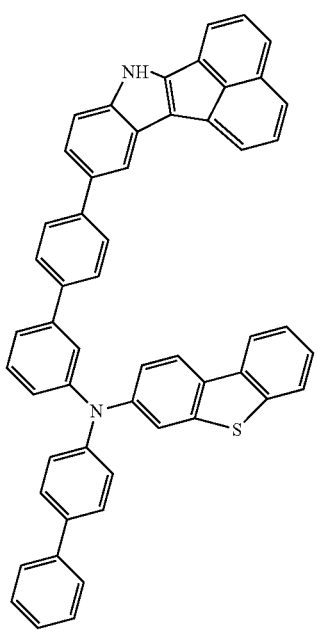

Sub 1-51
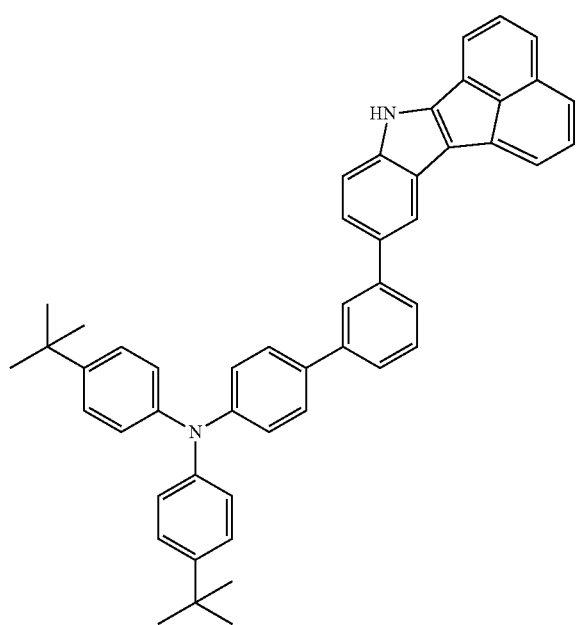
Sub 1-53
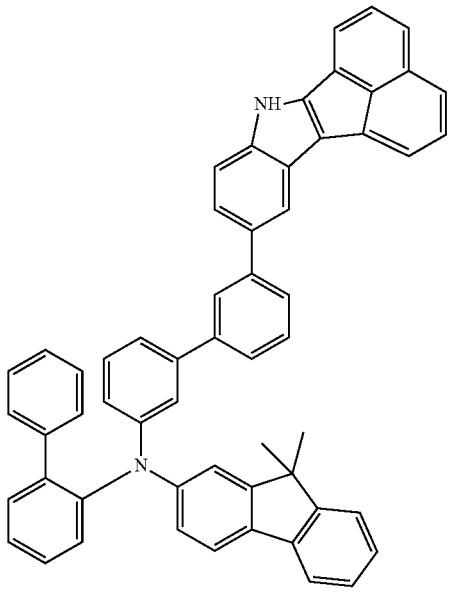
Sub 1-52
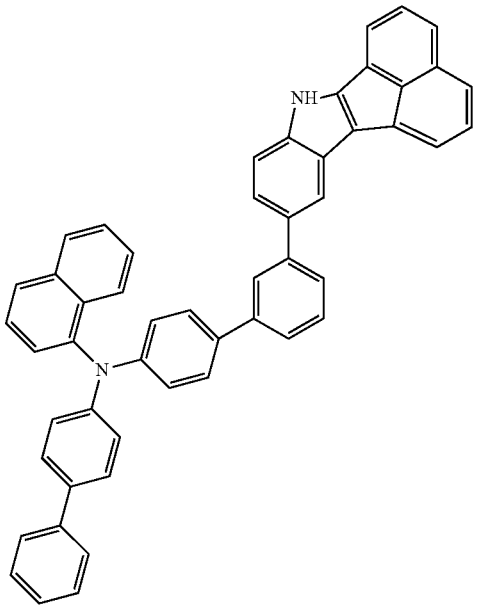
Sub 1-54
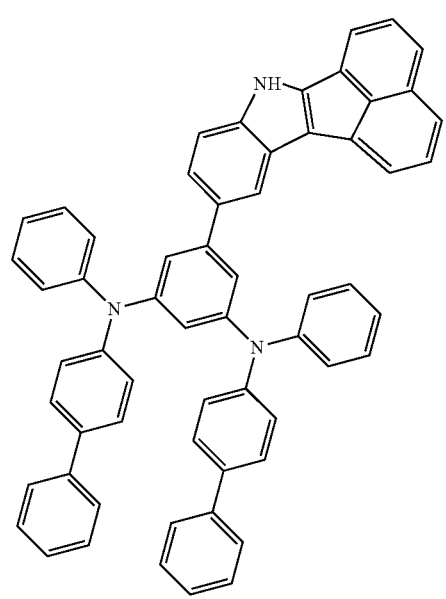

Sub 1-55
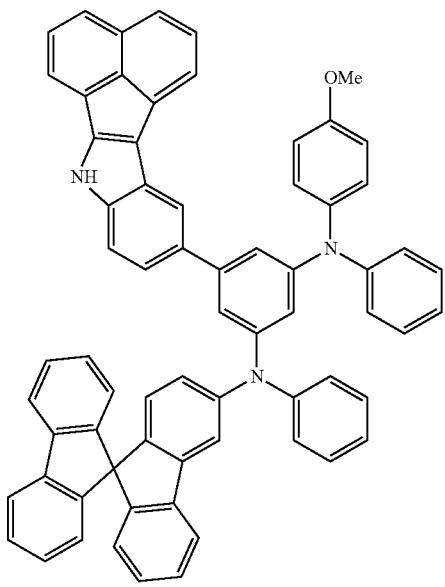
Sub 1-56
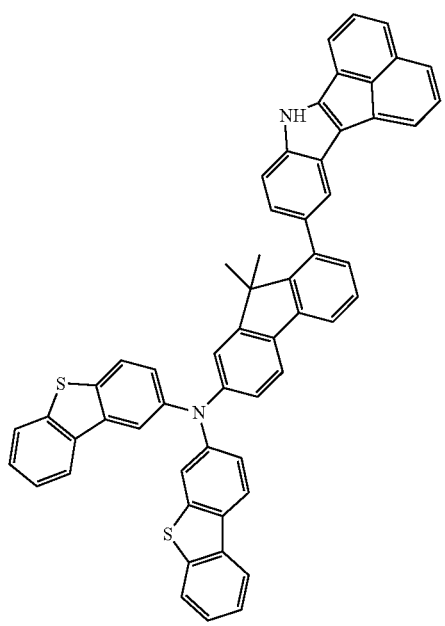
Sub 1-57
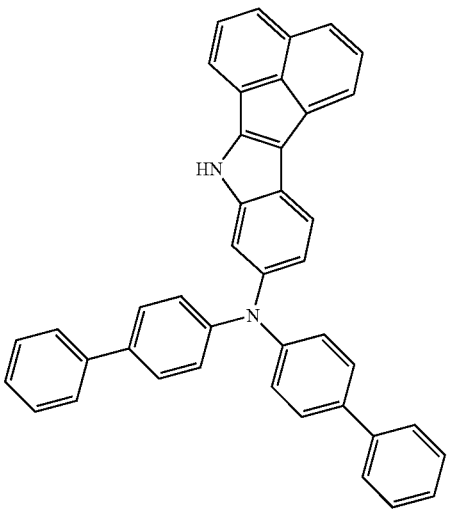
Sub 1-58
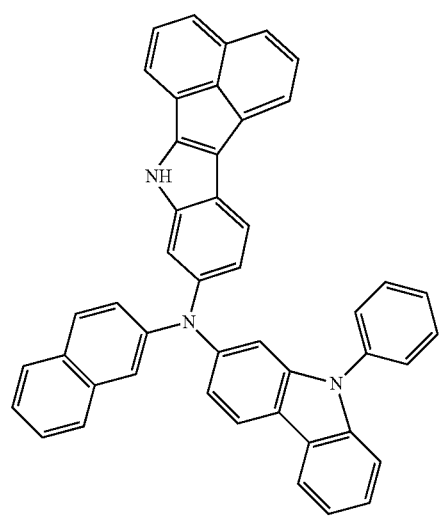
Sub 1-59
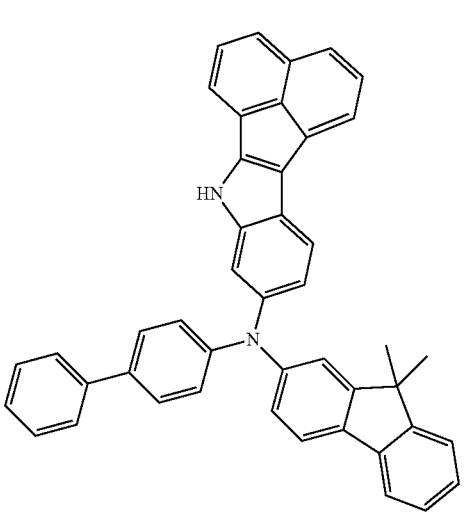

Sub 1-60
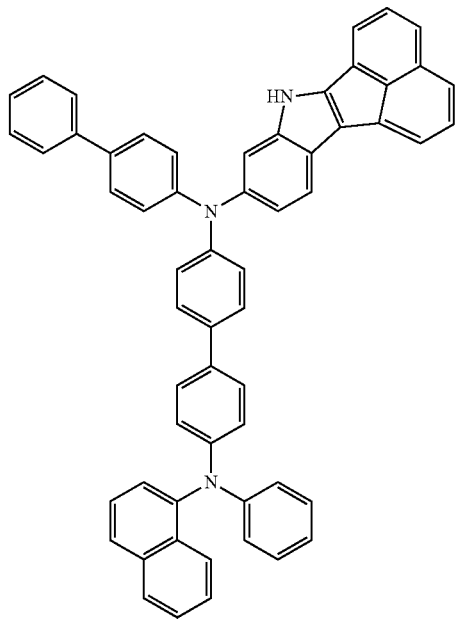
Sub 1-62
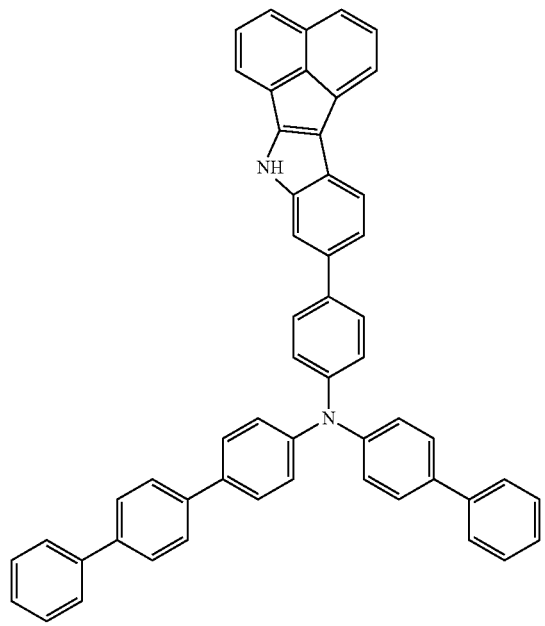
Sub 1-61
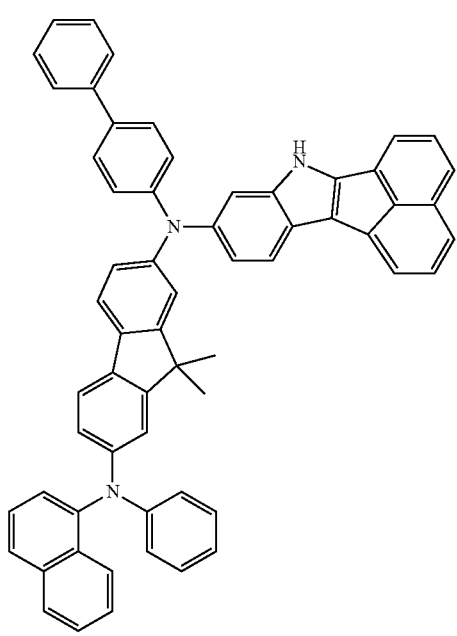
Sub 1-63
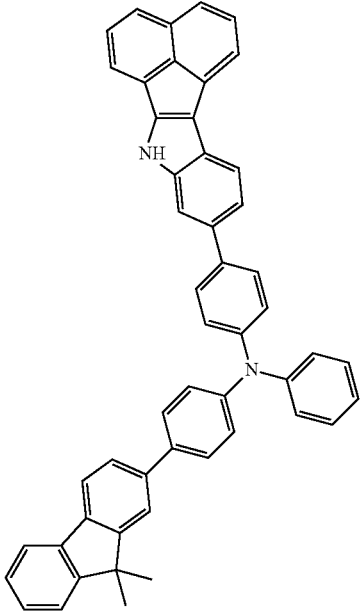

Sub 1-64
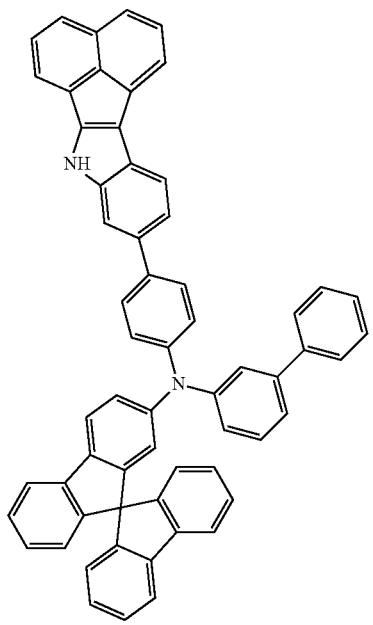
Sub 1-66
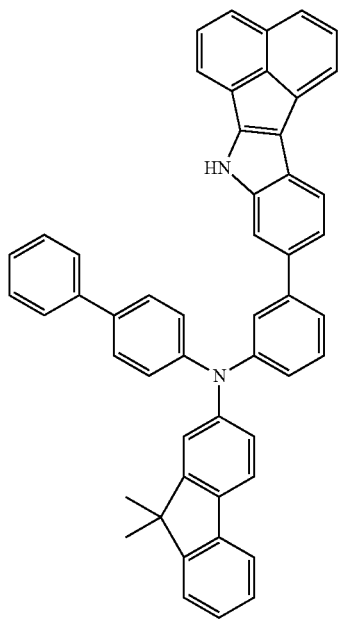
Sub 1-65
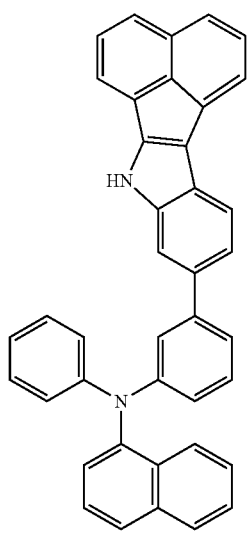
Sub 1-67
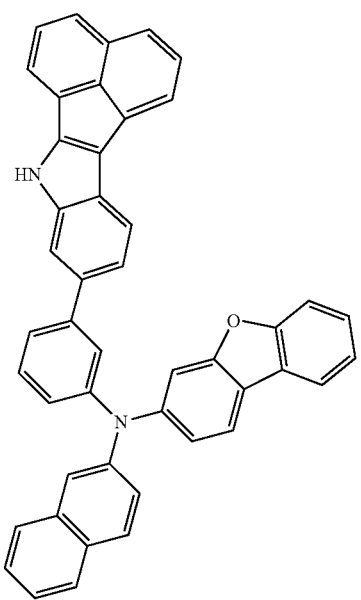

Sub 1-68
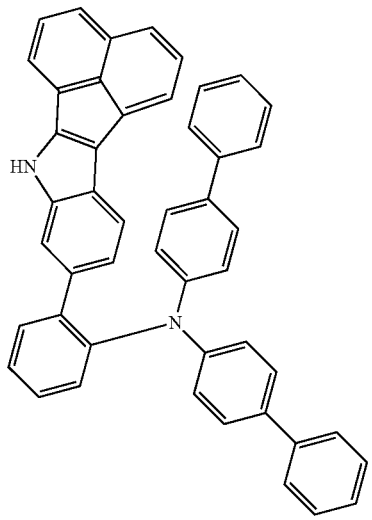
Sub 1-69
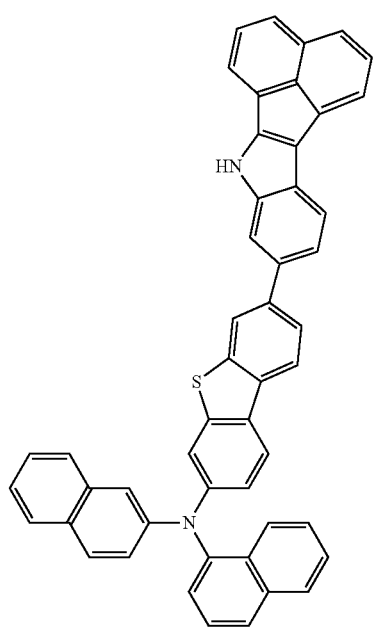
Sub 1-70
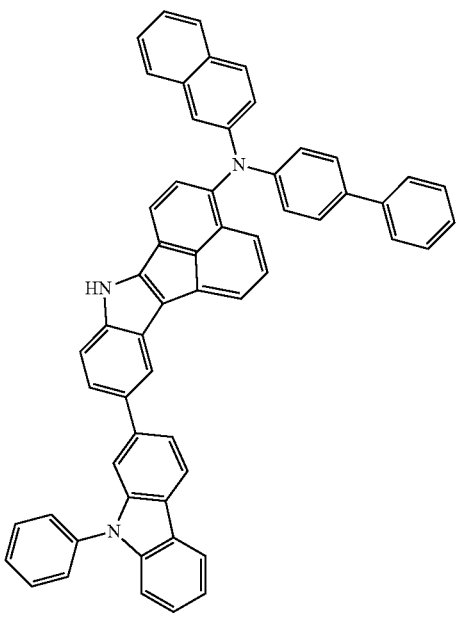
Sub 1-71
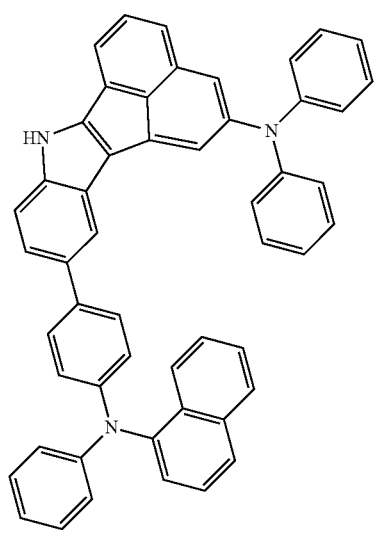
Sub 1-72

-continued
Sub 1-73
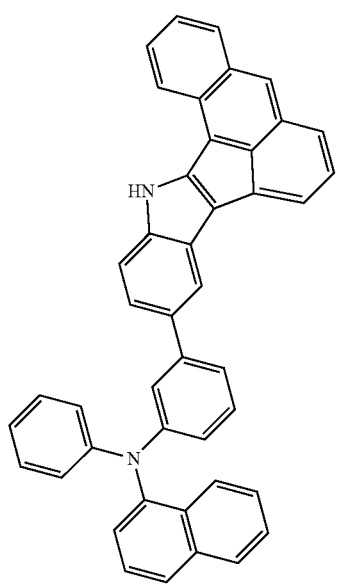
Sub 1-74
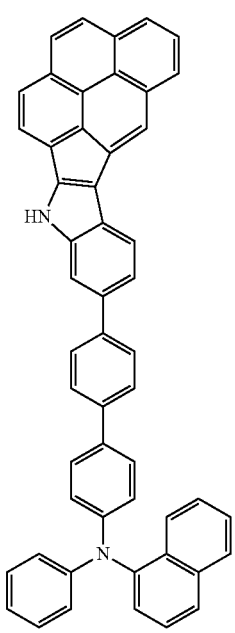
-continued
Sub 1-75
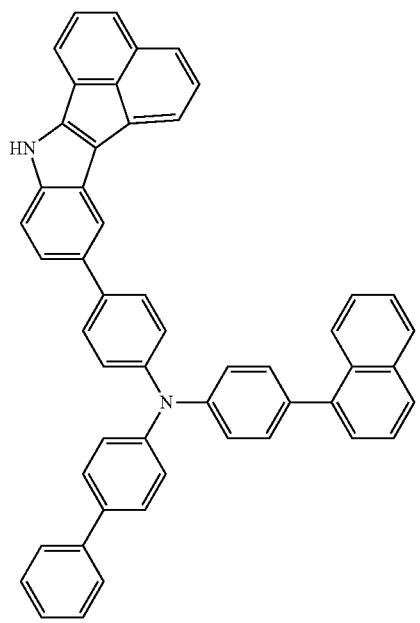
Sub 1-76
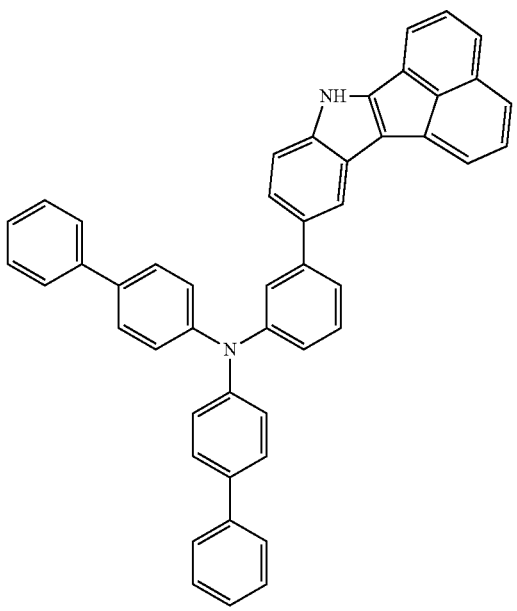

Sub 1-77

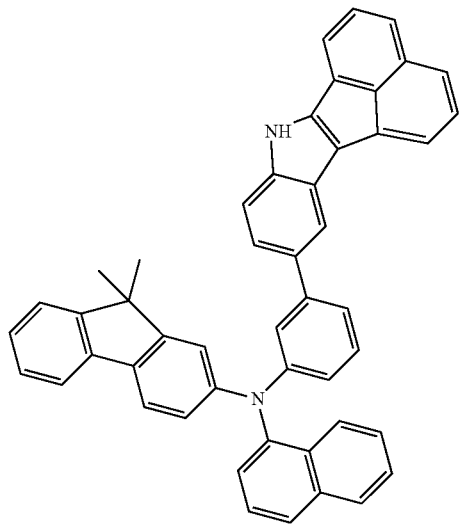

Sub 1-78

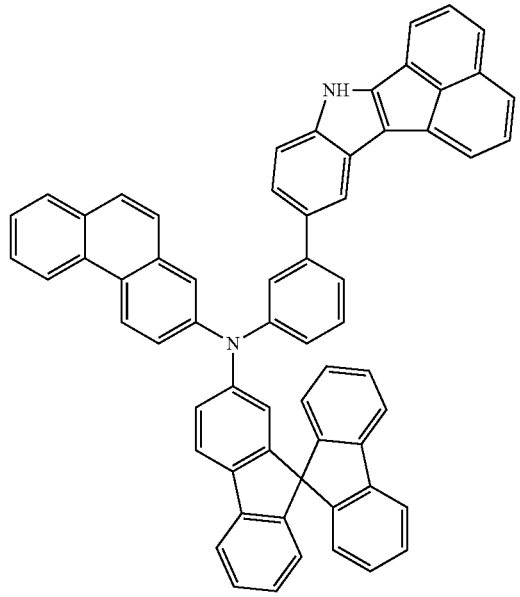

TABLE 1

| Compound | FD-MS | Compound | FD-MS |
|---|---|---|---|
| Sub 1-1 | m/z = 241.09($C_{18}H_{12}N$ = 241.29) | Sub 1-2 | m/z = 482.18($C_{36}H_{22}N_2$ = 482.57) |
| Sub 1-4 | m/z = 482.18($C_{36}H_{22}N_2$ = 482.57) | Sub 1-6 | m/z = 423.11($C_{30}H_{17}NS$ = 423.53) |
| Sub 1-7 | m/z = 407.13($C_{30}H_{17}NO$ = 407.48) | Sub 1-8 | m/z = 407.13($C_{30}H_{17}NO$ = 407.46) |
| Sub 1-9 | m/z = 433.18($C_{33}H_{23}N$ = 433.54) | Sub 1-11 | m/z = 610.22($C_{44}H_{26}N_4$ = 610.70) |
| Sub 1-18 | m/z = 543.20($C_{42}H_{25}N$ = 543.65) | Sub 1-19 | m/z = 406.15($C_{30}H_{18}N_2$ = 406.48) |
| Sub 1-23 | m/z = 664.20($C_{48}H_{28}N_2S$ = 664.83) | Sub 1-26 | m/z = 315.10($C_{24}H_{13}N$ = 315.37) |
| Sub 1-34 | m/z = 600.26($C_{45}H_{32}N_2$ = 600.77) | Sub 1-35 | m/z = 590.18($C_{42}H_{26}N_2S$ = 590.74) |
| Sub 1-37 | m/z = 817.35($C_{61}H_{43}N_3$ = 818.04) | Sub 1-40 | m/z = 484.19($C_{36}H_{24}N_2$ = 484.60) |
| Sub 1-41 | m/z = 636.26($C_{48}H_{32}N_2$ = 636.80) | Sub 1-47 | m/z = 650.27($C_{49}H_{34}N_2$ = 650.83) |
| Sub 1-50 | m/z = 742.24($C_{54}H_{34}N_2S$ = 742.94) | Sub 1-60 | m/z = 777.31($C_{58}H_{39}N_3$ = 777.97) |
| Sub 1-63 | m/z = 676.29($C_{51}H_{36}N_2$ = 676.86) | Sub 1-69 | m/z = 690.21($C_{50}H_{30}N_2S$ = 690.86) |
| Sub 1-70 | m/z = 775.30($C_{58}H_{37}N_3$ = 775.96) | Sub 1-72 | m/z = 701.28($C_{52}H_{35}N_3$ = 701.87) |
| Sub 1-74 | m/z = 684.26($C_{52}H_{32}N_2$ = 684.84) | | |

II. Synthesis of Sub 2

1. Synthesis Example of Sub 2-14

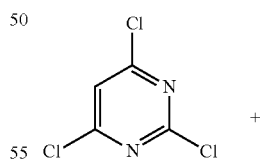

+

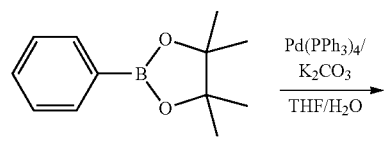

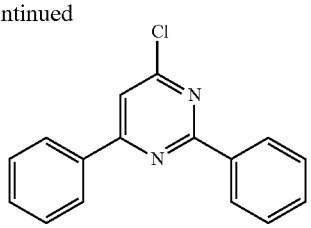

Sub 2-14

After phenylboronic acid pinacol ester (22.3 g, 109 mmol), THF (240 ml), Pd(PPh₃)₄ (3.8 g, 3.27 mmol), K₂CO₃ (45.2 g, 327 mmol) and water (120 ml) were added to 2,4,6-trichloropyrimidine (10 g, 54.5 mmol), the mixture was stirred at 90° C. When reaction was completed, the product was extracted with CH₂Cl₂ and water. Then, the organic layer was dried with MgSO₄ and concentrated. The concentrate was applied to silica gel column and recrystallized to obtain 9.5 g (yield: 65%) of the product.

2. Synthesis Example of Sub 2-20

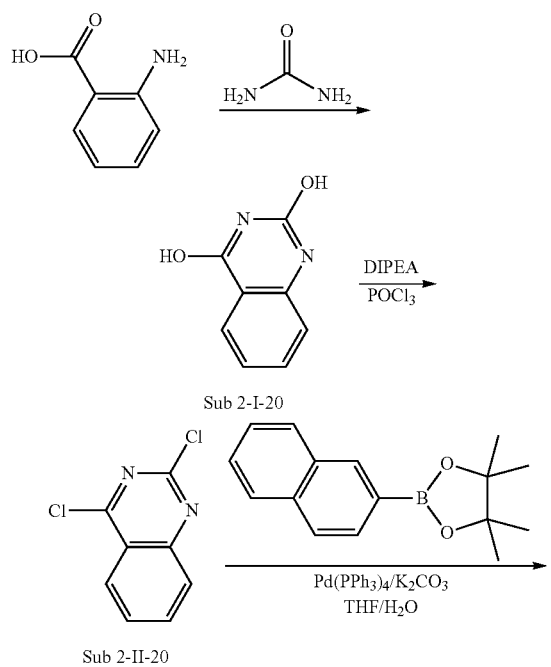

(1) Synthesis Example of Sub 2-I-20

2-aminobenzoic acid (15.22 g, 111 mmol) and urea (46.66 g, 776.9 mmol) were placed in a round bottom flask and the mixture was stirred at 160° C. After confirming the reaction by TLC, the reactant was cooled to 100° C. and water (55 ml) was added. Then, the mixture was stirred for 1 hour. When reaction was completed, the resulting solid was filtered under reduced pressure and washed with water. Then, the resultant was dried to obtain 14.58 g (yield: 81%) of the product.

(2) Synthesis Example of Sub 2-II-20

After Sub 2-I-20 (14.58 g, 89.9 mmol) was dissolved in POCl₃ (60 ml) in a round bottom flask at room temperature, N,N-Diisopropylethylamine (29.05 g, 224.8 mmol) was slowly added. Then, the mixture was stirred at 90° C. When reaction was completed, the product was concentrated and ice water (120 ml) was added thereto. The mixture was stirred at room temperature for 1 hour and the resulting solid was filtered under reduced pressure. Then, the resultant was dried to obtain 15.39 g (yield: 86%) of the product.

(3) Synthesis Example of Sub 2-20

THF (332 ml), 2,4-dichloroquinazoline (15 g, 75.36 mmol), Pd(PPh₃)₄ (1.3 g, 1.13 mmol), K₂CO₃ (15.62 g, 113 mmol) and water (166 ml) were added to 4,4,5,5-tetramethyl-2-(naphthalen-2-yl)-1,3,2-dioxaborolane (19.15 g, 75.36 mmol), and then 10.74 g (yield: 49%) of the product was obtained by the same method as in synthesis of Sub 2-14.

3. Synthesis Example of Sub 2-29

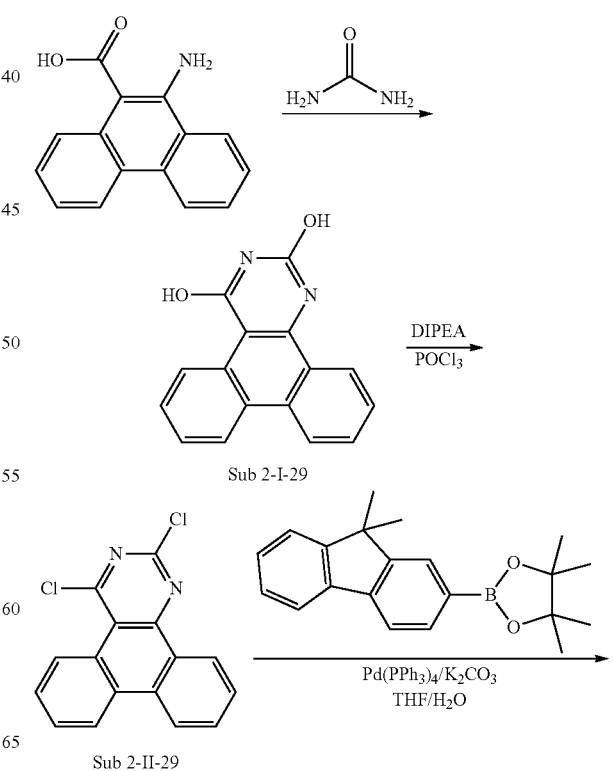

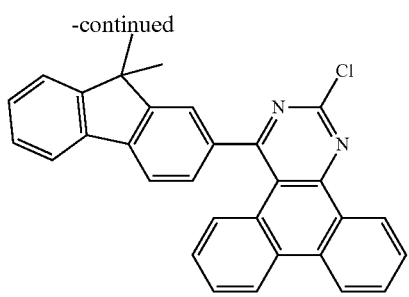

Sub 2-29

(1) Synthesis Example of Sub 2-I-29

Urea (106.71 g, 1776.8 mmol) and water (130 ml) were added to 10-aminophenanthrene-9-carboxylic acid (60.22 g, 253.8 mmol), and then 41.94 g (yield: 63%) of the product was obtained by the same method as in synthesis of Sub 2-I-20.

(2) Synthesis Example of Sub 2-II-29

$POCl_3$ (110 ml), N,N-Diisopropylethylamine (51.67 g, 399.8 mmol) was added to 4 Sub 2-I-29 (41.94 g, 159.9 mmol), and then 40.19 g (yield: 84%) of the product was obtained by the same method as in synthesis of Sub 2-II-20.

(3) Synthesis Example of Sub 2-29

2-(9,9-dimethyl-9H-fluoren-2-yl)-4,4,5,5-tetramethyl-1,3,2-dioxaborolane (13.92 g, 43.46 mmol), $Pd(PPh_3)_4$ (0.75 g, 0.65 mmol), $K_2CO_3$ (9.01 g, 65.18 mmol), THF (191 ml) and (96 ml) were added to Sub 2-II-29 (13.00 g, 43.46 mmol), and then 10.33 g (yield: 52%) of the product was obtained by the same method as in synthesis of Sub 2-14.

4. Synthesis Example of Sub 2-35

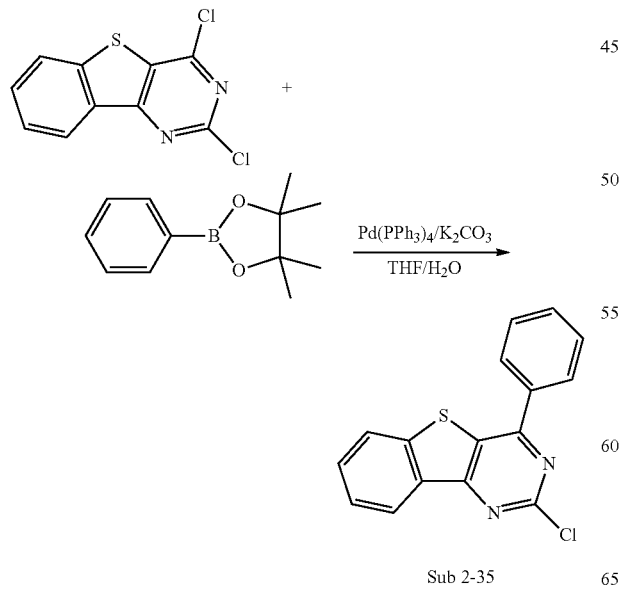

Sub 2-35

THF (293 ml), 2,4-dichlorobenzo[4,5]thieno[3,2-d]pyrimidine (17 g, 66.64 mmol), $Pd(PPh_3)_4$ (1.16 g, 1 mmol), $K_2CO_3$ (13.81 g, 99.95 mmol) and (147 ml) were added to Phenylboronic acid pinacol ester (13.60 g, 66.64 mmol), and then 8.70 g (yield: 44%) of the product was obtained by the same method as in synthesis of Sub 2-14.

The compound belonging to Sub 2 may be, but not limited to, the following compounds, and Table 2 shows FD-MS (Field Desorption-Mass Spectrometry) values of compounds belonging to Sub 2.

Sub 2-1

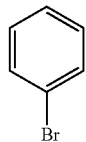

Sub 2-2

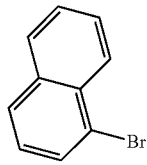

Sub 2-3

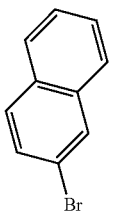

Sub 2-4

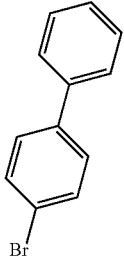

Sub 2-5

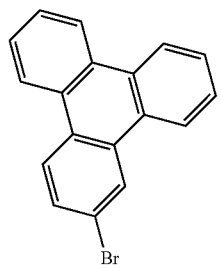

Sub 2-6

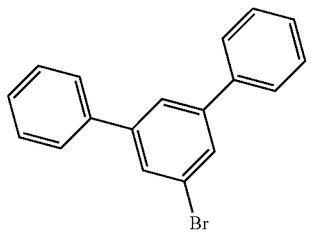

-continued
Sub 2-7
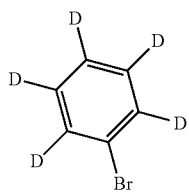
Sub 2-8
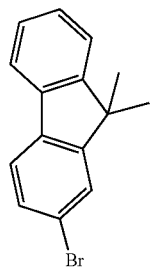
Sub 2-9
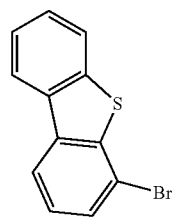
Sub 2-10
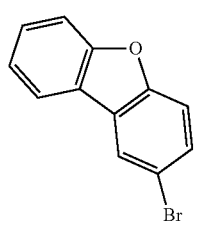
Sub 2-11
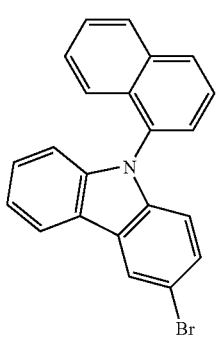
Sub 2-12
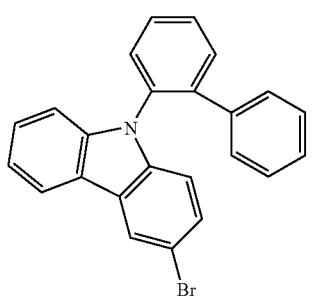
-continued
Sub 2-13
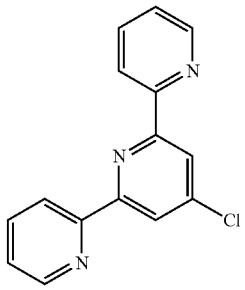
Sub 2-14
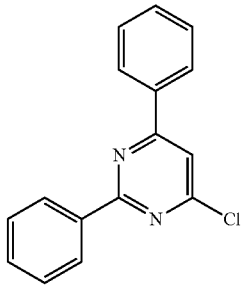
Sub 2-15
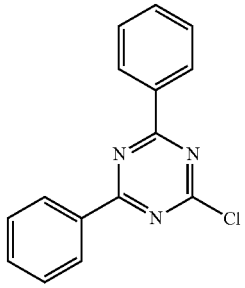
Sub 2-16
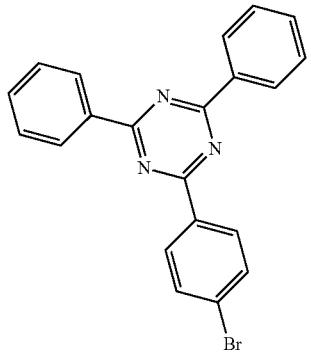
Sub 2-17
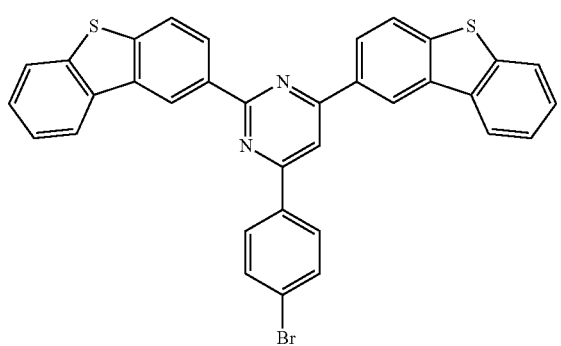

Sub 2-18
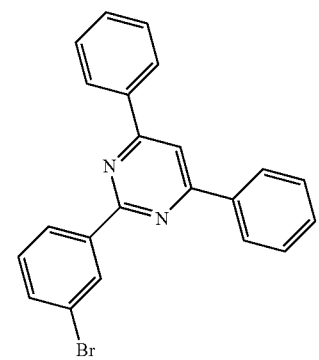
Sub 2-19
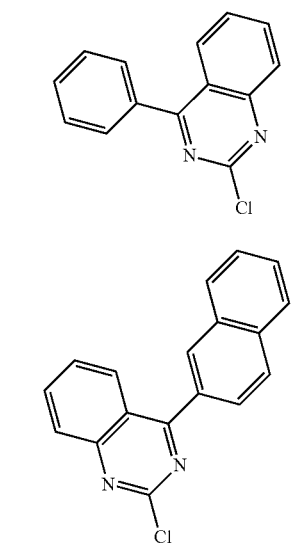
Sub 2-20
Sub 2-21
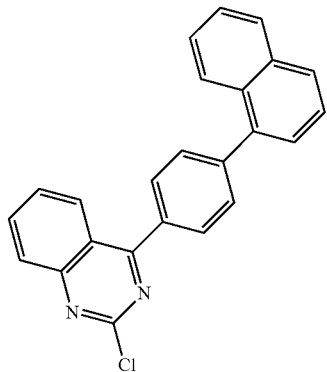
Sub 2-22
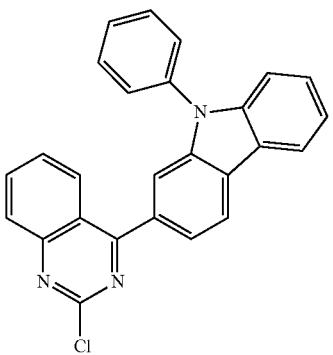
Sub 2-23
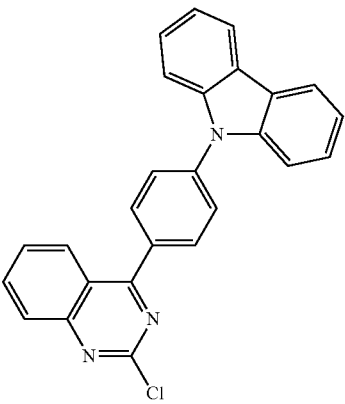
Sub 2-24
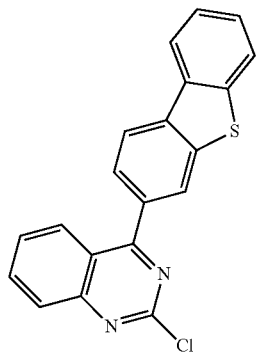
Sub 2-25
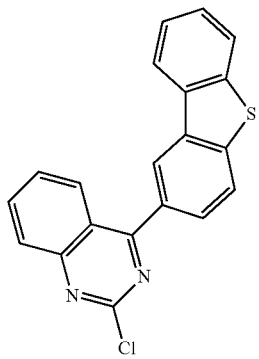
Sub 2-26
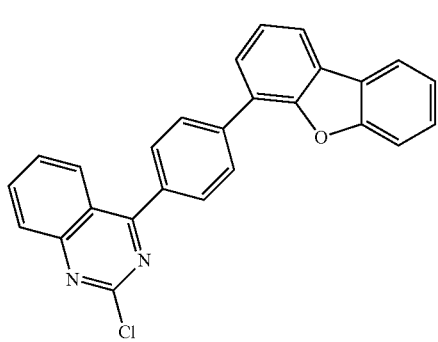

-continued
Sub 2-27
Sub 2-28
Sub 2-29
Sub 2-30
Sub 2-31
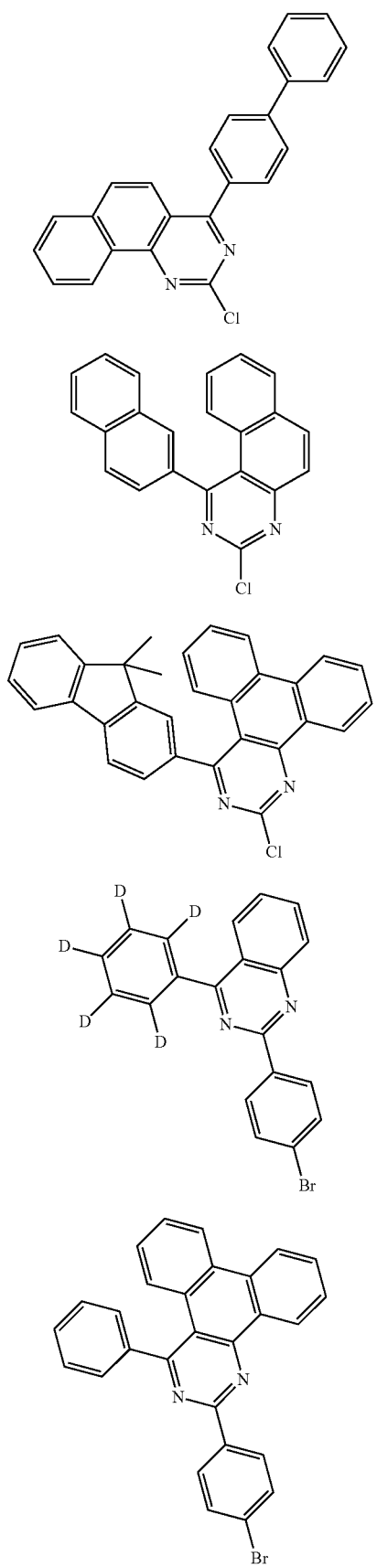
-continued
Sub 2-32
Sub 2-33
Sub 2-34
Sub 2-35
Sub 2-36
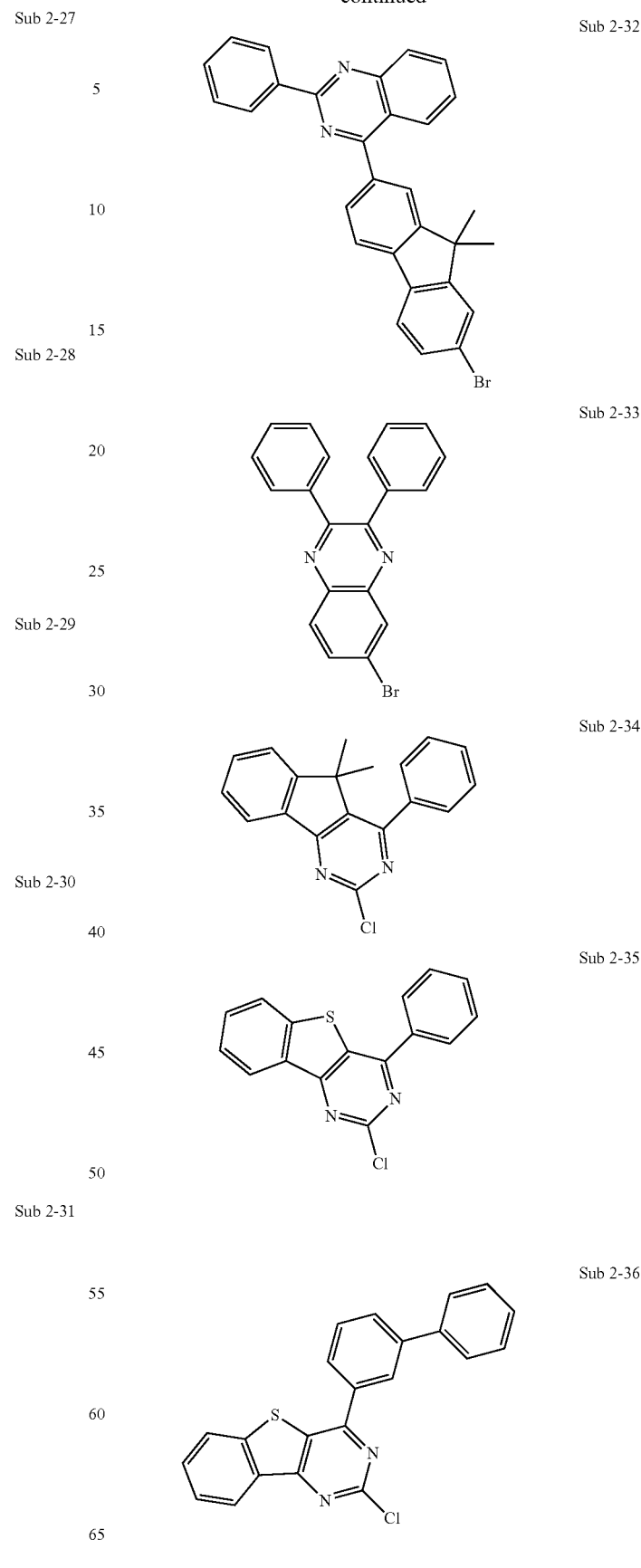

141
-continued
Sub 2-37
Sub 2-38
Sub 2-39
Sub 2-40
Sub 2-41
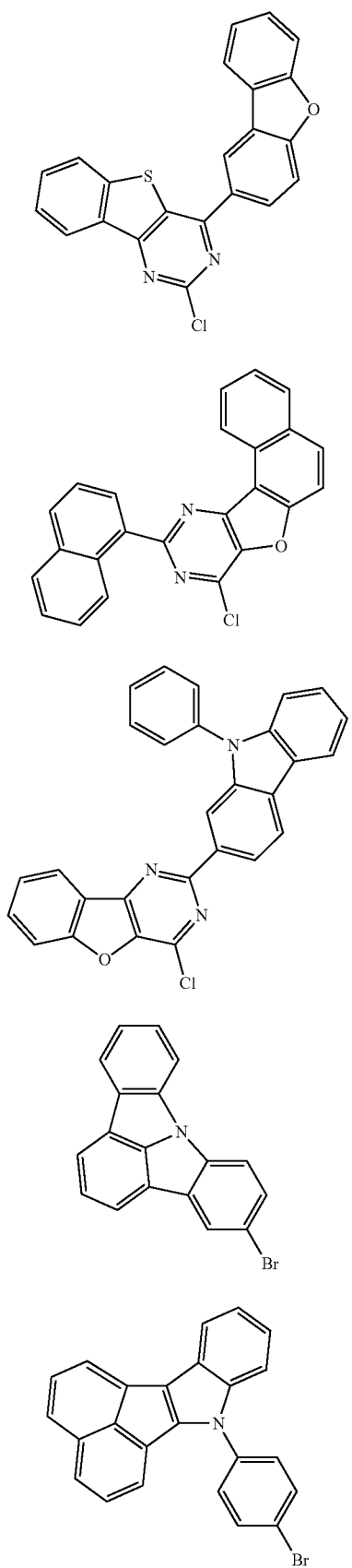
142
-continued
Sub 2-42
Sub 2-43
Sub 2-44
Sub 2-45
Sub 2-46
Sub 2-47
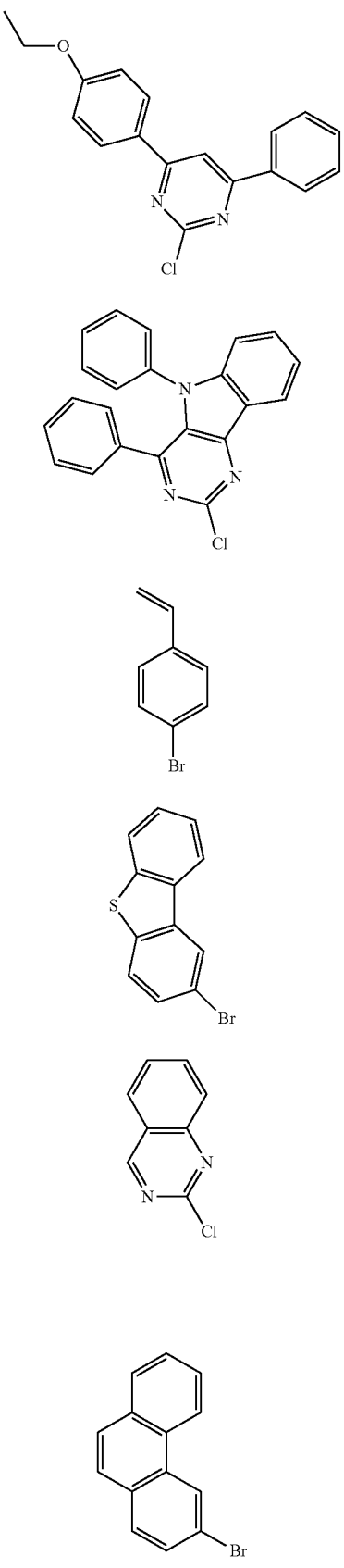

-continued

Sub 2-48

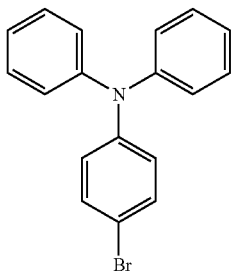

Sub 2-49

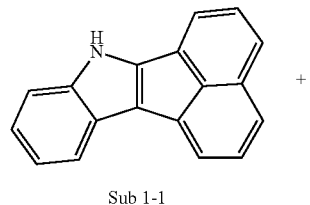

-continued

Sub 2-5

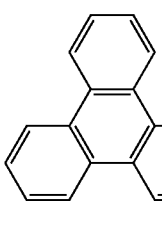

1-3

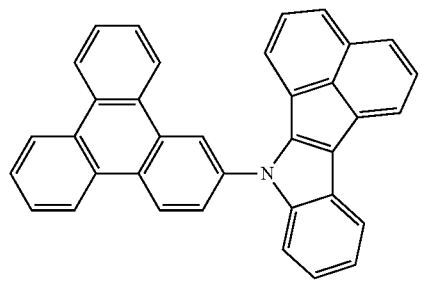

After Sub 1-1 (5.4 g, 22.38 mmol) was dissolved in Toluene (235 ml) in a round bottom flask, Sub 2-5 (6.87 g,

TABLE 2

| Compound | FD-MS | Compound | FD-MS |
|---|---|---|---|
| Sub 2-1 | m/z = 155.96($C_6H_5Br$ = 157.01) | Sub 2-2 | m/z = 205.97($C_{10}H_7Br$ = 207.07) |
| Sub 2-5 | m/z = 306.00($C_{18}H_{11}Br$ = 307.19) | Sub 2-6 | m/z = 308.02($C_{18}H_{13}Br$ = 309.21) |
| Sub 2-8 | m/z = 272.02($C_{15}H_{13}Br$ = 273.17) | Sub 2-10 | m/z = 245.97($C_{12}H_7BrO$ = 247.09) |
| Sub 2-14 | m/z = 266.06($C_{16}H_{11}ClN_2$ = 266.72) | Sub 2-19 | m/z = 240.05($C_{14}H_9ClN_2$ = 240.69) |
| Sub 2-20 | m/z = 290.06($C_{18}H_{11}ClN_2$ = 290.75) | Sub 2-27 | m/z = 366.09($C_{24}H_{15}ClN_2$ = 366.85) |
| Sub 2-29 | m/z = 456.14($C_{31}H_{21}ClN_2$ = 456.96) | Sub 2-32 | m/z = 476.09($C_{29}H_{21}BrN_2$ = 477.41) |
| Sub 2-33 | m/z = 360.03($C_{20}H_{13}BrN_2$ = 361.24) | Sub 2-35 | m/z = 296.02($C_{16}H_9ClN_2S$ = 296.77) |
| Sub 2-36 | m/z = 372.05($C_{22}H_{13}ClN_2S$ = 372.87) | Sub 2-45 | m/z = 261.95($C_{12}H_7BrS$ = 263.15) |
| Sub 2-46 | m/z = 164.01($C_8H_5ClN_2$ = 164.59) | Sub 2-48 | m/z = 323.03($C_{18}H_{14}BrN$ = 324.22) |

III. Synthesis Examples of Final Products

After Sub 1 (1 eq.) was dissolved in toluene in a round bottom flask, Sub 2 (1 eq.), $Pd_2(dba)_3$ (0.03 eq.), $P(t-Bu)_3$ (0.0.6 eq.) and NaOt-Bu (3 eq.) were added and the mixture was stirred at 100° C. When the reaction was completed, the product was extracted with $CH_2Cl_2$ and water. The organic layer was dried with $MgSO_4$ and concentrated. The concentrate was applied to silica gel column and recrystallized to obtain a final product.

1. Synthesis Example of 1-3

22.38 mmol), $Pd_2(dba)_3$ (1.02 g, 1.12 mmol), $P(t-Bu)_3$ (0.45 g, 2.24 mmol) and NaOt-Bu (6.45 g, 67.14 mmol) were added and the mixture was stirred at 100° C. When the reaction was completed, the product was extracted with $CH_2Cl_2$ and water. The organic layer was dried with $MgSO_4$ and concentrated. The concentrate was applied to silica gel column and recrystallized to obtain 7.01 g (yield: 67%) of the product.

2. Synthesis Example of 1-5

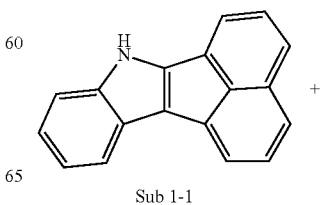

Sub 1-1

-continued

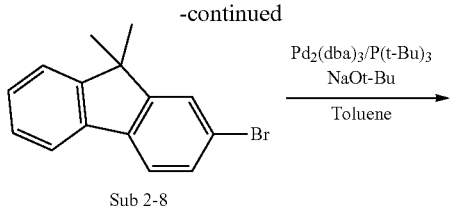

Sub 2-8

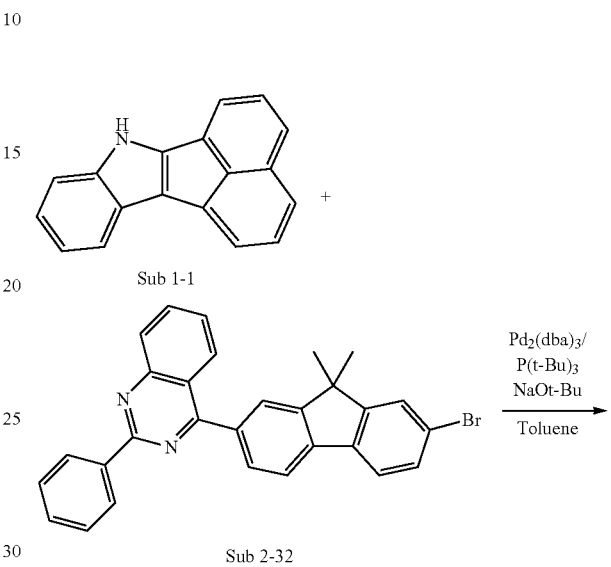

1-5

Toluene (226 ml), Sub 2-8 (5.89 g, 21.55 mmol), Pd₂(dba)₃ (0.99 g, 1.08 mmol), P(t-Bu)₃ (0.44 g, 2.16 mmol) and NaOt-Bu (6.21 g, 64.65 mmol) were added to Sub 1-1 (5.2 g, 21.55 mmol), and then 7.10 g (yield: 76%) of the product was obtained by the same method as in synthesis of the product 1-3.

3. Synthesis Example of 1-19

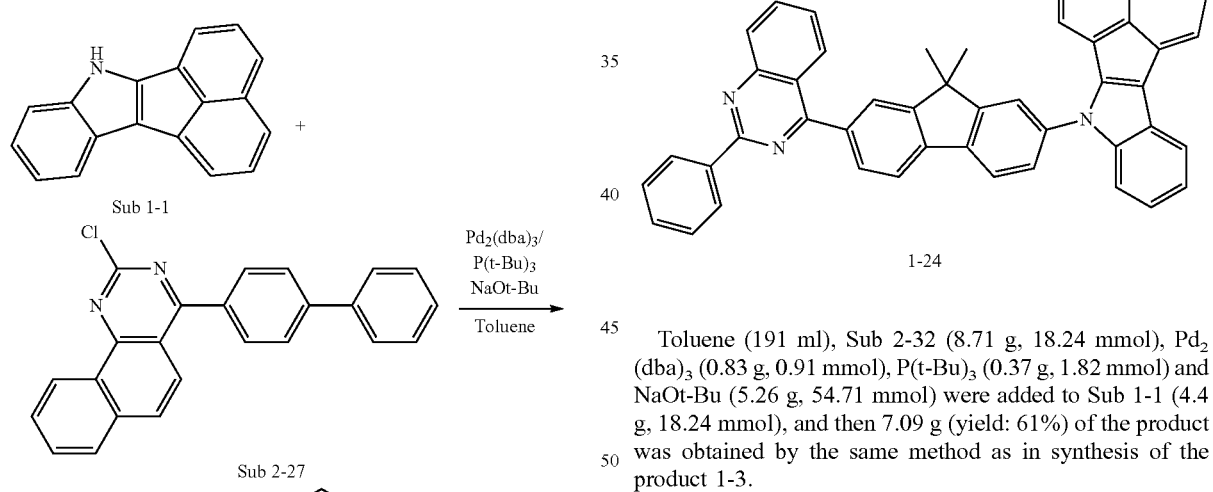

Sub 1-1

Sub 2-27

1-19

Sub 2-27 (6.39 g, 17.41 mmol), Pd₂(dba)₃ (0.8 g, 0.87 mmol), P(t-Bu)₃ (0.35 g, 1.74 mmol) and NaOt-Bu (5.02 g, 52.22 mmol) were added to Sub 1-1 (4.2 g, 17.41 mmol) dissolved in Toluene (183 ml), and then 7.16 g (yield: 72%) of the product was obtained by the same method as in synthesis of the product 1-3.

4. Synthesis Example of 1-24

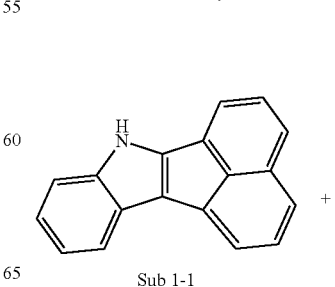

Sub 1-1

+

Sub 2-32

1-24

Toluene (191 ml), Sub 2-32 (8.71 g, 18.24 mmol), Pd₂(dba)₃ (0.83 g, 0.91 mmol), P(t-Bu)₃ (0.37 g, 1.82 mmol) and NaOt-Bu (5.26 g, 54.71 mmol) were added to Sub 1-1 (4.4 g, 18.24 mmol), and then 7.09 g (yield: 61%) of the product was obtained by the same method as in synthesis of the product 1-3.

5. Synthesis Example of 1-25

Sub 1-1

+

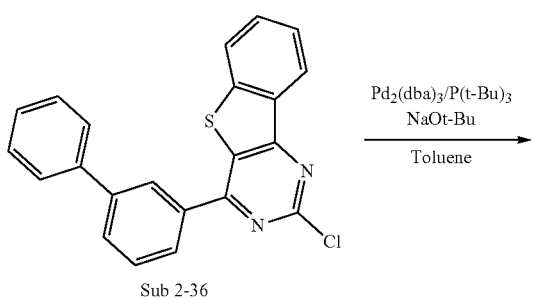

Sub 2-36

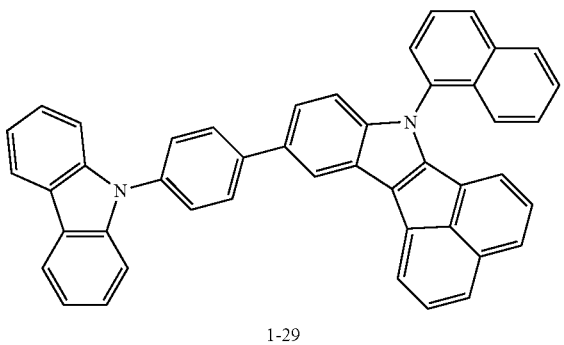

1-29

Toluene (146 ml), Sub 2-2 (2.87 g, 13.88 mmol), Pd$_2$(dba)$_3$ (0.64 g, 0.69 mmol), P(t-Bu)$_3$ (0.28 g, 1.39 mmol) and NaOt-Bu (4 g, 41.65 mmol) were added to Sub 1-2 (6.7 g, 13.88 mmol), and then 7.01 g (yield: 83%) of the product was obtained by the same method as in synthesis of the product 1-3.

7. Synthesis Example of 1-36

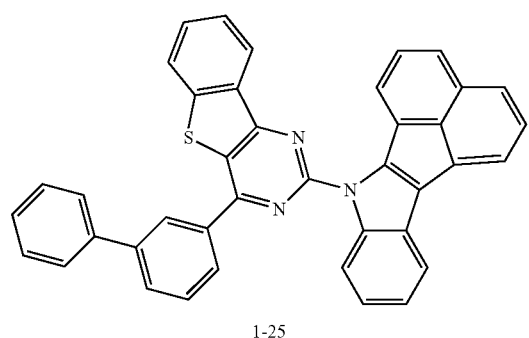

1-25

Toluene (187 ml), Sub 2-36 (6.64 g, 17.82 mmol), Pd$_2$(dba)$_3$ (0.82 g, 0.89 mmol), P(t-Bu)$_3$ (0.36 g, 1.78 mmol) and NaOt-Bu (5.14 g, 53.46 mmol) were added to Sub 1-1 (4.3 g, 17.82 mmol), and then 7 g (yield: 68%) of the product was obtained by the same method as in synthesis of the product 1-3.

6. Synthesis Example of 1-29

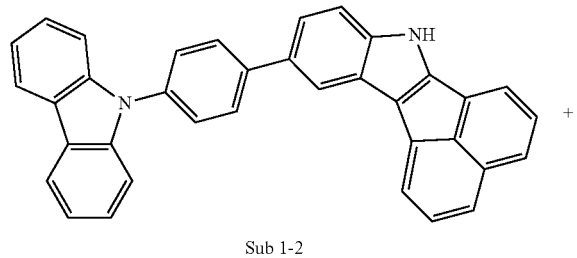

Sub 1-2

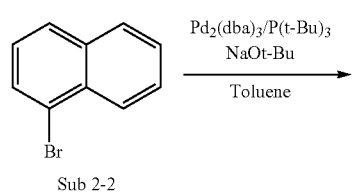

Sub 2-2

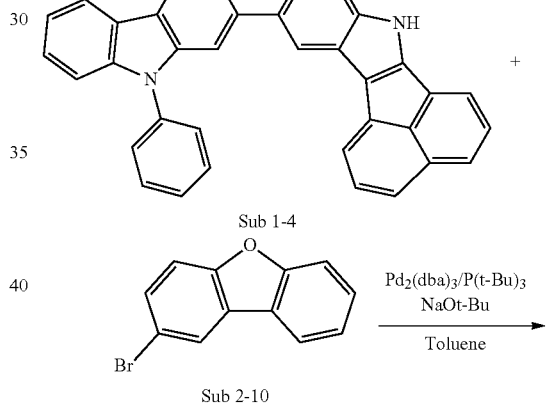

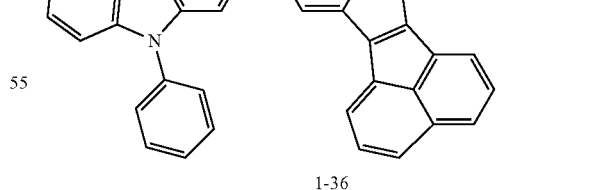

1-36

Toluene (144 ml), Sub 2-10 (3.38 g, 13.68 mmol), Pd$_2$(dba)$_3$ (0.63 g, 0.68 mmol), P(t-Bu)$_3$ (0.28 g, 1.37 mmol) and NaOt-Bu (3.94 g, 41.03 mmol) were added to Sub 1-4 (6.6 g, 13.68 mmol), and then 7.01 g (yield: 79%) of the product was obtained by the same method as in synthesis of the product 1-3.

8. Synthesis Example of 1-42

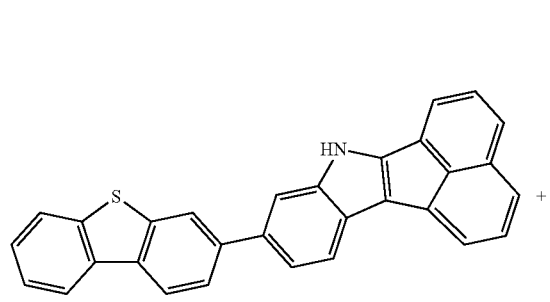

Sub 1-6

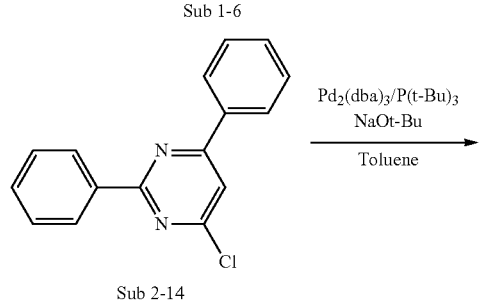

Sub 2-14

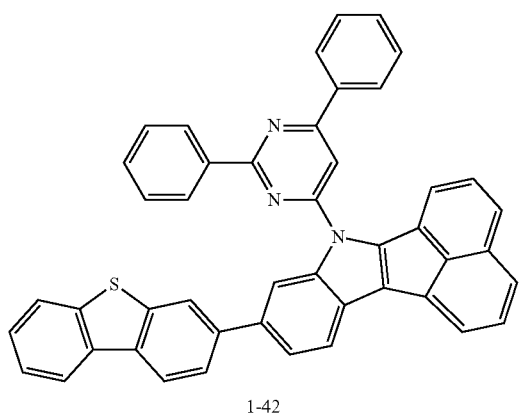

1-42

Toluene (154 ml), Sub 2-14 (3.9 g, 14.64 mmol), Pd₂(dba)₃ (0.67 g, 0.73 mmol), P(t-Bu)₃ (0.3 g, 1.46 mmol) and NaOt-Bu (4.22 g, 43.92 mmol) were added to Sub 1-6 (6.2 g, 14.64 mmol), and then 7.08 g (yield: 74%) of the product was obtained by the same method as in synthesis of the product 1-3.

9. Synthesis Example of 1-53

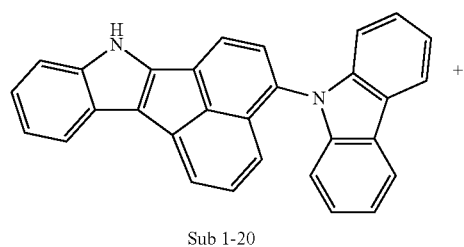

Sub 1-20

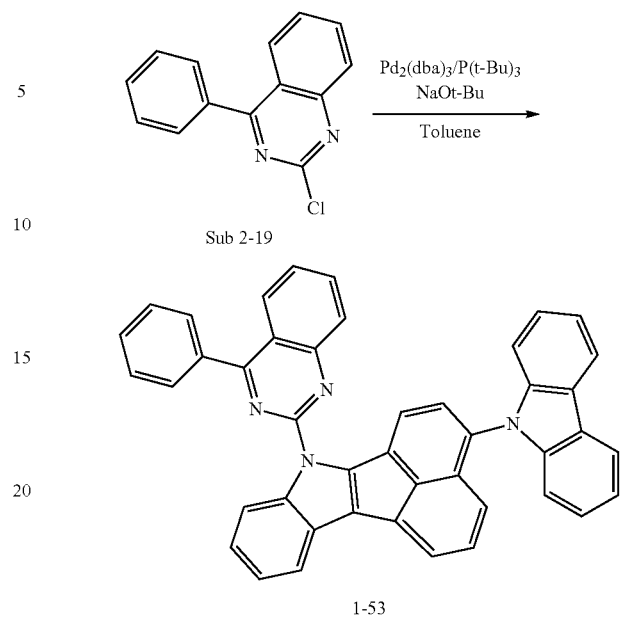

Sub 2-19

1-53

Toluene (157 ml), Sub 2-19 (3.61 g, 15.01 mmol), Pd₂(dba)₃ (0.69 g, 0.75 mmol), P(t-Bu)₃ (0.3 g, 1.5 mmol) and NaOt-Bu (4.33 g, 45.02 mmol) were added to Sub 1-20 (6.1 g, 15.01 mmol), and then 7.06 g (yield: 77%) of the product was obtained by the same method as in synthesis of the product 1-3.

10. Synthesis Example of 1-60

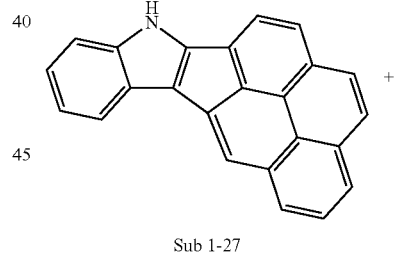

Sub 1-27

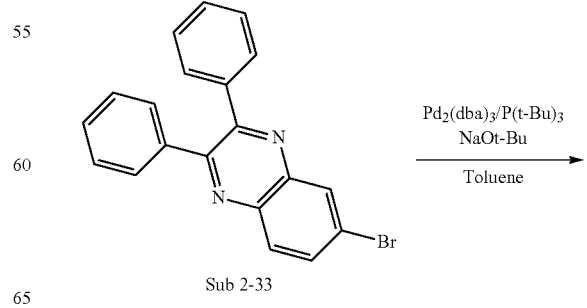

Sub 2-33

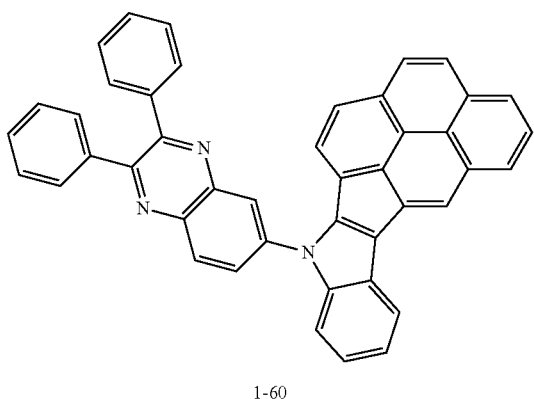

1-60

Toluene (201 ml), Sub 2-33 (4.62 g, 19.19 mmol), Pd$_2$(dba)$_3$ (0.88 g, 0.96 mmol), P(t-Bu)$_3$ (0.39 g, 1.92 mmol) and NaOt-Bu (5.53 g, 57.57 mmol) were added to Sub 1-27 (6.1 g, 15.01 mmol), and then 7.03 g (yield: 60%) of the product was obtained by the same method as in synthesis of the product 1-3.

11. Synthesis Example of 1-70

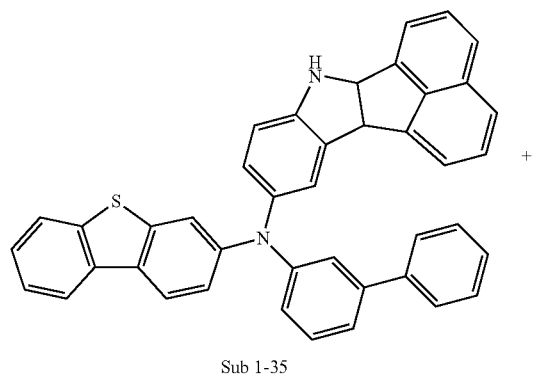

Sub 1-35

+

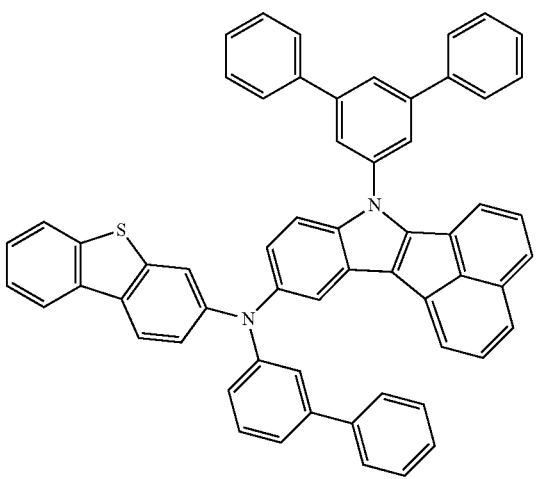

1-70

Toluene (115 ml), Sub 2-6 (3.4 g, 1 mmol), Pd$_2$(dba)$_3$ (0.3 g, 0.33 mmol), P(t-Bu)$_3$ (0.18 g, 0.88 mmol) and NaOt-Bu (3.17 g, 32.99 mmol) were added to Sub 1-35 (6.50 g, 11 mmol), and then 6.39 g (yield: 71%) of the product was obtained by the same method as in synthesis of the product 1-3.

12. Synthesis Example of 1-76

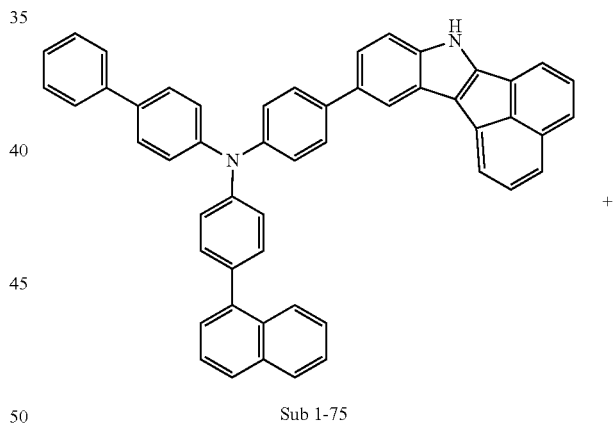

Sub 1-75

+

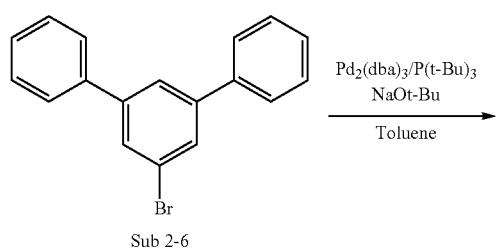

Sub 2-6

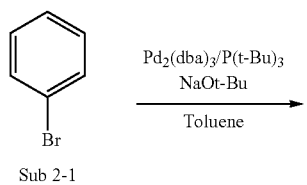

Sub 2-1

153
-continued

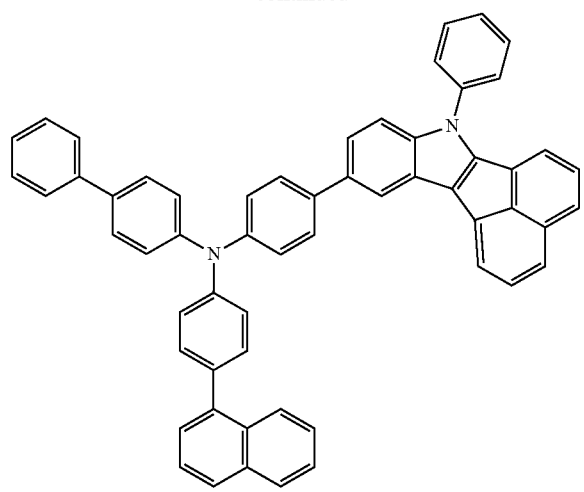

1-76

Toluene (107 ml), Sub 2-1 (1.6 g, 10.19 mmol), Pd₂(dba)₃ (0.28 g, 0.31 mmol), P(t-Bu)₃ (0.16 g, 0.82 mmol) and NaOt-Bu (2.94 g, 30.57 mmol) were added to Sub 1-75 (7 g, 10.19 mmol), and then 6.45 g (yield: 83%) of the product was obtained by the same method as in synthesis of the product 1-3.

13. Synthesis Example of 1-85

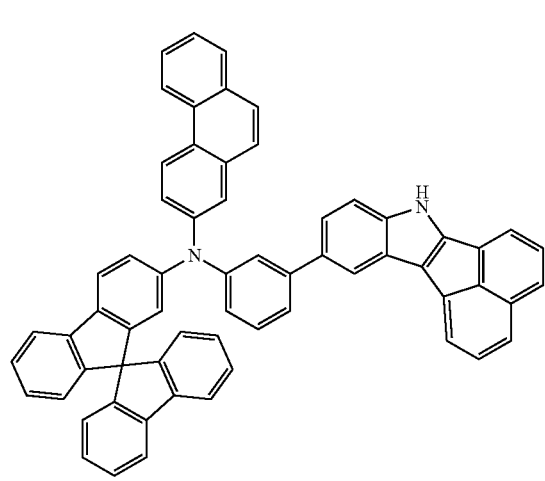

Sub 1-78

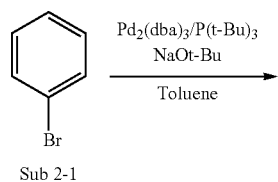

Sub 2-1

154
-continued

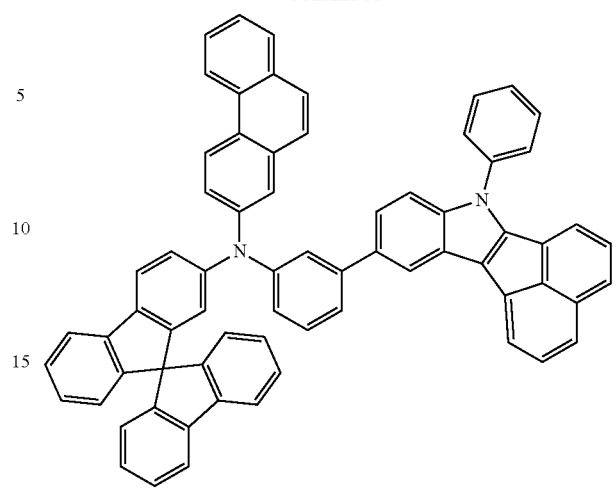

1-85

Toluene (94 ml), Sub 2-1 (1.4 g, 8.92 mmol), Pd₂(dba)₃ (0.24 g, 0.27 mmol), P(t-Bu)₃ (0.14 g, 0.71 mmol) and NaOt-Bu (2.57 g, 26.75 mmol) were added to Sub 1-78 (7.34 g, 8.92 mmol), and then 6.25 g (yield: 78%) of the product was obtained by the same method as in synthesis of the product 1-3.

14. Synthesis Example of 1-98

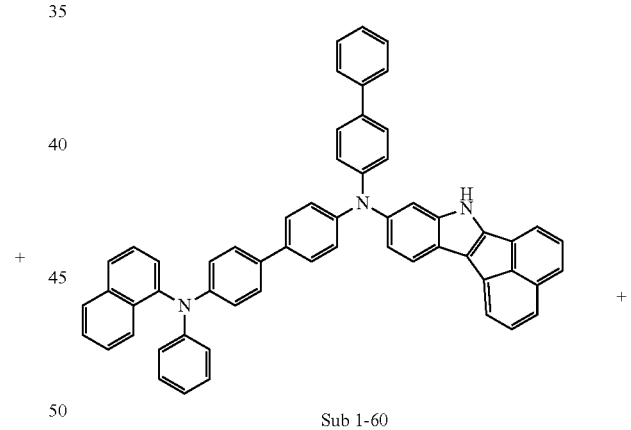

Sub 1-60

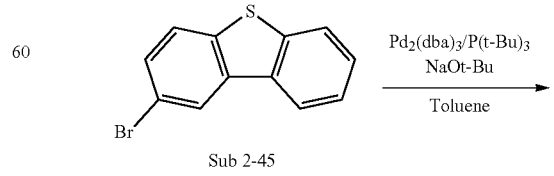

Sub 2-45

-continued

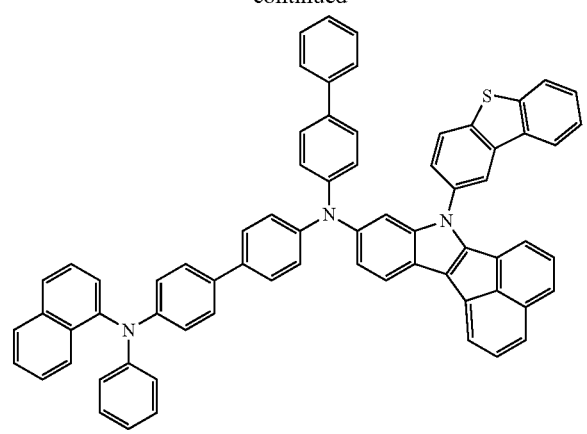

1-98

Toluene (100 ml), Sub 2-45 (2.5 g, 9.5 mmol), Pd₂(dba)₃ (0.26 g, 0.29 mmol), P(t-Bu)₃ (0.15 g, 0.76 mmol) and NaOt-Bu (2.74 g, 28.50 mmol) were added to Sub 1-60 (7.39 g, 9.5 mmol), and then 6.66 g (yield: 78%) of the product was obtained by the same method as in synthesis of the product 1-3.

15. Synthesis Example of 1-101

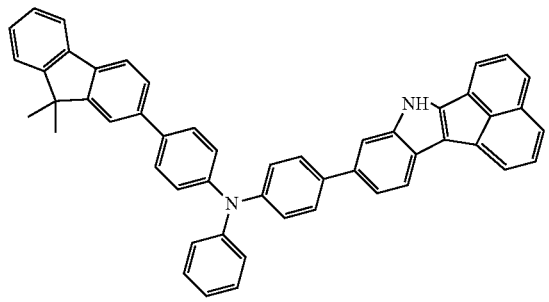

Sub 1-63

+

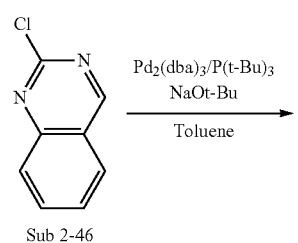

Sub 2-46

-continued

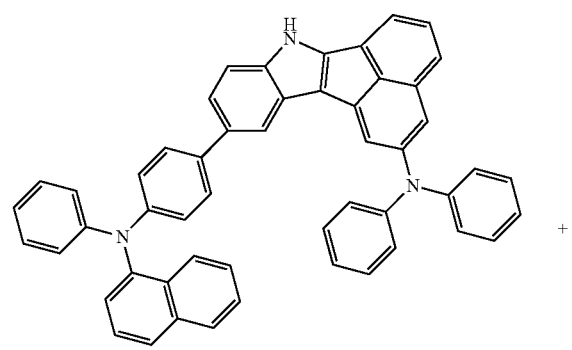

1-101

Toluene (121 ml), Sub 2-46 (1.9 g, 11.54 mmol), Pd₂(dba)₃ (0.32 g, 0.35 mmol), P(t-Bu)₃ (0.19 g, 0.92 mmol) and NaOt-Bu (3.33 g, 34.63 mmol) were added to Sub 1-63 (7.81 g, 11.54 mmol), and then 6.41 g (yield: 69%) of the product was obtained by the same method as in synthesis of the product 1-3.

16. Synthesis Example of 1-110

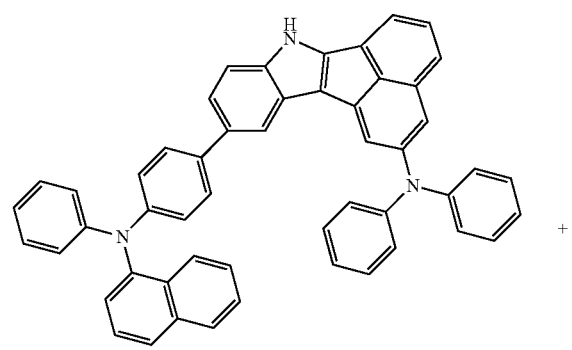

Sub 1-72

+

17. Synthesis Example of 1-112

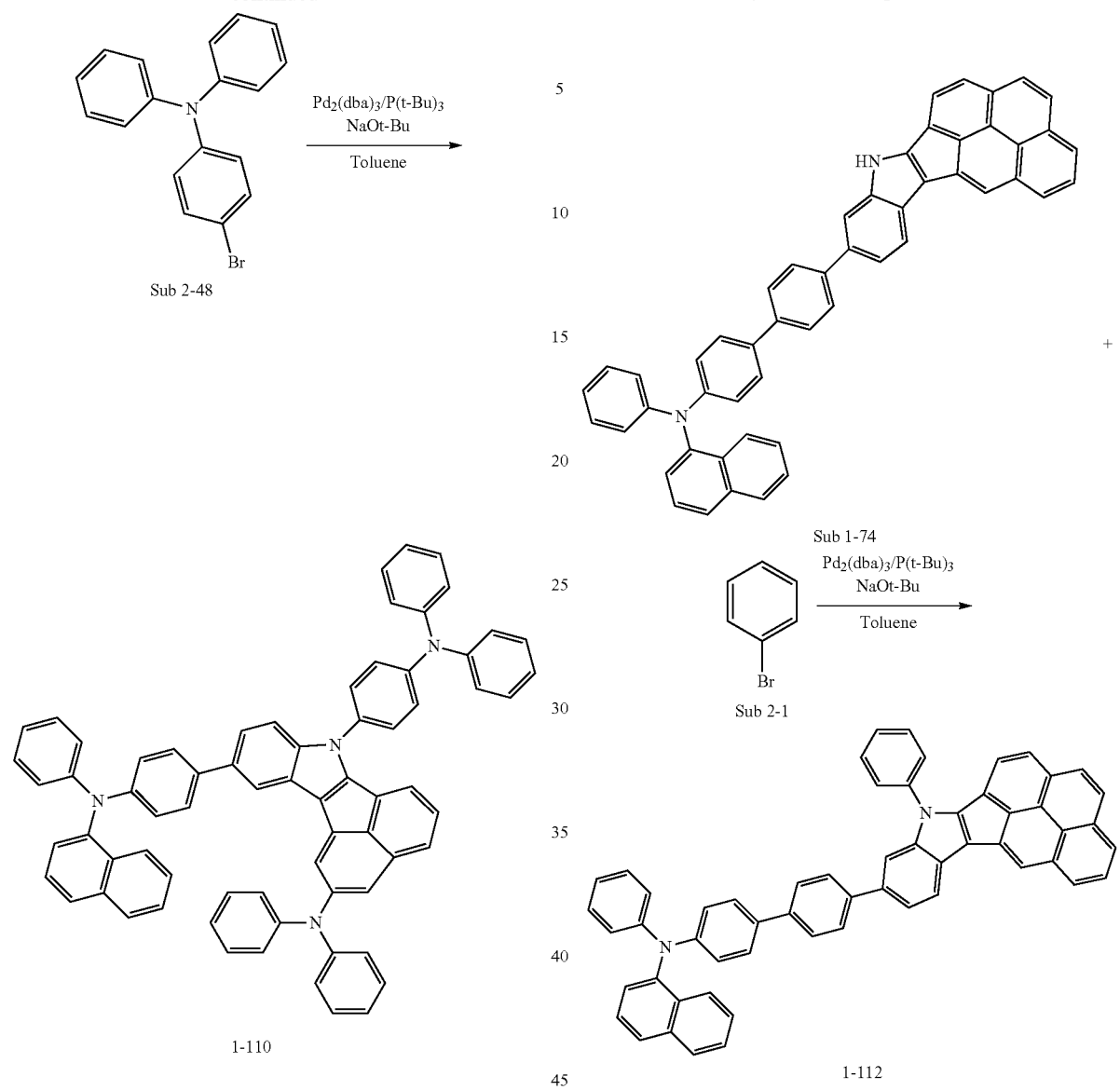

Toluene (104 ml), Sub 2-48 (3.2 g, 9.87 mmol), Pd$_2$(dba)$_3$ (0.27 g, 0.3 mmol), P(t-Bu)$_3$ (0.16 g, 0.79 mmol) and NaOt-Bu (2.85 g, 29.61 mmol) were added to Sub 1-72 (6.93 g, 9.87 mmol), and then 6.81 g (yield: 73%) of the product was obtained by the same method as in synthesis of the product 1-3.

Toluene (134 ml), Sub 2-1 (2 g, 12.74 mmol), Pd$_2$(dba)$_3$ (0.35 g, 0.38 mmol), P(t-Bu)$_3$ (0.21 g, 1.02 mmol) and NaOt-Bu (3.67 g, 38.21 mmol) were added to Sub 1-74 (8.72 g, 12.74 mmol), and then 7.95 g (yield: 82%) of the product was obtained by the same method as in synthesis of the product 1-3.

TABLE 3

| Compound | FD-MS | Compound | FD-MS |
|---|---|---|---|
| 1-3 | m/z = 467.17(C$_{36}$H$_{21}$N = 467.56) | 1-5 | m/z = 433.18(C$_{33}$H$_{23}$N = 433.54) |
| 1-6 | m/z = 482.18(C$_{36}$H$_{22}$N$_2$ = 482.59) | 1-7 | m/z = 423.11(C$_{30}$H$_{17}$NS = 423.53) |
| 1-8 | m/z = 407.13(C$_{30}$H$_{17}$NO = 407.47) | 1-10 | m/z = 472.17(C$_{33}$H$_{20}$N$_4$ = 472.55) |
| 1-12 | m/z = 547.20(C$_{40}$H$_{25}$N$_3$ = 547.66) | 1-13 | m/z = 445.16(C$_{32}$H$_{19}$N$_3$ = 445.53) |
| 1-14 | m/z = 571.20(C$_{43}$H$_{25}$N$_3$ = 571.68) | 1-15 | m/z = 610.22(C$_{44}$H$_{26}$N$_4$ = 610.72) |
| 1-17 | m/z = 551.15(C$_{38}$H$_1$N$_3$S = 551.67) | 1-18 | m/z = 611.20(C$_{44}$H$_{25}$N$_3$O = 611.70) |
| 1-19 | m/z = 571.20(C$_{42}$H$_{25}$N$_3$ = 571.67) | 1-20 | m/z = 545.19(C$_{40}$H$_{23}$N$_3$ = 545.65) |
| 1-21 | m/z = 661.25(C$_{49}$H$_{31}$N$_3$ = 661.81) | 1-22 | m/z = 526.22(C$_{38}$H$_{18}$D$_5$N$_3$ = 526.65) |
| 1-23 | m/z = 621.22(C$_{46}$H$_{27}$N$_3$ = 621.74) | 1-24 | m/z = 637.25(C$_{47}$H$_{31}$N$_3$ = 637.77) |
| 1-25 | m/z = 577.16(C$_{40}$H$_{23}$N$_3$S = 577.70) | 1-27 | m/z = 585.18(C$_{42}$H$_{23}$N$_3$O = 585.67) |
| 1-29 | m/z = 608.23(C$_{46}$H$_{28}$N$_2$ = 608.73) | 1-30 | m/z = 558.21(C$_{42}$H$_{26}$N$_2$ = 558.68) |
| 1-31 | m/z = 549.16(C$_{40}$H$_{23}$NS = 549.69) | 1-33 | m/z = 708.26(C$_{54}$H$_{32}$N$_2$ = 708.86) |

TABLE 3-continued

| Compound | FD-MS | Compound | FD-MS |
|---|---|---|---|
| 1-35 | m/z = 724.25($C_{54}H_{32}N_2O$ = 724.86) | 1-36 | m/z = 648.22($C_{48}H_{28}N_2O$ = 648.75) |
| 1-37 | m/z = 615.20($C_{45}H_{29}NS$ = 615.79) | 1-38 | m/z = 686.25($C_{50}H_{30}N_4$ = 686.82) |
| 1-39 | m/z = 677.19($C_{48}H_{27}N_3S$ = 677.83) | 1-40 | m/z = 717.19($C_{50}H_{27}N_3OS$ = 717.85) |
| 1-41 | m/z = 713.26($C_{51}H_{31}N_5$ = 713.84) | 1-42 | m/z = 653.19($C_{46}H_{27}N_3$ = 653.79) |
| 1-44 | m/z = 686.25($C_{50}H_{30}N_4$ = 686.82) | 1-45 | m/z = 713.26($C_{51}H_{31}N_5$ = 713.84) |
| 1-46 | m/z = 792.23($C_{56}H_{33}N_4S$ = 792.96) | 1-49 | m/z = 593.21($C_{46}H_{27}N$ = 593.73) |
| 1-51 | m/z = 619.23($C_{48}H_{29}N$ = 619.77) | 1-53 | m/z = 610.22($C_{44}H_{26}N_4$ = 610.70) |
| 1-54 | m/z = 736.26($C_{54}H_{32}N_4$ = 736.88) | 1-57 | m/z = 788.29($C_{58}H_{36}N_4$ = 788.95) |
| 1-59 | m/z = 545.19($C_{40}H_{23}N_3$ = 545.65) | 1-60 | m/z = 595.20($C_{44}H_{25}N_3$ = 595.69) |
| 1-68 | m/z = 534.21($C_{40}H_{26}N_2$ = 534.66) | 1-69 | m/z = 752.32($C_{57}H_{40}N_2$ = 752.96) |
| 1-70 | m/z = 818.28($C_{60}H_{38}N_2S$ = 819.04) | 1-71 | m/z = 903.36($C_{68}H_{45}N_3$ = 904.13) |
| 1-72 | m/z = 969.41($C_{73}H_{51}N_3$ = 970.23) | 1-73 | m/z = 883.30($C_{64}H_{41}N_3S$ = 884.11) |
| 1-75 | m/z = 560.23($C_{42}H_{28}N_2$ = 560.70) | 1-76 | m/z = 762.30($C_{58}H_{38}N_2$ = 762.96) |
| 1-77 | m/z = 726.30($C_{55}H_{38}N_2$ = 726.92) | 1-78 | m/z = 876.35($C_{67}H_{44}N_2$ = 877.10) |
| 1-79 | m/z = 798.30($C_{61}H_{38}N_2$ = 798.99) | 1-80 | m/z = 742.24($C_{54}H_{34}N_2S$ = 742.94) |
| 1-83 | m/z = 712.29($C_{54}H_{36}N_2$ = 712.90) | 1-84 | m/z = 726.30($C_{55}H_{38}N_2$ = 726.92) |
| 1-85 | m/z = 898.33($C_{69}H_{42}N_2$ = 899.11) | 1-87 | m/z = 925.38($C_{73}H_{48}N_2$ = 953.20) |
| 1-88 | m/z = 818.28($C_{60}H_{38}N_2S$ = 819.04) | 1-90 | m/z = 762.30($C_{58}H_{38}N_2$ = 762.96) |
| 1-95 | m/z = 636.26($C_{48}H_{32}N_2$ = 636.80) | 1-96 | m/z = 699.27($C_{52}H_{33}N_3$ = 699.86) |
| 1-97 | m/z = 752.32($C_{57}H_{40}N_2$ = 752.96) | 1-98 | m/z = 959.33($C_{70}H_{45}N_3S$ = 960.21) |
| 1-100 | m/z = 788.32($C_{60}H_{40}N_2$ = 788.99) | 1-101 | m/z = 804.33($C_{59}H_{40}N_4$ = 805.00) |
| 1-102 | m/z = 874.33($C_{67}H_{42}N_2$ = 875.09) | 1-103 | m/z = 610.24($C_{46}H_{30}N_2$ = 610.76) |
| 1-104 | m/z = 852.35($C_{65}H_{44}N_2$ = 853.08) | 1-108 | m/z = 825.33($C_{64}H_{41}N_3$ = 852.05) |
| 1-109 | m/z = 742.24($C_{54}H_{34}N_2S$ = 742.94) | 1-110 | m/z = 944.39($C_{70}H_{48}N_4$ = 945.18) |
| 1-111 | m/z = 660.26($C_0H_3N_2$=) | 1-112 | m/z = 760.29($C_{58}H_{36}N_2$ = 760.94) |

Even though an exemplary synthesis example of the present invention represented by the Formula 1 are described, all of them are based on Buchwald-Hartwig cross coupling reaction, Pd(II)-catalyzed oxidative cyclization reaction (Org. Lett. 2011, 13, 5504), and Suzuki cross-coupling reaction. It will be understood by those skilled in the art that the above reaction proceeds even when other substituents (substituents of $R^1 \sim R^3$, $L^1$, $Ar^1$ and the like) defined in Formula 1 are bonded, in addition to the substituents described in the specific synthesis example.

Meanwhile, bromination methods for the synthesis of M 1, M 1', M 1" are available by referring to SYNTHETIC COMMUNICATIONS, 11 (3), 253-259 (1981), J. Nat. Prod. 2006, 69, 1596-1600.

Fabrication and Evaluation of Organic Electronic Element

[Example 1] Red OLED (a Phosphorescent Host)

Organic light emitting diodes (OLEDs) were fabricated according to a conventional method by using a compound of the present invention as luminous host material of the light emitting layer. First, an ITO layer (anode) was formed on a glass substrate, and then 4,4',4"-Tris[2-naphthyl(phenyl) amino]triphenylamine (hereinafter, "2-TNATA") was vacuum-deposited on the ITO layer to form a hole injection layer with a thickness of 60 nm. And 4,4'-bis[N-(1-naphthyl)-N-phenylamino]biphenyl (hereinafter, "NPD") was vacuum-deposited on the hole injection layer to form a hole transport layer with a thickness of 60 nm.

Subsequently, a light emitting layer with a thickness of 30 nm was vacuum-deposited on the hole transport layer by using compound 1-13 of the present invention as a host material and bis-(1-phenylisoquinoline)iridium(III)acetylacetonate (hereinafter, "(piq)$_2$Ir(acac)" as a dopant material in a weight ratio of 95:5.

Subsequently, (1,1'-biphenyl-4-olato)bis(2-methyl-8-quinolinolato)aluminum (hereinafter, "BAlq") was vacuum-deposited with a thickness of 10 nm on the light emitting layer to form a hole blocking layer, and tris-(8-hydroxyquinoline)aluminum (hereinafter, "Alq$_3$") was vacuum-deposited with a thickness of 40 nm on the hole blocking layer to form an electron transport layer.

Next, halogenated alkali metal of LiF was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 20] Red OLED

In case of Examples 2 to 20, the OLEDs were fabricated in the same manner as described in Example 1 except that compounds of the present invention described in Table 4, instead of the compound 1-13 of the present invention, were used as the red host material of a light emitting layer.

[Comparative Example 1] and [Comparative Example 2]

In case of Comparative Examples 1 and 2, the OLEDs were fabricated in the same manner as described in Example 1 except that one of the comparative compounds 1 and 2, instead of the compound 1-13 of the present invention, were used as the red host material of a light emitting layer.

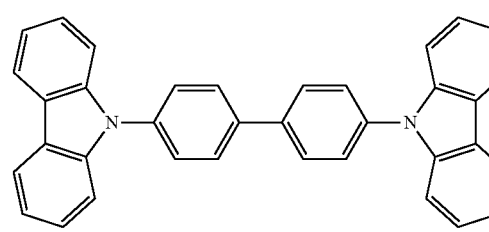

<Comp. compd 1>

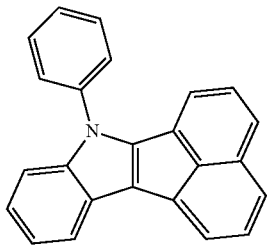
<Comp. compd 2>

Electroluminescence (EL) characteristics were measured with a PR-650 (Photoresearch) by applying a forward bias DC voltage to the OLEDs prepared in Examples 1 to 20 of the present invention and Comparative Examples 1 and 2. And, the T95 life time was measured using a life time measuring apparatus manufactured by Macscience Inc. at reference brightness of 2500 cd/m². The measurement results are shown in Table 4 below.

electrons in the electron transport layer, resulting in improved charge balance in the light emitting layer, and thus driving voltage is lowered, efficiency and life time are increased. Therefore, this suggests that the chemical and physical properties may be significantly changed by substituting a heterocyclic group having an ET characteristic in the core of the present invention.

Further, it is confirmed that Examples 14 to 18, wherein the inventive compounds used in Examples 14 to 18 correspond to the case where $Ar^1$ is a heterocyclic group and at least one of $R^1$ to $R^3$ is the substituent other than hydrogen, showed increased efficiency and decreased life time, comparing Examples 1 to 13. Furthermore, it is confirmed that Examples 19 and 20, wherein the inventive compounds used in Examples 19 and 20 correspond to the case where $Ar^1$ is benzene ring (Comparative Example 2) and at least one of $R^1$ to $R^3$ is the substituent other than hydrogen, showed increased efficiency and life time, comparing Comparative Example 2.

In particular, it is found that the efficiency is increased when $R^1$ to $R^3$ are carbazole, dibenzofuran or dibenzothi-

TABLE 4

|  | Compound | Voltage (V) | Current Density (mA/cm²) | Brightness (cd/m²) | Efficiency (cd/A) | Lifetime T(95) | CIE x | y |
|---|---|---|---|---|---|---|---|---|
| comp. Ex (1) | comp. Com 1 | 6.5 | 35.2 | 2500 | 7.1 | 69.2 | 0.66 | 0.32 |
| comp. Ex (2) | comp. Com 2 | 6.3 | 30.5 | 2500 | 8.2 | 83.4 | 0.66 | 0.31 |
| Ex.(1) | Com. 1-13 | 5.2 | 18.4 | 2500 | 13.6 | 124.0 | 0.65 | 0.32 |
| Ex.(2) | Com. 1-14 | 5.2 | 18.8 | 2500 | 13.3 | 123.5 | 0.66 | 0.32 |
| Ex.(3) | Com. 1-15 | 5.4 | 19.6 | 2500 | 12.8 | 118.3 | 0.66 | 0.31 |
| Ex.(4) | Com. 1-17 | 5.5 | 19.8 | 2500 | 12.6 | 119.5 | 0.66 | 0.32 |
| Ex.(5) | Com. 1-18 | 5.4 | 19.2 | 2500 | 13.0 | 118.2 | 0.65 | 0.32 |
| Ex.(6) | Com. 1-19 | 5.4 | 18.9 | 2500 | 13.2 | 120.7 | 0.66 | 0.31 |
| Ex.(7) | Com. 1-20 | 5.2 | 18.5 | 2500 | 13.5 | 121.2 | 0.66 | 0.32 |
| Ex.(8) | Com. 1-21 | 5.3 | 19.5 | 2500 | 12.8 | 121.8 | 0.65 | 0.32 |
| Ex.(9) | Com. 1-22 | 5.3 | 20.0 | 2500 | 12.5 | 118.5 | 0.66 | 0.32 |
| Ex.(10) | Com. 1-23 | 5.4 | 19.3 | 2500 | 12.9 | 119.6 | 0.66 | 0.32 |
| Ex.(11) | Com. 1-25 | 5.4 | 19.8 | 2500 | 12.6 | 119.5 | 0.65 | 0.31 |
| Ex.(12) | Com. 1-27 | 5.5 | 19.5 | 2500 | 12.8 | 119.2 | 0.65 | 0.32 |
| Ex.(13) | Com. 1-59 | 5.4 | 19.1 | 2500 | 13.1 | 122.0 | 0.66 | 0.31 |
| Ex.(14) | Com. 1-38 | 5.5 | 17.0 | 2500 | 14.7 | 106.7 | 0.65 | 0.32 |
| Ex.(15) | Com. 1-39 | 5.4 | 16.7 | 2500 | 15.0 | 106.9 | 0.66 | 0.31 |
| Ex.(16) | Com. 1-40 | 5.4 | 16.9 | 2500 | 14.8 | 107.7 | 0.66 | 0.32 |
| Ex.(17) | Com. 1-53 | 5.5 | 16.9 | 2500 | 14.8 | 106.6 | 0.65 | 0.31 |
| Ex.(18) | Com. 1-54 | 5.5 | 17.5 | 2500 | 14.3 | 109.9 | 0.65 | 0.32 |
| Ex.(19) | Com. 1-44 | 5.6 | 21.6 | 2500 | 11.6 | 96.4 | 0.66 | 0.32 |
| Ex.(20) | Com. 1-46 | 5.6 | 22.5 | 2500 | 11.1 | 94.1 | 0.65 | 0.32 |

From the measured results shown in Table 4 above, it is confirmed that the luminous efficiency, driving voltage and lifetime of OLED are remarkably improved when the compound according to an embodiment of the present invention was used as a phosphorescent host material of a light emitting layer.

That is, the Comparative compound 2 showed better device results than the Comparative compound 1, wherein the Comparative compound 1 is CBP commonly used as a host material, and the compound according to an embodiment of the present invention showed the lowest driving voltage, the highest luminous efficiency and the longest life time, and thus the inventive compound showed the best device results, wherein the inventive compound is a compound in which a heterocyclic ring is substituted for the same core as the Comparative compound 2.

It seems that this is because LUMO energy value is relatively lowered while the heterocyclic group having the electron transfer (ET) property is substituted for the core of the present invention (Examples 1 to 13) to easily receive ophene and the efficiency and life time are maximized when the secondary substituent of the carbazole is heterocyclic group.

This suggests that even though the compound has the same core, due to the introduction of a specific substituent, the chemical properties such as the energy level of the compound are changed and the device characteristics such as the packing density are changed, and thus, the device characteristics may be significantly changed.

Particularly, in the case of phosphorescent host, because the correlation of the hole transport layer and the dopant is grasped, even if a similar core is used, it will be very difficult to deduce the characteristics of the inventive compound showing in the phosphorescent host.

[Example 21] Green OLED (a Phosphorescent Host)

Organic light emitting diodes (OLEDs) were fabricated according to a conventional method by using a compound of the present invention as luminous host material of the light emitting layer. First, an ITO layer (anode) was formed on a glass substrate, and then 2-TNATA was vacuum-deposited on the ITO layer to form a hole injection layer with a thickness of 60 nm. And NPD was vacuum-deposited on the hole injection layer to form a hole transport layer with a thickness of 60 nm.

Subsequently, a light emitting layer with a thickness of 30 nm was vacuum-deposited on the hole transport layer by using compound 1-10 of the present invention as a host material and Ir(ppy)$_3$ as a dopant material in a weight ratio of 95:5.

Subsequently, BAlq was vacuum-deposited with a thickness of 10 nm on the light emitting layer to form a hole blocking layer, and Alq$_3$ was vacuum-deposited with a thickness of 40 nm on the hole blocking layer to form an electron transport layer. Next, halogenated alkali metal of LiF was deposited with a thickness of 0.2 nm on the electron transport layer to form an electron injection layer, and then Al was deposited with a thickness of 150 nm on the electron injection layer to form a cathode. In this way, the OLED was completed.

[Example 22] to [Example 32] Green OLED

In case of Examples 22 to 32, the OLEDs were fabricated in the same manner as described in Example 21 except that compounds of the present invention described in Table 5 instead of the compound 1-10 of the present invention were used as the green host material of a light emitting layer.

[Comparative Example 3] and [Comparative Example 4]

In case of Comparative Examples 3 and 4, the OLEDs were fabricated in the same manner as described in Example 21 except that one of the comparative compounds 1 and 2 instead of the compound 1-10 of the present invention were used as the green host material of a light emitting layer.

Electroluminescence (EL) characteristics were measured with a PR-650 (Photoresearch) by applying a forward bias DC voltage to the OLEDs prepared in Examples 21 to 32 of the present invention and Comparative Examples 3 and 4. And, the T95 life time was measured using a life time measuring apparatus manufactured by Macscience Inc. at reference brightness of 5000 cd/m$^2$. The measurement results are shown in Table 5 below.

From the measured results shown in Table 5 above, it is confirmed that OLED used the compound according to an embodiment of the present invention as a phosphorescent host material of a light emitting layer showed the lower driving voltage and the higher luminous efficiency and lifetime, comparing to OLED of Comparative Examples 3 and 4.

It seems that this is because LUMO energy value is relatively lowered while the heterocyclic group having the electron transfer (ET) property is substituted for the core of the present invention (Examples 21 to 22) to easily receive electrons in the electron transport layer, resulting in improved charge balance in the light emitting layer, and thus the driving voltage is lowered, the efficiency and life time are increased. Therefore, this suggests that the chemical and physical properties may be significantly changed by substituting a heterocyclic group having an ET characteristic in the core of the present invention.

Further, it is confirmed that Examples 23 and 24, wherein the inventive compounds used in Examples 23 and 24 correspond to the case where Ar$^1$ is a heterocyclic group and at least one of R$^1$ to R$^3$ is the substituent other than hydrogen, showed increased efficiency and decreased life time, comparing Examples 21 and 22. Furthermore, it is confirmed that Examples 28 to 30, wherein the inventive compounds used in Examples 28 to 30 correspond to the case where Ar$^1$ is benzene ring (Comparative Example 4) and at least one of R$^1$ to R$^3$ is the substituent other than hydrogen, showed increased efficiency and life time, comparing Comparative Example 4.

Therefore, it is found that the efficiency is increased when at least one of R$^1$ to R$^3$ is substituent other than hydrogen. Further, it is found that the efficiency and life time are maximized when the secondary substituent of the carbazole is heterocyclic group.

That is, this suggests that even though the compound has the same core, due to the introduction of a specific substituent, the chemical properties such as the energy level of the compound are changed and the device characteristics such as the packing density are changed, and thus, the device characteristics may be significantly changed.

Particularly, in the case of phosphorescent host, because the correlation of the hole transport layer and the dopant is grasped, even if a similar core is used, it will be very difficult to deduce the characteristics of the inventive compound showing in the phosphorescent host.

TABLE 5

| | Compound | Voltage (V) | Current Density (mA/cm$^2$) | Brightness (cd/m$^2$) | Efficiency (cd/A) | Lifetime T(95) | CIE X | Y |
|---|---|---|---|---|---|---|---|---|
| comp. Ex (3) | comp. Com 1 | 5.9 | 21.2 | 5000 | 23.6 | 56.4 | 0.31 | 0.6 |
| comp. Ex (4) | comp. Com 2 | 5.7 | 18.9 | 5000 | 26.4 | 87.6 | 0.31 | 0.61 |
| Ex.(21) | Com. 1-10 | 5.4 | 13.1 | 5000 | 38.2 | 126.6 | 0.3 | 0.60 |
| Ex.(22) | Com. 1-12 | 5.5 | 13.9 | 5000 | 36.1 | 124.7 | 0.31 | 0.61 |
| Ex.(23) | Com. 1-41 | 5.3 | 12.3 | 5000 | 40.8 | 119.2 | 0.30 | 0.60 |
| Ex.(24) | Com. 1-42 | 5.4 | 12.7 | 5000 | 39.3 | 116.3 | 0.31 | 0.61 |
| Ex.(25) | Com. 1-45 | 5.5 | 15.0 | 5000 | 33.4 | 102.6 | 0.30 | 0.61 |
| Ex.(26) | Com. 1-33 | 5.5 | 16.8 | 5000 | 29.8 | 100.9 | 0.31 | 0.61 |
| Ex.(27) | Com. 1-49 | 5.5 | 16.8 | 5000 | 29.8 | 93.3 | 0.30 | 0.60 |
| Ex.(28) | Com. 1-29 | 5.5 | 16.0 | 5000 | 31.2 | 99.5 | 0.31 | 0.60 |
| Ex.(29) | Com. 1-30 | 5.5 | 15.3 | 5000 | 32.7 | 97.3 | 0.30 | 0.60 |
| Ex.(30) | Com. 1-31 | 5.5 | 16.4 | 5000 | 30.5 | 95.2 | 0.31 | 0.61 |
| Ex.(31) | Com. 1-35 | 5.3 | 13.3 | 5000 | 37.5 | 111.5 | 0.30 | 0.60 |
| Ex.(32) | Com. 1-37 | 5.4 | 14.2 | 5000 | 35.2 | 104.7 | 0.31 | 0.61 |

[Example 33] Green OLED (Hole Transport Layer)

Organic light emitting diodes (OLEDs) were fabricated according to a conventional method by using a compound of the present invention as luminous host material of the light emitting layer. First, an ITO layer (anode) was formed on a glass substrate, and then 2-TNATA was vacuum-deposited on the ITO layer to form a hole injection layer with a thickness of 60 nm. And compound 1-68 of the present invention was vacuum-deposited on the hole injection layer to form a hole transport layer with a thickness of 60 nm.

Subsequently, a light emitting layer with a thickness of 30 nm was vacuum-deposited on the hole transport layer by using 4,4'-N,N'-dicarbazole-biphenyl (hereinafter, "CBP") as a host material and Ir(ppy)$_3$ as a dopant material in a weight ratio of 90:10.

Subsequently, BAlq was vacuum-deposited with a thickness of 10 nm on the light emitting layer to form a hole blocking layer, and Alq$_3$ was vacuum-deposited with a thickness of 40 nm on the hole blocking layer to form an electron transport layer. Next, halogenated alkali metal of LiF was deposited with a thickness of 0.2 nm on the electron transport layer to form an electron injection layer, and then Al was deposited with a thickness of 150 nm on the electron injection layer to form a cathode. In this way, the OLED was completed.

[Example 34] to [Example 59] Green OLED

In case of Examples 34 to 59, the OLEDs were fabricated in the same manner as described in Example 33 except that compounds of the present invention described in Table 6 instead of the compound 1-68 of the present invention were used as the material of a hole transport layer.

Comparative Example 5

The OLEDs were fabricated in the same manner as described in Example 33 except that the comparative compound 3 instead of the compound 1-68 of the present invention was used as the material of a hole transport layer.

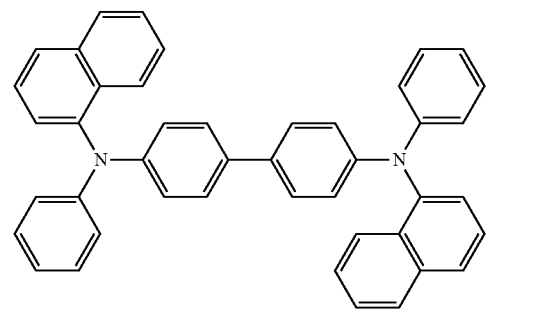

<Comp. compd 3>

Electroluminescence (EL) characteristics were measured with a PR-650 (Photoresearch) by applying a forward bias DC voltage to the OLEDs prepared in Examples 33 to 59 of the present invention and Comparative Example 5. And, the T95 life time was measured using a life time measuring apparatus manufactured by Macscience Inc. at reference brightness of 5000 cd/m$^2$. The measurement results are shown in Table 6 below.

TABLE 6

| | Compound | Voltage (V) | Current Density (mA/cm$^2$) | Brightness (cd/m$^2$) | Efficiency (cd/A) | Lifetime T(95) | CIE X | Y |
|---|---|---|---|---|---|---|---|---|
| comp. Ex (5) | comp. Com 1 | 6 | 21.6 | 5000 | 23.1 | 56.5 | 0.33 | 0.62 |
| Ex.(33) | Com. 1-68 | 5.4 | 16.5 | 5000 | 30.3 | 117.8 | 0.32 | 0.61 |
| Ex.(34) | Com. 1-69 | 5.5 | 16.6 | 5000 | 30.2 | 117.7 | 0.33 | 0.6 |
| Ex.(35) | Com. 1-71 | 5.4 | 14.2 | 5000 | 35.3 | 126.7 | 0.31 | 0.61 |
| Ex.(36) | Com. 1-72 | 5.5 | 14.4 | 5000 | 34.7 | 125.4 | 0.32 | 0.6 |
| Ex.(37) | Com. 1-73 | 5.5 | 14.7 | 5000 | 34.1 | 128.4 | 0.33 | 0.61 |
| Ex.(38) | Com. 1-75 | 5.5 | 15.3 | 5000 | 32.7 | 119.9 | 0.32 | 0.6 |
| Ex.(39) | Com. 1-77 | 5.4 | 16.6 | 5000 | 30.1 | 119.7 | 0.32 | 0.61 |
| Ex.(40) | Com. 1-78 | 5.5 | 16.7 | 5000 | 30 | 120.3 | 0.32 | 0.6 |
| Ex.(41) | Com. 1-79 | 5.5 | 16.7 | 5000 | 30 | 119.2 | 0.32 | 0.61 |
| Ex.(42) | Com. 1-80 | 5.5 | 16.4 | 5000 | 30.4 | 122.7 | 0.32 | 0.61 |
| Ex.(43) | Com. 1-83 | 5.4 | 15.8 | 5000 | 31.6 | 121.2 | 0.31 | 0.61 |
| Ex.(44) | Com. 1-84 | 5.5 | 15.3 | 5000 | 32.6 | 124 | 0.32 | 0.6 |
| Ex.(45) | Com. 1-87 | 5.5 | 16.1 | 5000 | 31.1 | 121 | 0.32 | 0.6 |
| Ex.(46) | Com. 1-88 | 5.5 | 14.7 | 5000 | 33.9 | 128.6 | 0.33 | 0.61 |
| Ex.(47) | Com. 1-90 | 5.4 | 14.0 | 5000 | 35.8 | 126.6 | 0.32 | 0.61 |
| Ex.(48) | Com. 1-95 | 5.5 | 16.8 | 5000 | 29.8 | 115.5 | 0.32 | 0.61 |
| Ex.(49) | Com. 1-96 | 5.6 | 16.0 | 5000 | 31.3 | 117.5 | 0.31 | 0.61 |
| Ex.(50) | Com. 1-97 | 5.6 | 16.9 | 5000 | 29.5 | 118.5 | 0.31 | 0.6 |
| Ex.(51) | Com. 1-98 | 5.4 | 14.7 | 5000 | 33.9 | 126 | 0.33 | 0.61 |
| Ex.(52) | Com. 1-100 | 5.5 | 14.4 | 5000 | 34.7 | 126.4 | 0.32 | 0.6 |
| Ex.(53) | Com. 1-102 | 5.4 | 14.5 | 5000 | 34.5 | 127 | 0.32 | 0.6 |
| Ex.(54) | Com. 1-103 | 5.5 | 16.4 | 5000 | 30.4 | 120 | 0.32 | 0.61 |
| Ex.(55) | Com. 1-104 | 5.4 | 15.9 | 5000 | 31.5 | 119.4 | 0.31 | 0.61 |
| Ex.(56) | Com. 1-108 | 5.6 | 16.2 | 5000 | 30.8 | 120.3 | 0.32 | 0.6 |
| Ex.(57) | Com. 1-109 | 5.6 | 16.4 | 5000 | 30.5 | 119.3 | 0.32 | 0.6 |
| Ex.(58) | Com. 1-111 | 5.5 | 16.3 | 5000 | 30.6 | 122.9 | 0.33 | 0.61 |
| Ex.(59) | Com. 1-112 | 5.6 | 16.8 | 5000 | 29.7 | 121.2 | 0.33 | 0.61 |

From the measured results shown in Table 6 above, it is confirmed that OLED used the compound according to an embodiment of the present invention as material of a hole transport layer showed the improved luminous efficiency and lifetime, comparing to OLED used the Comparative compound 3 as material of a hole transport layer.

This results show that the compound of the present invention can be used in a hole transport layer by applying the amine group ($-L^a-N(R^a)(R^b)$) to $R^1$ to $R^3$ groups bonded to the core of the present invention and the compound of the present invention has a deep HOMO energy level and a high T1 value, which are intrinsic properties. Therefore, it is believed that the efficiency of blocking electrons is enhanced and holes are smoothly transported to the light emitting layer, resulting in the efficiency is improved since the excitons are more easily generated in the light emitting layer.

$R^1$ to $R^3$ of the compound of the present invention makes it possible to use the compound as a hole transport layer. The deep HOMO energy Level and a high T 1 value, it is considered that the efficiency of blocking electrons is improved and at the same time, the holes are smoothly transported to the light emitting layer, and as a result, the excitons are more easily generated in the light emitting layer and the efficiency is improved.

Taken together with the deep HOMO energy level and the high T1 value described above, it can be confirmed that band gap, electrical characteristics, interface characteristics, etc. can be greatly changed when an amine group ($-L^a-N(R^a)(R^b)$) is applied to $R^1$ to $R^3$ bonded to the core of the inventive compound, and this is a major factor in improving the performance of the device.

Further, in the case of a hole transport layer, because the correlation of the hole transport layer and a light emitting layer is grasped, even if a similar core is used, it will be very difficult to deduce the characteristics showing in a light emitting layer employing the inventive compound.

Furthermore, although the device characteristics have been described from the viewpoints of the light emitting layer or the hole transporting layer in the evaluation results of the above-described device fabrication, the compound used as the material of the light emitting layer can be used in other layers of the organic material layer such as an electron transport layer, an electron injection layer, a hole injection layer and the like as a single material or a mixture with another material. Therefore, the compound of the present invention can be used as a single material or a mixture with other material other layers of the organic material layer besides a light emitting layer, for example, an electron transport layer, an electron injection layer, a hole injection layer, a hole transport layer and an emission-auxiliary layer and the like.

Although the exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed herein is intended to illustrate the scope of the technical idea of the present invention, and the scope of the present invention is not limited by the embodiments. The scope of the present invention shall be construed on the basis of the accompanying claims, and it shall be construed that all of the technical ideas included within the scope equivalent to the claims belong to the present invention.

The invention claimed is:
1. A compound of Formula 1:

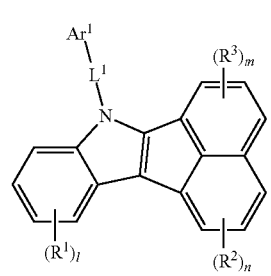

[Formula 1]

wherein,
$R^1$ to $R^3$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and $-L^a-N(R^a)(R^b)$, wherein neighboring $R^1$ groups, neighboring $R^2$ groups, neighboring $R^3$ groups, or $R^2$ and $R^3$ groups are optionally linked to each other to form a benzene or naphthelene ring, l is an integer of 0 to 4, and m and n are each an integer of 0 to 3, $L^1$ is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, $Ar^1$ is selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, $-L^a-N(R^a)(R^b)$, a $C_1$-$C_{30}$ alkoxyl group, and a $C_6$-$C_{30}$ aryloxyl group, with the proviso that: (i) a compound of Formula 1 wherein $L^1$ is a single bond, $Ar^1$ is methyl or phenyl, and l=m=n=0, is executed, (ii) a compound of Formula 1 wherein $L^1$-$Ar^1$ includes a quinazoline moiety, is excluded, and (iii) a compound of Formula 1 wherein $L^1$-$Ar^1$ includes a $C_6$-$C_{12}$ aryl group bonded to the N atom, has at least one of $R_1$ to $R_3$ being selected from the group consisting of a $C_{14}$-$C_{60}$ aryl group, fluorenyl group, a $C_{12}$-$C_{60}$ heterocyclic group and $L^a$-$N(R^a)(R^b)$, $L^a$ is each independently selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, $R^a$ and $R^b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, -L'-N(R')(R''), and a $C_6$-$C_{30}$ aryloxyl group, L' is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, R' and R'' are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, and the aryl group, fluorenyl group, heterocyclic group, alkyl group, fused ring group, alkenyl group, alkynyl group, alkoxyl group, aryloxyl group, arylene group, fluorenylene group, ring formed by linking between neighboring groups of $R^1$s to $R^3$s, and ring formed by linking between $R^2$ and $R^3$ are each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group, and a combination thereof.

2. The compound of claim 1 represented by the following Formula 2:

[Formula 2]

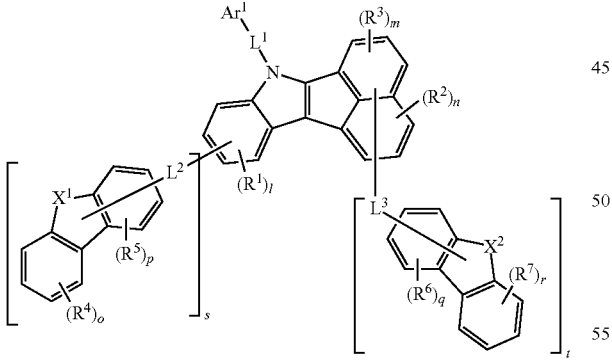

wherein,
$Ar^1$, $L^1$, $R^1$ to $R^3$, l, m, and n are the same as defined for Formula 1 in claim 1,
s is an integer of 0 to 4, t is an integer of 0 to 6, and s+t is 1 or more,
$L^2$ and $L^3$ are each independently selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, $X^1$ and $X^2$ are each independently N, N-$L^4$-$Ar^2$, O, S, C($R^8$)($R^9$) or Si($R^{10}$)($R^{11}$), $X^1$ is bonded to $L^2$ when $X^1$ is N, and $X^2$ is bonded to $L^3$ when $X^2$ is N, $R^4$ to $R^7$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_3$-$C_{60}$ aliphatic ring and a $C_6$-$C_{60}$ aromatic ring, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -$L^a$-N($R^a$)($R^b$), wherein neighboring groups of $R^4$ to $R^7$ are optionally linked to each other to form at least one ring, o, p, q and r are each an integer of 0 to 4, $L^4$ is independently selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, $Ar^2$ is selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-N($R^a$)($R^b$), a $C_1$-$C_{30}$ alkoxyl group, and a $C_6$-$C_{30}$ aryloxyl group, $R^8$ to $R^{11}$ are each independently selected from the group consisting of hydrogen, deuterium, a $C_1$-$C_{50}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group, a $C_1$-$C_{30}$ silyl group, a $C_6$-$C_{60}$ aryl group, a $C_2$-$C_{60}$ heterocyclic group containing at least one heteroatom selected from the group consisting of O, N, S, Si, and P, a fluorenyl group, and -$L^a$-N($R^a$)($R^b$), and $R^8$ and $R^9$, or $R^{10}$ and $R^{11}$ may be linked to each other to form a ring, and $L^a$, $R^a$ and $R^b$ are the same as defined in claim 1.

3. The compound of claim 1, wherein $Ar^1$ in the Formula 1 is selected from the following group:

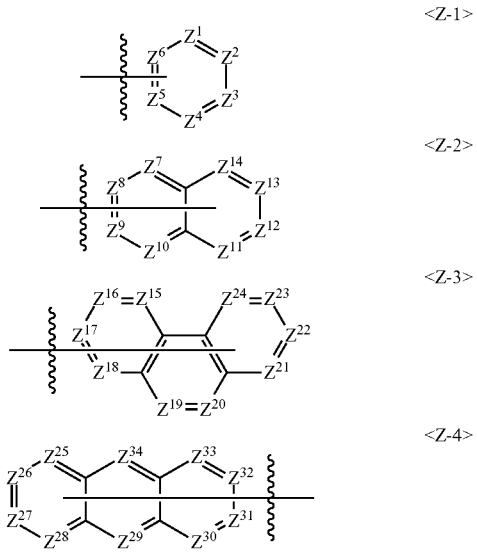

-continued

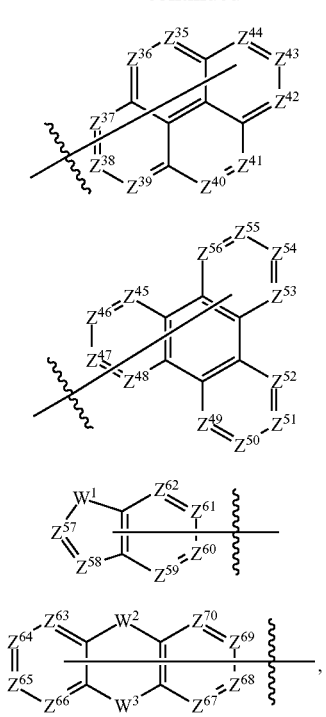

wherein $Z^1$ to $Z^{70}$ are each independently C, $CR^{12}$ or N, $W^1$ to $W^3$ are each independently a single bond, $C(R^{13})(R^{14})$, $N(Ar^3)$, O, S or $Si(R^{15})(R^{16})$, $R^{12}$ is independently selected from the group consisting of hydrogen, deuterium, a $C_1$-$C_{50}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group, a $C_1$-$C_{30}$ silyl group, a $C_6$-$C_{60}$ aryl group, a $C_2$-$C_{60}$ heterocyclic group containing at least one heteroatom selected from the group consisting of O, N, S, Si, and P, a fluorenyl group and -$L^a$-$N(R^a)(R^b)$, wherein neighboring groups of $R^{12}$ are optionally linked to each other to form at least one ring, $R^{13}$ to $R^{16}$ are independently selected from the group consisting of hydrogen, deuterium, a $C_1$-$C_{50}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxy group, a $C_1$-$C_{30}$ silyl group, a $C_6$-$C_{60}$ aryl group, a $C_2$-$C_{60}$ heterocyclic group containing at least one heteroatom selected from the group consisting of O, N, S, Si, and P, a fluorenyl group and -$L^a$-$N(R^a)(R^b)$, wherein $R^{13}$ and $R^{14}$, or $R^{15}$ and $R^{16}$ are optionally linked to each other to form a ring, $Ar^3$ is selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-$N(R^a)(R^b)$, a $C_1$-$C_{30}$ alkoxyl group, and a $C_6$-$C_{30}$ aryloxyl group, $L^a$, $R^a$ and $R^b$ are the same as defined in claim 1.

4. An organic electric element comprising a first electrode, a second electrode, and an organic material layer formed between the first electrode and the second electrode, wherein the organic material layer comprises the compound of claim 1.

5. The organic electric element of claim 4, wherein the compound is comprised in at least one layer of a hole injection layer, a hole transport layer, an emission-auxiliary layer, a light emitting layer, an electron transport-auxiliary layer and an electron transport layer, and the compound is comprised as a single compound or a mixture of two or more different kinds.

6. The organic electric element of claim 4, further comprising a layer for improving luminous efficiency formed on one side of the first electrode and/or one side of the second electrode, the side not facing the organic material layer.

7. The organic electric element of claim 4, wherein the organic material layer is formed by any one of the processes of spin coating, nozzle printing, inkjet printing, slot coating, dip coating and roll-to-roll.

8. An electronic device comprising a display device and a control unit for driving the display device, wherein the display device comprises the organic electric element of claim 4.

9. The electronic device of claim 8, wherein the organic electric element is an organic light emitting diode, an organic solar cell, an organic photo conductor, an organic transistor, or an element for monochromatic or white illumination.

10. The compound of claim 1, wherein Formula 1 is any one of the compounds below:

1-3

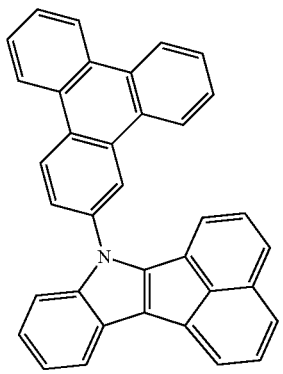

1-5

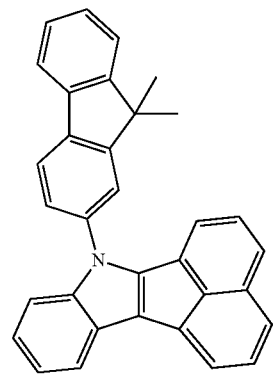

1-6
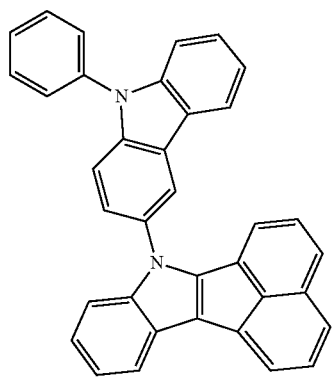
1-7
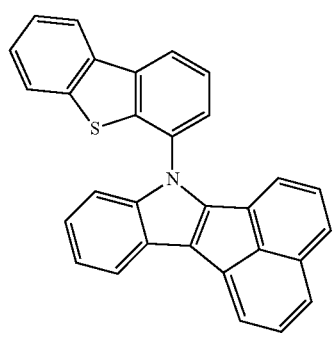
1-8
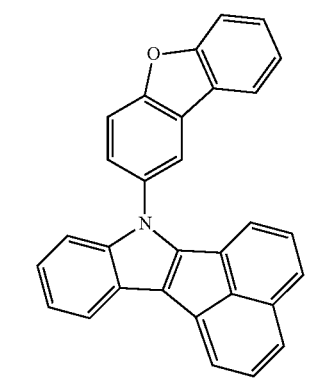
1-9
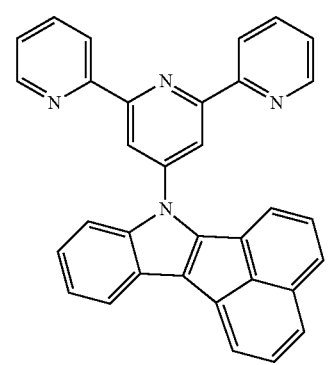
1-10
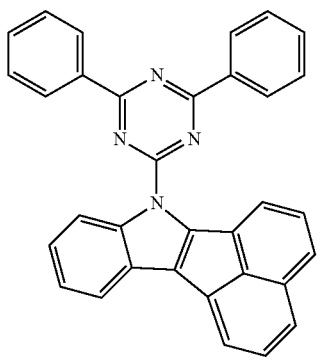
1-11
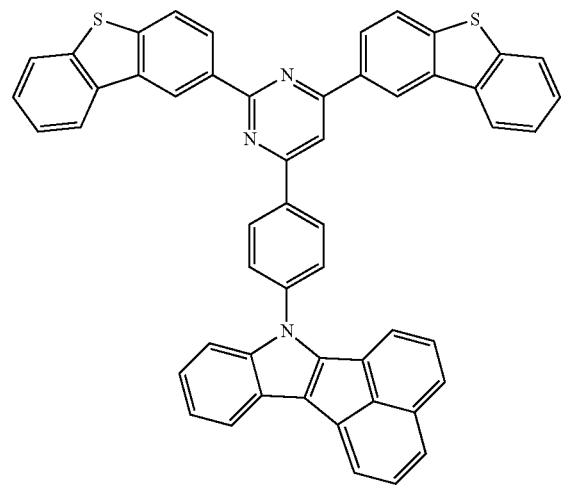
1-12
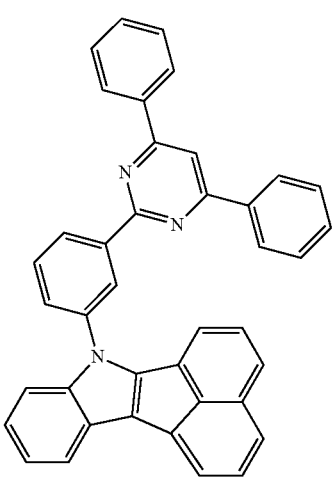

-continued
1-14
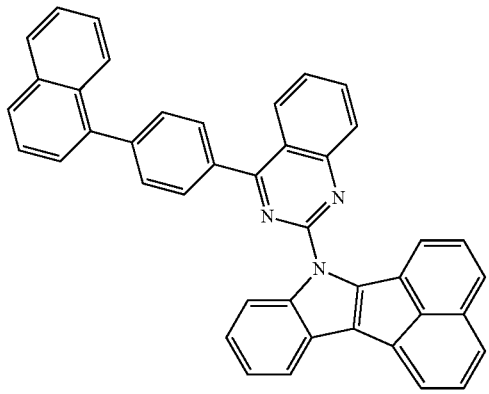
1-15
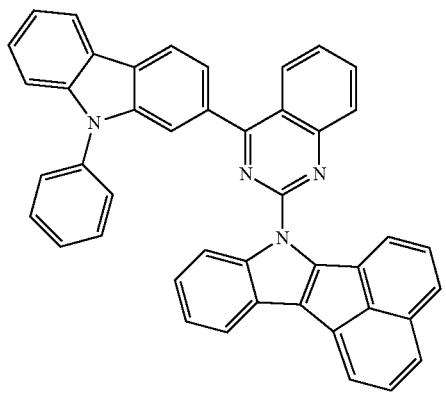
1-16
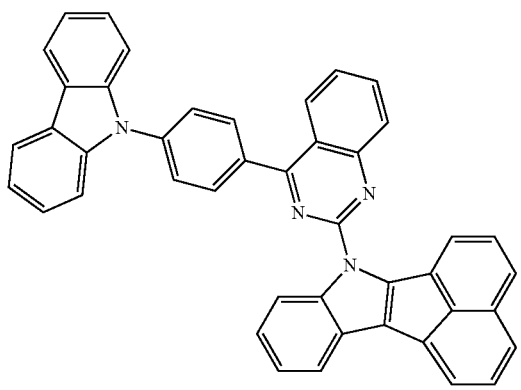
1-17
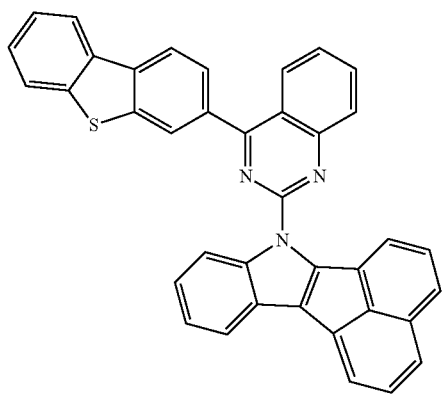
-continued
1-18
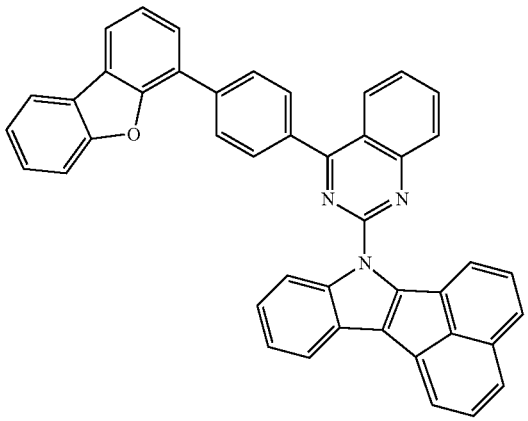
1-19
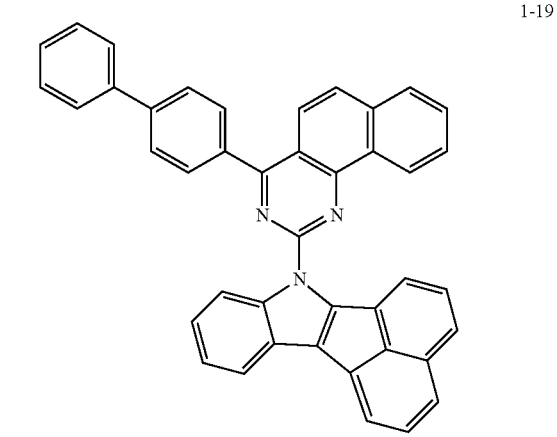
1-20
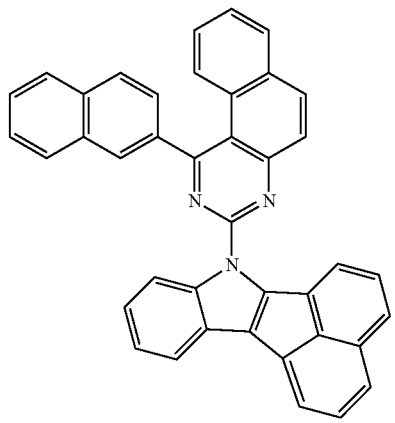

-continued
1-21
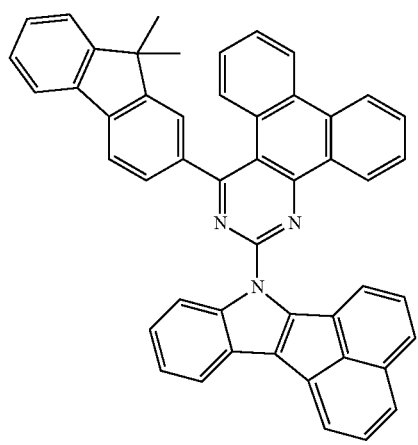
1-23
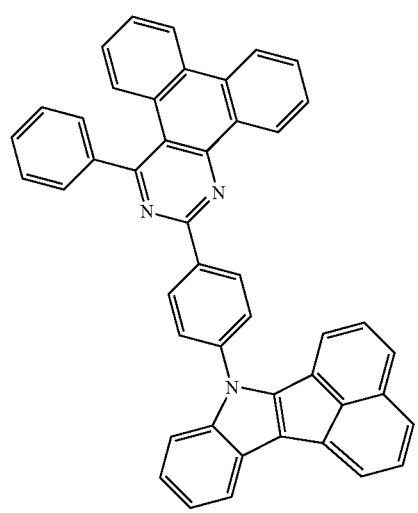
1-24
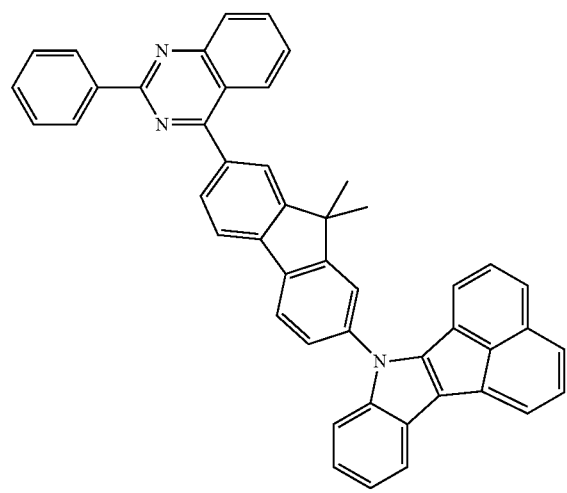
-continued
1-25
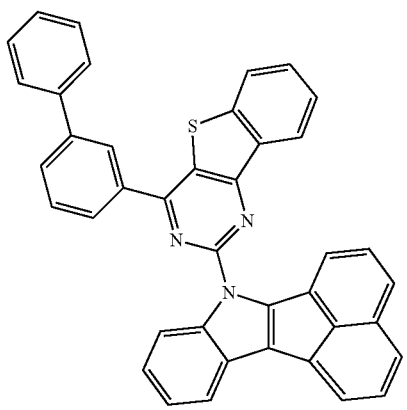
1-26
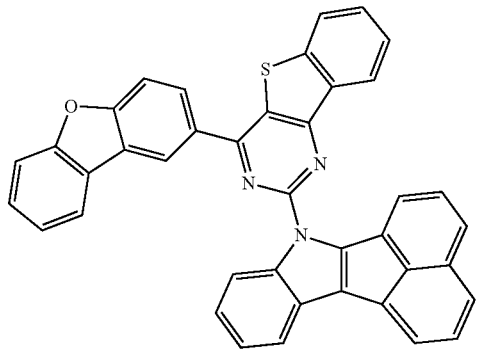
1-27
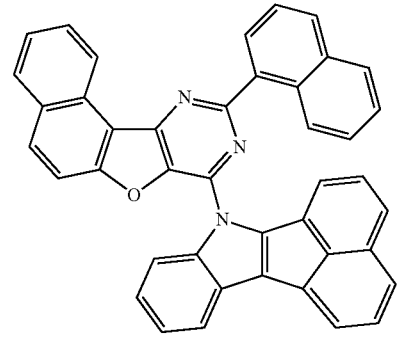
1-28
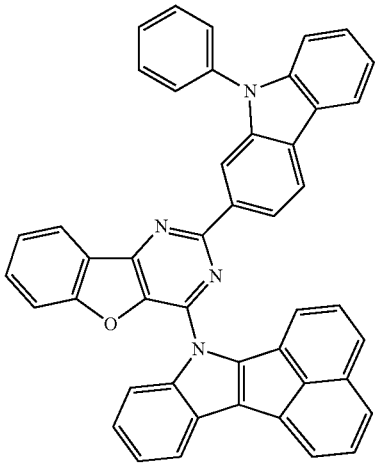

1-29
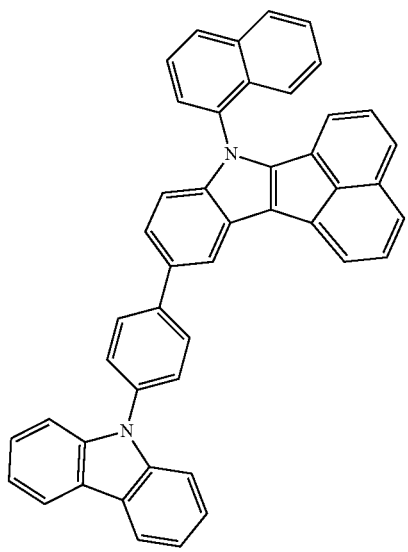
1-30
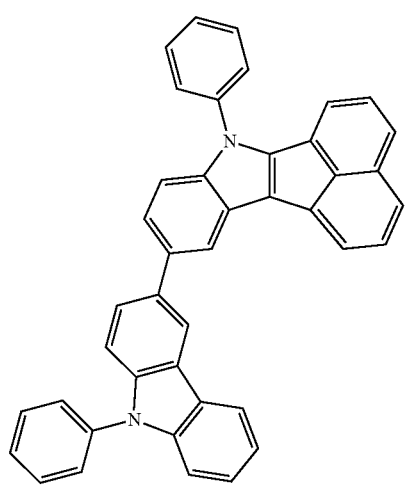
1-31
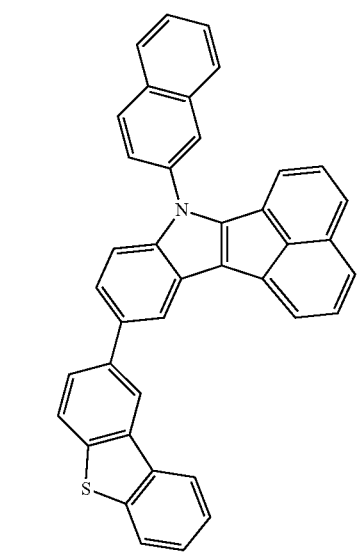
1-32
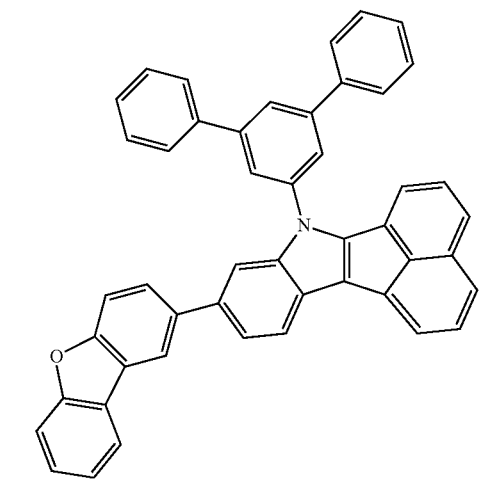
1-33
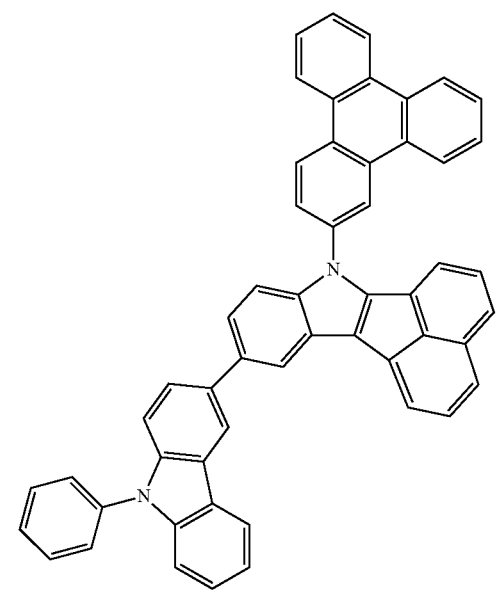
I-34
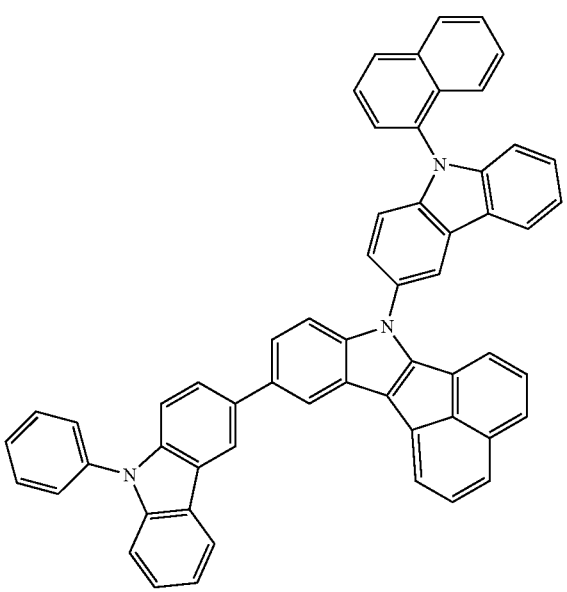

1-35
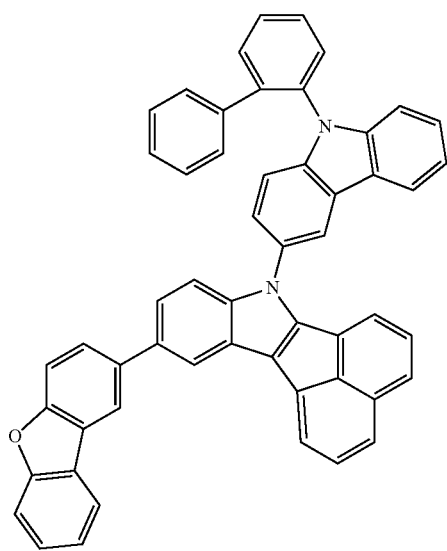
1-36
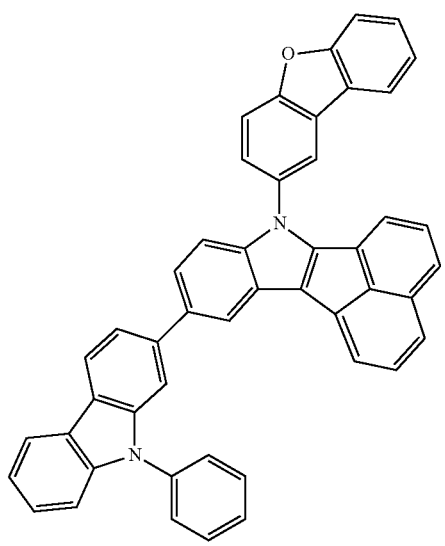
1-37
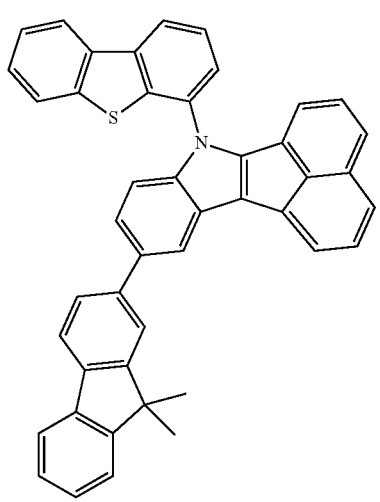
1-38
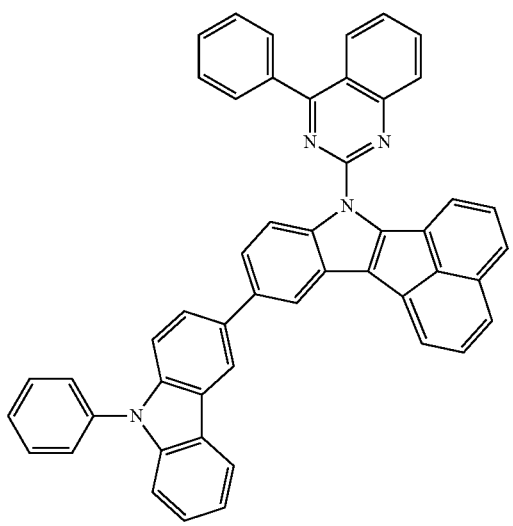
1-39
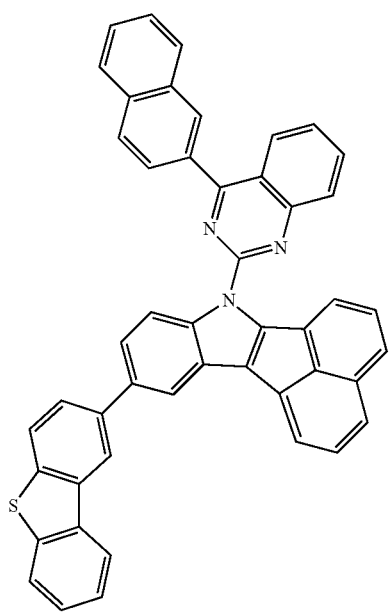

1-40
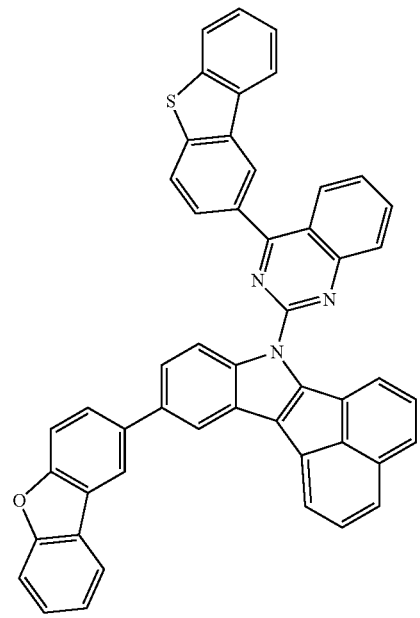
1-41
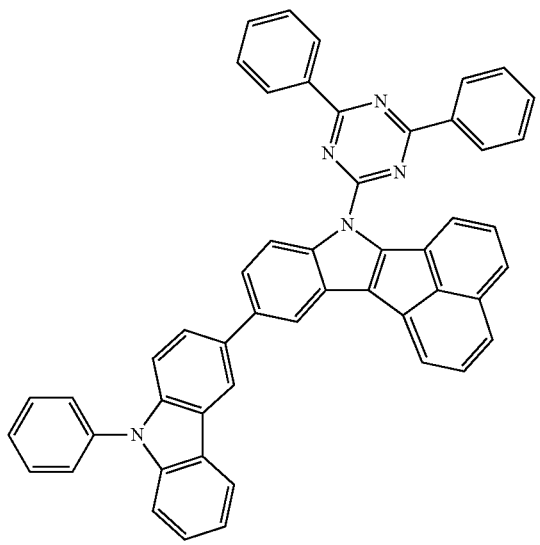
1-42
1-43
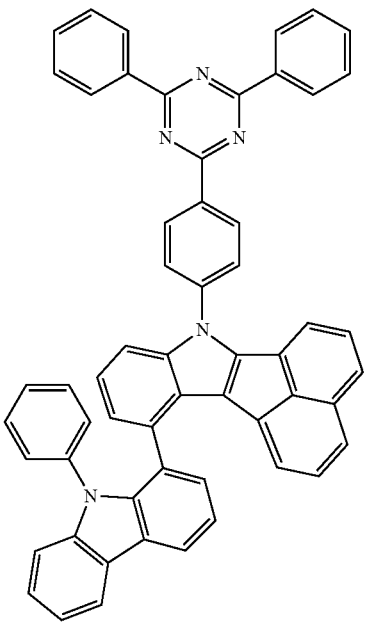
1-44
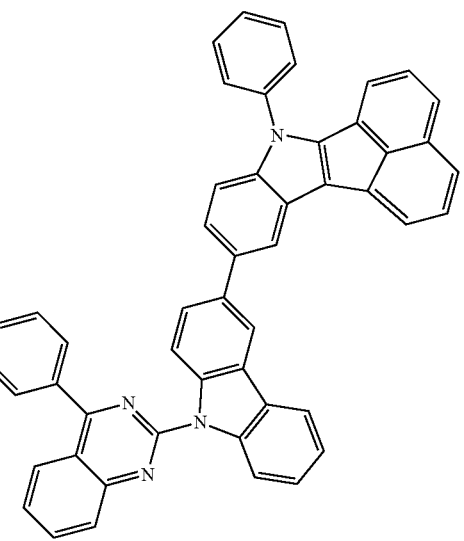

1-45
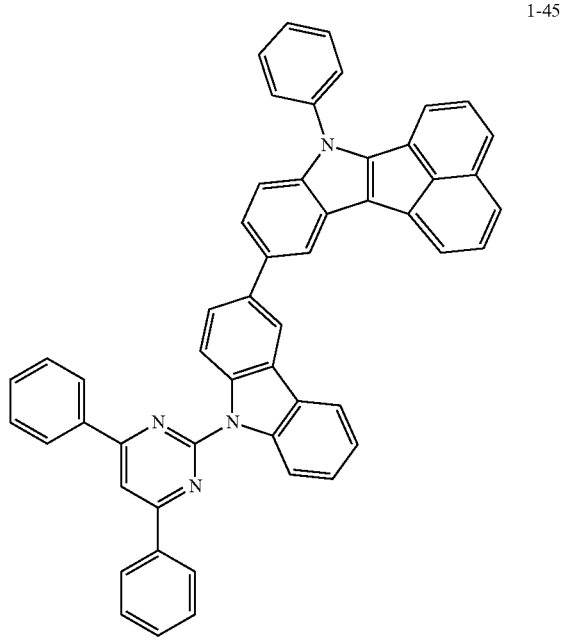
1-46
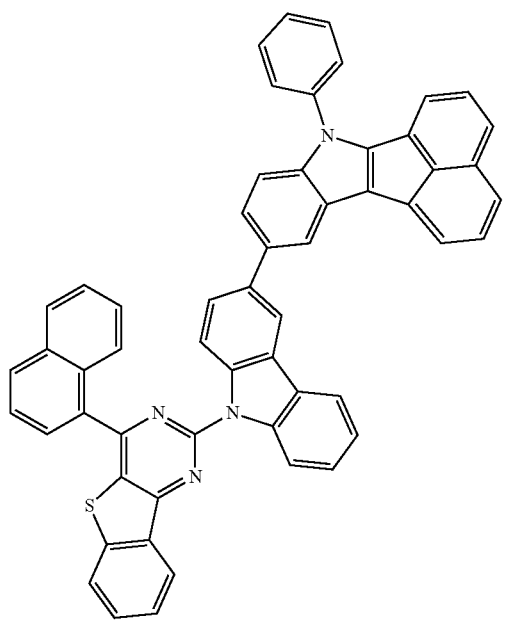
1-47
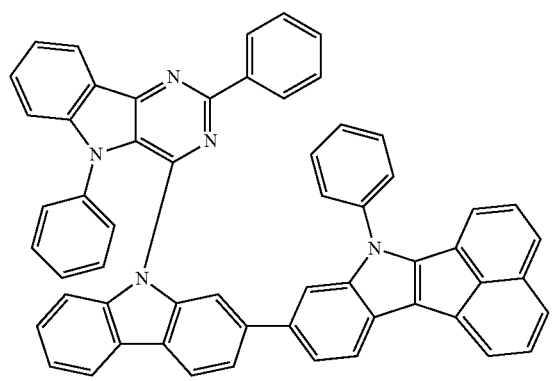
1-48
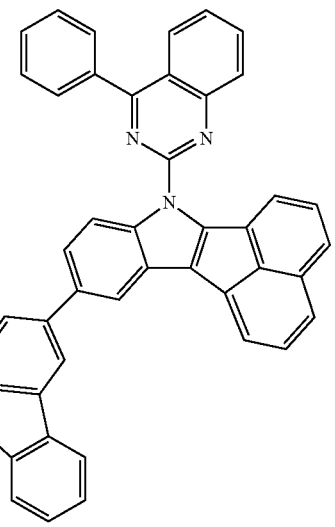
1-49
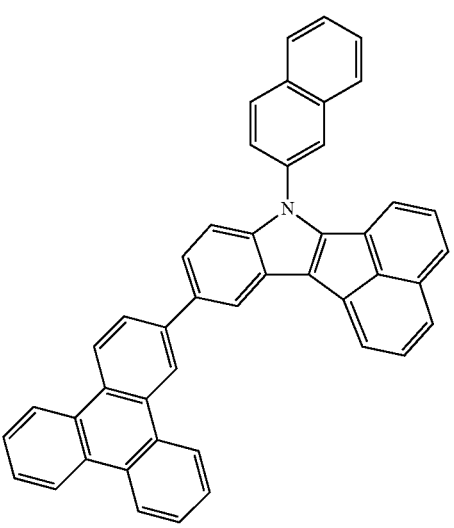
1-50
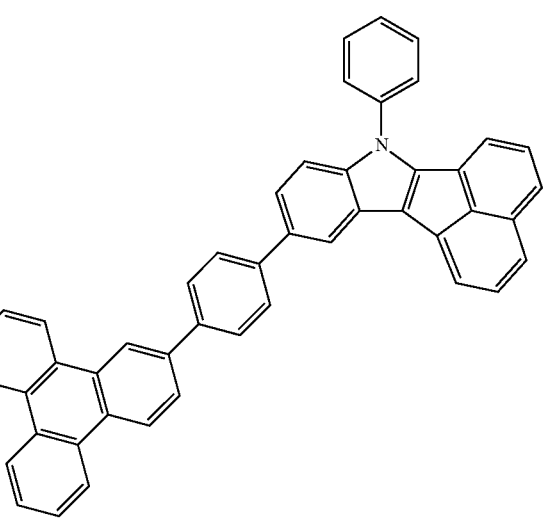

-continued
1-51
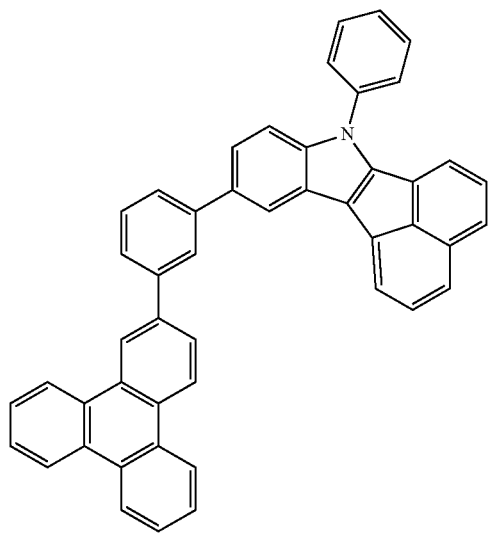
1-52
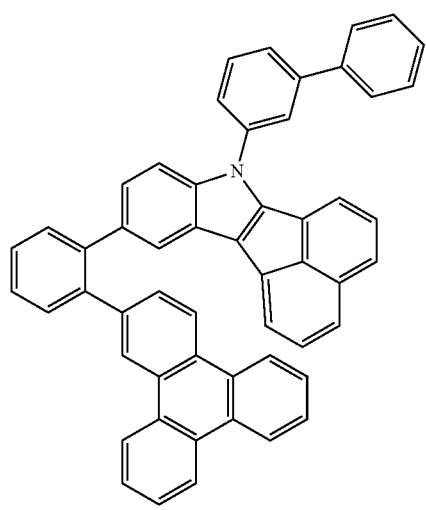
1-53
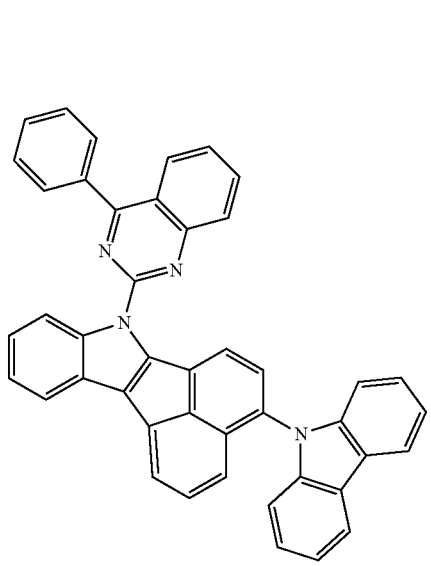
-continued
1-54
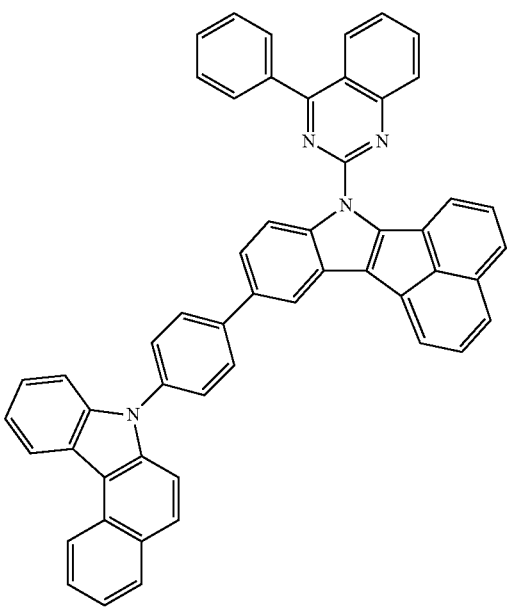
1-55
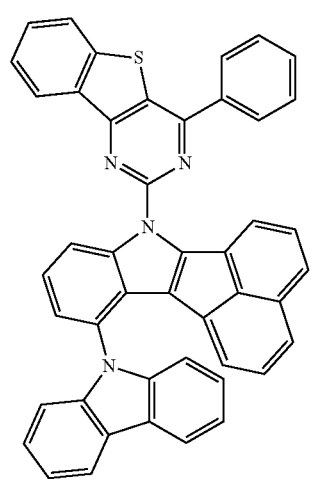

-continued
I-56
I-57
I-59
I-60
I-61
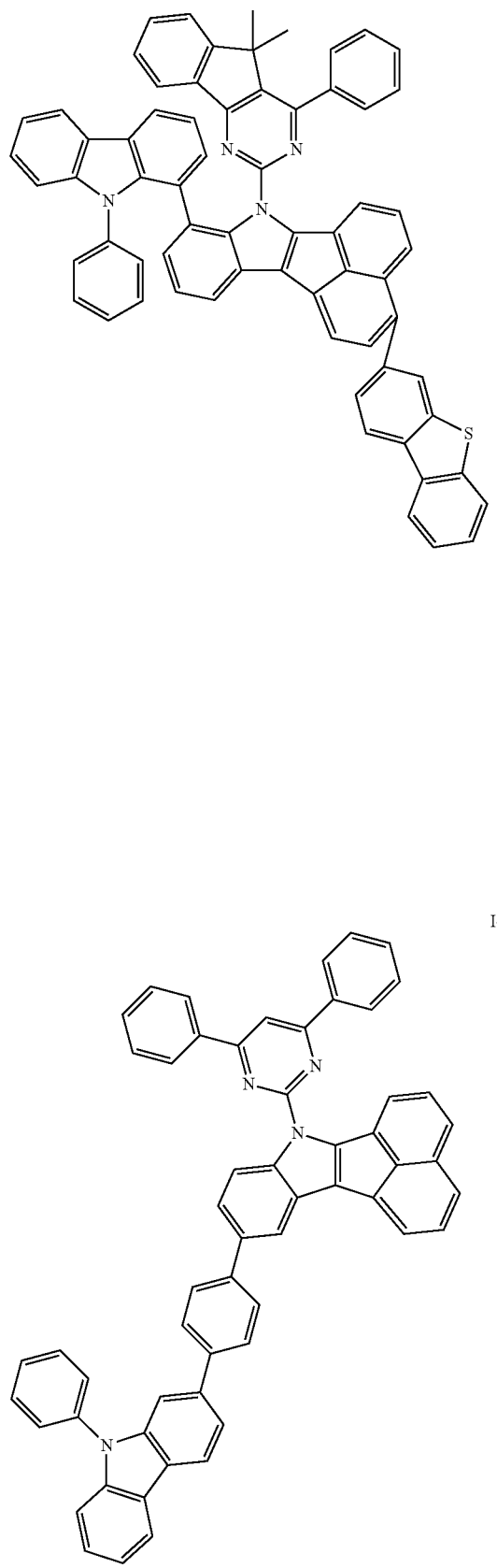
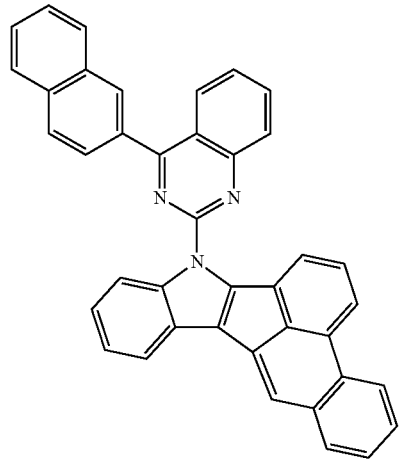
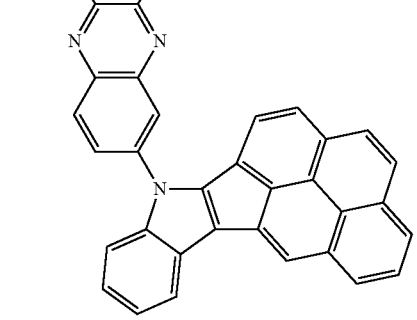
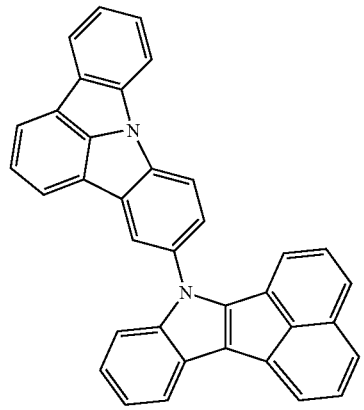

1-62
1-63
1-64
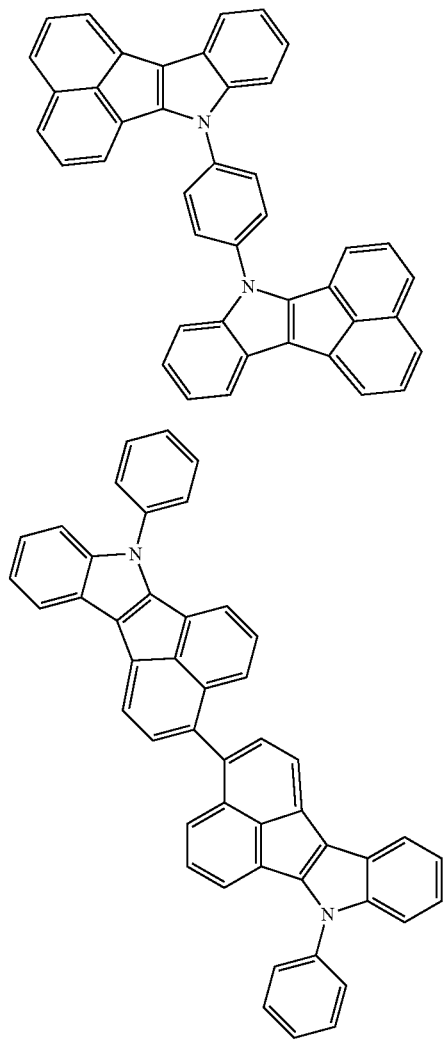
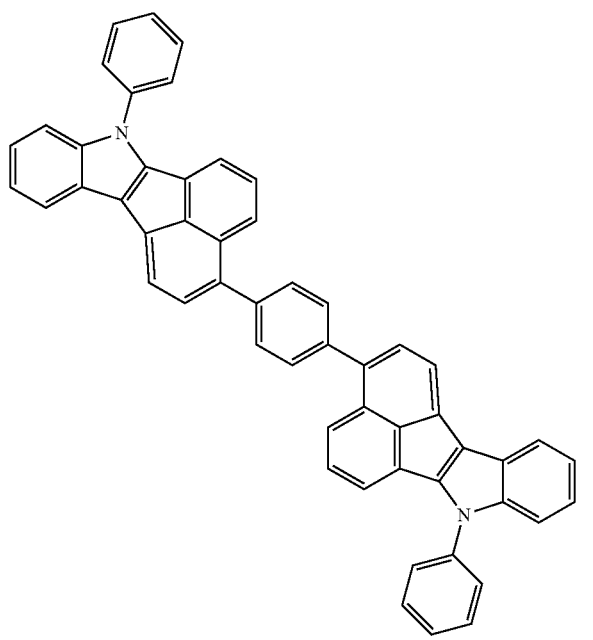
1-65
1-66
1-67
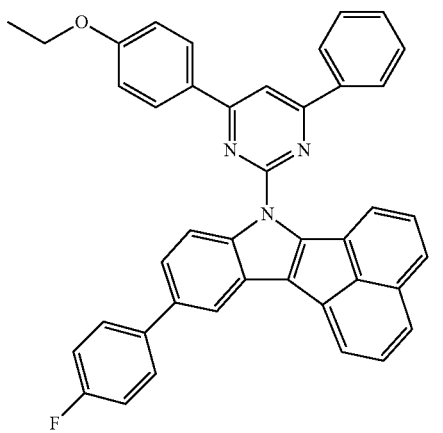
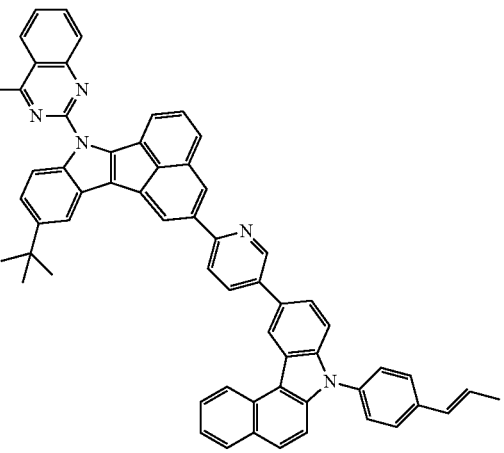
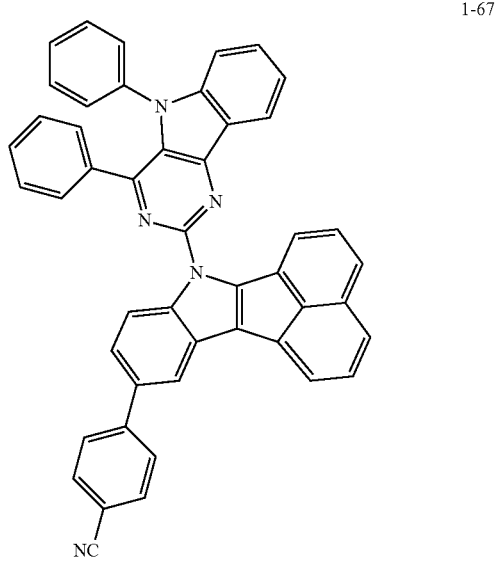

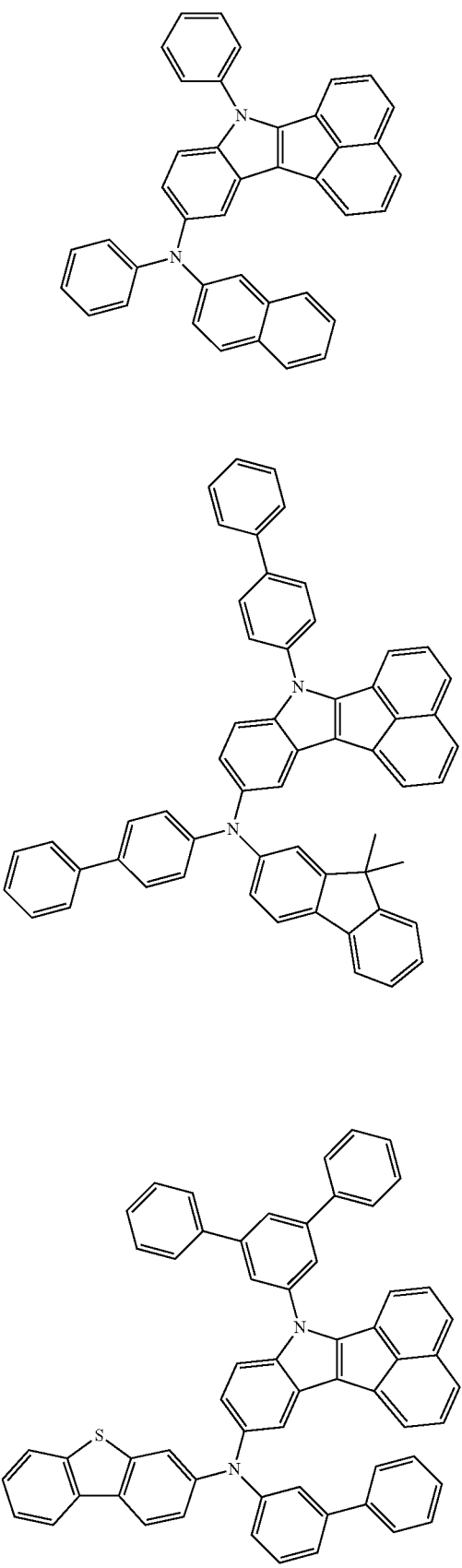

1-73
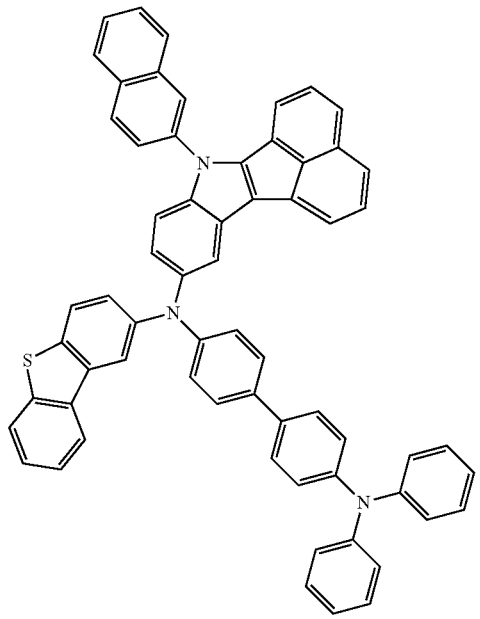
1-74
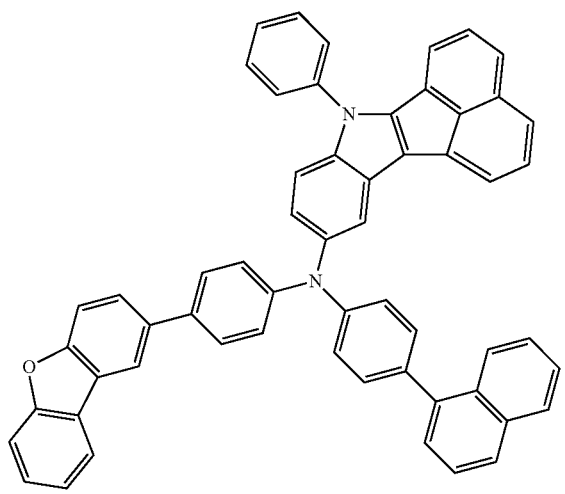
1-75
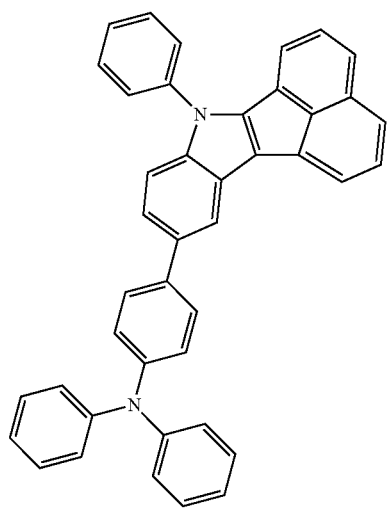
1-76
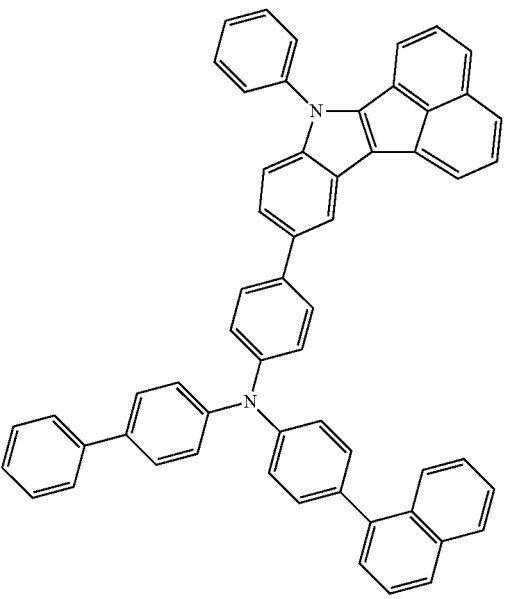
1-77
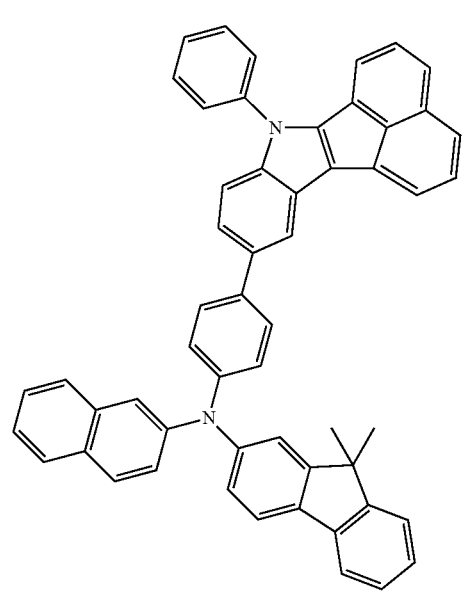

-continued
1-78
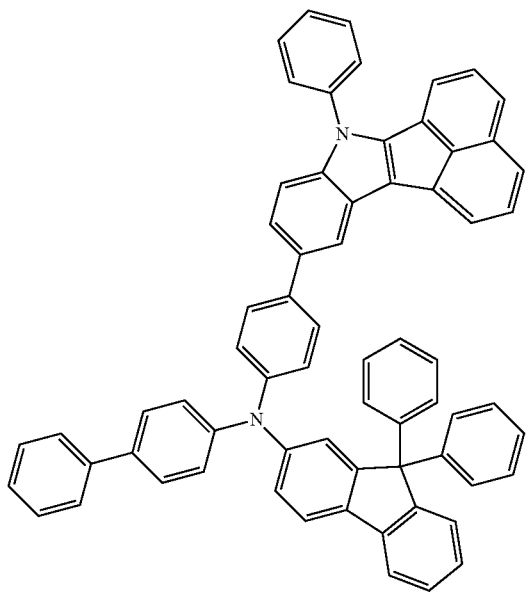
1-79
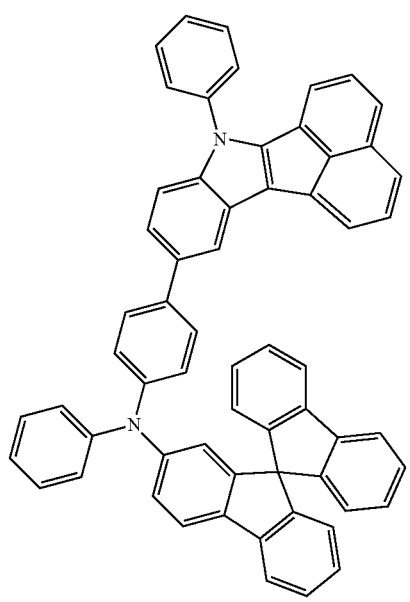
-continued
1-80
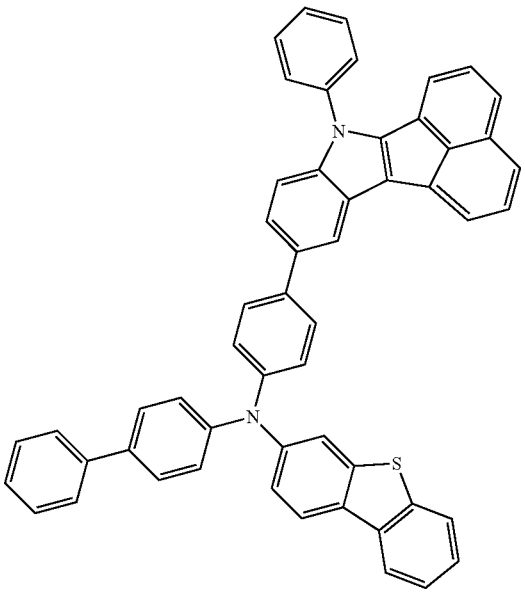
1-81
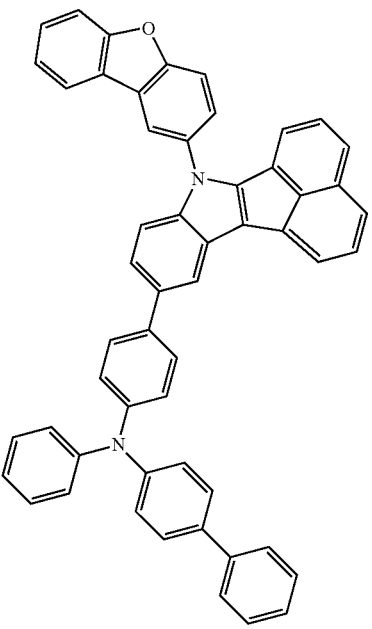

1-82
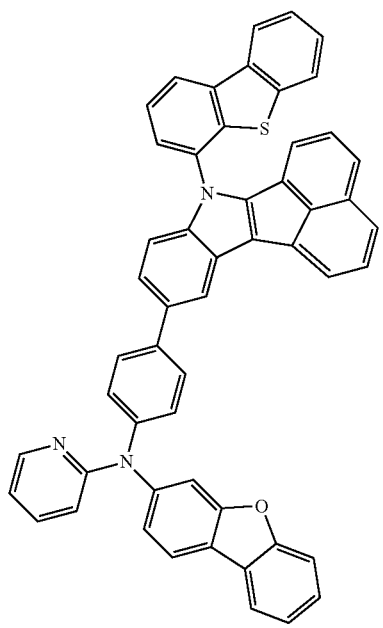
1-84
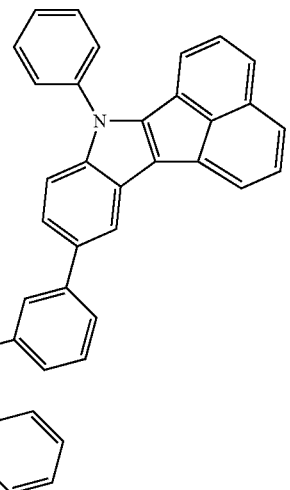
1-83
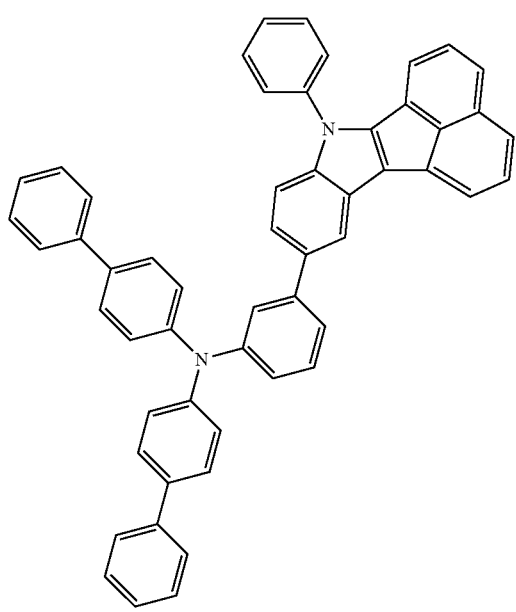
1-85
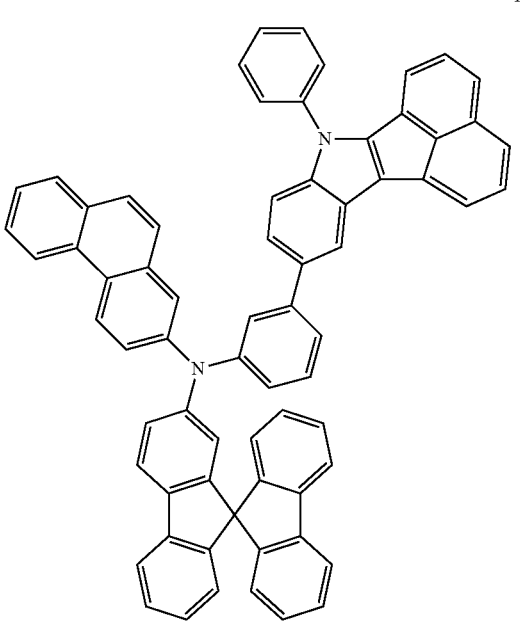

1-86
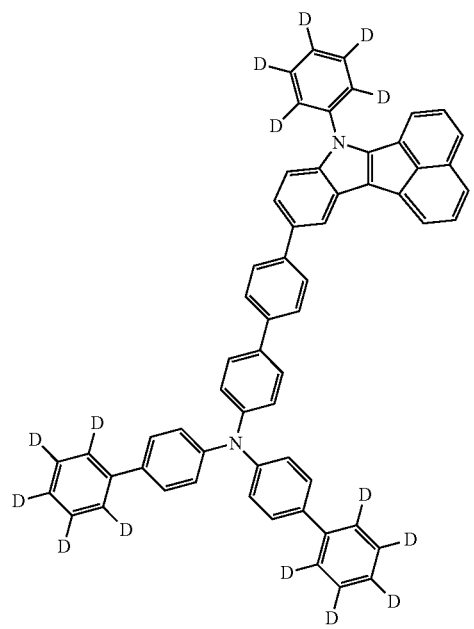
1-87
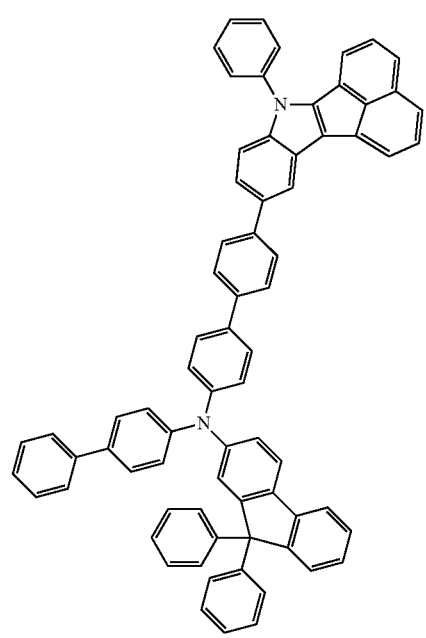
1-88
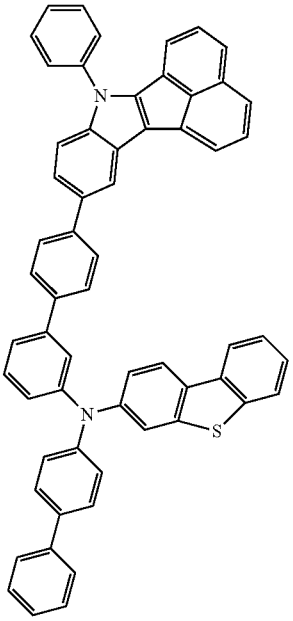
1-89
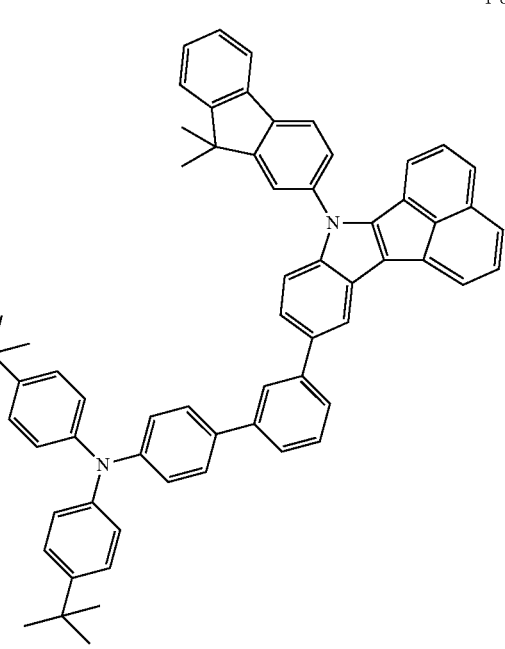

1-90
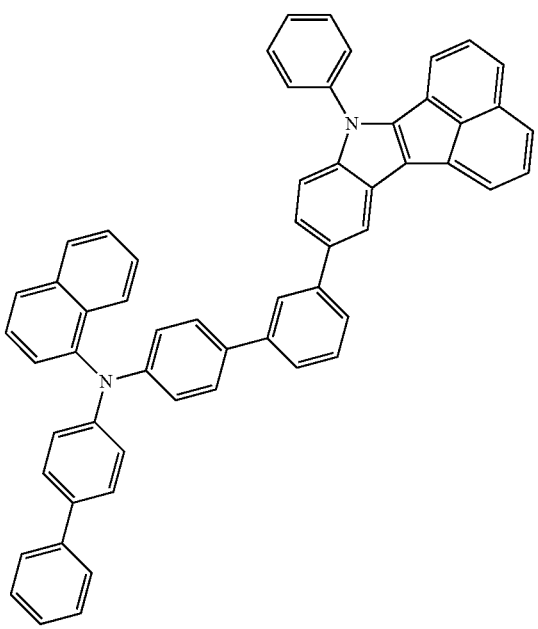
1-91
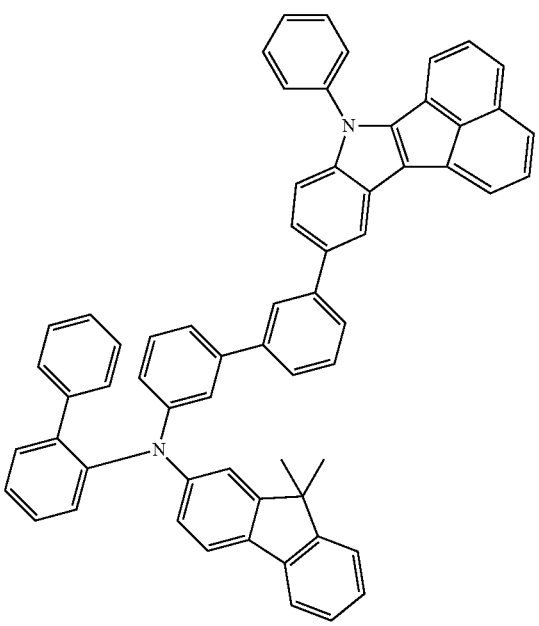
1-92
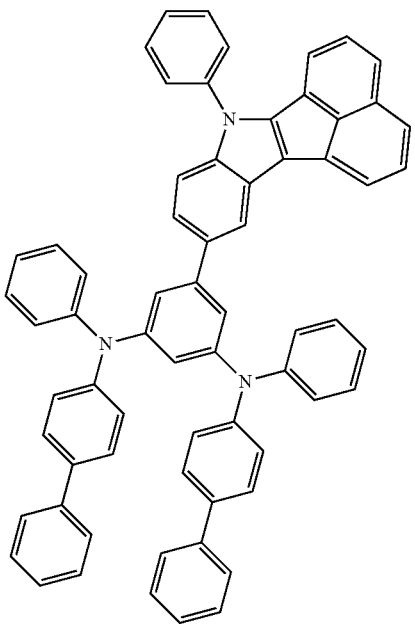
1-93
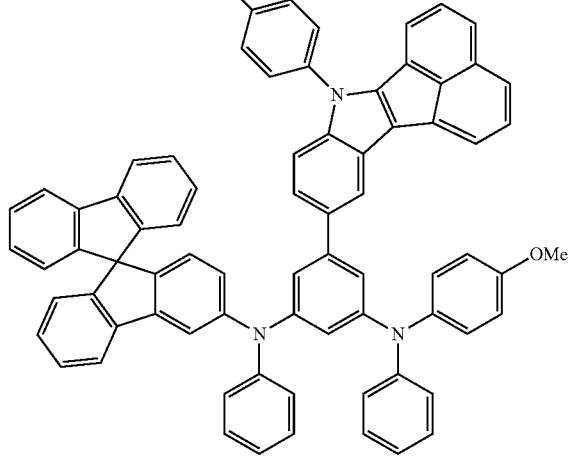

1-94
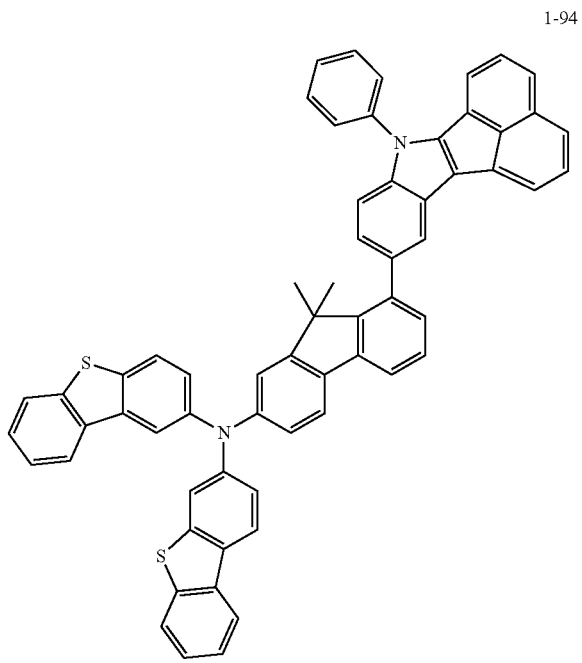
1-95
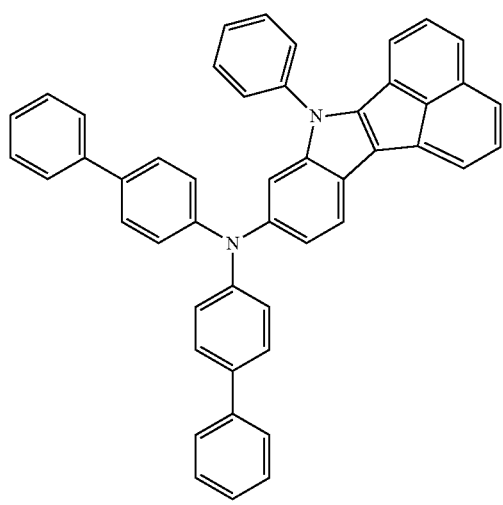
1-96
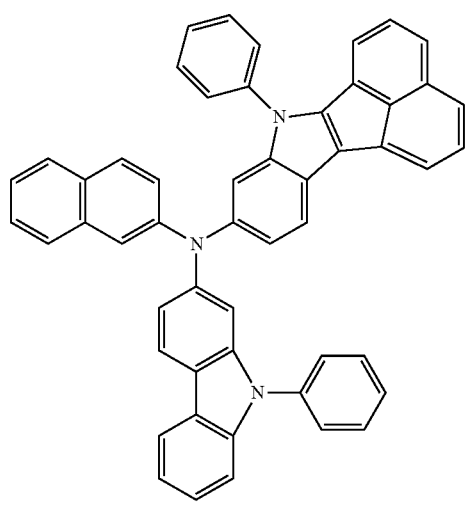
1-97
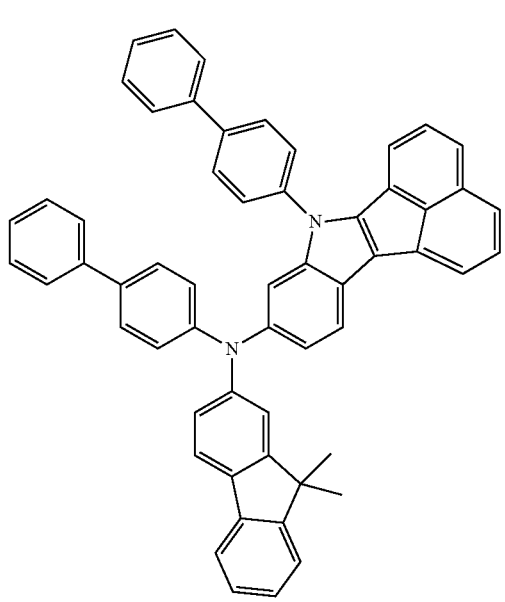
1-98
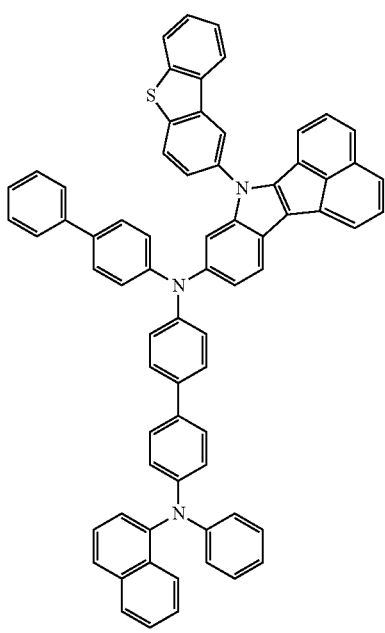

1-99
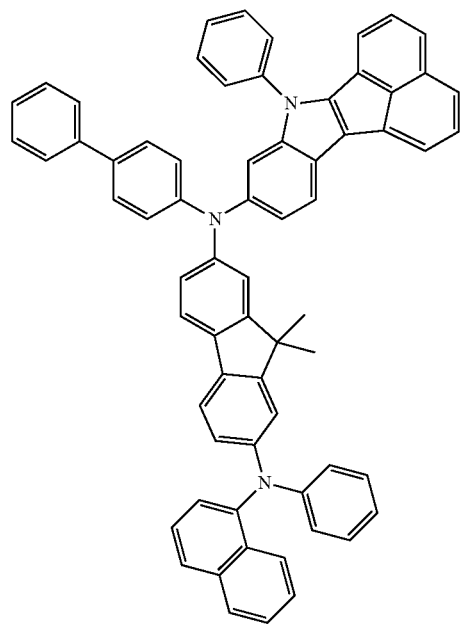
1-100
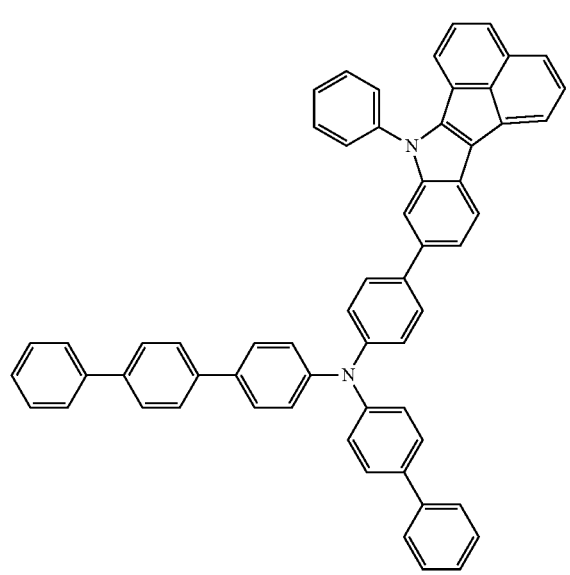
1-101
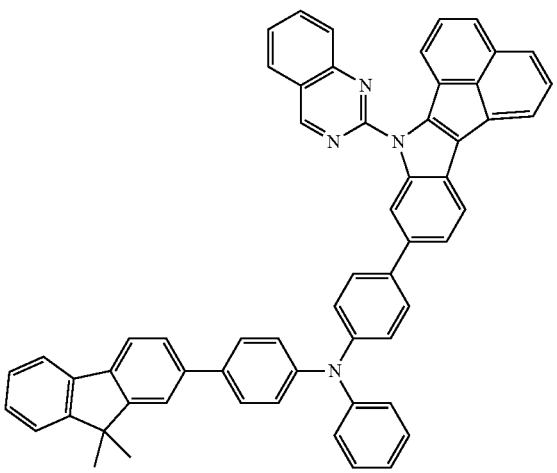
1-102
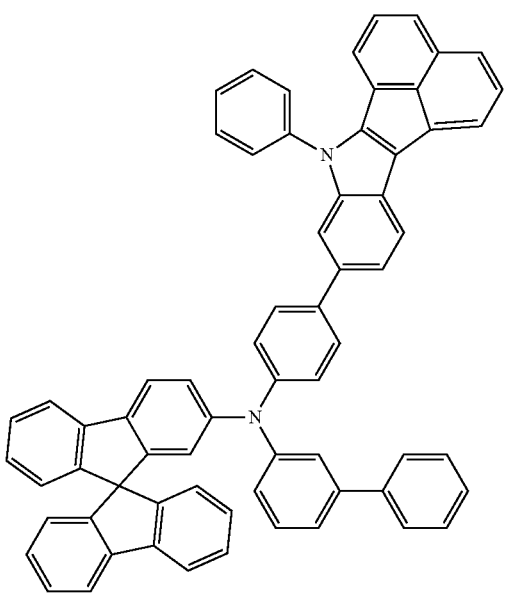
1-103
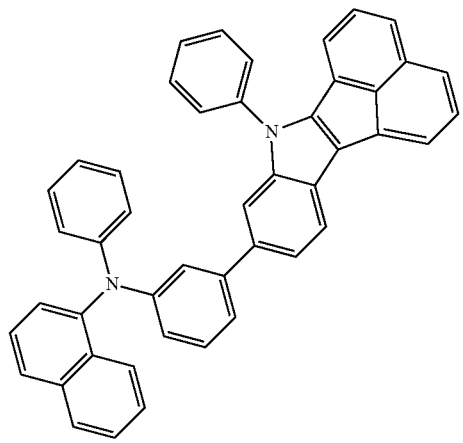

1-104
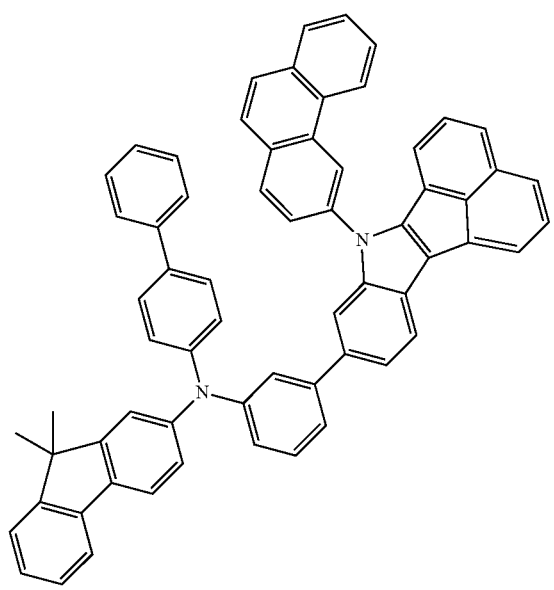
1-106
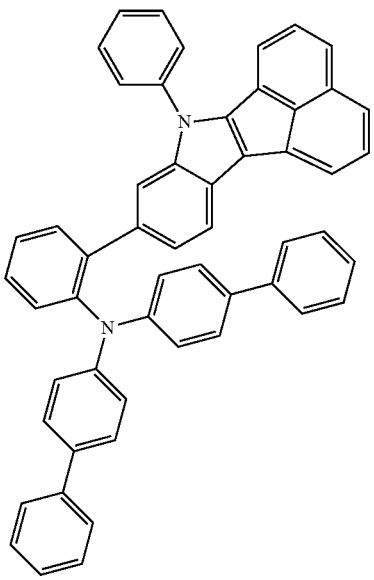
1-105
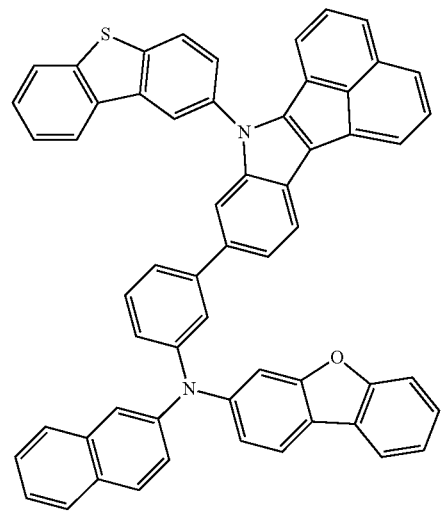
1-107
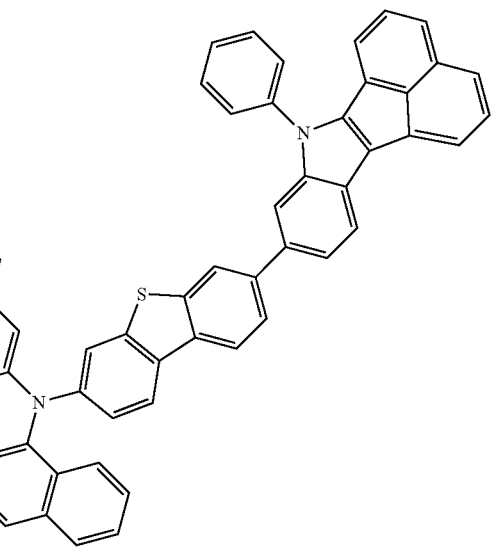

1-108
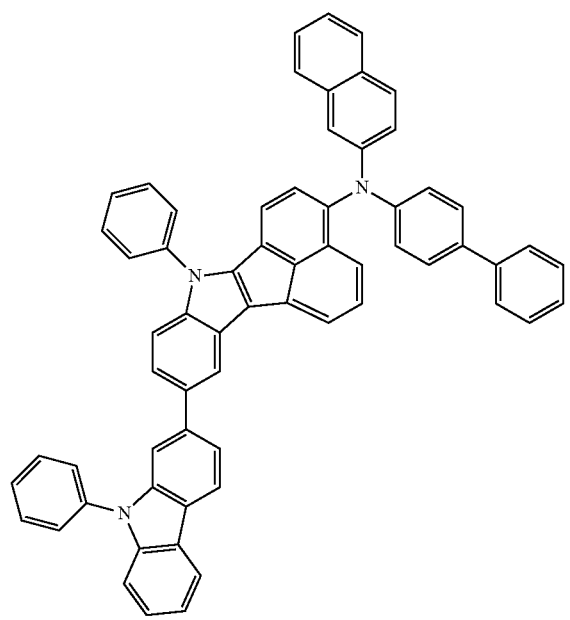
1-110
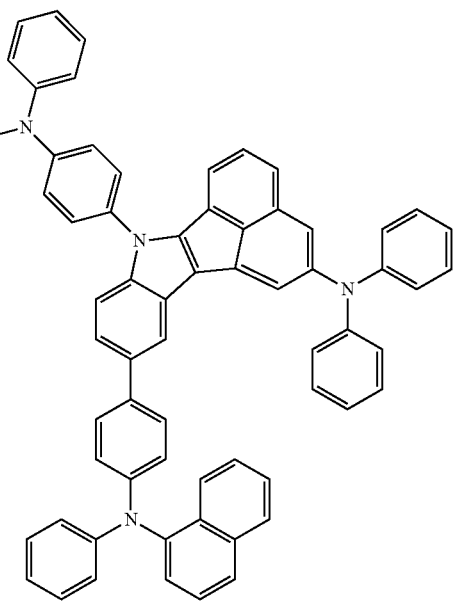
1-109
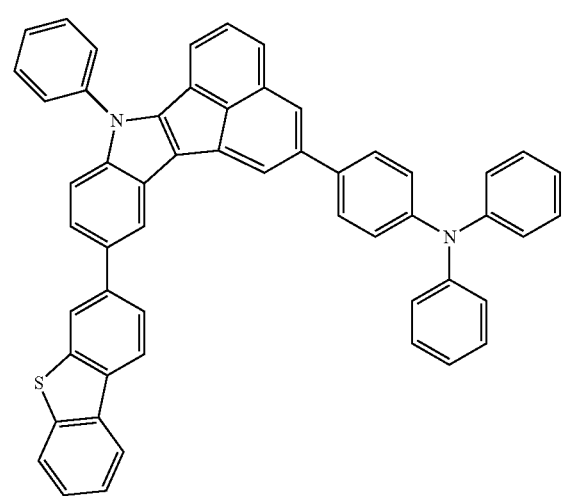
1-111
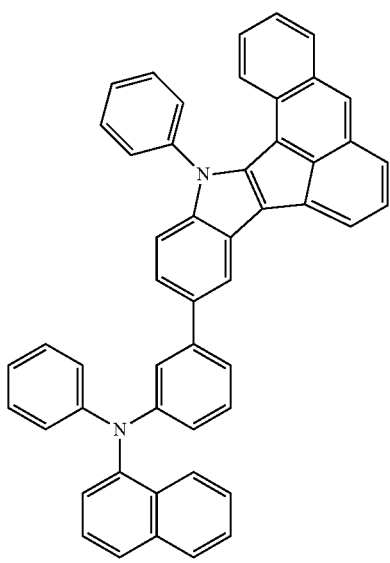

-continued 1-112
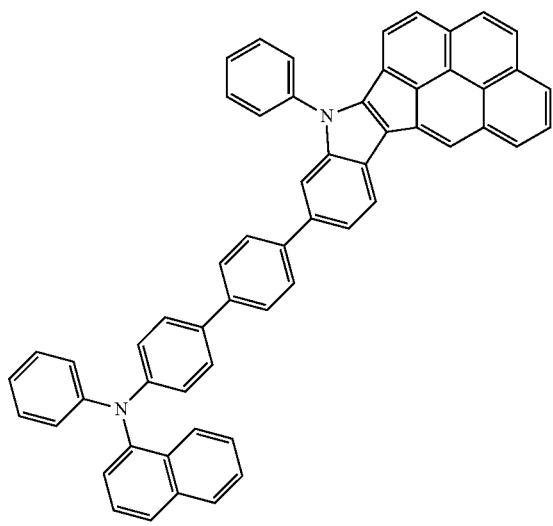

11. An organic electric element comprising a first electrode, a second electrode, and an organic material layer formed between the first electrode and the second electrode, wherein the organic material layer comprises the compound of claim 10.

12. An electronic device comprising a display device and a control unit for driving the display device, wherein the display device comprises the organic electric element of claim 11.

* * * * *